United States Patent
Abergel et al.

(10) Patent No.: US 12,002,595 B2
(45) Date of Patent: Jun. 4, 2024

(54) SEPARATION OF METAL IONS BY LIQUID-LIQUID EXTRACTION

(71) Applicant: The Regents of the University of California, Oakland, CA (US)

(72) Inventors: Rebecca J. Abergel, Oakland, CA (US); Gauthier J. P. Deblonde, Oakland, CA (US); Abel Ricano, Oakland, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 215 days.

(21) Appl. No.: 16/365,132

(22) Filed: Mar. 26, 2019

(65) Prior Publication Data

US 2019/0287691 A1    Sep. 19, 2019

Related U.S. Application Data

(63) Continuation-in-part of application No. PCT/US2017/048934, filed on Aug. 28, 2017.
(Continued)

(51) Int. Cl.
*G21F 9/12*    (2006.01)
*G21C 19/46*    (2006.01)
(Continued)

(52) U.S. Cl.
CPC ............. *G21F 9/125* (2013.01); *G21C 19/46* (2013.01); *G21F 9/00* (2013.01); *C07K 14/47* (2013.01); *Y02W 30/50* (2015.05)

(58) Field of Classification Search
CPC ............................. G21F 19/125; G21C 19/46
(Continued)

(56) References Cited

U.S. PATENT DOCUMENTS 3,323,857  A  *  6/1967  Bauer .................... C01F 17/276
                                                        423/21.5
3,634,113  A  *  1/1972  Fehrenbacher ......... C04B 35/46
                                                        501/103
(Continued)

FOREIGN PATENT DOCUMENTS

CN      104825389      8/2015
CN      104998251      10/2015
(Continued)

OTHER PUBLICATIONS

Extended European Search Report dated Jan. 19, 2021 in Application No. 17857076.8.
(Continued)

*Primary Examiner* — Melissa S Swain
(74) *Attorney, Agent, or Firm* — Knobbe, Martens, Olson & Bear, LLP

(57) ABSTRACT

Provided herein are separation processes for metal ions present in aqueous solutions based on methods involving liquid-liquid extraction. The separation process involves a chelator that can selectively bind to at least one of the metals at a relatively low pH. This can be used, for example, for recovery and purification of actinides from lanthanides, separation of metal ions based on their valence, and separation of metal ions based on the pH of the extraction conditions.

15 Claims, 106 Drawing Sheets

Related U.S. Application Data

(60) Provisional application No. 62/505,458, filed on May 12, 2017, provisional application No. 62/401,687, filed on Sep. 29, 2016.

(51) Int. Cl.
  *G21F 9/00* (2006.01)
  *C07K 14/47* (2006.01)

(58) Field of Classification Search
  USPC .......................................................... 423/8
  See application file for complete search history.

(56) References Cited

U.S. PATENT DOCUMENTS

| | | | |
|---|---|---|---|
| 4,025,602 A * | 5/1977 | Campbell | ............... C22B 59/00 423/7 |
| 4,278,559 A | 7/1981 | Levenson et al. | |
| 4,698,431 A * | 10/1987 | Raymond | ............ C07D 213/89 546/261 |
| 4,891,075 A | 1/1990 | Dakubu | |
| 5,442,116 A | 8/1995 | Welch et al. | |
| 5,482,570 A | 1/1996 | Saurer et al. | |
| 5,510,091 A * | 4/1996 | Rais | .................... C22B 60/0295 423/9 |
| 5,571,894 A | 11/1996 | Wels et al. | |
| 5,587,458 A | 12/1996 | King et al. | |
| 5,591,828 A | 1/1997 | Bosslet et al. | |
| 5,624,901 A | 4/1997 | Raymond et al. | |
| 5,634,901 A | 6/1997 | Alba et al. | |
| 5,753,204 A | 5/1998 | Huston et al. | |
| 5,826,161 A | 10/1998 | Madic et al. | |
| 5,869,046 A | 2/1999 | Presta et al. | |
| 5,892,029 A * | 4/1999 | Raymond | ............ C07D 213/81 546/256 |
| 6,221,476 B1 * | 4/2001 | Bruening | ........... B01D 67/0093 428/305.5 |
| 6,843,917 B1 | 1/2005 | Guy et al. | |
| 6,846,915 B2 | 1/2005 | Raymond et al. | |
| 8,361,794 B2 | 1/2013 | Jakobsen et al. | |
| 8,475,747 B1 | 7/2013 | Johnson et al. | |
| 8,557,601 B2 * | 10/2013 | Raymond | ............... C09K 11/06 530/391.1 |
| 8,933,526 B2 | 1/2015 | Tsakalakos et al. | |
| 9,123,846 B2 | 9/2015 | Le Perchec et al. | |
| 9,472,694 B2 | 10/2016 | Dionne et al. | |
| 9,556,122 B2 * | 1/2017 | Raymond | ............... C09K 11/06 |
| 10,982,136 B2 | 4/2021 | Agbo et al. | |
| 11,684,614 B2 | 6/2023 | Abergel et al. | |
| 2002/0122752 A1 | 9/2002 | Fukasawa et al. | |
| 2005/0008570 A1 | 1/2005 | Raymond et al. | |
| 2009/0184051 A1 | 7/2009 | Heres et al. | |
| 2009/0320646 A1 | 12/2009 | Yaita et al. | |
| 2010/0015725 A1 * | 1/2010 | Raymond | ............... H05B 33/14 530/391.1 |
| 2010/0261902 A1 | 10/2010 | Xu | |
| 2010/0317117 A1 * | 12/2010 | Peterson | ............ B01D 67/0009 436/57 |
| 2011/0250138 A1 | 10/2011 | Fan et al. | |
| 2012/0132277 A1 | 5/2012 | Sulima et al. | |
| 2012/0214843 A1 | 8/2012 | Durbin-Harvey et al. | |
| 2014/0039169 A1 * | 2/2014 | Raymond | ............... H05B 33/14 546/261 |
| 2014/0235680 A1 | 8/2014 | Bergeron et al. | |
| 2016/0289223 A1 | 10/2016 | Bergeron | |
| 2016/0362491 A1 | 12/2016 | Mudde et al. | |
| 2017/0298272 A1 | 10/2017 | Agbo et al. | |
| 2017/0360956 A1 * | 12/2017 | Butlin | ............... A61K 51/1096 |
| 2019/0183868 A1 | 6/2019 | Abergel et al. | |
| 2019/0287691 A1 | 9/2019 | Abergel et al. | |
| 2019/0382470 A1 | 12/2019 | Himmler et al. | |
| 2021/0009510 A1 | 1/2021 | Abergel et al. | |
| 2021/0283115 A1 | 9/2021 | Abergel et al. | |
| 2022/0152003 A1 | 5/2022 | Abergel et al. | |

FOREIGN PATENT DOCUMENTS

| | | |
|---|---|---|
| EP | 0404097 B1 | 6/1990 |
| EP | 1755586 A2 | 2/2007 |
| EP | 3452040 A1 | 3/2019 |
| EP | 3509595 A1 | 7/2019 |
| EP | 3519034 A1 | 8/2019 |
| EP | 3520117 A2 | 8/2019 |
| EP | 3 520 117 B1 | 11/2023 |
| JP | 2008-525812 | 7/2008 |
| JP | 2019-514944 A | 6/2019 |
| JP | 2019-532040 A | 11/2019 |
| JP | 2019-532182 A | 11/2019 |
| WO | WO 1993/01161 A1 | 1/1993 |
| WO | WO 1993/16185 A2 | 8/1993 |
| WO | WO 2006/028523 | 3/2006 |
| WO | WO 2006/072620 A1 | 7/2006 |
| WO | WO 2007/098934 A1 | 9/2007 |
| WO | WO 2007/118904 | 10/2007 |
| WO | WO 2010/129962 | 11/2010 |
| WO | WO 2015/077655 A1 | 5/2015 |
| WO | WO 2017/105565 | 6/2017 |
| WO | WO 2017/192581 A1 | 11/2017 |
| WO | WO 2018/048812 A1 | 3/2018 |
| WO | WO 2018/063638 A1 | 4/2018 |
| WO | WO 2018/097871 A2 | 5/2018 |

OTHER PUBLICATIONS

Durbin, P. et al., "Octadentate catecholamide ligands for Pu (IV) based on linear or preorganized molecular backbones", Human Toxicology, Macmillan Publishers, Basingstoke GB, vol. 15, No. 4, pp. 352-360, 1996.

Gans, et al., GLEE, a new computer program for glass electrode calibration, Talanta, vol. 51, No. 1, pp. 33-37, 2000.

Uhlir, Linda et al., "Specific sequestering agents for the actinides. 21. Synthesis and initial biological testing of octadentate mixed catecholate-hydroxypyridinonate ligands", Journal of Medicinal Chemistry, vol. 36, No. 4, pp. 504-509, 1993.

Office Action dated Jul. 22, 2020 in U.S. Appl. No. 16/097,782.

European Search Report, re Application No. 17873523.9, dated Aug. 27, 2020.

Supplementary Partial European Search Report, re Application No. 17857076.8, dated Oct. 7, 2020.

Abergel, et al. Biomimetic Actinide Chelators: An Update on The Preclinical Development of The Orally Active Hydroxypyridonate Decorporation Agents 3,4,3-L/(1,2-HOPO) and 5-LIO(Me-3,2-HOPO). Health Physics, vol. 99, No. 3, pp. 401-417, 2010.

Abergel, et al. Using the Antenna Effect as a Spectroscopic Tool; Photophysics and Solution Thermodynamics of the Model Luminescent Hydroxypyridonate Complex [EuIIIQ,4,3-LI(1,2-HOPO))], Inorganic Chemistry, vol. 48, No. 23, pp. 10868-10870, 2009.

Abergel, et al., Multidentate Terephthalamidate and Hydroxypyridonate Ligands: Towards New Orally Active Chelators, Hemoglobin, vol. 35, No. 3, pp. 276-290, 2011.

Agbo et al., Enhanced ultraviolet photon capture in ligand-sensitized nanocrystals, ACS Photonics, vol. 3, pp. 547-552, 2016.

Agbo et al., Ligand-Sensitized Lanthanide Nanocrystals: Merging Solid-State Photophysics and Molecular Solution Chemistry, Inorganic Chemistry, vol. 55, No. 20, pp. 9973-9980, 2016.

Agency for Toxic Substances and Disease Registry (ATSDR), Toxicological profile for Plutonium. 2010, U.S. Department of Health and Human Services, Public Health Service: Atlanta, GA.

Alderighi, et al., Hyperquad Simulation and Speciation (HySS): A Utility Program for The Investigation of Equilibria Involving Soluble And Partially Soluble Species, Coordination Chemistry Reviews, vol. 184, pp. 311-318, 1999.

Allred, B. et al. Siderocalin-mediated recognition, sensitization, and cellular uptake of actinides. Proceedings of the National Academy of Sciences of the United States of America, vol. 112, pp. 10342, 2015.

An, et al., Elimination Profiles After Delayed Treatment With 3,4,3L/(1,2HOPO) in Female and Male Swiss-Webster Mice. International Journal of Radiation Biology, vol. 90, No. 11, pp. 1055-1061, 2014.

(56) References Cited

OTHER PUBLICATIONS

An, et al., From Early Prophylaxis To Delayed Treatment: Establishing The Plutonium Decorporation Activity Window of Hydroxypyridinonate Chelating Agents, Chemico-Biological Interactions, Elsevier Science Ireland, IR, vol. 267, pp. 80-88, 2016.
Ansari, et al., Extraction of actinides using N, N,N , N-Tetraoctyl Diglycolamide (TODGA): A Thermodynamic Study Radiochimica. Acta Journal, vol. 94, pp. 307-312, 2006.
Ansari, et al., N,N,N',N'-Tetraoctyl Diglycolamide (TODGA): A Promising Extractant for Actinide-Partitioning from High-Level Waste (HLW), Solvent Extraction and Ion Exchange, pp. 463-479, 2006.
Antonio, M. et al., Berkelium redox speciation, Radiochim. Acta, vol. 90, pp. 851-856, (2006).
Argonne National Laboratory Division of Biological and Medical Research, Annual Report, Argonne National Laboratory. Division of Biological and Medical Research: Argonne, Illinois. 1979.
Baco, et al., Diphenyl-Benzo[1,3]dioxole-4-Carboxylic Acid Pentafluorophenyl Ester: A Convenient Catechol Precursor in The Synthesis of Siderophore Vectors Suitable for Antibiotic Trojan Horse Strategies, Organic and Biomolecular Chemistry, vol. 12, pp. 749, 2014.
Banker, et al., Pharmaceutics and Pharmacy Practice, pp. 238-250, 1982.
Banski, M. et al., NaYF4 nanocrystals with TOPO ligands: synthesis-dependent structural and luminescent properties, Physical Chemistry Chemical Physics, vol. 15, No. 47, pp. 19232-19241, 2013.
Baral, T. et al., Experimental Therapy of African Trypanosomiasis With A Nanobody-Conjugated Human Trypanolytic Factor, Nature Medicine, vol. 12, pp. 580-584, 2006.
Barthelemy, et al., Journal of Biological Chemistry, pp. 3283-3639, 2008.
Baybarz, et al. Absorption Spectra of Bk(III) and Bk(IV) in Several Media, Journal of Inorganic and Nuclear Chemistry, Vo. 34, pp. 739-746, 1972.
Bhattacharyya, M. et al., Action of DTPA on Hepatic Plutonium: III. Evidence for a Direct Chelation Mechanism for DTPA-Induced Excretion of Monomeric Plutonium into Rat Bile, Radiation Research, vol. 80, pp. 108-115, 1979.
Binz, et al., Engineering Novel Binding Proteins From Nonimmunoglobulin Domains, Nature Biotechnology, vol. 23, pp. 1257-1268, 2005.
Bird, et al., Single-chain antigen-binding proteins, Science, vol. 242, No. 4877, pp. 423-426, 1988.
Boersma, et al., DARPins and Other Repeat Protein Scaffolds: Advances in Engineering and Applications, Current Opinion in Biotechnology, vol. 22, No. 4, pp. 849-857, 2011.
Bunin, et al., Dose-Dependent Efficacy and Safety Toxicology of Hydroxypyridinonate Actinide Decorporation Agents in Rodents: Towards A Safe And Effective Human Dosing Regimenm Radiation Research, vol. 179, No. 2, pp. 171-182, 2013.
Bünzlil, et al., Lanthanide Luminescence for Biomedical Analyses and Imaging, Chemical Reviews, vol. 110, No. 5, pp. 2729-2755, 2010.
Bünzlil, et al. Taking Advantage of Luminescent Lanthanide Ions, Chemical Society Reviews, vol. 34, No. 12, pp. 1048-1077, 2005.
Carnall, et al., A Systematic Analysis of The Spectra The Trivalent Actinide Chlorides in D3h Site Symetry, Argonne National Laboratory, Argonne , Illinois, USA, 1989.
Carott, et al., Distribution of plutonium, americium and interfering fission products between nitric acid and a mixed organic phase of TODGA and DMDOHEMA in kerosene, and implications for the design of the "EURO-GANEX" process, Hydrometallurgy, vol. 152, pp. 139-148, 2015.
Carrot, et al. Neptunium Extraction and Stability in the GANEX Solvent: 0.2 M TODGA/0.5 M DMDOHEMA/Kerosene, Solvent Extraction and Ion Exchange, 2012.

Captain, et al., Engineered Recognition of Tetravalent Zirconium and Thorium by Chelator-Protein Systems: Toward Flexible Radiotherapy and Imaging Platforms, Inorganic Chemistry, vol. 55, pp. 11930-11936, 2016.
Cassatt, et al., Medical Countermeasures Against Nuclear Threats: Radionuclide Decorporation Agents., Radiation Research, vol. 170, No. 4, pp. 540-548, 2008.
Chang, et al., Analytical Methods for the Bioavailability Evaluation of Hydroxypyridinonate Actinide Decorporation Agents in Pre-Clinical Pharmacokinetic Studies, Journal Chromatography Separation Technique Journal, 2012.
Chen, et al. Core/Shell NaGdF4:Nd3+/NaGdF4 Nanocrystals with Efficient Near-Infrared to Near-Infrared Downconversion Photoluminescence for Bioimaging Applications, ACS Nano, vol. 6, No. 4, pp. 2969-2977, 2012.
Choi, et al., Biodistribution of the Multidentate Hydroxypyridinonate Ligand (14)CJ-3,4,3-L/(1,2-HOPO), A Potent Actinide Decorporation Agent, Drug Development Research, vol. 76, No. 3, pp. 107-122, 2015.
Choi, et al., In vitro metabolism and stability of the actinide chelating agent 3,4,3-Lf {1,2-I-/OPO). Journal of pharmaceutical sciences, vol. 104, No. 5, pp. 1832-1838, 2015.
Choi, et al., Understanding the Health Impacts and Risks of Exposure to Radiation, in Reflections on the Fukushima Daiichi Nuclear Accident, Chemical Sciences Division, Lawrence Berkeley National Laboratory, pp. 259-281, 2015.
Chudinov, et al., The separation of berkelium (III) from cerium (III), Journal of Radioanalytical and Nuclear Chemistry, vol. 10, pp. 41-46, 1972.
Cortez-Retamozo, V. et al., Efficient Cancer Therapy with a Nanobody-Based Conjugate, Cancer Research, vol. 64, pp. 2853-2857, 2004.
Cotton, et al., Wiley, 2006. http://www.wiley.com/WileyCDA/WileyTitle/productCd-0470010053.html.
Daumann, et al. New Insights into Structure and Luminescence of Eu(III) and Sm(III) Complexes of the 3,4,3-Li(1,2-HOPO) Ligand, Journal of the American Chemical Society, vol. 137, pp. 2816-2819, 2015.
Deblonde, et al., A New Strategy for The Purification of Heavy Actinides and Medical Radioisotopes, Advanced Techniques in Actinide Spectroscopy, 2018.
Deblonde, et al., Chelation and stabilization of berkelium in oxidation state +IV, Nature Chemistry, vol. 9, pp. 843-849, 2017.
Deblonde, et al., Complexation, Characterization and Separation of the Lanthanides and Actinides: Shedding Light to Subtle Differences within the f-element Series, Actinides and Rare Earths Focus Topic, 2018.
Deblonde, et al., Solution Thermodynamic Stability of Complexes Formed with the Octadentate Hydroxypyridinonate Ligand 3,4,3-LI(1,2-HOPO): A Critical Feature for Efficient Chelation of Lanthanide(IV) and Actinide(IV) Ions, Inorganic Chemistry, vol. 52, pp. 8805-8811, 2013.
Deblonde, et al., 1387—Hydropyridinonate ligands: From iron(III) to berkelium(IV) chemistry, Abstract.
Deblonde, et al., Inducing Selectivity and Chirality in Group IV Metal Coordination With High-Denticity Hydroxypyridinones†, Dalton Transactions, No. 23, 2019.
Deblonde, et al., Solution Thermodynamics and Kinetics of Metal Complexation with a Hydroxypyridinone Chelator Designed for Thorium-227 Targeted Alpha Therapy, Inorganic Chemistry, vol. 57, pp. 14337-14346, 2018.
Deblonde, et al., Solution thermodynamics of hydropyridinonate 4f and 5f complexes, 28th Rare Earth Research Conference, 2017.
Deblonde, et al., Toxic heavy metal—Pb, Cd, Sn—complexation by the octadentate hydroxypyridinonate ligand archetype 3,4,3-LI(1,2-HOPO)†, New Journal of Chemistry, vol. 42, pp. 7649-7658, 2018.
Deblonde, et al., Ultra-selective Ligand-driven Separation of Strategic Actinides, Nature Communications, 2019.
Deblonde, et al., Inorganic chemistry, vol. 52, No. 15, pp. 8805-8811, 2013.

(56) References Cited

OTHER PUBLICATIONS

Delmau, et al., Extraction of Trivalent Actinides and Lanthanides from Californium Campaign Rework Solution Using TODGA-based Solvent Extraction System, Oak Ridge National Laboratory, 2017.

Deri, et al., Alternative Chelator for 89Zr Radiopharmaceuticals: Radiolabeling and Evaluation of 3,4,3-(LI-1,2-HOPO), Journal of Medicinal Chemistry, vol. 57, No. 11, pp. 4849-4860, 2014.

Deri, et al., Bioconjugate Chemistry, vol. 26, No. 12, pp. 2579-2591, 2015.

Deri, et al., A Superior Bifunctional Chelator for 89Zr ImmunoPET, Bioconjugate Chemistry, vol. 26, No. 12, pp. 2579-2591, 2015.

Designing a Process for Selecting a Site for a Deep-Mined, Geologic Repository for High Level Radioactive Waste and Spent Nuclear Fuel, United States Nuclear Waste Technical Review Board, pp. 1-228, 2015.

Durbin, et al. Actinides in Animals and Man, in The Chemistry of the Actinide and Transactinide Elements, L.R. Morss, N.M. Edelstein, and J. Fuger, Editors, pp. 3339-3340, 2006.

Durbin, et al., Gross Composition and Plasma and Extracellular Water Volumes of Tissues of a Reference Mouse, Health Physics, vol. 63, No. 4, pp. 427-442, 1992.

Durbin, et al., Lecture: The Quest For Therapeutic Actinide Chelators, Health Physics, vol. 95, No. 5, pp. 465-492, 2008.

Dutta, et al., Studies on separation of 90Y and 90Sr separation from hydrochloric acid solutions using TODGA as the extractant by SLM method, Procedia Chemistry, vol. 7, pp. 191-194, 2012.

Fritsch, et al., Simplified Structure of a New Model To Describe Urinary Excretion of Plutonium After Systemic, Liver or Pulmonary Contamination of Rats Associated With Ca-DTPA Treatments, Radiation Research, vol. 171, No. 6, pp. 674-686, 2009.

Fritsch, et al., Structure of a Single Model to Describe Plutonium and Americium Decorporation by DTPA treatments, Health Physics, vol. 99, No. 4, pp. 553-559, 2010.

Gans, et al., Investigation of Equilibria in Solution. Determination of Equilibrium Constants with the Hyperquad Suite of Programs, Taianta, vol. 43, pp. 1739-1753, 1996.

Gennaro, et al., Remington: The Science and Practice of Pharmacy, 20th ed, 2003.

Goetz, et al., The Neutrophil Lipocalin NGAL is a Bacteriostatic Agent That Interferes With Siderophore-Mediated Iron Acquisition, Molecular Cell, vol. 10, pp. 1033-1043, 2002.

Gorden, et al., Rational Design of Sequestering Agents for Plutonium and Other Actinides, Chemical Reviews, vol. 103, pp. 4207-4282, 2003.

Grappin, et al., Treatment of actinide exposures: A review oJCa-DTPA injections inside CEA-COGEMA plants, Radiation Protection Dosimetry, vol. 127, pp. 435-439, 2007.

Gregoric, et al., Characterization and Leaching of Neodymium Magnet Waste and Solvent Extraction of the Rare-Earth Elements Using TODGA, Journal of Sustain. Metall, vol. 3, pp. 638-645, 2017.

Grimes, et al., Trivalent Lanthanide/Actinide Separation Using Aqueous-Modified TALSPEAK Chemistry, Solvent Extraction and Ion Exchange, vol. 32, No. 4, pp. 378-390, 2014.

Gutmacher, et al., The absorption spectra of Bk3+ and Bk4+ in solution, Journal of Inorganic and Nuclear Chemistry, vol. 29, pp. 2341-2345, 1967.

Gutmacher, et al., Stability of Tetravalent Berkelium in Acid Solution and The Absorption Spectra of Bk(IV) and Bk(III), Journal of Inorganic and Nuclear Chemistry, pp. 979-994, 1973.

Harvey, Production of Actinium-225 via High Energy Proton Induced Spallation of Thorium-232. Final Technical Report DE-SC0003602, NorthStar Medical Radioisotopes, LLC, https//world wide web .osti.gov/scitech/servlets/purl/1032445/).

Hobart, et al., The Chemistry of the Actinide and Transactinide Elements—Chapter X—Berkelium, Springer, 2006.

Hoet, et al., Generation of High-Affinity Human Antibodies by Combining Donor-Derived and Synthetic Complementarity-Determining-Region Diversity, Nature Biotechnology, vol. 23, pp. 344-348, 2005.

Holliger, et al., Diabodies: small bivalent and bispecific antibody fragments, Proceedings of the National Academy of Sciences of the USA, vol. 90, pp. 6444-6448, 1993.

Hudson, et al., Engineered antibodies, Nature Medicine, vol. 9, pp. 129-134, 2003.

Husain, et al., Extraction chromatography of lanthanides using N,N,N',N'-tetraoctyl diglycolamide (TODGA) as the stationary phase, Desalination, vol. 229, pp. 294-301, 2008.

Huston, et al., Protein Engineering of Antibody Binding Sites: Recovery of Specific Activity in an Anti-Digoxin Single-Chain Fv Analogue Produced in *Escherichia coli*, Proceedings of the National Academy of Sciences of the USA, vol. 85, pp. 5879-5883, 1988.

Iqbal, et al., Synthesis and Am/Eu extraction of novel TODGA derivatives, Supramolecualr Chemistry, vol. 22, pp. 827-837, 2010.

Jang, et al. Bright dual-mode green emission from selective set of dopant ions in β-Na(Y,Gd)F4:Yb,Er/β-NaGdF4:Ce,Tb core/shell nanocrystals, Optics Express, vol. 20, No. 15, pp. 17107-17118, (2012).

Jarvis, et al., Significance of Single Variables in Defining Adequate Animal Models to Assess the Efficacy of New Radionuclide Decorporation Agents: Using the Contamination Dose as an Example. Drug Development Research, vol. 73, No. 5, pp. 281-299, 2012.

Burgada, et al., Journal of Labelled Compounds and Radiopharmaceuticals, vol. 44, pp. 13-19, 2001.

Jursich, et al., Laser induced fluorescence of 249 Bk 4+ in CeF 4, Inorganica Chim. Acta. vol. 139, pp. 273-274. 1987.

Konzen, et al., Development of the Plutonium-DTPA Biokinetic Model. Health Physics, vol. 108, No. 6, pp. 565-573, 2015.

Kurkoti, et al., Gadolinium and nephrogenic systemic fibrosis: Association or causation. 1-10 Nephrology, vol. 13, pp. 235-241, 2008.

Kullgren, et al., Actinide Chelation: Biodistribution and In Vivo Complex Stability of The Targeted Metal Ions, Toxicology Mechanisms and Methods, vol. 23, No. 1, pp. 18-26, 2013.

Lakowicz, et al., Energy Transfer, Principles of Fluorescence Spectroscopy, pp. 367-394, 2006.

Lake, et al., Construction and Binding Analysis of Recombinant Single-Chain TCR Derived From Tumor-Infiltrating Lymphocytes and a Cytotoxic T Lymphocyte Clone Directed Against MAGE-1, International Immunology, Vo. 11, pp. 745-751, 1999.

Lakshminarayana, et al., Cooperative downconversion luminescence in Pr3+/Yb3+:SiO2-Al2O3—BaF2—GdF3 glasses, Journal of Materials Research, vol. 23, Issue 11, pp. 3090-3095, 2008.

Li, et al., Engineering Homogeneous Doping in Single Nanoparticle to Enhance Upconversion Efficiency, Nano Lett., vol. 14, No. 6, pp. 3634-3639, 2014.

Li, et al., Enhanced NIR downconversion luminescence by precipitating nano Ca5(PO4)3F crystals in Eu2+-Yb3+ co-doped glass, Spectrochimica Acta Part A: Molecular and Biomolecular Spectroscopy, vol. 114, pp. 575-578, 2013.

Li, et al. Nd3+ Sensitized Up/Down Converting Dual-Mode Nanomaterials for Efficient In-vitro and In-vivo Bioimaging Excited at 800 nm, Scientific Reports, vol. 3, pp. 3536, 2013.

Liu, et al. A Strategy to Achieve Efficent Dual-Mode Luminescence of EU3+ in Lanthanides Doped Multifunctional NAGdF4 Nanocrystals, Adv Matter, vol. 22, pp. 3266-3271, 2010.

Liu, et al. Morphology and Phase-Controlled Synthesis of Monodisperse Lanthanide-Doped NaGdF4 Nanocrystals with Multicolor Photo Luminesence, Journal of Materials Chemistry, vol. 19, pp. 489-496, 2009.

Liu et al., Procedures for a fast separation of berkelium from complex mixtures of reaction products, J. Radioanal. Nucl. Chem. 76, pp. 119-124, 1983.

Lohithakshan, et al., Solvent extraction studies of plutonium(IV) and americium(III) in room temperature ionic liquid (RTIL) by di-2-ethyl hexyl phosphoric acid (HDEHP) as Extractant, Journal of Radioanalytical and Nuclear Chemistry, vol. 301, pp. 153-157, 2014.

(56) References Cited

OTHER PUBLICATIONS

Loomis, et al., Inorganic Chemistry, vol. 30, No. 5, pp. 906-911, 1991.
Lumetta, et al., An Advanced TALSPEAK Concept Using 2-Ethylhexylphosphonic Acid Mono-2-Ethylhexyl Ester as the Extractant, Solvent Extraction and Ion Exchange, vol. 33, No. 3, pp. 211-223, 2015.
Lundberg, et al., Structural Study of the N,N'-Dimethylpropyleneurea Solvated Lanthanoid(III) Ions in Solution and Solid State with an Analysis of the Ionic Radii of Lanthanoid(III) Ions, Inorganic Chemistry, vol. 49, pp. 4420-4432, 2010.
Lundberg, et al., The size of actinoid(III) ions—structural analysis vs. common misinterpretations, Coordination Chemistry Reviews, vol. 318, pp. 131-134, 2016.
Martell, et al., NIST Standard Reference Database; National Institute of Standards and Technology: Gaithersburg, MD.
Maynard, et al., High-Level Bacterial Secretion of Single-Chain Aβ T-Cell Receptors, Journal of Immunological Methods, vol. 306, pp. 51-67, 2005.
Mimum, et al., Bimodal imaging using neodymium doped gadolinium fluoride nanocrystals with near-infrared to near-infrared downconversion luminescence and magnetic resonance properties, Journals of Materials Chemistry B, vol. 1, pp. 5702-5710, 2013.
Milyukova, et al. Extraction of Bk(IV) with POM—Milyukova, 1986.pdf, J. Radioanal. Nucl. Chem. 104 pp. 81-90, (1986).
Modolo, et al., Recovery of Actinides and Lanthanides From High-Level Liquid Waste by Extraction Chromatography Using TODGA+TBP Impregnated Resins, Radiochimica Acta, vol. 95, pp. 391-397, 2007.
Modolo, et al., Development of a TODGA based Process for Partitioning of Actinides from a PUREX Raffinate Part I: Batch Extraction Optimization Studies and Stability Tests, Solvent Extraction and Ion Exchange, 2007.
Moore, et al. An octadentate luminescent Eu(III) 1,2-HOPO chelate with potent aqueous stability, Inorganic Chemistry, vol. 46, No. 14, pp. 5468-5470, 2007.
Moore, et al., Application of dual affinity retargeting molecules to achieve optimal redirected T-cell killing of B-cell lymphoma, Blood, Vo. 117, pp. 4542-4551, 2011.
Moore, et al. Liquid-liquid Extraction Method for The Separation of Cerium (IV) From Berkelium (IV) and Other Elements, Analytical Chemistry, vol. 41, pp. 1658-1661, 1969.
Moore, et al., New Method for Rapid Separation of Berkelium (IV) From Cerium (IV) by Anion Exchange, Analytical Chemistry, vol. 39, pp. 1874-1876, 1967.
Moos, et al., Radiation Drugs—A Hot Topic. Drug Development Research, vol. 73, No. 5, pp. 229-231, 2012.
Morita, et al. Development of Todga Extraction Process for High-Level Liquid Waste—Preliminary Evaluation of Actinide Separation by Calculation, 2000.
Morris, et al., Voltammetric Investigation of The Berkelium(IV/III) Couple in Concentrated Aqueous Carbonate Solutions, Radiochimica Acta, pp. 125-134, 1990.
Morss et al., The Chemistry of the Actinide and Transactinide Elements, 4th ed, Springer,(2010).
Nash, et al., The Chemistry of TALSPEAK: A Review of the Science, Solvent Extraction. Ion Exchange Journal, vol. 33, No. 1, pp. 1-55, 2015.
NCRP, Management of Persons Contaminated with Radionuclides: Handbook, in NCRP Publication. 2008: Bethesda.
Nord, et al., A combinatorial library of an α-helical bacterial receptor domain, Protein Engineering, Design and Selection, vol. 8, No. 6, pp. 601, 1995.
Nord, et al., Binding proteins selected from combinatorial libraries of an α-helical bacterial receptor domain, Nature Biotechnology, vol. 15, pp. 772-777, 1997.
Nord, et al., Recombinant human factor VIII-specific affinity ligands selected from phage-displayed combinatorial libraries of protein A, European Journal of Biochemistry, vol. 268, pp. 4269-4277, 2001.
Nugent, et al., Electron-transfer and fd Absorption Bands of Some Lanthanide and Actinide Complexes and The Standard (II-III) Oxidation Potential for Each Member of The Lanthanide and Actinide Series, The Journal of Physical Chemistry A, vol. 77, pp. 1528-1539, 1973.
Nugent, et al., Intramolecular Energy Transfer and Sensitized Luminescence in Actinide (III). Beta.-Diketone Chelates, The Journal of Physical Chemistry A, vol. 73, pp. 1540-1549, 1969.
Ostapenko, et al., Extraction Chromatographic Behavior of Actinium and REE on DGA, Ln and TRU Resins in Nitric Acid Solutions, Journal of Radioanalytical and Nuclear Chemistry, vol. 306, pp. 707-711, 2015.
Oxford Dictionary of Biochemistry and Molecular Biology Ed. Anthony Smith, Oxford University Press, Oxford, 2004.
Parker, S et al., The McGraw-Hill Dictionary of chemical Terms, 1985.
Payne, et al. Possible Stabilization of The Tetravalent Oxidation State of Berkelium and Californium in Acetonitrile With Triphenylarsine Oxide, Inorganica Chimica Acta, vol. 139 , pp. 111-112, 1987.
Peppard, et al. Isolation of Berkelium by Solvent Extraction of The Tetravalent Species, Journal of Inorganic and Nuclear Chemistry, vol. 4, pp. 344-348, 1957.
Pham, et al., A Macrocyclic Chelator with Unprecedented Th4+ Affinity, Journal of the American Chemical Society, vol. 136, No. 25, pp. 9106-9115, 2014.
Plueckthon The Pharmacology of Monoclonal Antibodies, vol. 113, Rosenburg and Moore, 269-315, 1994.
Pokhrel, et al. Stokes emission inGdF3:Nd3+ nanoparticles for bioimaging probe, Nanoscale, vol. 6, No. 3, pp. 1667-1674, 2014.
Pourmand, et al., Distribution coefficients of 60 elements on TODGA resin: Application to Ca, Lu, Hf, U and Th isotope geochemistry, Taianta, vol. 81, pp. 741-753, 2010.
Radchenko et al., Application of Ion Exchange and Extraction Chromatography to The Separation of Actinium From Proton-Irradiated Thorium Metal for Analytical Purposes, Journal of Chromatography, pp. 55-63, 2015.
Remington's Pharmaceutical Sciences, 18th Ed. Mack Printing Company, 1990.
Ricano, et al. Combinatorial Design of Multimeric Chelating Peptoids for Selective Metal Coordination, Chemical Science, 2019.
Shannon, et al., Revised Effective Ionic Radii and Systematic Studies of Interatomic Distances in Halides and Chalcogenides, Acta Crystallographica A32, pp. 751-757, 1976.
Shockley, et al. Detailed Balance Limit of Efficiency of p-n Junction Solar Cells, Journal of Applied Physics, vol. 32, No. 3, pp. 510-519, 1961.
Smith, et al., NIST Critically selected stability constants of metal complexes database, NIST standard reference database, 2004.
Stather, et al., Use of DTPA for increasing the rate of elimination of plutonium-238 and americium-241 from rodents after their inhalation as the nitrates, Human & Experimental Toxicology, vol. 4, No. 6, pp. 573-582, 1985.
Stockley, et al., Absorption Spectra of the Bk(IV)-Bk(III) in several media, Journal of Inorganic and Nuclear Chemistry, vol. 34, pp. 739-746, 1972.
Sturzbecher-Hoehne, et al., Highly Luminescent and Stable Hydroxypyridinonate Complexes: A Step Towards New Curium Decontamination Strategies, Chemistry—A European Journal, vol. 20, No. 32, pp. 9962-9968, 2014.
Sturzbecher-Hoehne, et al., Hydroxypyridinonate Complex Stability of Group (IV) Metals and Tetravalent f-Block Elements: The Key to the Next Generation of Chelating Agents for Radiopharmaceuticals, Inorganic chemistry, vol. 54, No. 7, pp. 3462-3468, 2015.
Sturzbecher-Hoehne, et al. 3,4,3-LI(1,2-HOPO): In vitroformation of highly stable lanthanide complexes translates into efficacious in vivo europium decorporation, Dalton Trans., vol. 40, No. 33, pp. 8340-8346, 2011.
Sturzbecher-Hoehne, et al. Intramolecular Sensitization of Americium Luminescence in Solution: Shining Light on Short-Lived Forbidden 5f Transitions, Dalton Transactions, vol. 45, pp. 9912-9919, 2016.

(56) References Cited

OTHER PUBLICATIONS

Sturzbecher-Hoehne, et al., Solution Thermodynamic Evaluation of Hydroxypyridinonate Chelators 3,4,3-LI(1,2-HOPO) and 5-LIO(Me-3,2-HOPO) for UO2(VI) and Th(IV) Decorporation, Radiochimica Acta, vol. 101 ,No. 6, pp. 359-366, 2013.
Suzuki, et al., Extraction and separation of Am(III) and Sr(II) by N,N,N N-tetraoctyl-3-oxapentanediamide (TODGA), Radiochimica Acta vol. 92, pp. 463-466, 2004.
Tachimori, et al. Modification of Todga-N-Dodecane Solvent With a Monoamide for High Loading of Lanthanides(III) and Actinides(III), Solvent Extraction and Ion Exchange, 2007.
Taylor, et al., Treatment of Human Contamination With Plutonium and Americium: Would Orally Administered Ca- or Zn—DTPA be effective? Radiation Protection Dosimetry, vol. 127, pp. 469-471, 2007.
Thompson, et al., Element 97, Physics Review, vol. 77, pp. 838, 1950.
Thompson, et al., Chemical properties of Berkelium, Journal of the American Chemical Society, vol. 72, pp. 2798-2801, 1950.
Trissel, L. et al., ASHP Handbook on Injectable Drugs 4th ed, pp. 622-630, 1986.
Turanov, et al., Synergistic Extraction of U(VI), Th(IV), and Lanthanides(III) from Nitric Acid Solutions Using Mixtures of TODGA and Dinonylnaphthalene Sulfonic Acid, Solvent Extraction and Ion Exchange, 2018.
Umeda, et al., Separation of Americium from Plutonium-Solvent Extraction Raffinate by Extraction Chromatography using TODGA Absorbent, Atlantate, 2004.
U.S. Food and Drug Administration, Guidance for Industry Calcium DTPA and Zinc DTPA Drug Products—Submitting a New Drug Application. 2004.
US. Food and Drug Administration, Guidance for Industry Internal Radioactive Contamination—Development of Decorporation Agents. 2006.
U.S. Food and Drug Administration, Guidance for Industry Product Development Under the Animal Rule 2015.
U.S. Food and Drug Administration, Approval of New Drugs When Human Efficacy Studies Are Not Ethical or Feasible. 2015, U.S. FDA: Washington, DC.
Van Der Ende, et al., Lanthanide ions as spectral converters for solar cells, Physical Chemistry Chemical Physics, vol. 11, pp. 11081-11095, 2009.
Van Wijngaarden, et al. Energy Transfer Mechanism for Downconversion in The (Pr3+, Yb3+) couple, Physics Review, vol. 81, Issue 15, pp. 155112, 2010.
Wadsworth, et al., Present Status of Cerium (IV)-Cerium (III) Potentials, Analytical Chemistry, vol. 29, pp. 1824-1825, 1957.
Wai, et al., Carboxylate-Derived Calixarenes With High Selectivity for Actinium-225, Chemical Communications pp. 377-378, 1998.
Wang, et al. Down- and Up-Conversion Photoluminescence, Cathodoluminescence and Paramagnetic Properties of NaGdF4 : Yb3+,Er3+ Submicron Disks Assembled From Primary nanocrystals, Journal of Materials Chemistry, Issue 16, pp. 3178-3185, 2010.
Wang, et al. Extraction of Trivalent Americium and Europium With TODGA Homologs From HNO3 Solution, Journal of Radioanalytical and Nuclear Chemistry, vol. 313, pp. 309-318, 2017.
Wang, et al. Preparation of Core-Shell NaGdF4 Nanoparticles Doped with Luminescent Lanthanide Ions to be Used as Upconversion-Based Probes, Nature Protocols, vol. 9, No. 7, pp. 1634-1644, 2014.
Wawrzynczyk, et al. Ligand-dependent luminescence of ultra-small Eu3+-doped NaYF4 nanoparticles, Journal of Nanoparticle Research, vol. 15, pp. 1707, 2013.
Weidle et al., The Emerging Role of New Protein Scaffold-based Agents for Treatment of Cancer, Cancer Genomics and Proteomics. vol. 10, pp. 155, 2013.
Weitl, et al., Specific sequestering agents for the actinides. 3. Polycatecholate ligands derived from 2,3-dihydroxy-5-sulfobenzoyl conjugates of diaza- and tetraazaalkanes, Journal of the American Chemical Society, vol. 102. No. 7, pp. 2289-2293, 1980.
Welcher, F. J. The analytical uses of ethylenediamine tetraacetic acid; 1958.
Wermuth, C. et al., Designing Prodrugs and Bioprecursors, pp. 561-586, 2003.
Whitaker, et al., Applications of Diglycolamide Based Solvent Extraction Processes in Spent Nuclear Fuel Reprocessing, Part 1: Todga, Solvent Extraction and Ion Exchange, 2018.
Whitcomb, et al., A Public Health Perspective on The U.S. Response to The Fukushima radiological emergency. Health Phys, vol. 108, No. 3, pp. 357-363, 2015.
White, et al., Specific Sequestering Agents for the Actinides. 16. Synthesis and Initial Biological Testing of Polydentate Oxohydroxypyridinecarboxylate Ligands, Journal of Medicinal Chemistry , vol. 31, No. 1, pp. 11-18, 1988.
Wilden, A. et al. Unprecedented Inversion of Selectivity and Extraordinary Difference in the Complexation of Trivalent f-Elements by Diastereomers of a Methylated Diglycolamide, Chemistry a European Journal, 2019.
Xu, et al., Specific Sequestering Agents for the Actinides. 28. Synthesis and Initial Evaluation of Multidentate 4-Carbamoyl-3-hydroxy-1-methyl-2(1H)-pyridinone Ligands for in Vivo Plutonium (IV) Chelation, Journal of Medicinal Chemistry, vol. 38, No. 14, pp. 2606-2614, 1988.
Yantasee, et al., Novel Sorbents for Removal of Gadolinium-Based Contrast Agents in Sorbent Dialysis and Hemoperfusion: Preventive Approaches to Nephrogenic Systemic Fibrosis (NSF), Nanomedicine, vol. 6, No. 1, pp. 1-8, 2010.
Ye, et al. Down conversion luminescence of Tb3+-Yb3+ codoped SrF2 precipitated glass ceramics, Journal of Non-Crystalline Solids, vol. 357, Issues 11-13, pp. 2268-2271, 2011.
Ye, et al. Enhanced cooperative quantum cutting in Tm3+-Yb3+ codoped glass ceramics containing LaF3nanocrystals, Optics Express, vol. 16, No. 12, pp. 8989-8994, 2008.
Zou, et al. Broadband Dye-Sensitized Upconversion of Near-Infrared Light, Nature Photonics, vol. 6, pp. 560-564, 2012.
Zhang et al., Novel enterobactin analogues as potential therapeutic chelating agents: Synthesis, thermodynamic and antioxidant studies Scientific Reports, vol. 6, pp. 1-12, 2016.
Zhu, et al. An active-core/active-shell structure with enhanced quantum-cutting luminescence in Pr—Yb co-doped monodisperse nanoparticles, Nanoscale, vol. 6, pp. 10500-10504, 2014.
Zhu, X et al. Cumulative study on solvent extraction of elements by N,N,N ,N-tetraoctyl-3-oxapentanediamide (TODGA) from nitric acid into n-dodecane, Analytica Chimica Acta 527, pp. 163-168, 2004.
International Preliminary Reporton Patentability dated Nov. 6, 2018 in International Patent Application No. PCT/US2017/030628.
International Preliminary Reporton Patentability dated Mar. 12, 2019 in International Patent Application No. PCT/US2017/050121.
International Preliminary Report on Patentability dated Apr. 11, 2019 in International Patent Application No. PCT/US2017/048910.
International Preliminary Report on Patentability dated Apr. 11, 2019 in International Patent Application No. PCT/US2017/048934.
International Search Report and Written Opinion dated Jul. 27, 2017 in International Patent Application No. PCT/US2017/030628.
International Search Report and Written Opinion dated Nov. 13, 2017 in International patent application PCT/US2017/050121.
International Search Report dated Dec. 21, 2017 in International Patent Application No. PCT/US2017/048910.
International Search Report dated May 11, 2018 in International Patent Application No. PCT/US2017/048934.
Office Action dated Nov. 21, 2018 in U.S. Appl. No. 15/442,441.
Office Action dated May 6, 2019 in U.S. Appl. No. 15/442,441.
Office Action dated Aug. 23, 2019 in U.S. Appl. No. 15/442,441.
Supplementary European Search Report, dated Nov. 15, 2019, in European Application No. EP 17793154.
Extended European Search Report dated Mar. 24, 2020 in European App. No. 17849400.1.
Sam II, AD et al. Safety of gadolinium contrast angiography in patients with chronic renal Insufficiency Journal of Vascular Surgery, vol. 38, pp. 313-318, (2003).
Office Action dated Jan. 2, 2020 in U.S. Appl. No. 15/442,441.
Office Action dated Apr. 9, 2020 in U.S. Appl. No. 15/442,441.

(56) References Cited

OTHER PUBLICATIONS

Office Action dated Mar. 10, 2020 in U.S. Appl. No. 16/097,782.
Office Action dated Oct. 15, 2019 in U.S. Appl. No. 16/097,782.
Office Action dated Jun. 25, 2019 in U.S. Appl. No. 16/097,782.
Supplementary Partial European Search Report, re Application No. 17873523.9, dated May 27, 2020.
Naasani, Imad et al., Improving the Oral Bioavailability of Sulpiride by Sodium Oleate in Rabbits, J. Pharm., vol. 47, pp. 469-473, 1995.
Office Action dated Jul. 13, 2021 in U.S. Appl. No. 16/330,601.
Office Action dated Jul. 28, 2021 in JP 2019-512761.
Office Action dated Oct. 26, 2021 in Japanese Application No. 2019-516989.
Office Action dated Dec. 14, 2021 in U.S. Appl. No. 16/336,665.
Japanese Office Action dated Oct. 26, 2021 in JP 2019-516989.
Corrected Notice of Allowability dated Nov. 10, 2021 in U.S. Appl. No. 16/330,601.
Notice of Reasons for Rejection dated Apr. 26, 2021 in Japanese Patent Application No. JP 2018-557384.
Office Action dated Aug. 16, 2021 in U.S. Appl. No. 16/097,782.
Office Action dated May 14, 2021 in European Patent Application No. 17793154.0.
Pharmaceutics, 1997, vol. 57 No. Suppl, pp. 62-63.
Office Action dated Jan. 19, 2022 in U.S. Appl. No. 16/097,782.
Notice of Allowance dated Nov. 26, 2021 in Japanese Patent Application No. 2019-512761.
Office Action dated Mar. 11, 2022 in Japanese Patent Application No. 2018-557384.
Carter et al., Developing scandium and yttrium coordination chemistry to advance theranostic radiopharmaceuticals, Communications Therapy, https://doi.org/10.1038/s42004-020-0307-0, pp. 1-7 (2020).
Moore et al., "Eu(III) complexes of functionalized octadentate 1-Hydroxypyridin-2-ones: Stability, bioconjugation, and luminescence resonance energy transfer studies", Inorg. Chem. vol. 49(21):9928-9939 (2010).
Rees et al., "Evaluating the potential of chelation therapy to prevent and treat gadolinium deposition from MRI contrast agents", Scientific Reports, published online Mar. 13, 2018, www.nature.com/scientificreports, in 9 pages.
Notice of Allowance dated Oct. 29, 2021 in U.S. Appl. No. 16/330,601.
Supplemental Notice of Allowability dated Dec. 14, 2021 in U.S. Appl. No. 16/330,601.
Notice of Allowance dated Mar. 16, 2022 in U.S. Appl. No. 16/330,601.
Notice of Allowance dated Jul. 27, 2022 in U.S. Appl. No. 16/330,601.
Final Office Action dated Jul. 15, 2022 in U.S. Appl. No. 16/336,665.
Office Action with English translation in Japanese Application No. 2019-516989, dated Aug. 5, 2022.
Decision to Grant in European Application No. 17849400.1, dated Oct. 7, 2022, in 2 pages.
Decision on Petition in U.S. Appl. No. 16/330,601, dated Jun. 23, 2022.
Office Action issued in European Application No. 17793154.0, dated Sep. 20, 2022, in 4 pages.
Decision of Refusal in Japanese Application No. 2018-557384, dated Sep. 29, 2022, with English translation, in 5 pages.
Corrected Notice of Allowability dated Nov. 28, 2022, in U.S. Appl. No. 16/330,601.
Notice of Allowance dated Nov. 7, 2022, in U.S. Appl. No. 16/330,601.
Office Action dated Jan. 31, 2023, in Japanese Application No. 2022-008581.
Chatterjee et al., Excipients and Active Pharmaceutical Ingredients, American Association of Pharmaceutical Scientists, Chapter 24, pp. 347-361 (2014).
Notice of Allowance in Japanese Application No. 2019-516989, dated Mar. 29, 2023.
Non-Final Office Action dated Mar. 30, 2023, in U.S. Appl. No. 16/097,782.
Non-Final Office Action dated Mar. 28, 2023, in U.S. Appl. No. 16/336,665.
Corrected Notice of Allowability dated Apr. 12, 2023, in U.S. Appl. No. 16/330,601.
Corrected Notice of Allowability dated May 19, 2023, in U.S. Appl. No. 16/330,601.
Office Action in Canadian Application No. 3,022,852, dated Jun. 22, 2023, in 6 pages.
Office Action in Japanese Application No. 2022-008581, dated Jun. 27, 2023, in 5 pages.
Final Office Action dated Aug. 1, 2023, in U.S. Appl. No. 16/097,782.
Intention to Grant dated May 30, 2023, in European application No. 17873523.9.
Notice of Allowance in Japanese Application No. 2022-8581, dated Oct. 16, 2023.
Office Action in Canadian Application No. 3,035,966, dated Oct. 23, 2023.
Office Action in Canadian Application No. 3,038,723, dated Oct. 27, 2023.
N,N-Dimethylacetamide, C4H9NO, CID 31374—PubChem, date unknown, in 3 pages.
Final Office Action in U.S. Appl. No. 16/336,665, dated Aug. 31, 2023.
Decision to Grant in European Application No. 17793154.0, dated Nov. 2, 2023.
Office Action in Canadian Application No. 3,038,670, dated Nov. 1, 2023.
Notice of Allowance in U.S. Appl. No. 16/097,782, dated Jan. 12, 2024, in 11 pages.
Office Action in Canadian application No. 3,022,852, dated Jan. 16, 2024, in 6 pages.
Office Action in Japanese application No. 2023-16016, dated Mar. 5, 2024, in 3 pages.
Office Action in U.S. Appl. No. 16/336,665, dated Mar. 14, 2024, in 24 pages.
Extended European Search report in European Application No. 23204493.3, dated Feb. 16, 2024, in 10 pages.

\* cited by examiner

Left to right and top to bottom: HHHC, CHHH, HCHH, HHCH, CHHC, HHCC

Left to right and top to bottom: CCHH, HCHC, HCCH, CHCH, HCCC, CHCC

Left to right and top to bottom: CCHC, CCCH, CCCC (uncomplexed), HHHH:Zr:Na

S

US 12,002,595 B2

SEPARATION OF METAL IONS BY LIQUID-LIQUID EXTRACTION

CROSS REFERENCE TO RELATED APPLICATIONS

This application is a Continuation-in-Part of International Application No. PCT/US2017/048934, filed Aug. 28, 2017, designating the U.S. and published as WO 2018/097871 A2 on May 31, 2018, which claims the benefit of U.S. Provisional Application No. 62/505,458, filed on May 12, 2017 and 62/401,687, filed on Sep. 29, 2016, which is hereby incorporated by reference in its entirety. Any and all applications for which a foreign or a domestic priority is claimed is/are identified in the Application Data Sheet filed herewith and is/are hereby incorporated by reference in their entireties under 37 C.F.R. § 1.57.

STATEMENT REGARDING FEDERALLY SPONSORED R&D

The invention was made with government support under Contract No. DE-AC02-05CH 11231 between the U.S. Department of Energy and the University of California. The government has certain rights in the invention. This work was supported by the U.S. Department of Energy, Office of Science, Office of Basic Energy Sciences, Chemical Sciences, Geosciences, and Biosciences Division at LBNL under Contract DE-AC02-05CH11231.

BACKGROUND

Field

The present disclosure is related to separation processes for metal ions.

Description of the Related Art

Owing to concerns related to global warming due to $CO_2$ emission by traditional energy sources, nuclear energy has emerged as an alternative energy source. However, disposing of nuclear waste is a major challenge.

A few processes, using liquid-liquid extraction, are under development with limited success in term of selectivity and efficacy: TALSPEAK process (USA), GANEX process (France), and DIAMEX-SANEX process (France). The purification of the element actinium ($Ac^{3+}$) is also catching growing attention. In fact, actinium isotopes are emerging radioactive sources for cancer treatments such as the "targeted alpha therapies." The methods of production of $Ac^{3+}$ isotopes generate $Ln^{3+}$ fission products in addition to the initial material that is usually made of thorium ($Th^{4+}$). Current purification protocols for actinium involve numerous chromatographic steps that require different chemical media in order to obtain a purified fraction of $Ac^{3+}$.

SUMMARY

In some embodiments, a method of processing spent nuclear fuel is provided. This comprises obtaining spent nuclear fuel dissolved in an acidic medium, contacting the dissolved spent nuclear fuel with an octadentate ligand and an organic phase to generate a mixture, and separating an aqueous phase enriched for $Pu^{4+}$ from the mixture.

In some embodiments, a method for enriching a metal ion is provided. The method comprises contacting a first aqueous phase with an organic phase to generate a mixture, wherein the first aqueous phase comprises: a plurality of metal ions; and an octadentate ligand, and wherein the aqueous phase has an acidic pH of less than 1. The method further includes separating from the mixture a second aqueous phase enriched for a metal ion of the plurality of metal ions.

In some embodiments, a method of preparing a medical isotope is provided. The method comprises obtaining a metallic precursor dissolved under an acidic condition, wherein the metallic precursor comprises a medical isotope; contacting the dissolved metallic precursor with an octadentate ligand and an organic phase to generate a mixture; and separating the medical isotope from one or more metal ions in the dissolved metallic precursor based on an interaction between the octadentate ligand and the medical isotope.

In some embodiments, a method of separating metal ions for nuclear forensics is provided. The method comprises obtaining a sample derived from a nuclear material, wherein the sample comprises $UO2^{2+}$, $Ac^{3+}$, $Pu^{4+}$, and $Np^{4+}$; contacting the sample with an octadentate ligand to generate a first mixture, wherein the first mixture has an acidic pH of 1 or lower; separating $UO2^{2+}$ and $Ac^{3+}$ from $Pu^{4+}$ and $Np^{4+}$ in the mixture based on an interaction or lack of interaction between the octadentate ligand and each of $UO_2^{2+}$, $Ac^{3+}$, $Pu^{4+}$, and $Np^{4+}$, to generate a second mixture comprising the $Pu^{4+}$ and $Np^{4+}$; and further separating each metal within both mixtures by classical techniques.

In some embodiments, a method of separating metal ions is provided. The method comprises contacting a liquid composition comprising a plurality of metal ions with an octadentate ligand to generate a mixture, under conditions sufficient to form a metal ion-ligand complex comprising a metal ion of the plurality of metal ions, and separating a first fraction of the mixture enriched for the metal ion-ligand complex from a second fraction depleted for the metal ion-ligand complex, wherein the first fraction of the mixture has an acidic pH of less than 1. The plurality of metal ions are selected from the group consisting of: a p-, d- or f-block element of period 5 or greater, a group 3 element, or a group 4 element In some embodiments, a method of separating trivalent metal ions from tetravalent metal ions is provided. The method comprises providing an aqueous solution comprising tetravalent metal ions and trivalent metal ions, wherein the solution has an acidic pH; adding a HOPO chelator to the aqueous solution; and performing an extraction against the aqueous solution, wherein the HOPO chelator functions as a holdback agent to keep the tetravalent metal ions in the aqueous solution, while allowing the trivalent metal ions to be removed via decanting at the end of the extraction.

In some embodiments, a method for separating metal ions is provided. The method comprises providing an aqueous solution comprising a first metal ion and a second metal ion, wherein the solution has an acidic pH; adding a HOPO chelator to the aqueous solution; and performing an extraction against the aqueous solution. The HOPO chelator functions as a holdback agent to selectively keep the first metal ion in the aqueous solution, while allowing the second metal ion to go into an organic phase during the extraction.

DETAILED DESCRIPTION

Provided herein are separation processes for metal ions in aqueous solutions. In some embodiments, this can be based on liquid-liquid extraction. In some embodiments, this allows for recovery and/or purification of actinides from lanthanides, based on their valence, and the pH of the extraction conditions.

Figure 2:
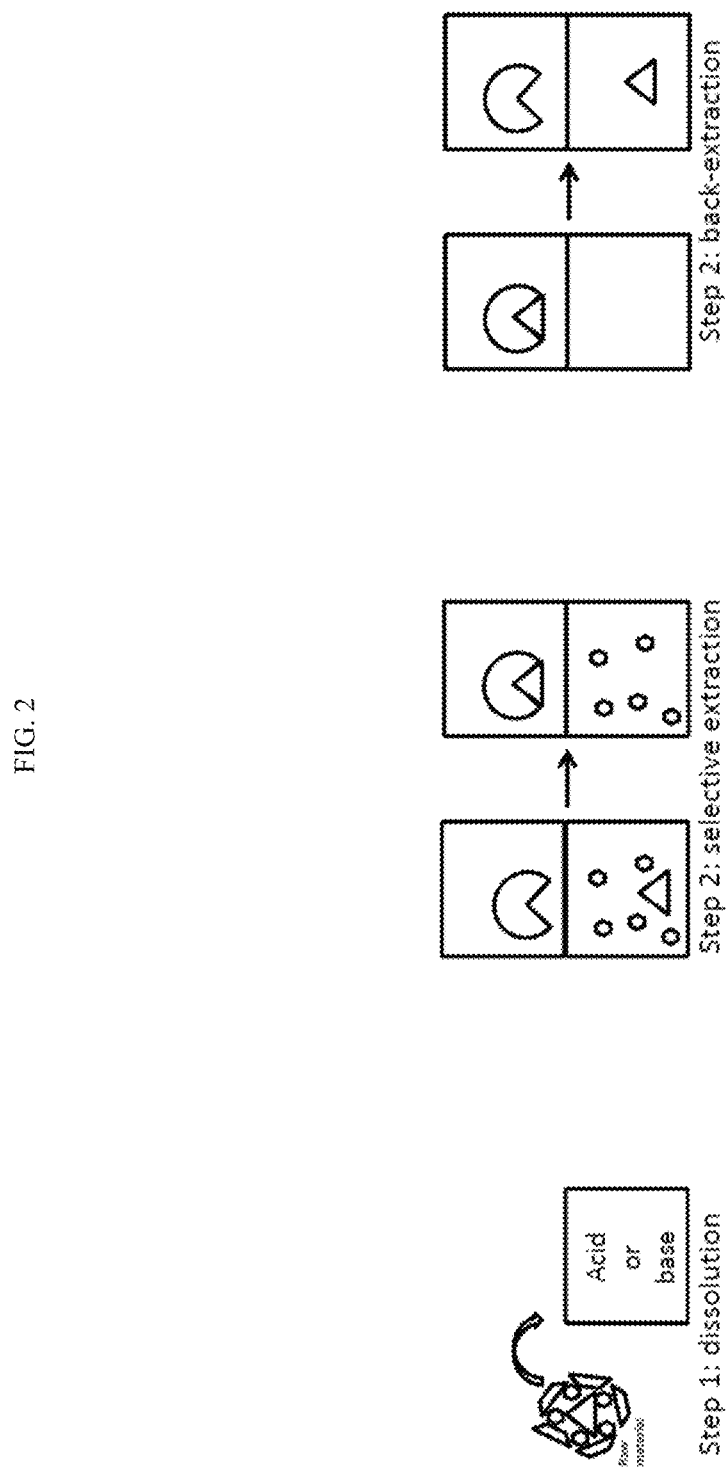
FIG. 2 shows extraction can be based on one or more principles.

In some embodiments, the extraction includes dissolving the raw material in an acidic or basic matrix and providing a chelator or ligand (such as a HOPO chelator) that selectively extracts the metal(s) ion(s) of interest. This can be done at a relatively low pH in some embodiments. For example, in some embodiments, the first step of the extraction is to dissolve the raw material in an acidic or basic matrix and the second step is to find a soluble species that selectively extracts (or back-extracts) the metal(s) ion(s) of interest (FIG. 2), such as a HOPO chelator or ligand. The metal associated with this chelator can then be extracted (or retained) via the properties of the ligand, while the metal not associated with the chelator can be removed (or retained). Furthermore, as disclosed herein, chelators such as HOPO molecules, allow binding of various metal ions, as a function of pH, even at low pH. This allows for pH manipulation to drive selective binding of particular metal ion species over different metal ion species (e.g., M$^{3+}$ vs M$^{4+}$). Thus, by using such a chelator, and adjusting the pH accordingly, one can selectively bind the metal ion desired, remove any remaining metal ion (via, e.g., a general "extracting agent" that will move to the organic phase), and then, once the organic phase is decanted, collect the metal desired metal ion and removing it from the chelator. The separation techniques can include liquid-liquid extraction (large scale), and/or chromatography or ion-exchange. In some embodiments, the various metal separation techniques can employ chromatography and/or a liquid-liquid extraction. In some embodiments, further steps that can occur include, for example liquid-liquid extraction, chromatography, and/or analytical techniques.

Definitions

The terms "pure," "purified," "substantially purified," and "isolated" as used herein refer to the compound of the embodiment being free of other, dissimilar compounds with which the compound, if found in its natural state (e.g., natural ores), as raw material(s), in waste for recycling, or man-made materials, would be associated in its natural state or as raw material(s). In certain embodiments described as "pure," "purified," "substantially purified," or "isolated" herein, the compound can comprise at least 0.5% to 1%, 1% to 5%, 5% to 10%, 10% to 20%, 20% to 50%, 50% to 70%, 70% to 90%, 90% to 95%, 95% to 99%, and 99% to 100%. In some embodiments, the amount of the compound will be at least 50% or 75% of the mass, by weight, of a given sample. A "functional purity" is a measurement of the amount of a particular compound in a sample or product in relation to other compounds in a sample that can adversely impact the function of the compound. Thus, other components in a sample that do not interfere with the compound's activity (e.g., water), will not be used in determining the purity of a sample or product.

The terms "derivative," "variant," or other similar term refers to a compound that is an analog of the other compound.

The term "and/or" designates both the option of "and" as well as the option of "or" in that particular circumstance. However, unless otherwise specified in the specification, the use of the term "or" or "and" encompasses a description of both option as well. Thus, the use of the term "or" should not be taken as excluding the option of "and", unless additional context indicates that it should (this definition does not apply to the language in the claims). The use of the singular or plural forms of a term encompasses both options (singlular or plural) as well as both options combined (singular and plural), unless indicated otherwise.

Methods

In some embodiments, a method of processing spent nuclear fuel is provided. This comprises obtaining spent nuclear fuel dissolved in an acidic medium, contacting the dissolved spent nuclear fuel with an octadentate ligand and an organic phase to generate a mixture, and separating an aqueous phase enriched for Pu$^{4+}$ from the mixture.

In some embodiments, a method for enriching a metal ion is provided. The method comprises contacting a first aqueous phase with an organic phase to generate a mixture, wherein the first aqueous phase comprises: a plurality of metal ions; and an octadentate ligand, and wherein the aqueous phase has an acidic pH of less than 1. The method further includes separating from the mixture a second aqueous phase enriched for a metal ion of the plurality of metal ions.

In some embodiments, a method of preparing a medical isotope is provided. The method comprises obtaining a metallic precursor dissolved under an acidic condition, wherein the metallic precursor comprises a medical isotope; contacting the dissolved metallic precursor with an octadentate ligand and an organic phase to generate a mixture; and separating the medical isotope from one or more metal ions in the dissolved metallic precursor based on an interaction between the octadentate ligand and the medical isotope.

In some embodiments, a method of separating metal ions for nuclear forensics is provided. The method comprises obtaining a sample derived from a nuclear material, wherein the sample comprises $UO_2^{2+}$, $Ac^{3+}$, $Pu^{4+}$, and $Np^{4+}$; contacting the sample with an octadentate ligand to generate a first mixture, wherein the first mixture has an acidic pH of 1 or lower; separating $UO_2^{2+}$ and $Ac^{3+}$ from $Pu^{4+}$ and $Np^{4+}$ in the mixture based on an interaction or lack of interaction between the octadentate ligand and each of $UO_2^{2+}$, $Ac^{3+}$, $Pu^{4+}$, and $Np^{4+}$, to generate a second mixture comprising the $Pu^{4+}$ and $Np^{4+}$; and further separating each metal within both mixtures by classical techniques.

In some embodiments, a method of separating metal ions is provided. The method comprises contacting a liquid composition comprising a plurality of metal ions with an octadentate ligand to generate a mixture, under conditions sufficient to form a metal ion-ligand complex comprising a metal ion of the plurality of metal ions, and separating a first fraction of the mixture enriched for the metal ion-ligand complex from a second fraction depleted for the metal ion-ligand complex, wherein the first fraction of the mixture has an acidic pH of less than 1. The plurality of metal ions are selected from the group consisting of: a p-, d- or f-block element of period 5 or greater, a group 3 element, or a group 4 element.

In some embodiments, a method of separating trivalent metal ions from tetravalent metal ions is provided. The method comprises providing an aqueous solution comprising tetravalent metal ions and trivalent metal ions, wherein the solution has an acidic pH; adding a HOPO chelator to the aqueous solution; and performing an extraction against the aqueous solution, wherein the HOPO chelator functions as a holdback agent to keep the tetravalent metal ions in the aqueous solution, while allowing the trivalent metal ions to be removed via decanting at the end of the extraction.

In some embodiments, a method for separating metal ions is provided. The method comprises providing an aqueous solution comprising a first metal ion and a second metal ion, wherein the solution has an acidic pH; adding a HOPO chelator to the aqueous solution; and performing an extraction against the aqueous solution. The HOPO chelator functions as a holdback agent to selectively keep the first metal ion in the aqueous solution, while allowing the second metal ion to go into an organic phase during the extraction.

In some embodiments, the acidic denotes a pH of between about 1 to about 0.

In some embodiments, the octadentate ligand is a hydroxypyridonate ligand. In some embodiments, the octadentate ligand is built on a spermine scaffold. In some embodiments, the octadentate ligand is 3,4,3-LI(1,2-HOPO).

In some embodiments, the method further comprises dissolving a metal in an acidic solution to obtain the liquid composition.

In some embodiments, the first fraction is enriched for a tetravalent metal ion and the second fraction is enriched for a trivalent metal ion and/or a divalent metal ion.

In some embodiments, the contacting further comprises contacting the sample with an organic phase.

In some embodiments, a method of separating trivalent metal ions from tetravalent metal ions is provided. The method comprises providing an aqueous solution comprising tetravalent metal ions and trivalent metal ions, wherein the solution has an acidic pH; adding a HOPO chelator to the aqueous solution; and performing an extraction against the aqueous solution, wherein the HOPO chelator functions as a holdback agent to keep the tetravalent metal ions in the aqueous solution, while allowing the trivalent metal ions to be removed via decanting at the end of the extraction.

In some embodiments, the method further comprises separating the HOPO chelator from the tetravalent metal to thereby collect the tetravalent metal.

In some embodiments, the method further comprises lowering a pH beneath 0 to separate tetravalent ions.

In some embodiments, separating comprises filtering, precipitating, liquid-liquid extraction or chromatography, or wherein the method further comprises filtering, precipitating, liquid-liquid extraction or chromatography.

In some embodiments, the first fraction is enriched for a first metal ion that has a charge that is different from a charge of a second metal ion enriched in the second fraction.

In some embodiments, 1) the separating comprises contacting the liquid composition with an organic phase or 2) further comprising contacting the liquid composition with an organic phase.

In some embodiments, the method does not comprise adjusting the pH of the liquid composition after dissolving the metal. In some embodiments, the method does not comprise raising the pH of the liquid composition after dissolving the metal.

In some embodiments, the organic phase comprises a non-selective extractant. In some embodiments, the organic phase does not comprise an extractant that selectively binds to the first or second metal ion. In some embodiments, the method does not comprise adjusting the pH of the dissolved spent nuclear fuel. In some embodiments, the extractant is selected from the group consisting of di-(2-ethylhexyl) phosphoric acid (HDEHP), a derivative of HDEHP, calixarenes, diglycoamide derivatives, carbamoylphosphine oxide derivatives, tributylphosphate (TBP), monoamide derivatives, and tertiary amines, and quaternary ammonium salts.

In some embodiments, the first metal ion is a tetravalent metal ion and the second metal ion is selected from the group consisting of a divalent metal ion and a trivalent metal ion. In some embodiments, the first metal ion is a trivalent metal ion and the second metal ion is a trivalent metal ion.

In some embodiments, a HOPO chelator binds to the first metal ion more effectively than it binds to the second metal ion at a given pH.

In some embodiments, the fuel, first aqueous phase, precursor, nuclear material, liquid composition, or solution comprises actinium. In some embodiments, the actinium is separated from a $M^{4+}$ metal. Actinium can be included in and/or isolated as a result of, any of the methods provided herein.

In some embodiments, the chelators provided herein are distinct form classical aqueous chelators such as citrate, EDTA (Ethylenediaminetetraacetic acid), DTPA (Diethylenetriaminepentaacetic acid) as classical chelators were not able to complex metal ions under highly acidic conditions. Due to that, traditional separation of metal ions relied on the selectivity of the extractant (organic molecule, such as TBP, dissolved in an organic phase) or on the selectivity of a solid support (in the case of chromatography). This selectivity is not required in some of the embodiments provided herein.

In some embodiments, the use of 3,4,3-LI(1,2-HOPO) allows one to be able to selectively bind to the tetravalent metal ions under highly acidic conditions. Results show that 3,4,3-LI(1,2-HOPO) stays bound to $Hf^{4+}$ and $Zr^{4+}$ from pH 8 to strongly acidic solutions (at least 6 M HCl). The same compound stays from pH 6 to 10 M HCl (at least) in the case of $Ti^{4+}$ and from pH 8 to 1 M HCl in the case of $Sn^{4+}$. Based on thermodynamic data (stability constant of the complex) one can expect $Pu^{4+}$, $Th^{4+}$ and $Ce^{4+}$ to behave like $Zr^{4+}$ and $Hf^{4+}$.

In some embodiments, the chelating agents are capable of binding or chelating, or capable of forming stable complexes with actinides and/or lanthanides, such as the cations of Eu, Pu, Np, Th, Am, and/or Cf, such as of $^{152}$Eu(III), $^{241}$Am(III), $^{238}$Pu(IV), $^{237}$Np(IV), $^{237}$Np(V), and $^{233}$U(VI).

As noted above, selective pH dependent binding, at an acidic pH range, can be achieved using HOPO molecules. Furthermore, thermodynamic studies have shown that 3,4,3-LI(1,2-HOPO) releases the trivalent metal ions ($M^{3+}$) and divalent uranyl ($UO_2^{2+}$) as soon as the pH value is lower than about 1. Thus, in some embodiments $M^{4+}$ metals can be separated from $M^{3+}$ and/or $M^{2+}$ via a HOPO ligand when subjected to lower pH values. In some embodiments, the ligand 3,4,3-LI(1,2-HOPO) could also be immobilized on a solid support (e.g., beads, nanoparticles, or other form of solid support).

In some embodiments, provided herein is a process involving a high acidity (directly after the metallic target dissolution) where 3,4,3-LI(1,2-HOPO) is used to selectively bind the tetravalent metal ions in the aqueous and acidic liquor. The separation of tetravalent ions (bound to the chelator) for the other ions (unbound) can then achieved by using a non-selective extractant for the remaining metal ions and performing a liquid-liquid extraction step (for example). The tetravalent ions stay in the aqueous phase whereas the rest are extracted in the organic phase. The selectivity of such a process can be extremely high since 3,4,3-LI(1,2-HOPO) specifically binds the tetravalent metal ions under acidic condition (but not the trivalent metal ions). In some embodiments, the concentration of HCl can range from about 0 M to about 4 M. In some embodiments, the concentration of HCl can range from about 4 M to about 8 M. In some embodiments, the concentration of HCl can range from about 8 M to about 12M. In some embodiments, the concentration of HCl is about 0, 1, 2, 3, 4, 5, 6, 7, 8, 9, or 10 M, or a value within a range defined by any two of the aforementioned values. The selectivity of the process can be due to the presence of 3,4,3-LI(1,2-HOPO) in the aqueous phase (See, TABLE 0.2). A non-selective extractant can be used in the organic phase.

In some embodiments, selective complexation of tetravalent ions is achieved by 3,4,3-LI(1,2-HOPO) under very acidic conditions, e.g., less than pH 3, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, 0.1, 0, or lower.

In some embodiments, the strategy for metal ion separation provided herein aims at using innovative chelators (e.g., HOPO containing molecules), for metal ion separation processes. In some embodiments, processes that are more selective, more efficacious and more flexible than the current state-of-the-art are provided.

In some embodiments, one or more of the processes disclosed herein can be used to separate $M^{2+}$ from $M^{3+}$ from $M^{4+}$, where each M is a metal. In some embodiments, $M^{2+}$ is first separated from a $M^{3+}/M^{4+}$ mixture, and then the $M^{3+}$ is separated from $M^{4+}$ via a different technique, such as chromatography. In some embodiments, one or more of the processes disclosed herein can be employed to separate a first $M^{4+}$ from a second $M^{4+}$ or a first $M^{3+}$ from a second $M^{3+}$. In some embodiments, the separation is of Actinium from other metals. The separation is achieved by different affinities of each metal ion for the chelator. This may, or may not, also be driven in a pH dependent manner (that is, affinity changes as a function of pH for the various metal ions as well).

In some embodiments, the separation can be of lanthanides from actinides. In some embodiments, separation is of element actinium from both lanthanides and actinides.

The separation of trivalent lanthanide ions (examples: $Gd^{3+}$, $Eu^{3+}$, etc. herein referred to as $Ln^{3+}$) from the trivalent actinide ions (Examples: $Ac^{3+}$, $Am^{3+}$, $Cm^{3+}$, $Bk^{3+}$, $Cf^{3+}$, etc. Here after referred to as $An^{3+}$) can be challenging because these two classes of metal ions exhibit similar chemical properties. Nonetheless, there is value in efficient processes able to separate $Ln^{3+}$ from $An^{3+}$. Indeed, $Ln^{3+}$ and $An^{3+}$ are both present in the nuclear spent fuels (civilian and military) and their separation could allow for two developments. First, the presence of $An^{3+}$ impairs the long-term storage of the nuclear waste because it would generate too much heat in hypothetical underground repositories. The removal of $An^{3+}$ from the main nuclear waste would therefore facilitate the storage and reduce the cost. Second, the minor actinides $An^{3+}$ could be transmuted into less toxic elements in the next generation of nuclear reactors but this transmutation is only possible in the absence of lanthanide fission products $Ln^{3+}$. The separation $Ln^{3+}/An^{3+}$ is therefore beneficial to obtain closed nuclear fuel cycles (with recycling of U and Pu, transmutation of $An^{3+}$, and storage of $Ln^{3+}$).

Figure 1:
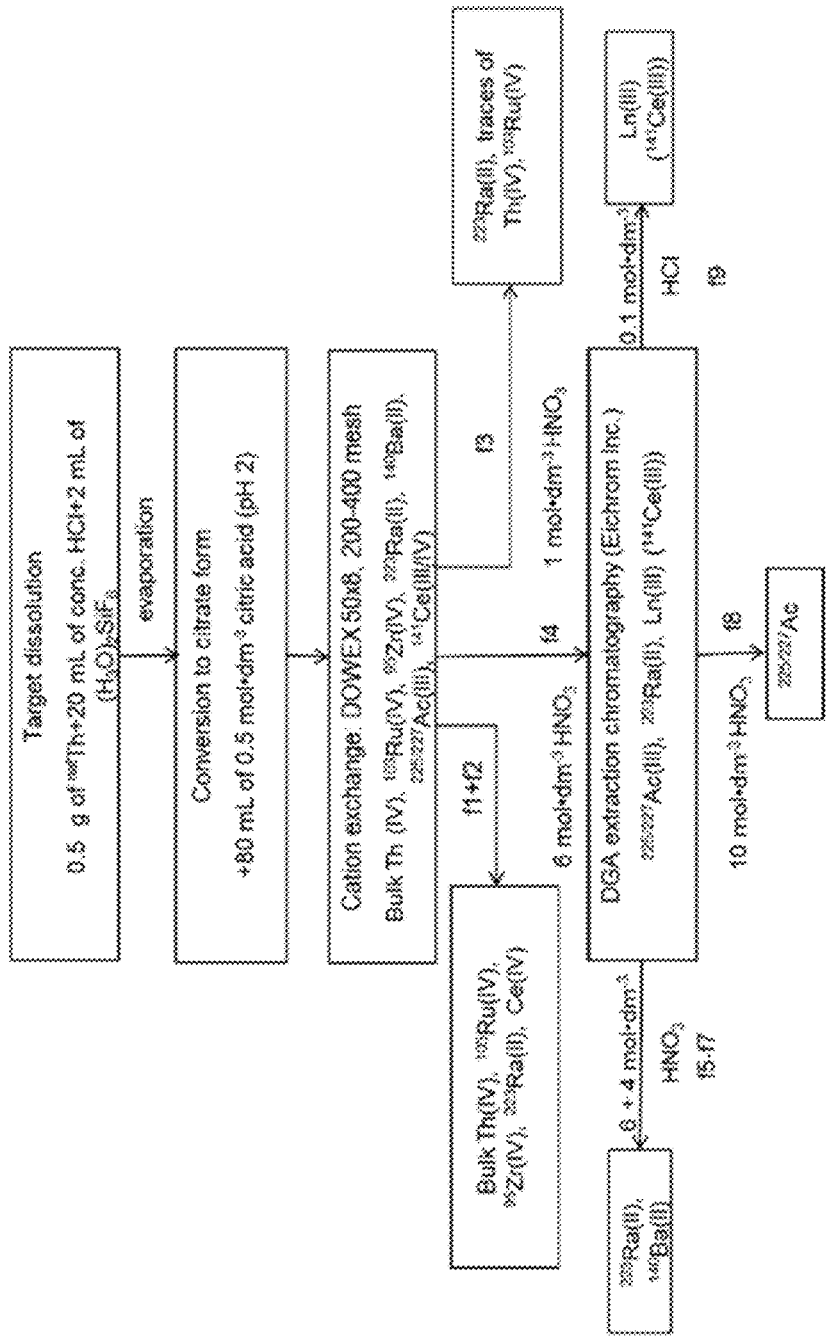
FIG. 1 shows current state-of-the-art purification of 227/225Ac.

In some embodiments, separation of metal ions is beneficial during mining for natural resources. In some embodiments, separation of metal ions is involved during mining for recycling of valuable waste. In some embodiments, separation of metal ions is required during mining for purification of medical and/or research isotopes, e.g., $^{177}$Lu, $^{223}$Ra, $^{225}$Ac, and $^{227}$Th. In some embodiments, the metal ion separation can be for mining from natural stones, recycling of valuable wastes, purification of medical and/or research isotopes such as $^{177}$Lu, $^{223}$Ra, $^{225}$Ac, and $^{227}$Th. An example of purification of $^{227/225}$Ac is shown in FIG. 1 (Radchenko et al 2015 Journal of Chromatography A, 55-63, which is hereby incorporated by reference in its entirety).

In some embodiments, the method for separation of metal ions include, without limitations, liquid-liquid extraction and chromatography or ion-exchange-based methods. In some embodiments, the methods are large scale. In some embodiments, the methods are small scale. In some embodiments, liquid-liquid extraction methods are large scale. In some embodiments, chromatography or ion-exchange-based methods are small scale. In some embodiments, countercurrent liquid-liquid extraction can be employed.

Figure 3:
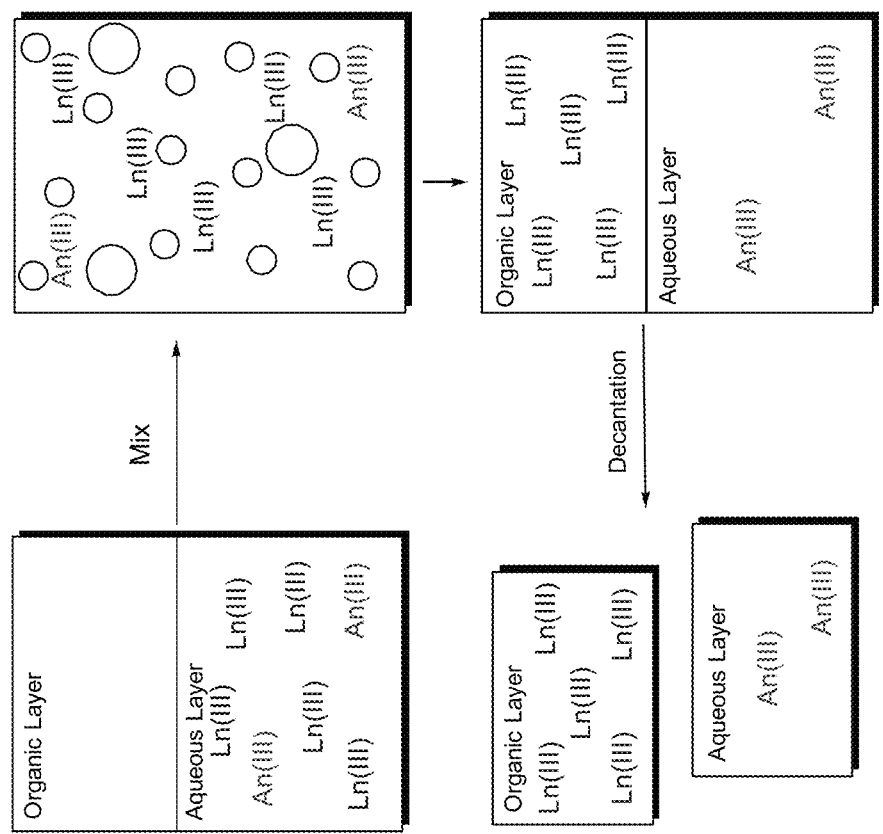
FIG. 3 shows an embodiment of the principle of liquid-liquid extraction process.

Liquid-liquid extraction (FIG. 3) processes involve two immiscible phases (one aqueous, one organic) between which the elements of interest are selectively transferred. In some embodiments, one can use one or more chelators in the aqueous phase (also called hold-back reagent) and use, preferentially, a non-selective extractant to pull some or all of the other metals into the organic phase.

In some embodiments, the present disclosure provides liquid-liquid extraction with ligands based on the binding units 1,2-HOPO that can selectively bind or release targeted elements ($Ac^{3+}$, $Am^{3+}$, $Gd^{3+}$, etc.) in aqueous media. As disclosed herein, the affinity of the 1,2-HOPO ligands for a given metal ion also depends on the acidity of the aqueous media. Thus, modifying the acidity allows for selective binding or release of HOPO chelators to the metal of choice. Furthermore, the selectivity of the HOPO ligands is usually superior to that of the chelators currently used for this type of application (e.g., DTPA). Thus, in some embodiments, depending on the chemical conditions, a given element can be selectively extracted in the organic from a mixture of elements by using specific chemical conditions in the aqueous phase containing the HOPO ligand and a non-specific extractant in the organic phase.

In some embodiments, a new strategy for the complexation and purification of tetravalent metal ions from other ions (not exhibiting a 4+ charge) is provided. Examples of elements that naturally form tetravalent ions are: plutonium ($Pu^{4+}$), thorium ($Th^{4+}$), titanium ($Ti^{4+}$), zirconium ($Zr^{4+}$), hafnium ($Hf^{4+}$), cerium ($Ce^{4+}$), tin ($Sn^{4+}$), platinum ($Pt^{4+}$), iridium ($Ir^{4+}$). Examples of elements that can be stabilized as tetravalent ions under specific conditions are: berkelium ($Bk^{4+}$), uranium ($U^{4+}$), and lead ($Pb^{4+}$). Thus, any of the elements can be used in the present methods. In some embodiments, actinium can be separated from any of these metals.

In some embodiments, the separation techniques can employ altering and/or controlling the pH of a solution so as to allow $M^{3+}$ to be separated from $M^{4+}$. In some embodiments, the pH of a solution can be varied from ~8 to very strong acidic solutions (pH~0) in order to separate various components within the solution. In some embodiments, a metal species is formed when the pH of the solution is between 0 and 6 and other species are formed when the pH of the solution is between 6 and 8.

Figure 4:
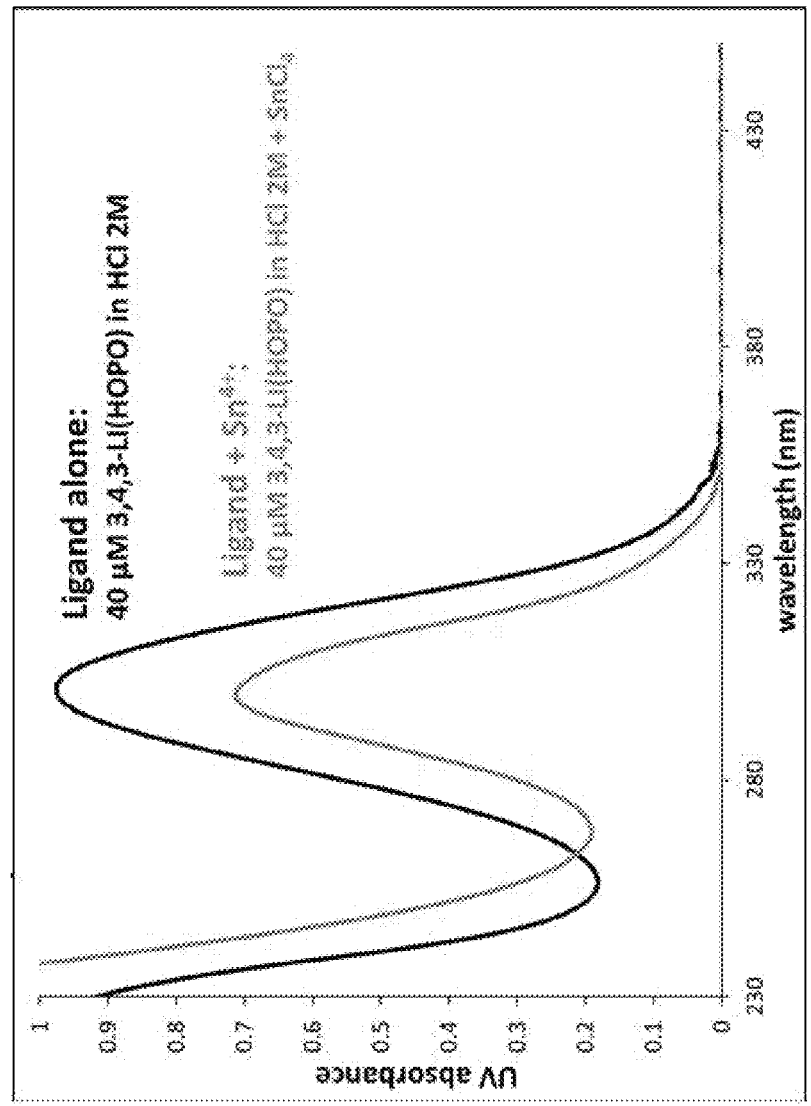
FIG. 4 shows spectroscopic characterization of $Sn^{4+}$ complexation in 2 M HCl.

In some embodiments, a $M^{3+}$ can be separated from a $M^{4+}$ via a pH dependent process. In some embodiments, this can comprise dropping the pH of the solution to less than 2, which allows for trivalent metals to be separated from tetravalent metals. That is, in some embodiments, $M^{4+}$ and $M^{3+}$ can be separated by pH differences. While $M^{4+}$ ions are still bound at pH<0, $M^{3+}$ ions are released at pH<2, which is shown by the complexation of $Sn^{4+}$ in 2 M HCl (FIG. 4). Other examples include $Ce^{4+}$ and $Th^{4+}$ complexes studied in 0.05 M $H_2SO_4$, and $Zr^{4+}$ and $Pu^{4+}$ complexes studied in 0.05-0.5 M $H_2SO_4$ (*Inorg. Chem.* 2013 & *Inorg. Chem.* 2015 which are hereby incorporated by reference in their entireties). Thus, $M^{4+}$ metals will remain associated with the chelator (e.g., 3,4,3-LI(1,2-HOPO)), while $M^{3+}$ metals will still be free in solution. These $M^{3+}$ metal ions can then be removed, for example, by addition of an organic metal binding compound that will be extracted into the organic phase of an extraction process. The HOPO ligand (with the $M^{4+}$ metal ion) will stay in the aqueous phase). In some embodiments, the $M^{3+}$ is actinium.

In some embodiments, any of these options involve the use of a highly acidic aqueous media as a feed solution. In some embodiments, where the HOPO ligand is adequately selective for the method, the aqueous solution need not be acidic.

Examples of commercial and non-selective extractant for liquid-liquid extraction under highly acidic conditions include, but are not limited to, trioctyl amine, quaternary ammonium salts (such as Aliquat® 336), TODGA, Cyanex®, HDEHP, CMPO, etc.

In some embodiments, non-limiting characteristics of the extractant include an ability to transfer the targeted material from the aqueous phase to the organic phase, and solubility in an organic diluent and insoluble in aqueous media. In some embodiments, mixtures of two or more extractants can be used. In some embodiments, a pure form of the extractant can be expensive and, in most case, too viscous. Therefore, in some embodiments, the extractant is diluted in an organic diluent. In some embodiments, the diluent is usually an inert and inexpensive liquid (non-limiting examples include dodecane, toluene, etc.) and is only there to convey the diluted extractant.

In some embodiments, a solution comprising one or more of $M^{2+}$, $M^{3+}$ and $M^{4+}$ can be separated into one or more part (e.g., $M^{2+}$ only, $M^{3+}$ only, $M^{2+}$ and $M^{3+}$, $M^{3+}$ and $M^{4+}$ etc.), via the addition of a HOPO chelator, wherein the HOPO chelator will bind to the metal in a pH dependent manner.

In some embodiments, the metal ion is released from the chelator by lowering the pH beneath a level which allows for the metal binding. Thus, a pH of approximately −1 can be used to release the tetravalent metal from the HOPO molecule. Other non-limiting options include the pH be increased to about 10 in order to release the $M^{+4}$ ions. In some embodiments, if the targeted metal is very valuable, the $M^{4+}$/HOPO solution can be evaporated and calcinated in order to burn the HOPO ligand and recover the metal. In some embodiments, the metal to be separated is Actinium.

Applications

In some embodiments, the process can be applied to the recycling of nuclear fuels (civilian and military) to the production of medical isotopes, and also analytical devices, production of radiation sources, etc. In some embodiments, typical examples of metal ions separation by liquid-liquid extraction would include the separation of plutonium ($Pu^{4+}$) from lanthanide fission products ($Ln^{3+}$), uranyl ($UO_2^{2+}$) and minor actinides ($Am^{3+}$, $Cm^{3+}$) in the frame of nuclear waste reprocessing.

This type of technology can be useful, for example, to reduce the environmental impact of nuclear energy the need for closed nuclear fuel cycles will become more critical. Thus far, the proposed plan for spent nuclear fuel in the United States has been long-term storage at a yet to be decided repository.$_1$ Storage of spent nuclear fuel becomes an issue because of longer-lived actinide (An) isotopes, like americium (Am) and curium (Cm), which are intense alpha-emitters and dominate the thermal heat load in spent fuels. See, Travis S. Grimes, Richard D. Tillotson, and Leigh R. Martin, "Trivalent Lanthanide/Actinide Separation Using Aqueous-Modified TALSPEAK Chemistry," Solvent Extr. Ion Exch. 32(4), 378-390 (2014); Kenneth L. Nash, "The Chemistry of TALSPEAK: A Review of the Science," Solvent Extr. Ion Exch. 33(1), 1-55 (2015).

Repositories must then be larger and better ventilated for longer periods of time, thus more expensive, to accommodate the minor actinide species from an open fuel cycle. Fast-breeder reactors are the next generation of nuclear reactors and will have the potential to transmute Am and Cm into shorter-lived radionuclides, which will reduce the storage time, heat generated, and radiotoxicity of the spent fuels. However, lanthanide (Ln) fission products compete with An metals for neutrons and render the transmutation process less efficient. See, Kenneth L. Nash, "The Chemistry of TALSPEAK: A Review of the Science," Solvent Extr. Ion Exch. 33(1), 1-55 (2015).

Minor actinides can be separated from lanthanides for the transmutation process but this separation can be challenging since Ln, Am, and Cm predominate as trivalent ions in solution and exhibit similar ionic-radii, thus almost identical chemistries. See, Travis S. Grimes, Richard D. Tillotson, and Leigh R. Martin, "Trivalent Lanthanide/Actinide Separation Using Aqueous-Modified TALSPEAK Chemistry," Solvent Extr. Ion Exch. 32(4), 378-390 (2014). Some embodiments provided herein allow for the separation of some of the metals from one another.

Another typical example would be the purification of actinium ($Ac^{3+}$) thorium ($Th^{4+}$), and vice versa, in the frame of medical isotope production.

Another example would be separation of lutetium ($Lu^{3+}$) from hafnium ($Hf^{4+}$) or the separation of yttrium ($Y^{3+}$) from zirconium ($Zr^{4+}$) in the frame of medical isotope productions.

In some embodiments, the processes herein can be applied to separation of Sn/Zr or Sn/Hf in an acidic media. In some embodiments, the process can separate Sn/Ti at pH of about 7. In some embodiments, the process can separate Ti/Zr or Ti/Hf at pH 6-11. In some embodiments, the process can separate Sn/Zr or Sn/Hf in acidic media. In some embodiments, the process can further separate Sn/Ti at pH 7.

In some embodiments, the process provides for industrial processes that are simpler and more efficient than the current ones, for the separation and/or purification of metal ions.

The applications of the invention are numerous, going from the recycling of nuclear fuels (civilian and military) to the production of medical isotopes, and also analytical devices, production of radiation sources, etc. Typical examples of metal ions separation by liquid-liquid extraction can include the separation of lanthanide fission products ($Ln^{3+}$) from minor actinides ($Am^{3+}$, $Cm^{3+}$) in the frame of nuclear waste reprocessing. Another typical example would be the purification of actinium ($Ac^{3+}$) from lanthanide ($Ln^{3+}$ and $Ce^{4+}$) and actinides ($Th^{4+}$, $Am^{3+}$, etc) in the frame medical isotope production. In some embodiments, this can be scaled-up to an industrial process and be simpler and more efficient than the current ones, for the separation and/or purification of lanthanide and actinide elements.

In some embodiments, one or more of the processes disclosed herein can be used to separate Bk from Ce, such as $Ce^{4+}$ from $Bk^{4+}$. In some embodiments, one or more of the processes disclosed herein can be used to separate $Bk^{4+}$ from $An^{3+}$. In some embodiments, one or more of the processes disclosed herein can be used to separate Pu from other An, such as in nuclear fuel waste processing. In some embodiments, one or more of the processes disclosed herein can be used for nuclear forensics.

In some embodiments, one or more of the processes disclosed herein can be used to separate medical isotopes, such as Sc and/or Ac from Th, including $Sc^{3+}$ and/or $Ac^{3+}$ from $Th^{4+}$.

In some embodiments, one or more of the processes disclosed herein can be used to separate ions for nuclear forensics, including $UO_2^{2+}$ from $Pu^{4+}$ from $Np^{4+}$. Pu can be separated from Np via chromatography. In some embodiments, one or more of the processes disclosed herein can be used to separate $UO_2^{2+}$ from $Pu^{4+}$ and $Np^{4+}$.

In some embodiments, one or more of the processes disclosed herein can be used to separate $Ce^{4+}$ from $Tm^{3+}$, such as in the processing of medical isotopes.

In some embodiments, one or more of the processes disclosed herein can be used to separate $Zr^{4+}$ from $Y^{3+}$, such as in the processing of medical isotopes.

In some embodiments, a mixture of metal ions exhibiting different charges is obtained and these metal ions are to be separated in order to obtain the final product. For example, when reprocessing the nuclear spent fuels, the nuclear spent fuel rods are dissolved in highly acidic solutions (usually concentrated $HNO_3$). These acidic solutions contain $Pu^{4+}$ but also trivalent lanthanide fission products ($Ln^{3+}$), trivalent actinides ($Am^{3+}$, $Cm^{3+}$), divalent uranyl ions ($UO_2^{2+}$) and monovalent neptunyl ($[NpO_2]^+$). $Pu^{4+}$ eventually has to be separated from the other ions in order to reuse the plutonium material for other applications. The separation of $Pu^{4+}$ from the other ions is currently performed at an industrial scale by using the liquid-liquid extraction process called "PUREX."

Figure 5:
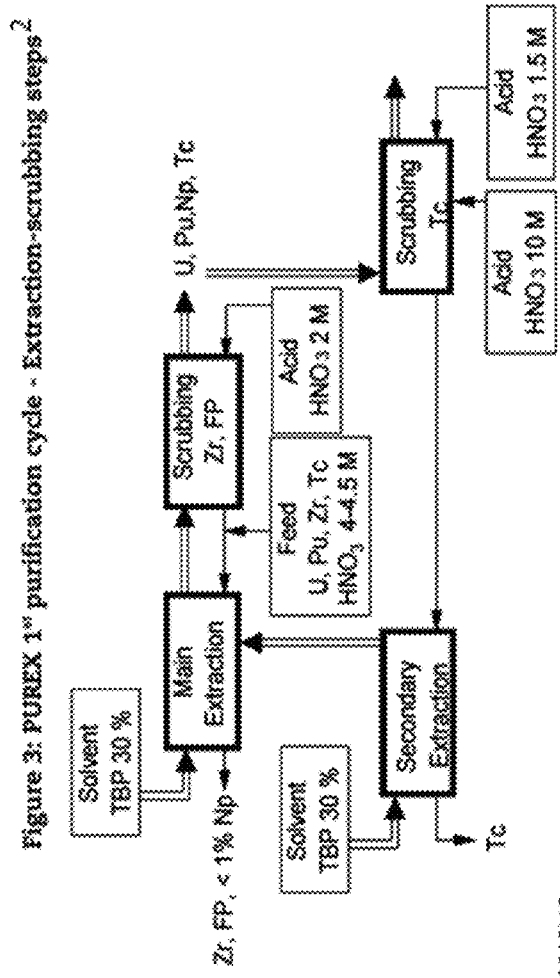
FIG. 5 shows an embodiment of the PUREX process, which can be modified by one or more of the HOPO chelators as described herein.

In some embodiments, the separation of metal ions involves a variation of the PUREX process (FIG. 5). The PUREX process involves recovery of U and Pu from nuclear spent fuel. The basic principle of the PUREX process involves the use of TBP which extracts $Pu^{4+}$ and $UO_2^{2+}$ but not $M^{3+}$. It is estimated that approximately 5040 t of nuclear fuel reprocessed annually in the UK, France, Japan, and Russia.

The PUREX process is based on the simultaneous extraction of $Pu^{4+}$ and $UO_2^{2+}$ in an organic phase comprising the molecule TBP (tributylphosphophate) while letting the $Ln^{3+}$, $Am^{3+}$, $Cm^{3+}$ and $[NpO_2]^+$ ions in the original solution comprising nitric acid. The separation of $Pu^{4+}$ from $UO_2^{2+}$ requires further liquid-liquid extraction or back-extraction steps. The selectivity of such a process is based on differences in the affinity of TBP (present in the organic phase) for the different metal ions (initially in the organic phase). No reagent in the aqueous phase need be added to improve the selectivity of the process. In some embodiments, the PUREX process is modified in that one employs pH dependent HOPO chelating agent instead of TBP, under acidic conditions, to allow the HOPO ligand to selectively chelate to $Pu^{4+}$ under acidic conditions, while not chelating the trivalent metals. The $Pu^{4+}$ will remain in the aqueous phase, while the other metals will instead be moved to the organic phase. Thus, in this modified PUREX approach, the $Pu^{4+}$ will remain in the acidic aqueous phase.

In some embodiments, trivalent actinium ions ($Ac^{3+}$) can be separated from thorium ($Th^{4+}$) in the frame of medical isotope production. The goal can be either to recover $Ac^{3+}$ isotopes or $Th^{4+}$ isotopes. Medical isotope productions sometimes also require to separate $Zr^{4+}$ from yttrium ($Y^{3+}$). These processes usually involve dissolving a metallic target (containing the isotopes of interests, the initial metallic target material, and the impurities generated during the isotope production) in an acidic solution, such as HCl or $HNO_3$, before separating the different metal ions by chromatographic or ion-exchange techniques.

TALSPEAK was developed in the 60's at Oak Ridge National Lab. See, Kenneth L. Nash, "The Chemistry of TALSPEAK: A Review of the Science," Solvent Extr. Ion Exch. 33(1), 1-55 (2015). TALSPEAK is a liquid-liquid extraction process that, in principle, allows the complete extraction of lanthanides from actinides by using a nonselective extractant and a hold-back reagent.

Figure 7:
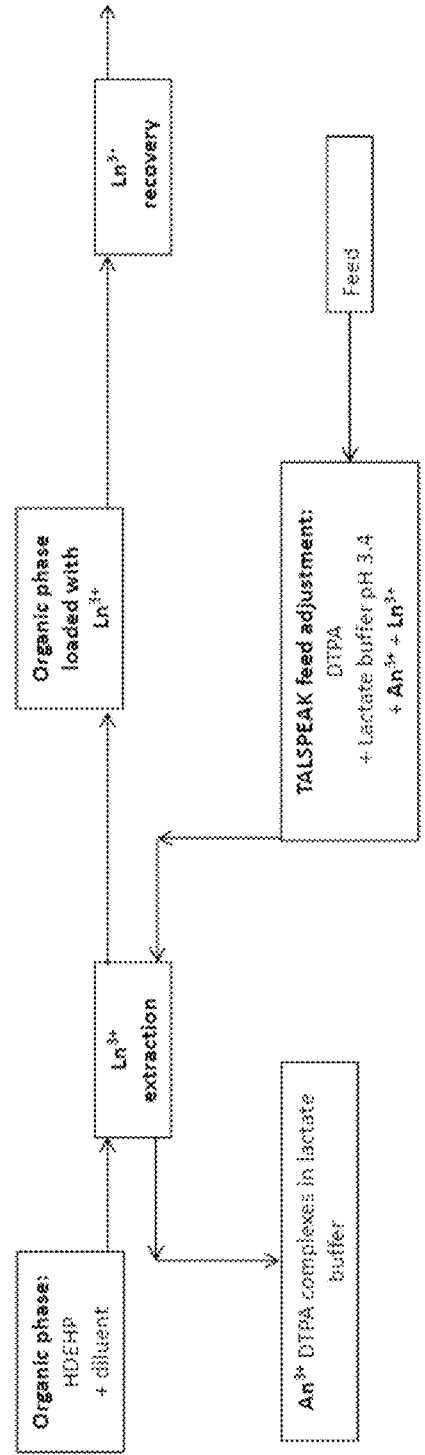
FIG. 7 shows an embodiment of the TALSPEAK process, which can be modified by one or more of the HOPO chelators as described herein.

In some embodiments, TALSPEAK is used for the separation of $An^{3+}$ or $Ln^{3+}$ after PUREX process. The TALSPEAK process can also be varied given the disclosure herein. In some embodiments, the goal is to recover Am, Cm, Bk, Cf isotopes to ease the radioactive waste storage. The TALSPEAK process is still under development and has not been applied at an industrial level because of a few drawbacks: i) extraction efficiency decreases with increasing pH, ii) slow extraction kinetics, and iii) narrow set of conditions for optimum efficiency. See, Kenneth L. Nash, "The Chemistry of TALSPEAK: A Review of the Science," Solvent Extr. Ion Exch. 33(1), 1-55 (2015). Much of the effort in improving the TALSPEAK process has revolved around tackling the aforementioned issues and simplifying the implementation of this process into the nuclear cycle scheme. FIG. 7 shows an embodiment of the TALSPEAK process (adapted from Johnson and Maloney 2013 U.S. Pat. No. 8,475,747 B1, which is hereby incorporated by reference in its entirety).

The metal ion separation process can be described according to Equation (1),3 where M=$An^{3+}$ or $Ln^{3+}$, H5DTPA is the pentaprotic hold-back reagent, and HDEHP is the non-selective extractant. The selectivity in the process arises from the hold-back reagent, which can be for example, Diethylenetriamine-N, N, N', N", N"-pentaacetic acid (DTPA). Actinides exhibit a higher degree of covalency with respect to their 4-f analogues4, thus will form stronger complexes with DTPA. Therefore, for trivalent actinides and lanthanides the equilibrium in the Equation (1) will lie to the left and right, respectively.

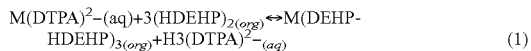

$$M(DTPA)^{2-}_{(aq)} + 3(HDEHP)_{2(org)} \leftrightarrow M(DEHP-HDEHP)_{3(org)} + H3(DTPA)^{2-}_{(aq)} \quad (1)$$

The structures of DTPA and HDEHP are as follows:

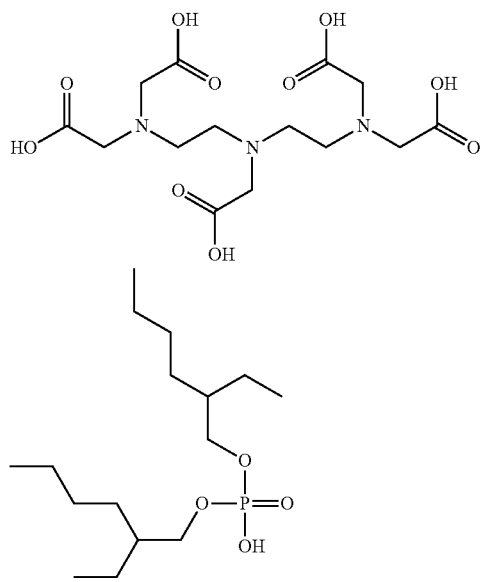

with Diethylenetriamine-N, N, N', N", N"-pentaacetic acid (DTPA) shown to the left and di(2-ethylhexyl)phosphoric acid (HDEHP) to the right.

Figure 37:
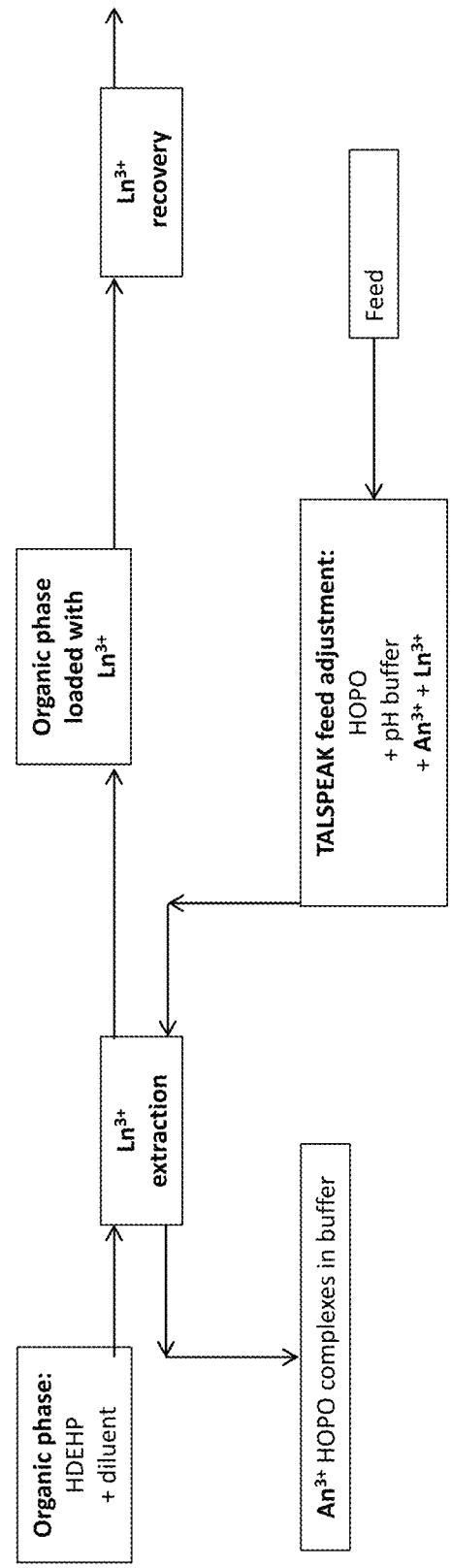
FIG. 37 shows an embodiment of the TALSPEAK process with a HOPO chelator.

In some embodiments, 3,4,3-LI(1,2-HOPO) can be used as a replacement for DTPA in the TALSPEAK process. Non-limiting example of the TALSPEAK process with a HOPO chelator is shown in FIG. 37. In some embodiments, the process can be a TALSPEAK process, but be at a pH of 0-3 (rather than 3-4), e.g., a pH of 0.2. 9, 0-2.8, 0-2.7, 0-2.6, 0-2.5, 0.5-2, etc.

The Trivalent Actinide-Lanthanide Separation by Phosphorous reagent Extraction from Aqueous Komplexes (TALSPEAK) process addresses the issue by selectively removing the long-lived minor actinides (Am, Cm) from fission products using liquid-liquid extractions, thus decreasing the storage size and time, and radiotoxicity of the raffinate. In some embodiments, this TALSPEAK process can be modified by using a HOPO chelator shown to form stronger complexes than the current hold-back reagent: diethylenetriamine-N,N,N',N",N"-pentaacetic acid (DTPA). Evidence was observed for the selective extraction Ac(III) over Gd(III) and Am(III) at pH>2.5. Furthermore, the separation of Gd(III) over Am(III) can be achieved when using HOPO chelators under conditions similar to that of the TALKSPEAK process.

Figure 6:
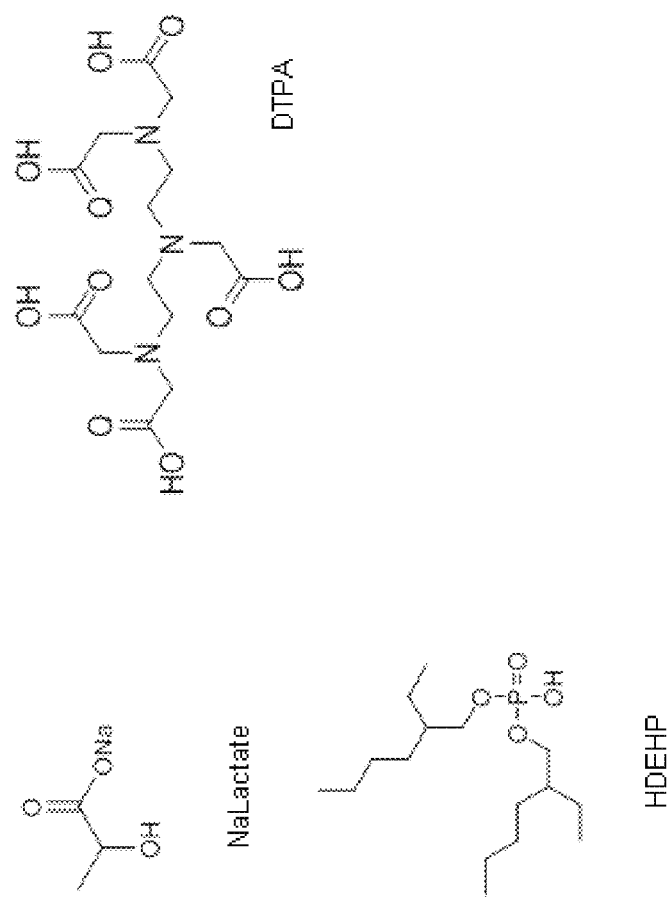
FIG. 6 shows structures of compounds used in the TAL-SPEAK process, which can be modified by one or more of the HOPO chelators inspired by the siderophore Enterboactin, as described herein.

In the TALSPEAK scheme, lactate serves as a buffering agent and to speed up transfer kinetics, bis-2-ethylhexyl phosphoric acid (HDEHP) is a nonselective extractant in the organic phase, DTPA is the current TALSPEAK hold-back reagent in the aqueous phase, and enterobactin is a naturally found iron chelator (FIG. 6).

Figure 8:
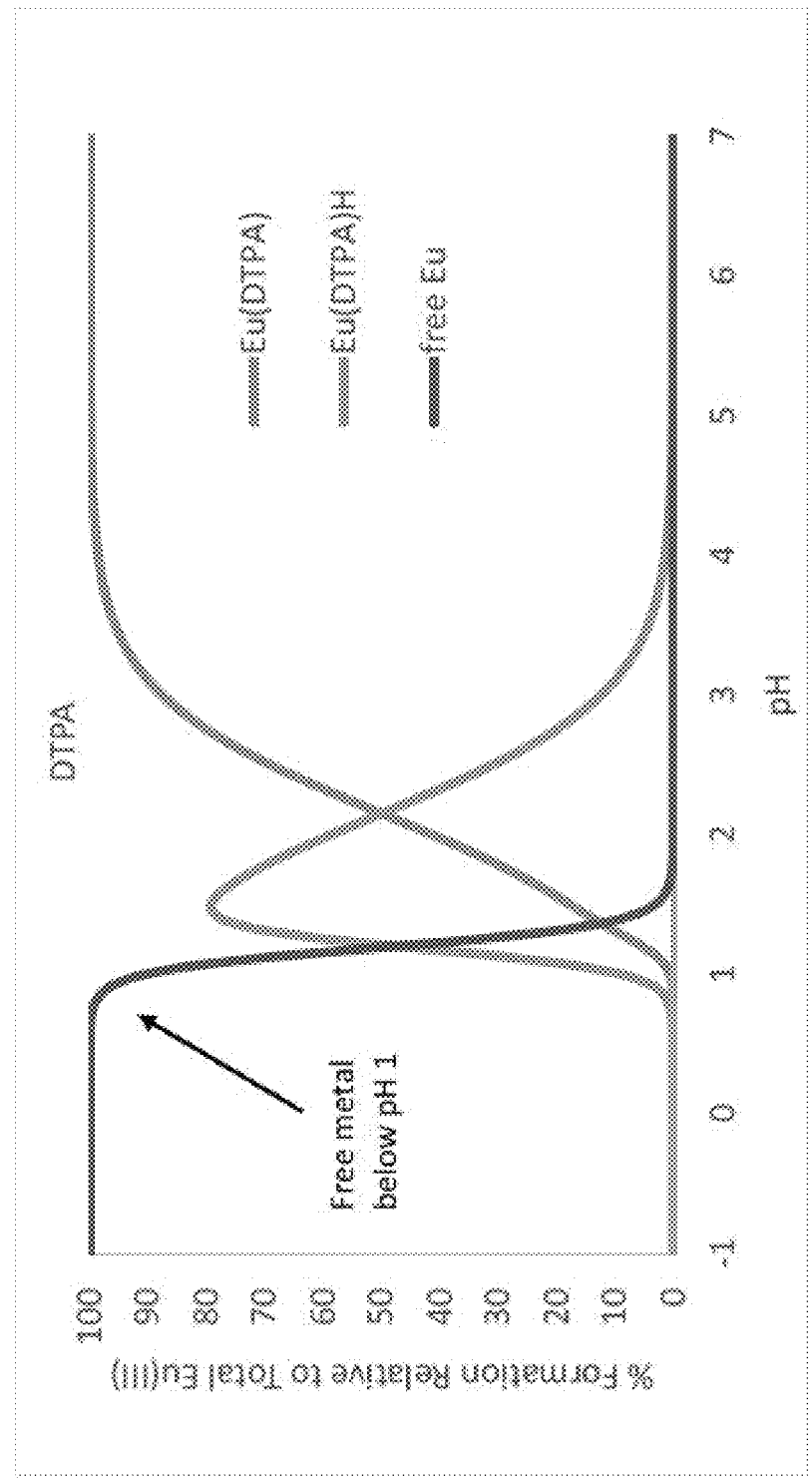
FIG. 8 shows a Eu(III) speciation diagram in the presence of excess DTPA (I=0.1 M at 25° C.).
Figure 9:
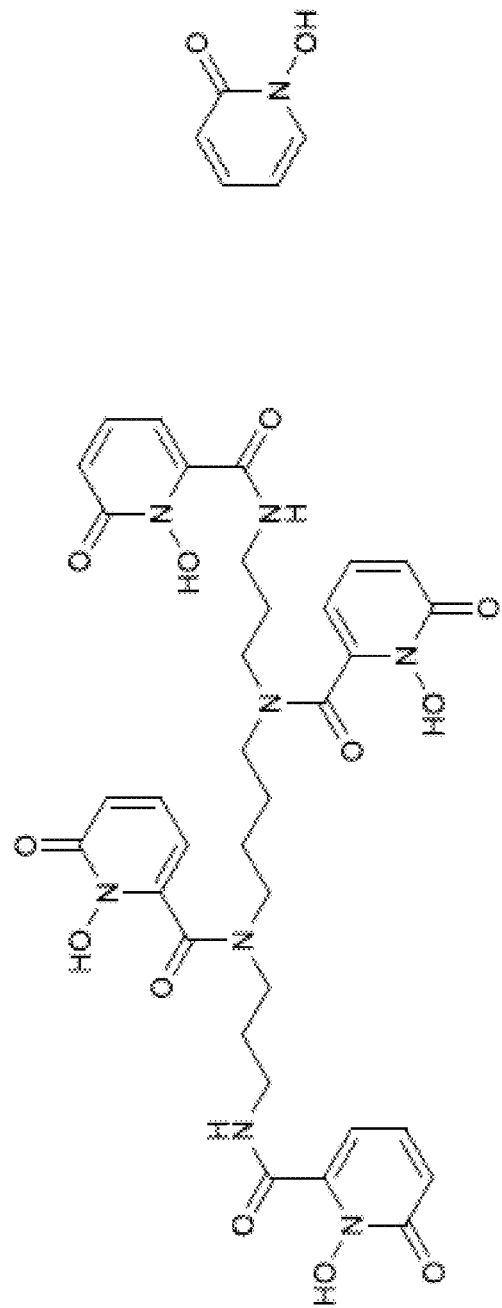
FIG. 9 shows structures of the aqueous octadentate ligand chelator 3,4,3-LI(1,2-HOPO) (left) and of the binding moiety 1,2-HOPO (right). Particular protons are labile and lead to the formation of $[3,4,3\text{-LI}(1,2\text{-HOPO})]^{4-}$ upon deprotonation for binding to a metal ion. HOPO=hydroxypyridinone.
Figure 26:
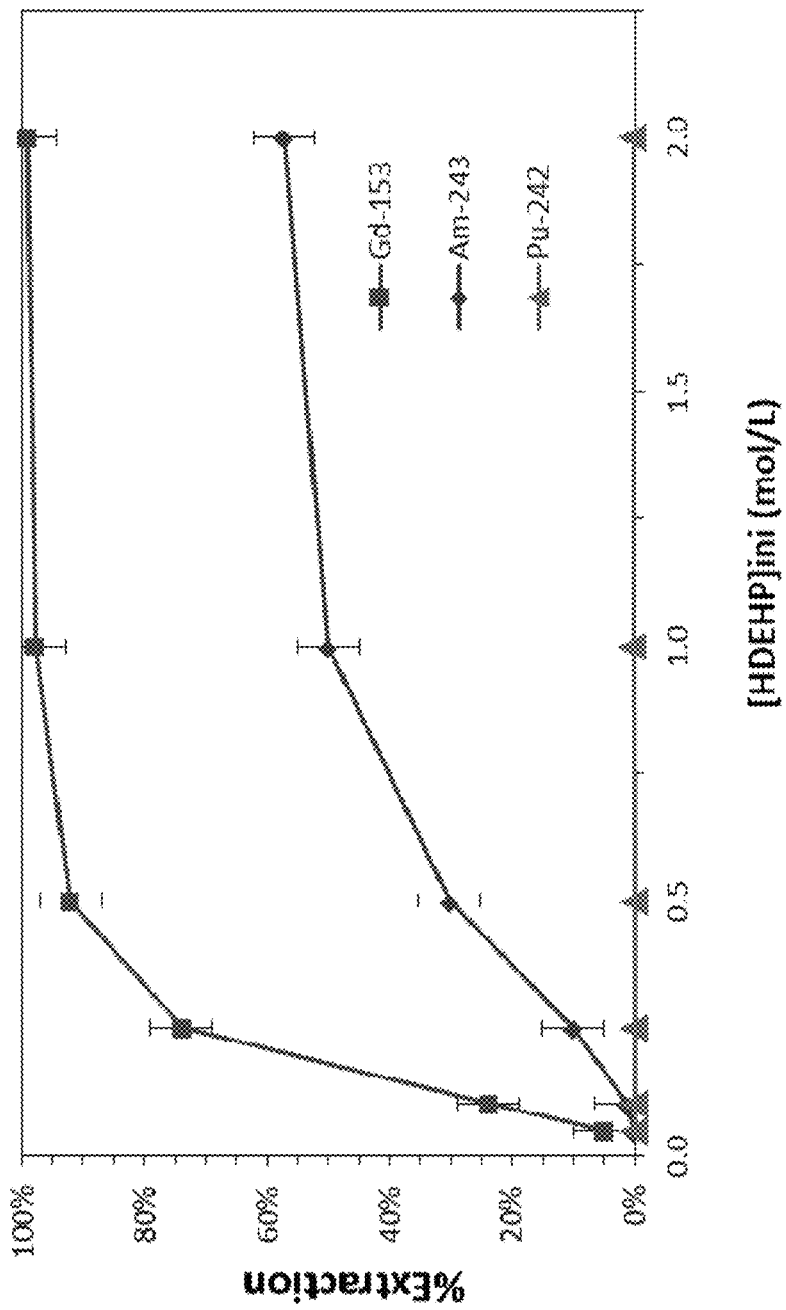
FIG. 26 shows percentage of extraction of plutonium(IV), americium(III), and gadolinium(III) by HDEHP at constant pH and using 3,4,3-LI(1,2-HOPO) as hold-back reagent.

Preliminary studies were done by modeling the species in solution as a function of pH for 40 mM hold-back reagent and 500 µM Eu(III) (FIG. 8 and FIG. 9). Europium was used in the speciation diagram since the stability constants with 3,4,3-LI(1,2-HOPO) have been well characterized. See, Rebecca J. Abergel, Anthony D'Aleo, Clara Ng Pak Leung, David K. Shuh, and Kenneth N. Raymond, "Using the Antenna Effect as a Spectroscopic Tool: Photophysics and Solution Thermodynamics of the Model Luminescent Hydroxypyridonate Complex [Eum(3,4,3-LI(1,2-HOPO))]-," Inorg. Chem. 48, 10868-10870 (2009). The binding of Eu(III) by DTPA and 3,4,3-LI(1,2-HOPO) by using available thermodynamic data at 0.1 M ionic strength at 25° C. were compared. Typical TALSPEAK conditions are >0.1 M ionic strength, due to needing strict pH control which is provided by sodium lactate (0.5-2.0 M). See, Kenneth L. Nash, "The Chemistry of TALSPEAK: A Review of the Science," Solvent Extr. Ion Exch. 33(1), 1-55 (2015). Therefore, extensive investigations of Ln-lactate stability constants have been obtained at high ionic strength, which are lacking for HOPO chelators. Nonetheless, this can be used to get an overview of the region where metal complexation is expected to occur. The calculations were made in the absence of lactate since lactate (log $\beta_{130}$=5.88 for Eu(III), I=2.0 M at 25° C.) (See, Kenneth L. Nash, "The Chemistry of TALSPEAK: A Review of the Science," Solvent Extr. Ion Exch. 33(1), 1-55 (2015)) is a much weaker chelator than 3,4,3-LI(1,2-HOPO) (log $\beta_{111}$=24.8 for Eu(III), I=0.1 M at 25° C.)6 and DTPA (log $\beta_{111}$=22.56 for Eu(III), I=2.0 M at 25° C.) (See, Kenneth L. Nash, "The Chemistry of TALSPEAK: A Review of the Science," Solvent Extr. Ion Exch. 33(1), 1-55 (2015)). In FIG. 26, 3,4,3-LI(1,2-HOPO) binds Eu(III) at pH as low as 0, whereas with DTPA (FIG. 8) free metal was present below pH 1. Thus, FIG. 8 shows that DTPA shows no binding at pH<1, i.e., Free Eu(III) is observed at pH<1. Stability constants obtained from NIST database. See, Rebecca J. Abergel, Anthony D'Aleo, Clara Ng Pak Leung, David K. Shuh, and Kenneth N. Raymond, "Using the Antenna Effect as a Spectroscopic Tool: Photophysics and Solution Thermodynamics of the Model Luminescent Hydroxypyridonate Complex [Eu$^{III}$(3,4,3-LI(1,2-HOPO))]," Inorg. Chem. 48, 10868-10870 (2009). In contrast, FIG. 26 shows that 3,4,3-LI(1,2-HOPO) shows evidence for binding Eu(III) at low pH.

The model supports the use of 3,4,3-LI(1,2-HOPO) as metal complexing agent even at low pH, which is advantageous to the TALSPEAK process since the raffinate begins in high acid media. Moreover, working at lower pH would be beneficial from an industrial point of view since the use of a buffering agent may be avoided and the pH control would more robust. Additionally, the protonated 3,4,3-LI(1, 2-HOPO):Eu complex is the dominant species over a relatively large pH range (0-4), forming a neutral species and potentially allowing for more favorable phase-transfer kinetics, which in the classic process lactate has been implicated in. See, Kenneth L. Nash, "The Chemistry of TALSPEAK: A Review of the Science," Solvent Extr. Ion Exch. 33(1), 1-55 (2015)

Figure 21:
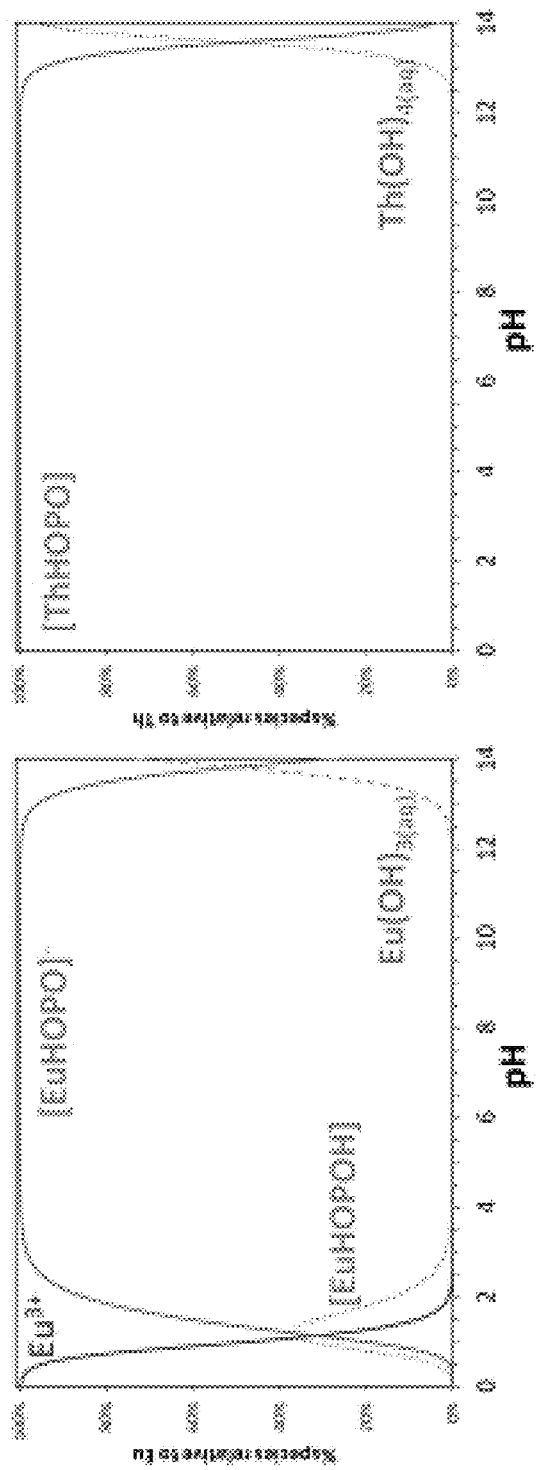
FIG. 21 shows a speciation diagram for solutions containing 3,4,3-LI(1,2-HOPO) and one equivalent of $Eu^{3+}$ or $Th^{4+}$ (I=0.1 M at 25° C.), showing use of 3,4,3-LI(1,2-HOPO) to suppress the extraction of $M^{4+}$ and selective extraction of $M^{3+}$.

FIG. 21 shows a pH extraction profile of Gd(III)-153, Ac(III)-225, and Am(III)-243 with [Gd(III)-153]=0.21 nM) DTPA as hold-back reagent. At [Ac(III)-225]=0.4 nM, [Gd (III)]=500 µM, [Am(III)-243]=40.4 nM, selective extraction of Gd(III) at pH 3-4, just as expected for this system under TALSPEAK conditions is observed. In some embodiments, the same applies to different isotopes, including, for example, 153, 225, and 243.

Figure 24:
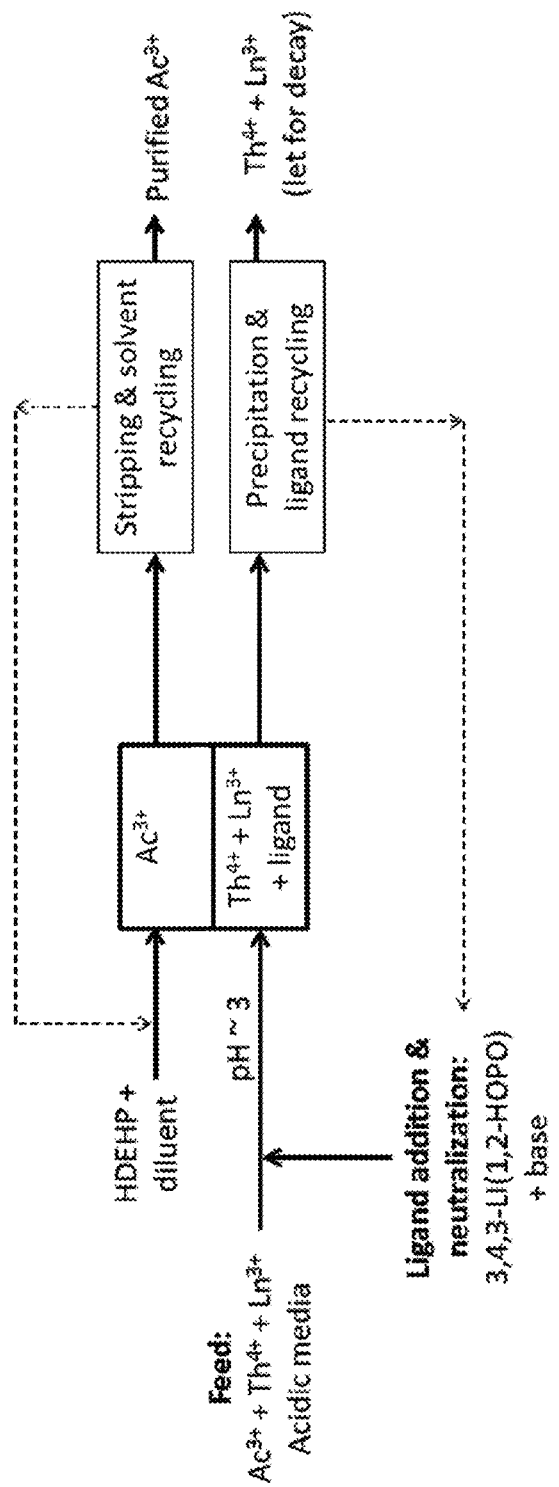
FIG. 24 shows an embodiment of a general process flowsheet proposed for the purification of actinium isotopes using 3,4,3-LI(1,2-HOPO) and HDEHP.
Figure 28:
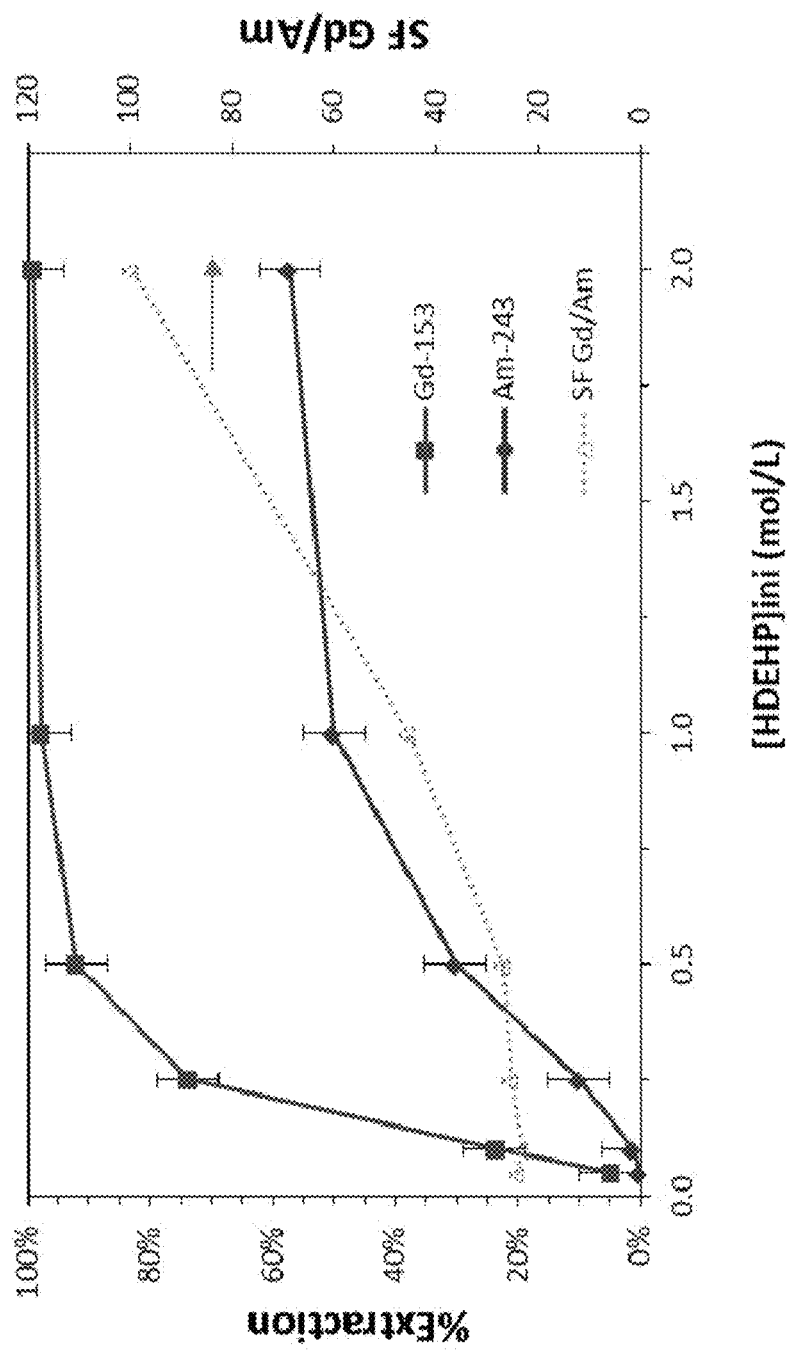
FIG. 28 shows percentage of extraction of americium(III), and gadolinium(III) by HDEHP at constant pH and using 3,4,3-LI(1,2-HOPO) as hold-back reagent.

FIG. 28 shows a pH extraction profile of of Gd(III)-153, Ac(III)-225, and Am(III)-243 with 3,4,3-LI(1,2-HOPO) as hold-back reagent. With [Gd(III)-153]=0.21 nM, [Ac(III)-225]=0.4 nM, [Gd(III)Total]=500 µM, [Am(III)-243]=40.4 nM, selective extraction of Ac(III) over Gd(III) and Am(III)-243 is seen above pH 2.5. FIG. 24 shows evidence for the selective extraction of Gd(III) over Am(III) with 3,4,3-LI (1,2-HOPO) as hold-back reagent. In some embodiments, the same applies to different isotopes, including, for example, 153, 225, and 243.

In some embodiments, DTPA chelator is a relatively weak complexing agent for Ac(III). Separation of Ac(III) from Gd(III) and Am(III) can be achieved by using a HOPO chelator at pH>2.5. Also observed was evidence for the selective extraction of Gd(III) over Am(III) between pH 1-2.5.

In some embodiments, one can separate Nd(III) and Am(III), which is often the limiting pair in the Ln(III)/An (III) extractions.

Figure 10:
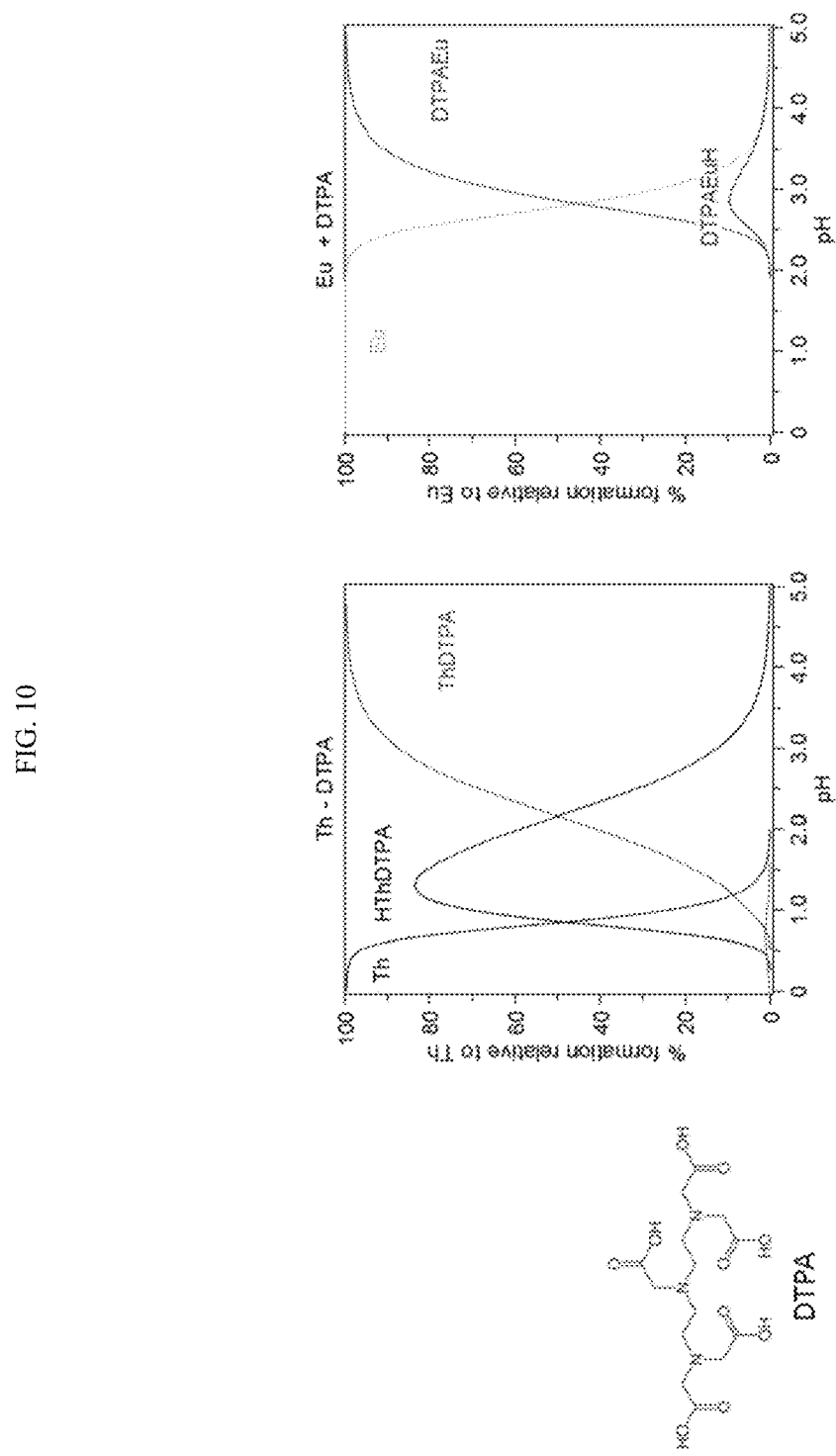
FIG. 10 shows binding of DTPA (left) to $M^{n+}$ in acidic solutions.

As described above, metal extraction processes rely on the selectivity of the ligands and organic extractants. In some embodiments, the initial feeds in a metal extraction process are highly acidic in order to allow for dissolution of the feeds. Ligands used for the aqueous phases in the metal extraction processes are essentially carboxylic acids. However, aqueous ligands are usually not able to bind $M^{n+}$ in acidic solutions (e.g., FIG. 10 for DTPA). An exception is HOPO ligands (FIG. 9). HOPO ligands are suitable for nuclear operations, are highly soluble, and need not have F or Cl atoms. In addition, 3,4,3-L1(1,2-HOPO) has an extreme affinity and selectivity for 4+ metal ions (TABLE 1).

TABLE 1

COMPARISON OF HOPO WITH DTPA

| | Log $\beta_{110}$ (Th$^{4+}$) | Log $\beta_{110}$ (Eu$^{3+}$) | Δ log β | Last pKa |
|---|---|---|---|---|
| 3,4,3-LI(1,2-HOPO)$^{4-}$ | 40.1 | 20.2 | 19.9 | 6.64 |
| DTPA$^{5-}$ | 28.7 | 22.4 | 6.3 | 10.4 |

In some embodiments, the TALSPEAK process can be modified by using 3,4,3-LI(1,2-HOPO), a promising f-element chelator shown to form stronger complexes than the current hold-back reagent: diethylenetriamine-N,N,N',N'',N''-pentaacetic acid (DTPA).

Given the lack of data on the lightest actinide element, actinium (Ac), extraction experiments under TALSPEAK conditions were also run for this actinide (Ac(III)-225 and Ac(III)-227). Evidence for the quantitative and selective extraction of Ac(III) over Gd(III) and Am(III) at pH>3 when using 3,4,3-LI(1,2-HOPO) was obtained. Thus, separation between metals of the same charge is also possible via this technique, as the various metals display varied affinity for the 3,4,3-LI(1,2-HOPO) ligand.

Figure 11:
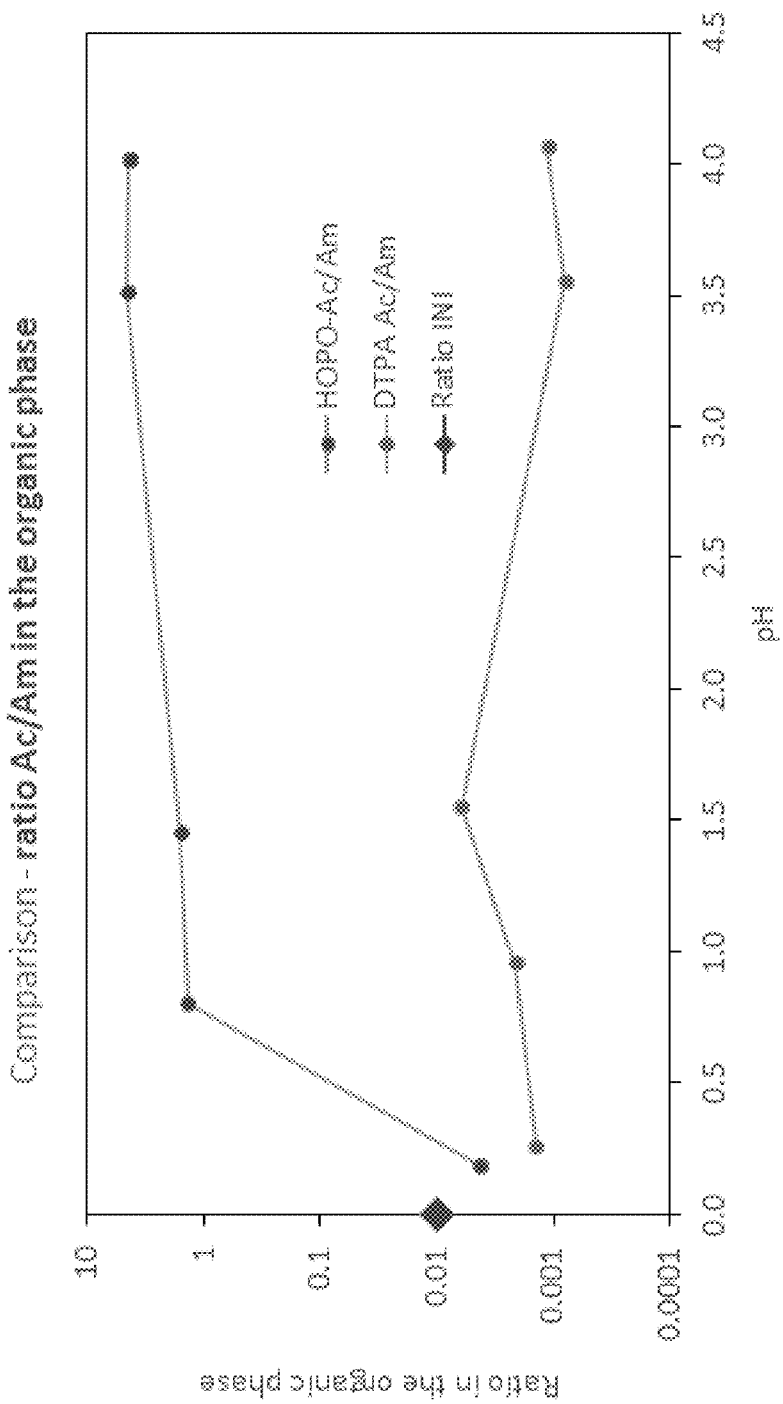
FIG. 11 shows comparison of ratio Ac/Am in organic phase for 3,4,3-LI(1,2-HOPO) and DTPA.
Figure 12:
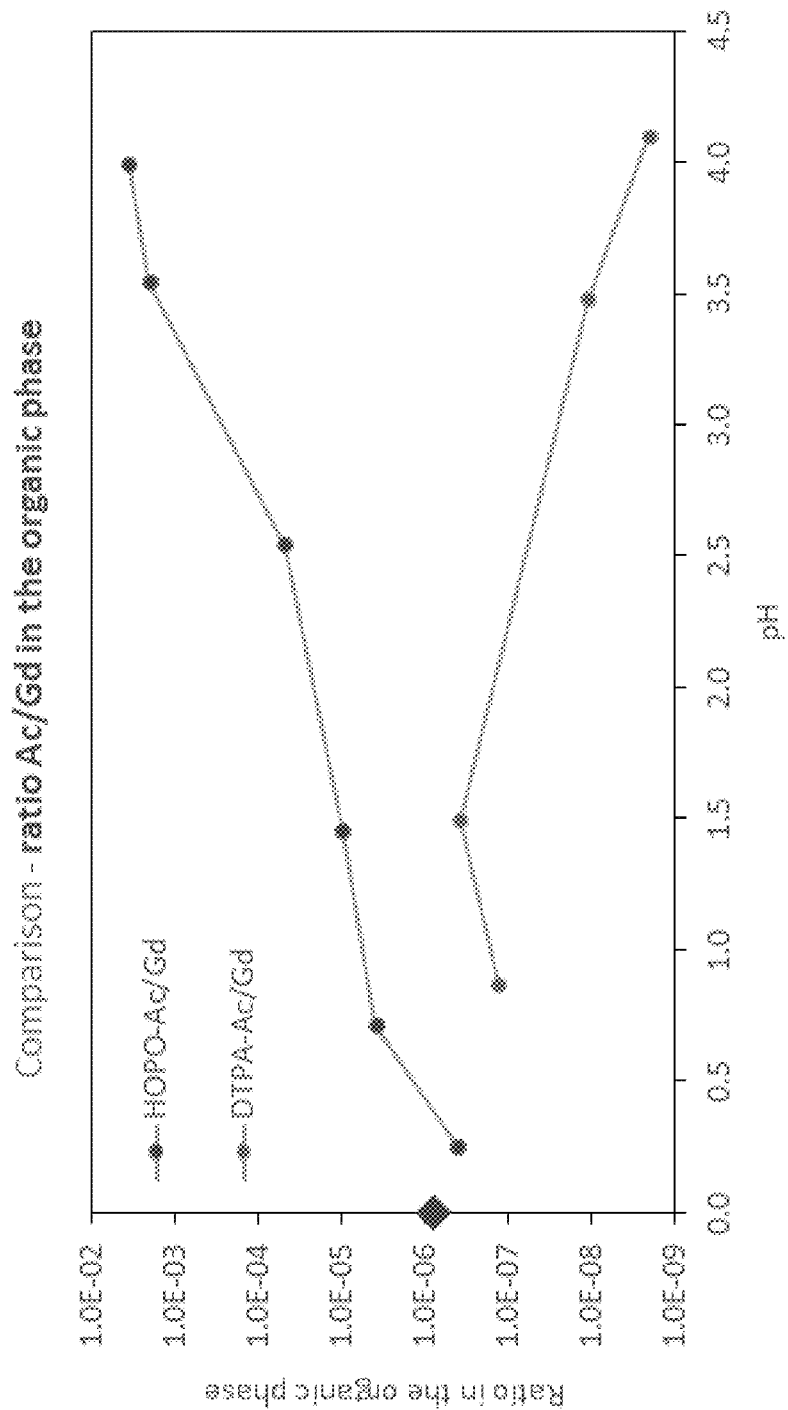
FIG. 12 shows comparison of ratio Ac/Gd in organic phase for 3,4,3-LI(1,2-HOPO) and DTPA.
Figure 13:
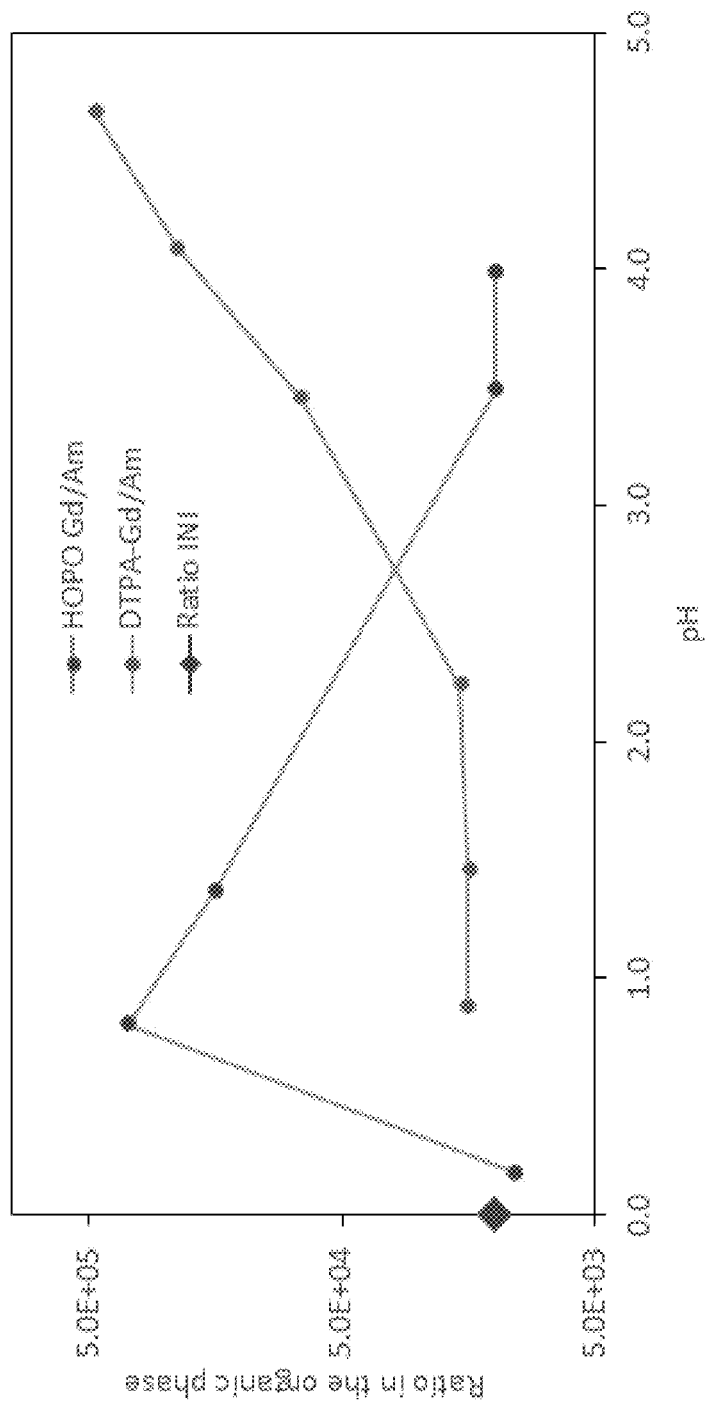
FIG. 13 shows comparison of ratio Gd/Am in organic phase for 3,4,3-LI(1,2-HOPO) and DTPA.
Figure 14:
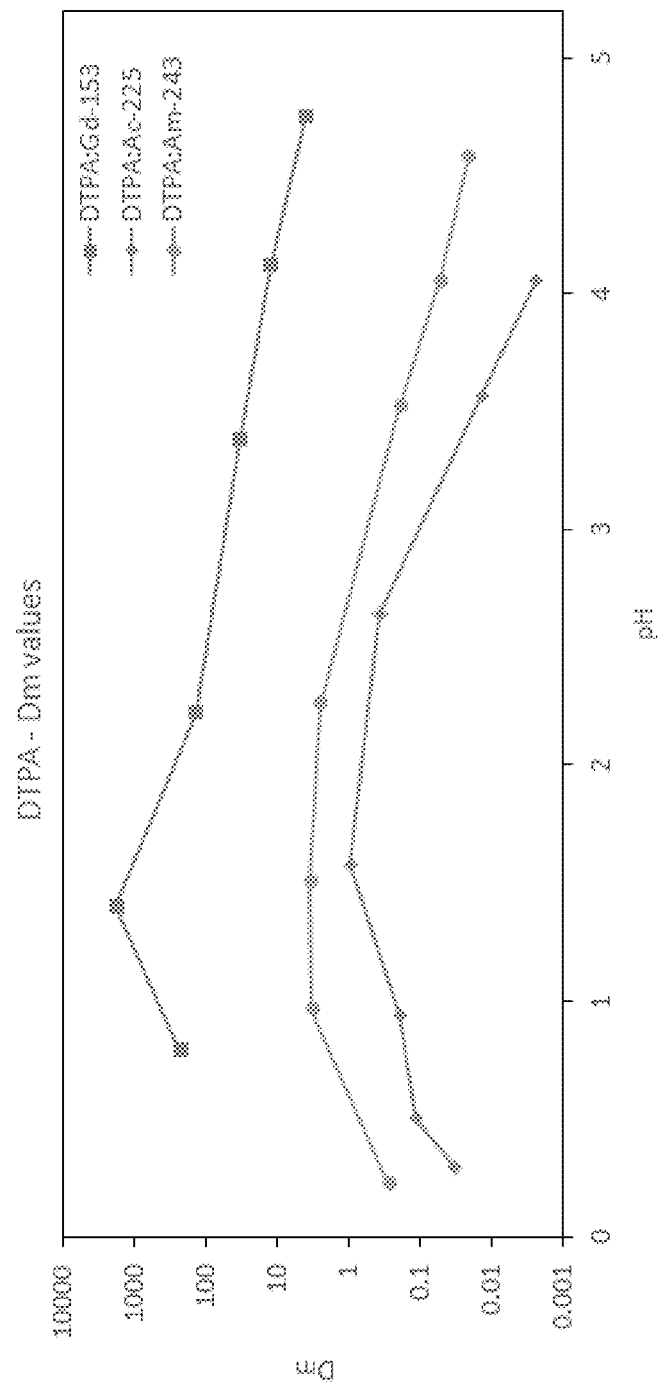
FIG. 14 shows a graph of extraction coefficient for DTPA for Gd, Ac and Am.
Figure 15:
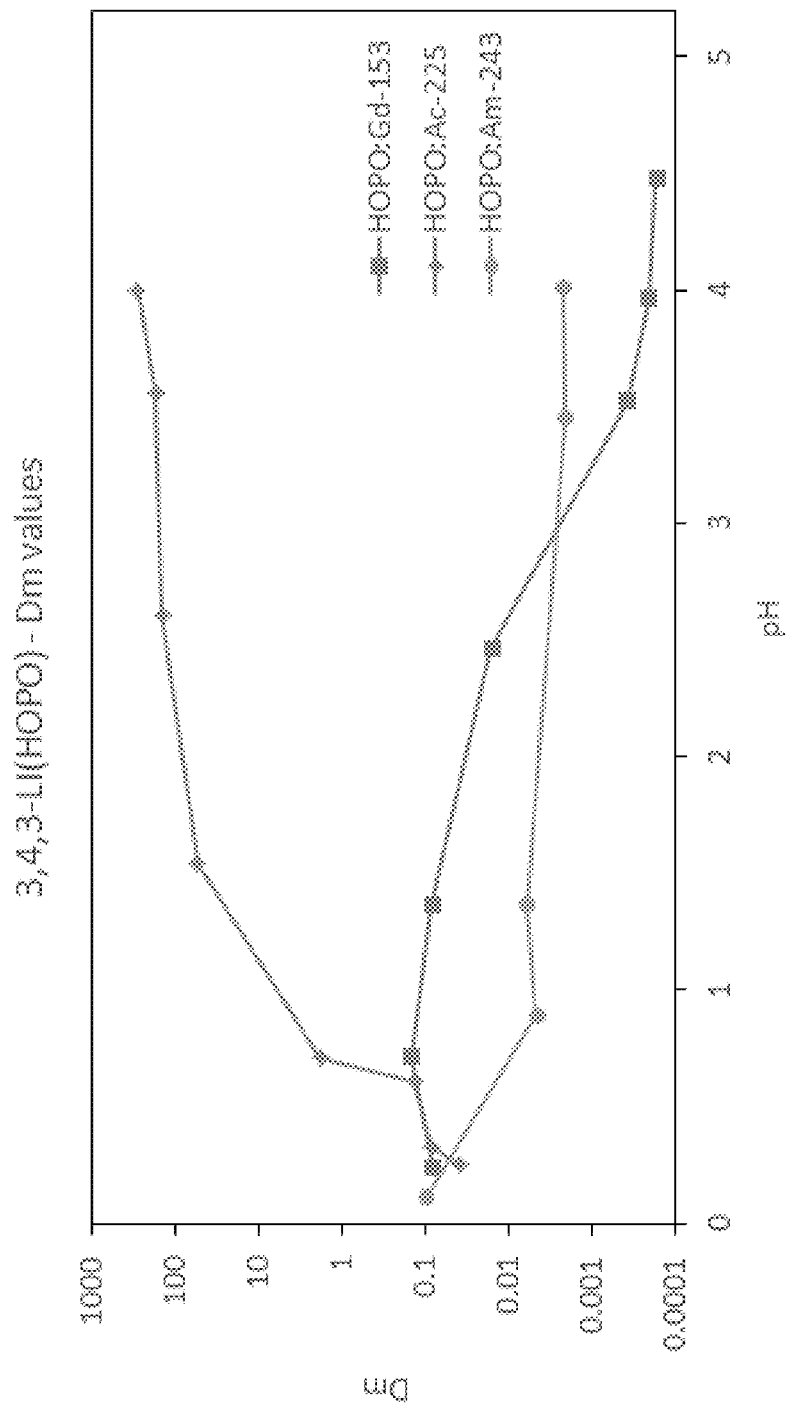
FIG. 15 shows a graph of extraction coefficient for 3,4,3-LI(1,2-HOPO) for Gd, Ac, and Am.

In some embodiments, one or more of the processes disclosed herein can be employed to separate a first $M^{3+}$ from a second $M^{3+}$. FIG. 11, FIG. 12 and FIG. 13 display the selectivity of 3,4,3-LI(1,2-HOPO) compared to DTPA. They give the calculated ratio between metals in the organic phase after extraction (what one recovers if one wants to purify something) if one had started with mixtures of Ac/Gd, Ac/Am or Gd/Am, respectively. FIG. 14 and FIG. 15 outline the extraction coefficient values comparing DTPA and 3,4,3-LI(1,2-HOPO), respectively.

In some embodiments, it is possible to obtain selective extraction of Ac(III) over Gd(III) and Am(III) at pH>3. Furthermore, it was possible to obtain higher extraction of Gd(III) over Am(III) at a lower pH range when using 3,4,3-LI(HOPO) as the hold-back reagent compared to DTPA and upon further optimization of the extraction condition expect to extract trivalent lanthanides over trivalent actinides Furthermore, in some embodiments, higher extraction of Gd(III) over Am(III) at a lower pH range when using 3,4,3-LI(1,2-HOPO) as the hold-back reagent compared to DTPA. The separation factors Gd/Am were also higher in the case of 3,4,3-LI(1,2-HOPO). In some embodiments, trivalent lanthanides are extracted over trivalent actinides at lower pH which is a significant optimization of the TALSPEAK process.

Traditionally, actinium cannot be purified from a mixture of $Ac^{3+}$, $Ln^{3+}$ and $An^{3+}$ when using DTPA as a hold-back reagent because the metals would be partially extracted at the same time. Chelators of the DTPA family (i.e., carboxylic acids) that are commonly used in separation processes, such as EDTA, NTA and, DOTA, are likely to exhibit a similar non-selectivity toward actinium. In contrast, in some embodiments, a HOPO-based method combines two features: (i) quantitative extraction for actinium, and (ii) a very high decontamination capability. In some embodiments, HOPO ligands provide very high separation factors between actinium and the lanthanides or actinides, after only 1 extraction step.

3,4,3-LI(1,2-HOPO) was investigated as a replacement for DTPA in the TALSPEAK process along with the behavior of Ac(III) with both hold-back reagents. Ac(III) was observed to behave similarly to Am(III) when using DTPA as the aqueous complexing agent and serves to show the dexterity of DTPA in the TALSPEAK process but lacks a pH range where selective extraction of Ac(III) over Am(III) is observed. Complete and selective extraction of Ac(III) in the liquid-liquid extractions with 3,4,3-LI(1,2-HOPO) was observed while retaining both Am(III) and Gd(III) in the aqueous phase. A selective, effective, and simplified separation process of Ac(III) from An(III) and Ln(III) can be envisioned from 3,4,3-LI(1,2-HOPO)'s behavior. Additionally, evidence for the selective extraction of Gd(III) over Am(III) at low pH is seen, a practical advantage to DTPA. Further probing of 3,4,3-LI(1,2-HOPO) with other f-elements is warranted to fully characterize it as a hold-back reagent. In some embodiments, the conditions used in the liquid-liquid extractions were from the classical TALSPEAK process but serve as a good starting point for the replacement of DTPA. Upon optimization of extraction conditions, 3,4,3-LI(1,2-HOPO) is expected to selectively separate An(III) (Am, Cm) from Ln fission products.

HOPO Ligands for Metal Ion Separation Processes

A structure of an embodiment of a HOPO molecule is as follows:

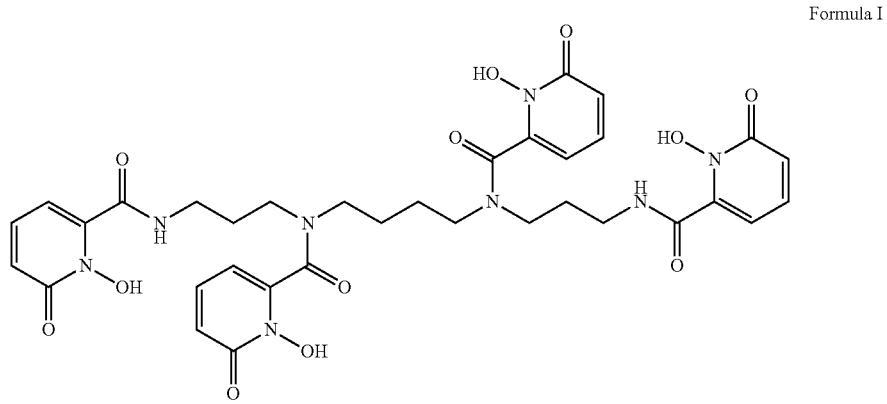 [SMILES: O=C(NCCCN(CCCCN(CCCNC(=O)c1cccc(=O)n1O)C(=O)c1cccc(=O)n1O)C(=O)c1cccc(=O)n1O)c1cccc(=O)n1O]

Formula I

Suitable 1,2-HOPO chelating agent include, but are not limited to, molecules defined by the structure:

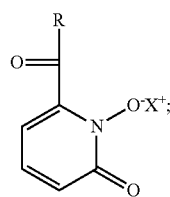

wherein R is a hydroxy group or

$R_1$ where $R_1$ and $R_2$ are selected from the group consisting of H, —$CH_3$, —$CH_2CH_3$ and —$CH_2$-φ, and X is either hydrogen, an alkali metal ion, or a quaternary ammonium ion.

Suitable 1,2-HOPO chelating agent include, but are not limited to, molecules incorporating a plurality of HOPO-type structures, including:

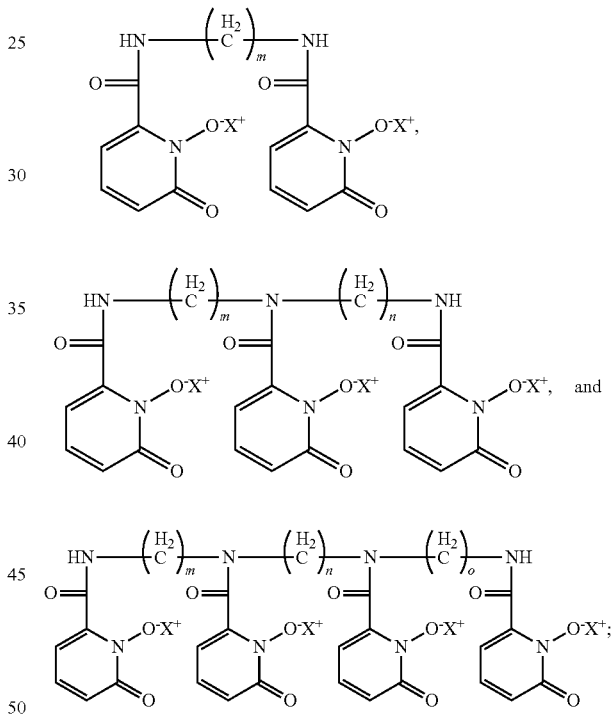

wherein l, m and n are integers between one and twenty. In some embodiments, there can be 5 HOPO groups instead of 4 (shown above).

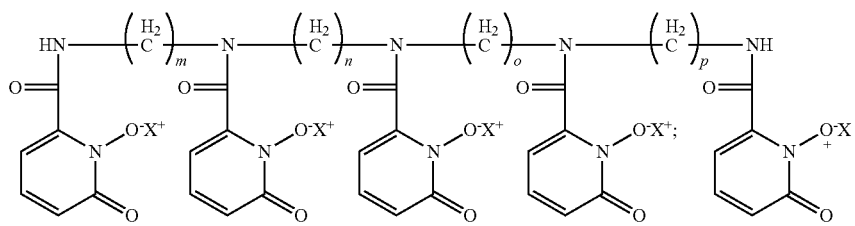

In some embodiments, the —(CH2)m- chains can contain ether bonds —(CH2-O—CH2)- or ramifications. —(CH2-CHR'—CH2)-, or hydroxyl groups —(CH2-CH(OH)'—CH2)- etc. In some embodiments, one can substitute one or both of the oxygens on the HOPO ring with a sulfur.

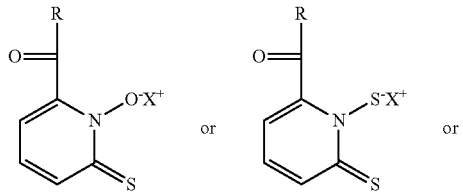

or

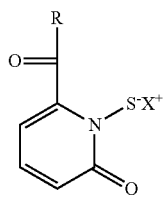

In a particular embodiment of the invention, m is three. In a particular embodiment of the invention, m is three and n is four. In a particular embodiment of the invention, 1 and n are three, and m is four. The 1,2-HOPO and 3,2-HOPO chelating agents suitable for use are also taught in U.S. Pat. No. 4,698,431 ("Hydroxypyridonate Chelating Agents"), U.S. Pat. No. 5,634,901 ("3-Hydroxy-2(1H)-pyridonate Chelating Agents"), and U.S. Pat. No. 5,892,029 ("3-Hydroxy-2(1H)-pyridonate Chelating Agents"), all of which are hereby incorporated by reference. Examples of appropriate chelators useful for the present methods described herein are shown in the Figures, Structure I, exemplary embodiments 1-51, and can include any of the HOPO formula provided herein, or other disclosed chelating formula, including those in FIGS. 38B-38E, 39, and 44-45D and the claims as filed. Any of the chelators provided herein can be applied to the various methods of extraction provided herein relating to the various pH manipulations.

Suitable 1,2-HOPO and 3,2-HOPO chelating agents include, but are not limited to, a chelating agent comprised of a plurality of chelating functional units joined by one or more linking members, said chelating functional units independently selected from the group consisting of

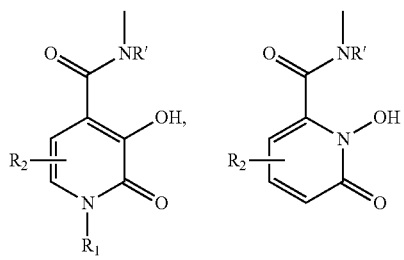

in which at least one of said plurality of chelating functional units on said chelating agent is

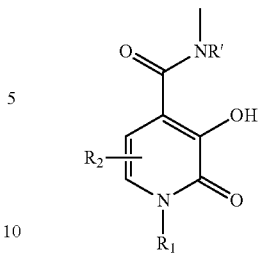

wherein $R_1$ and $R_2$ are independently selected from the group consisting of hydrogen, $C_{1-4}$ aliphatic hydrocarbon groups, and $C_{1-4}$ aliphatic hydrocarbon groups substituted by a single halide, hydroxy, carboxy, acrylamido group or an aryl group, and R' is a member selected from the group consisting of a bond to a linking member, a hydrogen atom, $C_{1-8}$ aliphatic hydrocarbon groups, aryl groups, and $C_{1-8}$ aliphatic hydrocarbon groups substituted by amino, carboxy, or hydroxy groups.

Suitable 3,2-HOPO chelating agents include, but are not limited to, a chelating agent having the structure:

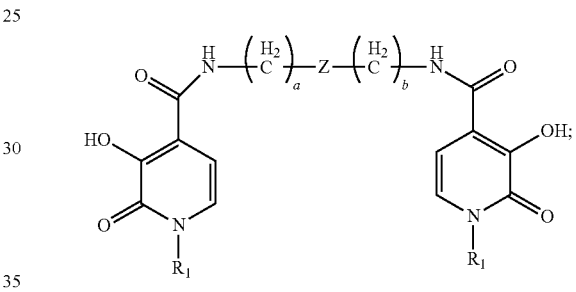

wherein $R_1$ is a member selected from the group consisting of hydrogen, $C_{1-4}$ aliphatic hydrocarbon groups, and $C_{1-4}$ aliphatic hydrocarbon groups substituted by a single halide, hydroxy, carboxy, or aryl group; Z is a member selected from the group consisting of O, NH, N-alkyl, and N-aryl; a is 2-4; and b is 2-4.

The methods for synthesizing the 1,2-HOPO and 3,2-HOPO chelating agents are taught in U.S. Pat. Nos. 4,698, 431; 5,634,901; and 5,892,029, all of which are hereby incorporated by reference.

In some embodiments, any siderophore based chelator that binds at a low pH can be employed in any of the processes provided herein.

In some embodiments, "3,4,3-LI(1,2-HOPO)" (FIG. 9; left) can be used as the chelator. This water-soluble chelator has previously been investigated for the complexation, in vitro or in vivo, of various metal ions, including: uranyl, lanthanide(III) ions, americium(III), curium(III), zirconium (IV), cerium(IV), thorium(IV), plutonium(IV) and, berkelium(IV). The solution thermodynamic properties of this molecule are therefore well documented. See, M. Sturzbecher-Hoehne, G. J.-P. Deblonde, R. J. Abergel, Solution thermodynamic evaluation of hydroxypyridinonate chelators 3,4,3-LI(1,2-HOPO) and 5-LIO(Me-3,2-HOPO) for UO2(VI) and Th(IV) decorporation, Radiochim. Acta. 101 (2013) 359-366. doi:10.1524/ract.2013.2047; R. J. Abergel, A. D'Alo, C. Ng Pak Leung, D. K. Shuh, K. N. Raymond, Using the Antenna Effect as a Spectroscopic Tool: Photophysics and Solution Thermodynamics of the Model Luminescent Hydroxypyridonate Complex [Eu(III)(3,4,3-LI(1,2-HOPO))]-, Inorg. Chem. 48 (2009) 10868-10870. doi:

10.1021/ic9013703; M. Sturzbecher-Hoehne, C. Ng Pak Leung, A. D'Aldo, B. Kullgren, A.-L. Prigent, D. K. Shuh, K. N. Raymond, R. J. Abergel, 3,4,3-LI(1,2-HOPO): In vitro formation of highly stable lanthanide complexes translates into efficacious in vivo europium decorporation, Dalton Trans. 40 (2011) 8340. doi:10.1039/c1dt10840a; M. Sturzbecher-Hoehne, P. Yang, A. D'Aldo, R. J. Abergel, Intramolecular sensitization of americium luminescence in solution: shining light on short-lived forbidden 5f transitions, Dalton Trans. (2016). doi:10.1039/C6DT00328A; M. Sturzbecher-Hoehne, B. Kullgren, E. E. Jarvis, D. D. An, R. J. Abergel, Highly Luminescent and Stable Hydroxypyridinonate Complexes: A Step Towards New Curium Decontamination Strategies, Chem.—Eur. J. 20 (2014) 9962-9968. doi:10.1002/chem.201402103; M. Sturzbecher-Hoehne, T. A. Choi, R. J. Abergel, Hydroxypyridinonate Complex Stability of Group (IV) Metals and Tetravalent f-Block Elements: The Key to the Next Generation of Chelating Agents for Radiopharmaceuticals, Inorg. Chem. 54 (2015) 3462-3468. doi:10.1021/acs.inorgchem.5b00033; G. J.-P. Deblonde, M. Sturzbecher-Hoehne, R. J. Abergel, Solution Thermodynamic Stability of Complexes Formed with the Octadentate Hydroxypyridinonate Ligand 3,4,3-LI(1,2-HOPO): A Critical Feature for Efficient Chelation of Lanthanide(IV) and Actinide(IV) Ions, Inorg. Chem. 52 (2013) 8805-8811. doi:10.1021/ic4010246; G. J.-P. Deblonde, M. Sturzbecher-Hoehne, P. B. Rupert, D. D. An, M.-C. Illy, C. Y. Ralston, J. Brabec, W. A. de Jong, R. K. Strong, R. J. Abergel, Chelation and stabilization of berkelium in oxidation state+IV, Nat. Chem. (2017). doi: 10.1038/nchem.2759.

Figure 20:
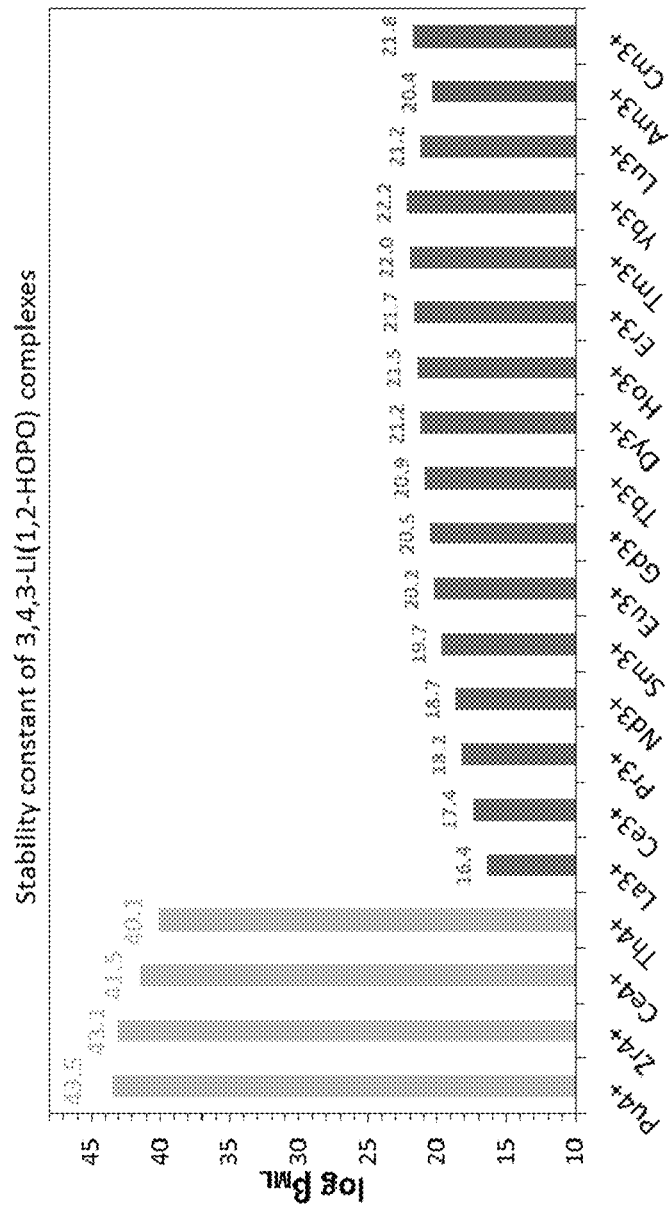
FIG. 20 shows the stability constant values published for the complexes of 3,4,3-LI(1,2-HOPO).

The ligand 3,4,3-LI(1,2-HOPO) exhibits an unprecedented affinity for a broad variety of metal ions and it is particularly efficient for tetravalent ions such as $Th^{4+}$ and $Pu^{4+}$. FIG. 20 shows the stability constant values published for the complexes of 3,4,3-LI(1,2-HOPO). Stability constant values (log $\beta_{ML}$) for various complexes of 3,4,3-LI(1,2-HOPO). FIG. 20 shows that the ligand forms extremely stable complexes with trivalent and tetravalent ions but it also keeps a high selectivity toward tetravalent ions. $\beta_{ML} = [ML]_{eq}/([M^{x+}]_{eq}[L^{n-}]_{eq})$. Data collected at 25° C.

This particular chelator combines several features, including but not limited to (i) formation of extremely stable complexes for both trivalent and tetravalent ions, (ii) high selectivity toward tetravalent metal ions, and (iii) very fast complexation kinetics (metal ions bound within a few seconds). In some embodiments, the ligand has one or more of these properties.

Another feature of the 3,4,3-LI(1,2-HOPO) molecule is that it is able to bind the tetravalent ions (e.g., $Th^{4+}$, $Pu^{4+}$) even at high acidity. In some embodiments, results 3,4,3-LI (1,2-HOPO) stays bound to $M^{4+}$ ions in solutions containing, at least, up to 6 mol/L $H_3O+$. This feature is unprecedented and unmatched by any of the common chelators used in the nuclear chemistry field such as ethylenediaminetetraacetic acid (EDTA), diethylentriamine-pentaacetic acid (DTPA), or tetraaza-cyclododecane-1,4,7,10-tetraacetic acid (DOTA).

Separation Aspects

FIG. 21 shows the speciation for solutions containing the ligand and one equivalent of $Eu^{3+}$ or $Th^{4+}$ showing what species are found in aqueous solutions of 3,4,3-LI(1,2-HOPO). FIG. 21 shows a speciation diagram for 3,4,3-LI (1,2-HOPO) solutions of $Eu^{3+}$ (left) and $Th^{4+}$ (right). Conditions: [Metal]=[ligand]=1 mM. Hydroxide stability constants taken from the NIST database. See, A. E. Martell, R. M. Smith, R. J. Motekaitis, NIST Standard Reference Database 46, (n.d.). In the near-neutral pH region, the trivalent metal ions form a negatively charged complex $[M(III)L]^-$ whereas the tetravalent metal ions form a neutral complex $[M(IV)L]$. However, in the acidic pH range, below pH ~2, the trivalent lanthanide ions are released by 3,4,3-LI(1,2-HOPO). In contrast, the tetravalent ions remain complexed to the ligand even at pH lower than 0. This clear difference in terms of metal speciation (i.e. free $M^{3+}$ versus bound $M^{4+}$) can be leveraged for separating trivalent ions from tetravalent ions as, for example, when purifying actinium from $Ac^{3+}/Th^{4+}$ mixtures.

Figure 22:
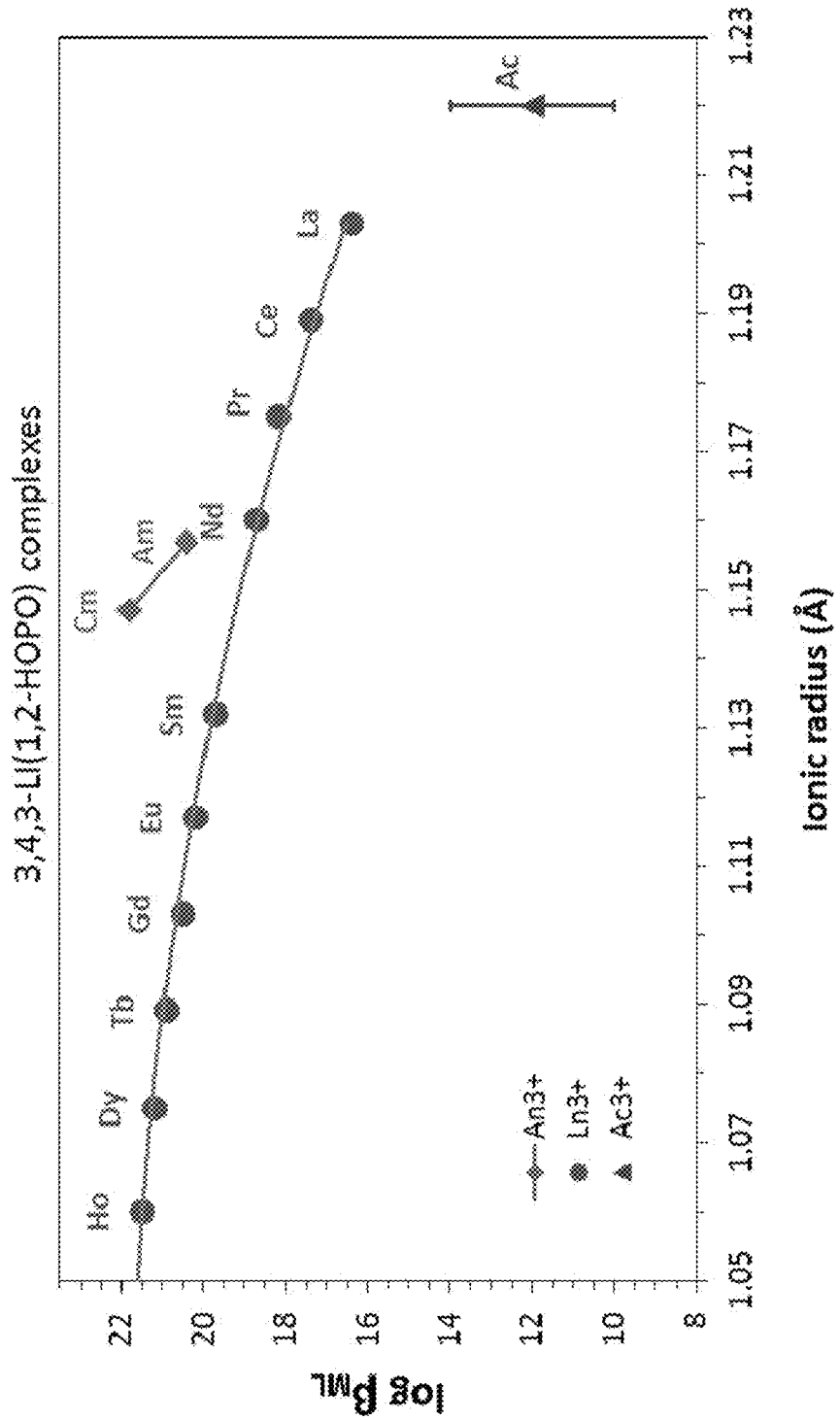
FIG. 22 shows relationship between ionic radius and stability constants for 3,4,3-LI(1,2-HOPO) for other actinide and lanthanide ions.

Thus far, no stability constant has been published for the actinium ($Ac^{3+}$) complex of 3,4,3-LI(1,2-HOPO). Based on the ionic radius of $Ac^{3+}$ (1.22 Å; See, D. Lundberg, I. Persson, The size of actinoid(III) ions—structural analysis vs. common misinterpretations, Coord. Chem. Rev. 318 (2016) 131-134. doi:10.1016/j.ccr.2016.04.003) and stability constants determined for other actinide and lanthanide ions, the stability of the $Ac^{3+}$ complex is expected to be very low, with a log $\beta_{[AcL]}$- value of about 12 (FIG. 22). Stability of constant of 3,4,3-LI(1,2-HOPO) complexes with trivalent ions as a function of the ionic radius of the metal is shown in FIG. 22. This graph shows that the stability of the actinium complex is expected to be low. Ionic radius values taken from Lundberg et al. for nona-coordinated metal ions. The $Ac^{3+}$ data point is an estimate. See, Lundberg, I. Persson, The size of actinoid(III) ions—structural analysis vs. common misinterpretations, Coord. Chem. Rev. 318 (2016) 131-134. doi:10.1016/j.ccr.2016.04.003; D. Lundberg, I. Persson, L. Eriksson, P. D'Angelo, S. De Panfilis, Structural Study of the N,N'-Dimethylpropyleneurea Solvated Lanthanoid(III) Ions in Solution and Solid State with an Analysis of the Ionic Radii of Lanthanoid(III) Ions, Inorg. Chem. 49 (2010) 4420-4432. doi:10.1021/ic100034q. Hence, this weak stability compared to the other complexes can be used for separation purposes.

Given the solution thermodynamics of the 3,4,3-LI(1,2-HOPO) complexes, some embodiments provided involve highly selective processes based on the difference in affinity that 3,4,3-LI(1,2-HOPO) exhibits for the metal ions. The affinity of the ligand for the metals ions follows the order: $M^{4+}>>>Cm^{3+}>Am^{3+}>Lu^{3+}—La^{3+}>>Ac^{3+}$. One can then expect to sequester selectively the impurities present in a given media ($Th^{4+}$, $Ln^{3+}$, etc.) while leaving the actinium ions unbound. In some embodiments, any of the metal ions can be separated from one another via their differences in affinity to the HOPO molecule, based on variables such as the amount of time of the extraction, amount of chelator added, pH value, amount of extractant in the organic phase, ratio between the organic phase and aqueous phase.

In the case of a liquid-liquid extraction process, the unbound $Ac^{3+}$ ions can then be extracted in an organic phase while letting the impurities remain in the aqueous phase. Since the selectivity of the process comes from the aqueous chelator 3,4,3-LI(1,2-HOPO), any extractant able to transfer $Ac^{3+}$ into an organic phase can be used and there is no need to develop a selective organic extractant for actinium. The separation method can then rely on commercially available compounds that are usually used in hydrometallurgy processes.

In some embodiments, the extract for $Ac^{3+}$ ions into an organic phase can be one or more of: di-(2-ethylhexyl) phosphoric acid (HDEHP), calixarenes (See, C. Wai, D. Fisher, others, Carboxylate-derived calixarenes with high selectivity for actinium-225, Chem. Commun. (1998) 377-378), diglycoamide derivatives (See, V. Radchenko, J. W. Engle, J. J. Wilson, J. R. Maassen, F. M. Nortier, W. A. Taylor, E. R. Birnbaum, L. A. Hudston, K. D. John, M. E.

Fassbender, Application of ion exchange and extraction chromatography to the separation of actinium from proton-irradiated thorium metal for analytical purposes, J. Chromatogr. A. 1380 (2015) 55-63. doi:10.1016/j.chroma.2014.12.045), carbamoylphosphine oxide derivatives (See, V. Ostapenko, A. Vasiliev, E. Lapshina, S. Ermolaev, R. Aliev, Y. Totskiy, B. Zhuikov, S. Kalmykov, Extraction chromatographic behavior of actinium and REE on DGA, Ln and TRU resins in nitric acid solutions, J. Radioanal. Nucl. Chem. 306 (2015) 707-711. doi:10.1007/s10967-015-4331-y), and quaternary ammonium salts (See, L. R. Morss, N. M. Edelstein, J. Fuger, The Chemistry of the Actinide and Transactinide Elements, 4th ed., Springer, 2010).

Figure 29:
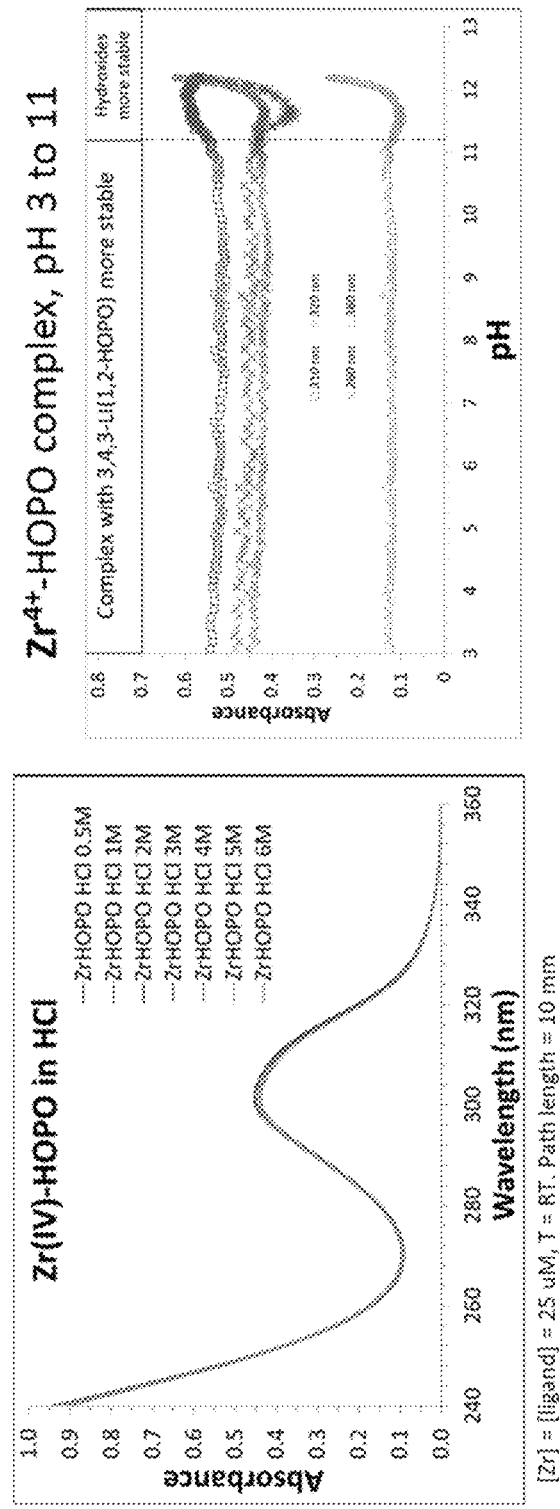
FIG. 29 shows the effects of acid and pH on $Zr^{4+}$-3,4,3-L1(1,2-HOPO) interactions.

In some embodiments, HOPO can be used for $Zr^{4+}$ extraction. In some embodiments, $Zr^{4+}$-3,4,3-L1(1,2-HOPO) complexes are stable from 6 M HCl (FIG. 29). In some embodiments, $Zr^{4+}$-3,4,3-L1(1,2-HOPO) complexes are stable to pH 11 (FIG. 29).

In some embodiments, HOPO can be used for $Hf^{4+}$ extraction. In some embodiments, $Hf^{4+}$-3,4,3-L1(1,2-HOPO) complexes are stable from 6 M HCl. In some embodiments, $Hf^{4+}$-3,4,3-L1(1,2-HOPO) complexes are stable to pH 11.

Figure 30:
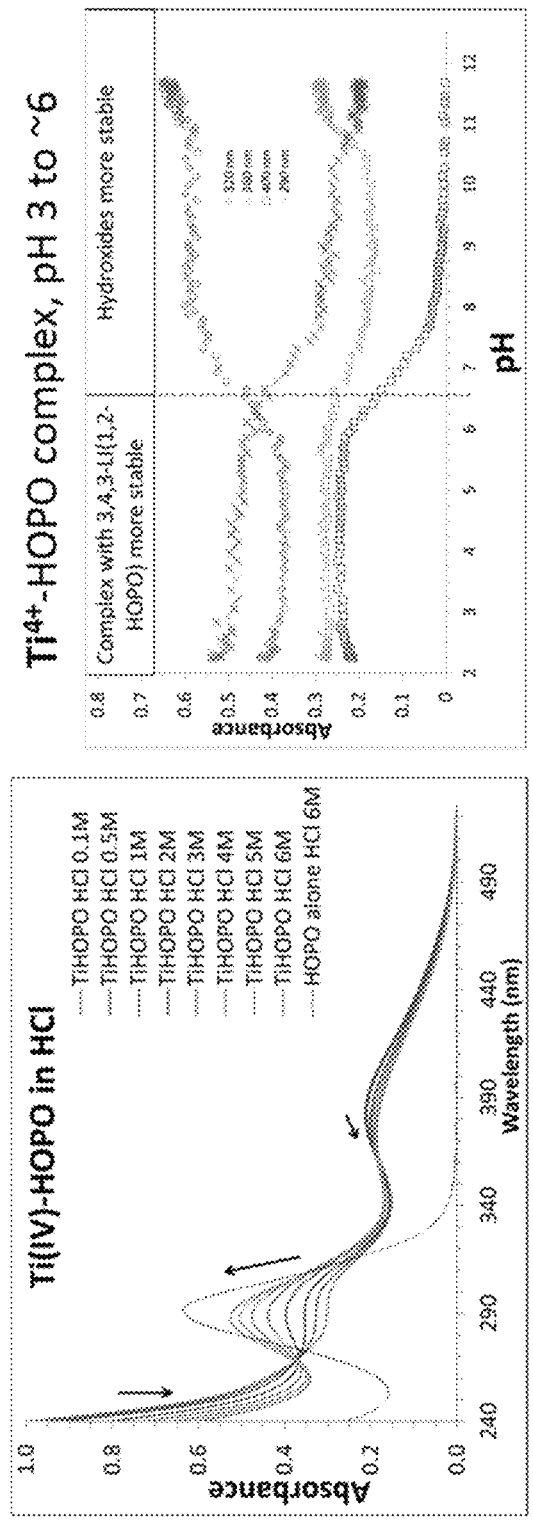
FIG. 30 shows the effects of acid and pH on $Ti^{4+}$-3,4,3-L1(1,2-HOPO) interactions.

In some embodiments, $Ti^{4+}$-3,4,3-L1(1,2-HOPO) complexes are stable, at least, from ~6 M HCl (FIG. 30). In some embodiments, $Ti^{4+}$-3,4,3-L1(1,2-HOPO) complexes are stable to ~pH 6 (FIG. 30). In some embodiments, separation of Ti/Zr or Ti/Hf is possible at pH 6-11 using HOPO.

Figure 31:
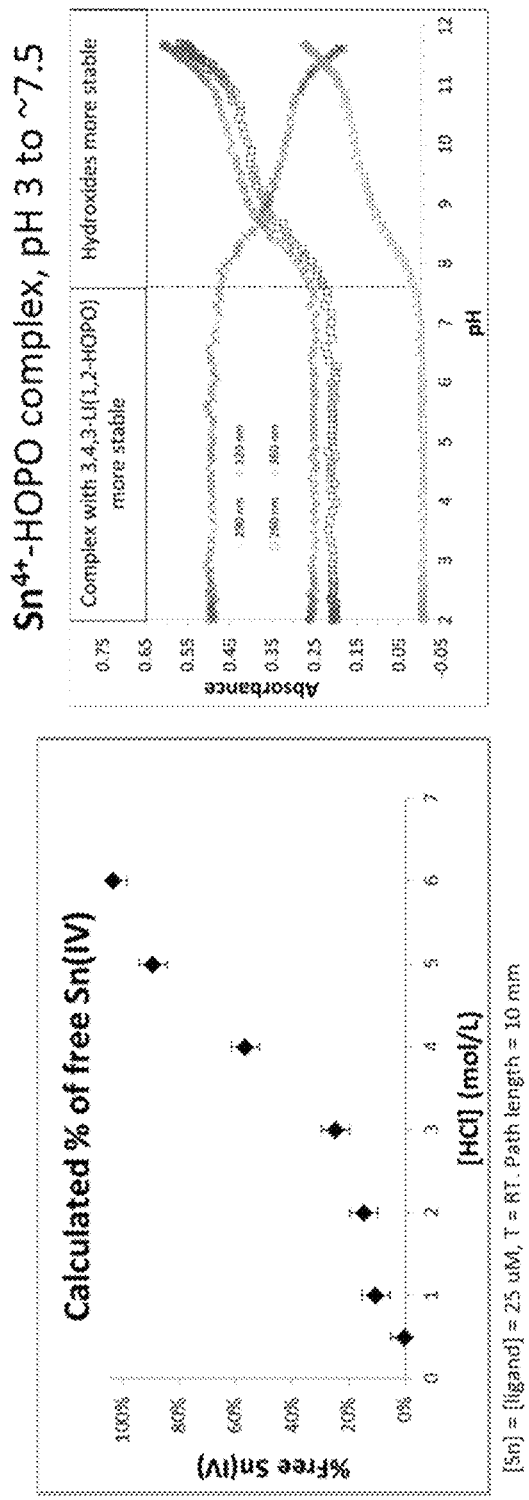
FIG. 31 shows the effects of acid and pH on $Sn^{4+}$-3,4,3-L1(1,2-HOPO) interactions.

In some embodiments, $Sn^{4+}$-3,4,3-L1(1,2-HOPO) complexes are stable from ~1 M HCl (FIG. 31). In some embodiments, $Sn^{4+}$-3,4,3-L1(1,2-HOPO) complexes are stable to ~pH 8 (FIG. 31). In some embodiments, separation of Sn/Zr or Sn/Hf is possible in acidic media using HOPO. In some embodiments, separation of Sn/Ti is possible at pH ~7 using HOPO.

Figure 32:
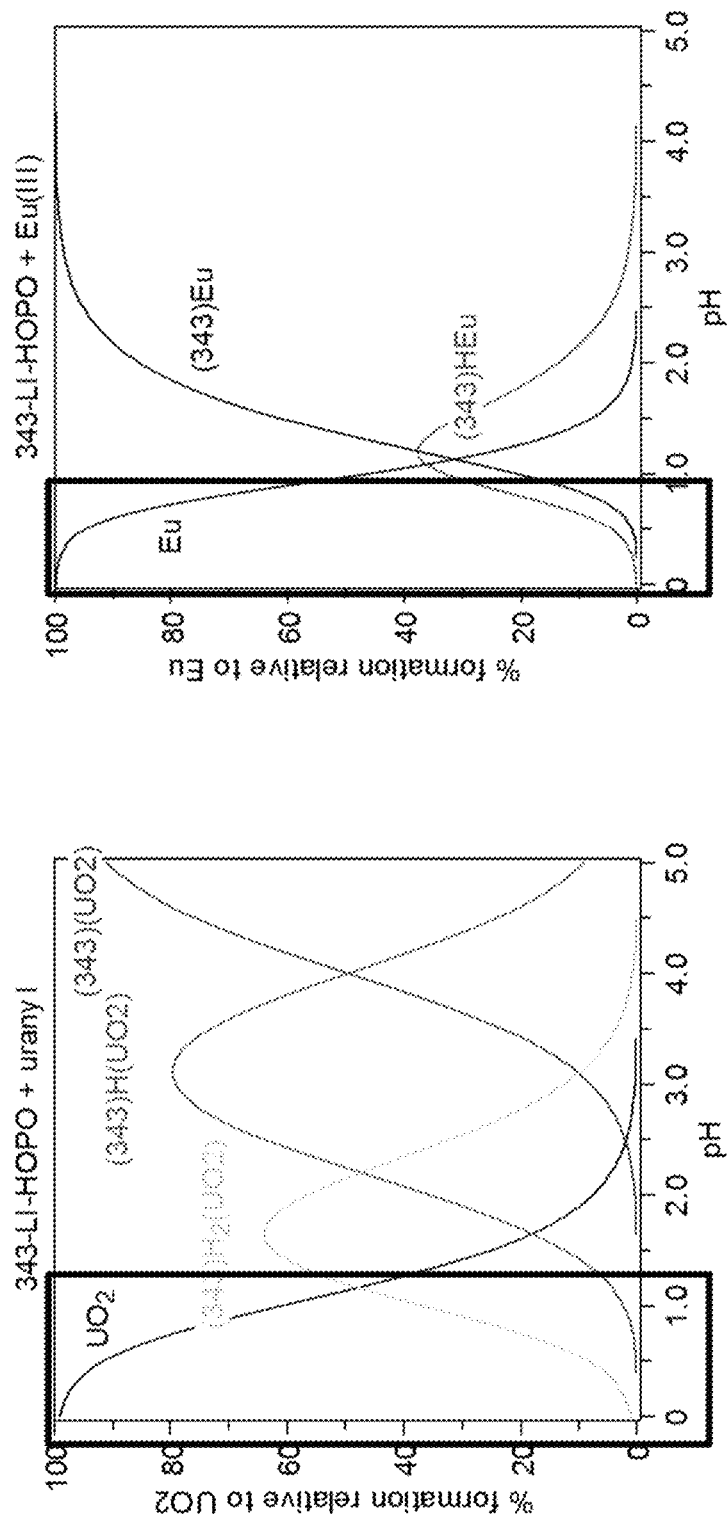
FIG. 32 shows speciation of $M^{3+}$ or $M^{2+}$ versus $M^{4+}$ ions in the presence of 3,4,3-L1(1,2-HOPO).

In some embodiments, speciation of $M^{3+}$ or $M^{2+}$ versus $M^{4+}$ ions is readily different in the presence of 3,4,3-L1(1,2-HOPO) (FIG. 32). In some embodiments, $Ln^{3+}$, $An^{3+}$ and $UO_2^{2+}$ are released below pH ~1 (FIG. 32).

Figure 33:
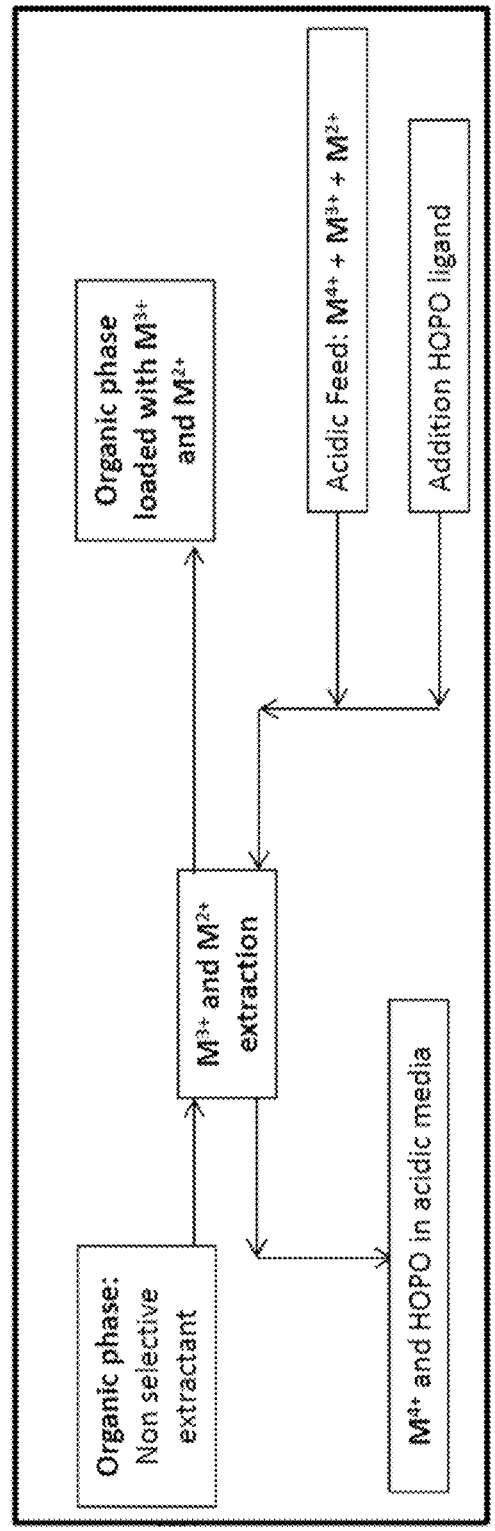
FIG. 33 shows an embodiment of a strategy for grouped separation of $M^{4+}$ ions versus others ions at low pH.

In some embodiments, a possible application of 3,4,3-L1(1,2-HOPO) is for grouped separation of $M^{4+}$ ions versus others ions at low pH. In some embodiments, a separation strategy is shown in FIG. 33. Non-limiting examples of applications of the separation strategy of FIG. 33 include separation of $^{227}Th^{4+}$ from $^{227}Ac^{3+}$ and $^{223}Ra^{2+}$, $Pu^{4+}$ from $Ln^{3+}$, $An^{3+}$, $TcO_4^-$, $UO_2^{2+}$, $NpO_2^+$, $Sn^{4+}$ from $Pb^{2+}$, $Hf^{4+}$ from $^{177}Lu^{3+}$, $Ti^{4+}$ from $Sc^{3+}$, and $Bk^{4+}$ from $Cf^{3+}$.

In some embodiments, 3,4,3-LI(1,2-HOPO) is a chelator that binds $M^{4+}$ in really acidic conditions. The speciation of $M^{4+}/M^{3+}$ is readily different under acidic conditions. Therefore, in some embodiments, 3,4,3-LI(1,2-HOPO) can be used to suppress the extraction of $M^{4+}$.

In some embodiments, selective extraction of $M^{3+}$ in the presence of 3,4,3-LI(1,2-HOPO) is possible (FIG. 26), for example, with classical REE extractants (e.g., HDEHP, CMPO, etc.).

In some embodiments, based on the results provided in the examples below, processes can be established for the recovery and/or purification of actinium from a mixture of actinium, thorium and lanthanides. The starting material is considered to be an acidic solution since spallation Th target are likely to be dissolved in a mineral acid aqueous solution.

In some embodiments, a first strategy would involve extracting solely actinium in an organic phase using HDEHP while letting the 3,4,3-LI(1,2-HOPO) complexes of lanthanide(III) and thorium(IV) in the aqueous phase (FIG. 24). A pH adjustment to ~3 would be necessary due to the use of HDEHP. The actinium ions would then be back-extracted by common procedures (contact with HCl or $HNO_3$) and the solvent would be recycled into the extraction step. The aqueous phase containing $Th^{4+}$ and $Ln^{3+}$ complexes could then be neutralized in order to precipitate the $Th^{4+}$ and $Ln^{3+}$ hydroxides and to recycle 3,4,3-LI(1,2-HOPO). The solid material could then be let for decay of the short-lived isotopes ($^{227}Th$ and lanthanide fission products) and then reprocessed to make a new $^{232}Th$ spallation target.

Figure 25:
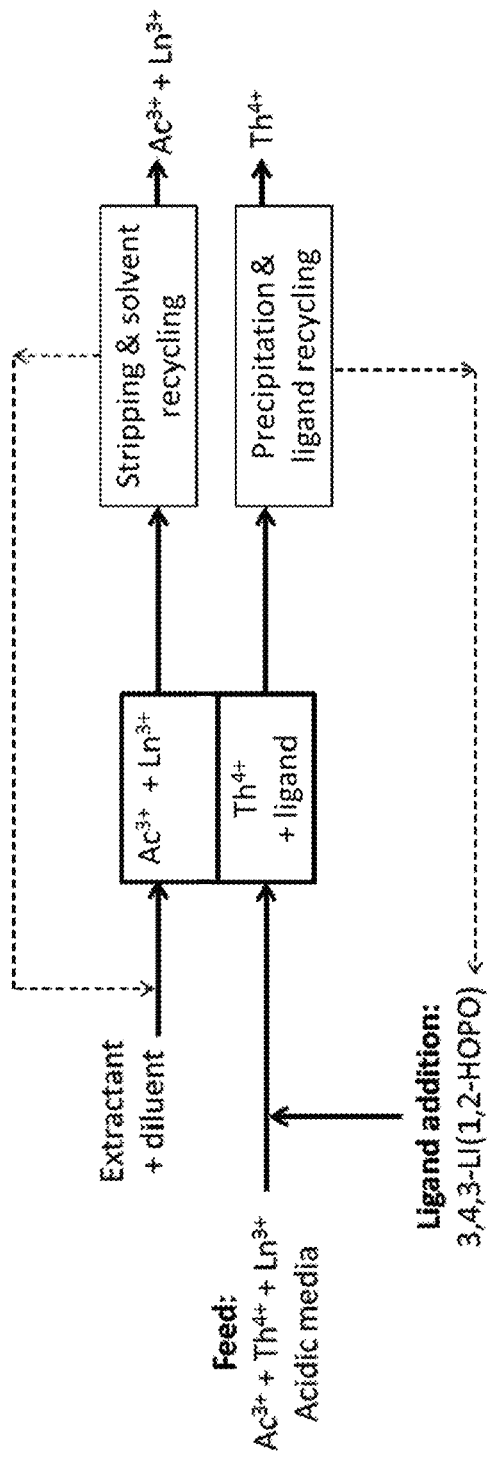
FIG. 25 shows an embodiment of another process proposed for the recovery of actinium using 3,4,3-LI(1,2-HOPO) and a non-selective extractant.

In some embodiments, another strategy (FIG. 25) would involve of working directly on the acidic feed solution without pH adjustment. Under highly acidic conditions, (e.g., 3-7.5 M $HNO_3$), the lanthanide and actinium complexes of 3,4,3-LI(1,2-HOPO) will not be formed whereas the thorium(IV) complex will be formed. Due to this, $Ac^{3+}$ ions could be extracted selectively from $Th^{4+}$ but the $Ln^{3+}$ ions are also likely to be transferred into the organic phase (depending on the acidity and extractant used). In that case, the process would serve as an actinium recovery method as well as an $Ac^{3+}/Th^{4+}$ separation step. Further processing of the organic phase can be done in order to do the final $Ac^{3+}/Ln^{3+}$ separation, such as the one described in FIG. 31 or by the mean of a chromatography column (See, J. T. Harvey, Production of Actinium-225 via High Energy Proton Induced Spallation of Thorium-232. Final Technical Report DE-SC0003602, NorthStar Medical Radioisotopes, LLC, https://world wide web.osti.gov/scitech/servlets/purl/1032445/).

ADDITIONAL EMBODIMENTS

TABLE 3 gives the formation constants of 3,4,3-LI(1,2-HOPO) complexes with various metal ions. As provided herein, the high affinity of 3,4,3-LI(1,2-HOPO) toward $Ln^{3+}$, $An^{3+}$ and $An^{4+}$ ions so that the chelator acts as a hold-back reagent for these ions while letting actinium being transferred into an organic phase.

TABLE 3

Stability constant ($\beta_{ML}$ = [ML]/([M][L])) of different complexes of the ligand 3,4,3-LI(1,2-HOPO).

| Ion | Ionic radius (Å. CN = 8) | log $\beta_{ML}$ |
|---|---|---|
| $UO_2^{2+}$ | / | 18.0 ± 0.4 |
| $Pb^{2+}$ | 1.29 | 18.0 ± 0.2 |
| $Cd^{2+}$ | 1.10 | 16.1 ± 0.3 |
| $La^{3+}$ | 1.16 | 16.4 ± 0.4 |
| $Gd^{3+}$ | 1.05 | 20.5 ± 0.1 |
| $Lu^{3+}$ | 0.98 | 21.2 ± 0.1 |
| $Am^{3+}$ | 1.09 | 20.4 ± 0.2 |
| $Th^{4+}$ | 1.05 | 40.1 ± 0.5 |
| $Ac^{3+}$ | 1.12 | 10-14 |
| $Ra^{2+}$ | 1.48 | Unknown |

The chemical interactions between radium ions ($Ra^{2+}$) and the chelator 3,4,3-LI(1,2-HOPO) or its derivatives can be extrapolated from data related to interaction between 3,4,3-LI(1,2-HOPO) with other metal ions (i.e. $Cd^{2+}$, $Pb^{2+}$, $UO_2^{2+}$, and $Sr^{2+}$).

The behavior of $Ra^{2+}$ ions is driven by two phenomena: (1) the ability of 3,4,3-LI(1,2-HOPO) to bind $Ra^{2+}$ ions in the aqueous phase; (2) the ability of the chosen extractant to transfer non-complexed $Ra^{2+}$ ions into the organic phase.

The ligand 3,4,3-LI(1,2-HOPO) usually exhibits a lower affinity for divalent cations compared to trivalent and tetravalent ions (TABLE 3). This ligand is also a hard donor and has a lower affinity for soft metal ions, as exemplified by the lower stability of the $Cd^{2+}$ complex when compared to the $Pb^{2+}$ complex (TABLE 3). With their large ionic radius, $Ra^{2+}$ ions are expected to be weakly bound, or even not bound at all, by 3,4,3-LI(1,2-HOPO). Thus, the ligand is not expected to hold-back $Ra^{2+}$ ions throughout the pH scale and especially not in the acidic region where competition with protons can occur. Hence, the main parameter to take into account for predicting the behavior of radium is the ability of the extractant to transfer $Ra^{2+}$ ions into the organic phase.

Figure 34:
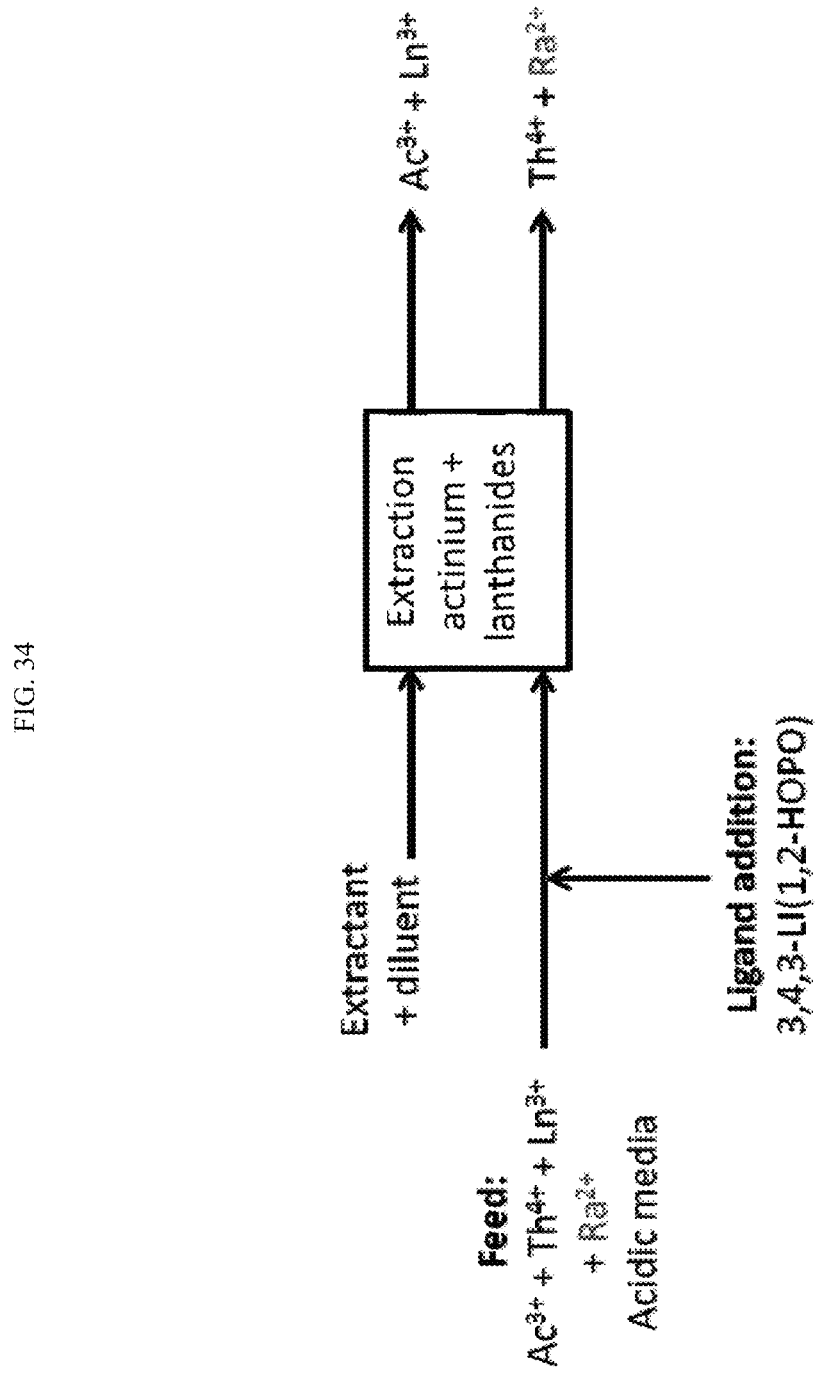
FIG. 34 shows a flowsheet for acidic feed solutions for selective extraction step using 3,4,3-LI(1,2-HOPO) as hold-back reagent for thorium.
Figure 35:
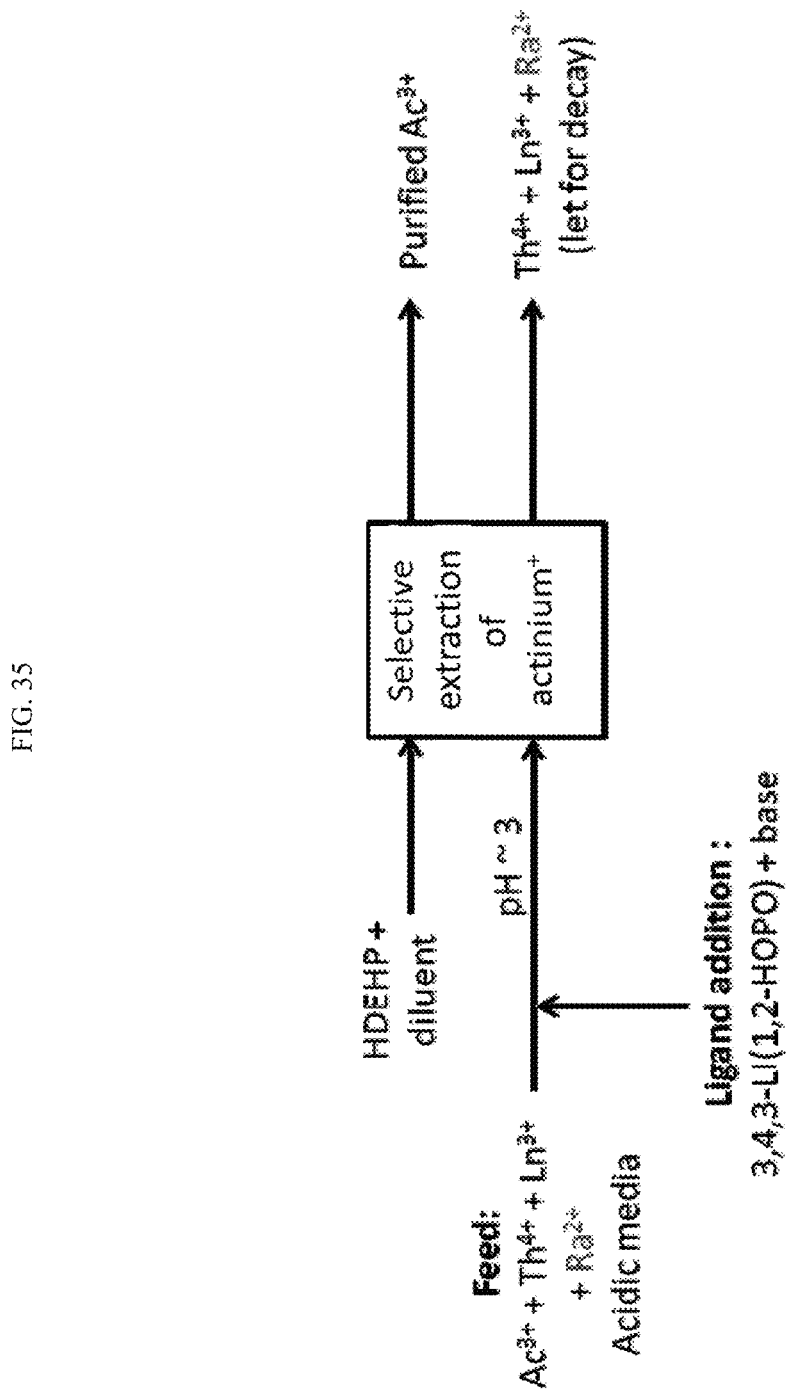
FIG. 35 shows a flowsheet for feed solutions at pH near 3 and using HDEHP as extractant for selective extraction step using 3,4,3-LI(1,2-HOPO) as hold-back reagent for thorium.

$Ra^{2+}$ ions do not readily form coordination compounds with organic chelators. Conversely, the purification of radium is usually done by extracting the other ions present in the media into the organic phase while letting radium in the aqueous phase. With the exception of crown ethers that form fairly strong complexes with radium and also strontium, classical organic extractants, like HDEHP, are not able to extract $Ra^{2+}$ ions. Considering the process flowsheets proposed in the prior note, radium will most likely not be extracted and will be separated from actinium. FIG. 34 and FIG. 35 highlight the most likely behavior of radium ions during the extraction step of the proposed processes. As radium will end up in the aqueous raffinate, additional steps could eventually be developed for the selective recovery of radium. For example, selective precipitation of $Ra^{2+}$ using barium sulfate is a common technique for the selective recovery of radium.

Another option, would involve storing the aqueous raffinate (containing thorium, radium and eventually the lanthanide fission products (FIG. 34 and FIG. 35) until the in-growth of Ac-225 from Ra-225 is deemed adequate and simply perform another extraction step in order to harvest a second batch of Ac-225. The cycle can eventually be repeated until the radium parent isotope has completely decayed.

In some embodiments, one lets thorium in the aqueous phase instead of extracting it. Likewise, actinium can be extracted in the proposed process, in some embodiments.

When thorium represents the main metal ion present in the spallation target, the volume of the feed aqueous solution (coming from the dissolution step) will be dictated by the solubility of the complex formed by 3,4,3-LI(1,2-HOPO) and $Th^{4+}$.

The solubility of the complex is also expected to vary with the pH value.

The aqueous solubility of the ligand itself was determined experimentally as 1 mol/L at room temperature. It has also been observed experimentally that a few percent's of dimethylformamide (DMF) or dimethlysulfoxide (DMSO) can increase the solubility of the ligand and its metal complexes.

In some embodiments, the dissolution step itself can be performed on a lower volume and the addition of the ligand and the downstream steps can be performed independently. A separate dissolution step could allow the use of a higher concentration of acid and consequently fasten the dissolution of the metallic target.

In some embodiments, since the process can extract microgram-quantities of actinium, the subsequent extraction steps can use a low ratio O/A (organic flow/aqueous flow). This has the advantage of minimizing the volume of actinium-containing solutions (loaded organic phase) as it concentrates the actinium flow. The downstream process would therefore require volumes in the range of hundreds of mL.

Figure 36:
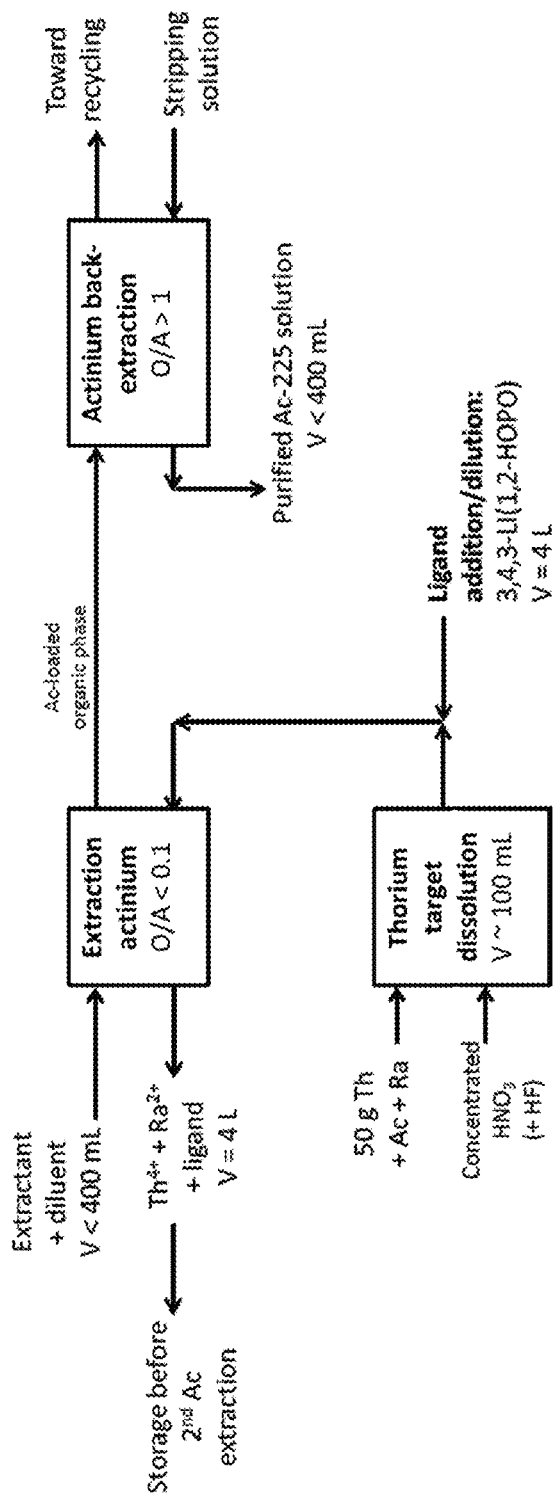
FIG. 36 shows an embodiment of a general process strategy for the recovery and purification of Ac-225 from a Th spallation target.

Some embodiments for the recovery and purification of actinium starting from a thorium spallation target is given in FIG. 36. In some embodiments, the actinium extraction part would use a low ratio O/A as mentioned above. In some embodiments, the number of stages to obtain a quantitative extraction of actinium can be determined by the McCabe & Thiele method. In some embodiments, the number of stages is low (1 to 3 stages). Indeed, experimental results already obtained show very high extraction efficiencies for actinium due to the low affinity of 3,4,3-LI(1,2-HOPO) for $Ac^{3+}$ ions. In some embodiments, only micrograms of actinium need to be extracted, which is favorable for not saturating the organic phase and, as a consequence, will allow using a low number of extraction stages and a low O/A ratio. In some embodiments, larger amounts of $Ac^{3+}$ ions can be extracted Regarding the back extraction of actinium, since only micrograms quantities will need to be stripped from the loaded organic phase, a low number of back-extraction stages is expected (1 to 3). The dimensioning of the actinium back-extraction can also be evaluated by the McCabe & Thiele method in a near future. A high ratio O/A could potentially be used so that the final Ac-225 purified solution is as concentrated as possible. Preliminary results show the potential for using a biologically compatible buffer for the stripping of actinium from HDEHP-based organic solvents.

Extraction Aspects

In some embodiments, the aqueous phase can be made up of water. In some embodiments, the aqueous phase also includes a HOPO-type chelator, a buffering agent to control the pH, dissolved inorganic salts or mineral acids (ex: $NaNO_3$, $HNO_3$, HCl, NaCl, $H_2SO_4$ etc.), and/or solubility improver (a few percent's of DMF or DMSO).

In some embodiments, the organic phase can be any organic solution or solvent, as long as it does not ineffectively dissolve or merge into the aqueous phase. In some embodiments, the organic phase can also include one or several extractant(s), an inert diluent (Ex: dodecane, kerosene, TPH, Elixore®, toluene, etc.), and/or a phase modifier in order to help the phases decant. In some embodiments, the volume ratio (or flows) of the organic phase and aqueous phase (usually called "O/A") can be different from 1. In some embodiments, the organic phase is selected from the group consisting of octanol, dodecanol, dichloromethane, chloroform, toluene, dimethylformamide, dimethylsulfoxide, octane, dodecane, kerosene.

In some embodiments, the aqueous volume is at least 1 mL, e.g., 1-100 or 1-1000 mL. In some embodiments, the aqueous volume is at least 1 L, e.g., 1-10 L, 1-100, 1-1000, 1-10000, 10-10000, 10-100000, or 100-1000000 L, or larger volumes. In some embodiments, the organic volume is at least 1 mL, e.g., 1-100 or 1-1000 mL. In some embodiments, the organic volume is at least 1 L, e.g., 1-10 L, 1-100, 1-1000, 1-10000, 10-10000, 10-100000, or 100-1000000 L, or larger volumes. In some embodiments, the organic phase is larger than the aqueous phase, e.g., 1.1, 1.5, 2, 5, 10, 20, 100, 1000 fold larger. In some embodiments, the volumes of the two phases are about the same. In some embodiments, the aqueous phase is larger than the organic phase, e.g., 1.1, 1.5, 2, 5, 10, 20, 100, 1000 fold larger.

In some embodiments, the two phases are mixed at room temperature. In some embodiments, they are mixed at a temperature of freezing to just below boiling. In some embodiments, the mixture occurs at 1, 10, 20, 30, 40, 50, 60, 70, 80, 90, or 99 degrees Celsius.

In some embodiments, the extraction and/or mixing occurs for as long as effective or necessary and can be repeated as many times as desired in order to obtain the purification and/or enrichment desired. In some embodiments, this is for 1-10 minutes, 1-60 minutes, 1 hour or more, e.g., 1, 2, 3, 4, 5, 6, 10, 20 or 24 hours, or 1 day or more. In some embodiments, the extraction mixing can occur 1, 2, 3, 4, 5, 6, 7, 8, 9, 10 or more times. In some embodiments, the extraction process (add, agitate, decant) can occur 1 or more times, e.g., 1, 2, 3, 4, 5, 6, 7, 8, 9, 10 or more times.

As will be appreciated by one of skill in the art, often the present disclosure refers to the metal being chelated by the HOPO molecule as the desired metal for enrichment, isolation, collection. However, each of these embodiments can equally be applied to the other metal that is separated from the HOPO chelator (into the organic phase) for various embodiments. Thus, each process disclosed herein regarding a chelator separation, is envisioned not only as an option for collecting the metal associated with the chelator (in the aqueous phase) but also as an option for collecting the metal that is separated therefrom (in the organic phase). This applies for all embodiments provided herein.

Although this disclosure is in the context of certain embodiments and examples, those skilled in the art will understand that the present disclosure extends beyond the specifically disclosed embodiments to other alternative embodiments and/or uses of the embodiments and obvious modifications and equivalents thereof. In addition, while several variations of the embodiments have been shown and described in detail, other modifications, which are within the scope of this disclosure, will be readily apparent to those of skill in the art based upon this disclosure. It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes or embodiments of the disclosure. Thus, it is intended that the scope of the present disclosure herein disclosed should not be limited by the particular disclosed embodiments described above. For example, chemical conditions (e.g., acidity, concentrations, etc.) could be carried to match those of interest for various applications. In some embodiments, the ligand 3,4,3-LI(1,2-HOPO) could also be immobilized on a solid support if the chromatographic technique is preferred over the liquid-liquid extraction methods. Thus, in some embodiments, any extraction process described herein can instead be performed instead via a solid support and a chromatographic technique. Additionally, one or more embodiments herein can be combined with any one or more of the other embodiments herein.

In particular embodiments, chelators can include a number of metal-coordinating atoms that bond with a metal. The metal-coordinating atoms can bond with metals having cations with a +1 charge. The metal-coordinating atoms can also bond with metals having cations with a +2 charge. Additionally, the metal-coordinating atoms can bond with metals having cations with a +3 charge. Further, the metal-coordinating atoms can bond with metals having cations with a +4 charge. The chelators described herein can, in some cases, include siderophores.

In particular embodiments, the metal-coordinating atoms of the chelators described herein can be included in one or more functional groups of the chelators. In some examples, the metal-coordinating atoms of the chelators can be included in one or more catecholate (CAM) groups. A CAM group can include at least a phenyl ring substituted by hydroxyl groups on adjacent carbon atoms. According to some illustrative embodiments, a CAM group can include:

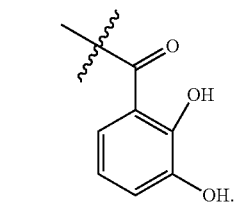 [SMILES: *C(=O)c1cccc(O)c1O]

In some embodiments, the metal-coordinating atoms of the chelators can be included in one or more hydroxamate (HA) groups. According to some embodiments, a HA group can include:

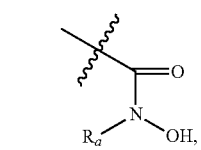

where $R_a$ can include H or an alkyl group including no greater than 5 carbon atoms. For example, $R_a$ can include a methyl group, an ethyl group, a propyl group, an isopropyl group, a butyl group, a sec-butyl group, an iso-butyl group, a tert-butyl group, a pentyl group, a tert-pentyl group, a neopentyl group, or an iso-pentyl group.

In some embodiments, the metal-coordinating atoms of the chelators can be included in one or more hydroxypyridinone (HOPO) groups. A HOPO group can include a pyridinone ring substituted by a hydroxyl group on the N atom. In some cases, a HOPO group can include a 1,2-HOPO group. According to some illustrative embodiments, a 1,2-HOPO group can include:

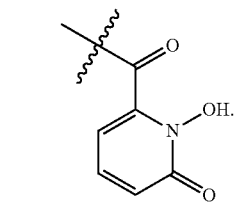 [SMILES: *C(=O)c1cccc(=O)n1O]

The metal-coordinating atoms of the chelators can be included in combinations of two or more of one or more CAM groups, one or more HA groups, or one or more HOPO groups. In illustrative examples, the metal-coordinating atoms of the chelators can be included in one or more CAM groups and one or more HA groups. In other illustrative examples, the metal-coordinating atoms of the chelators can be included in one or more CAM groups and one or more HOPO groups. In additional illustrative examples, the metal-coordinating atoms of the chelators can be included in one or more HA groups and one or more HOPO groups. In further illustrative examples, the metal-coordinating atoms of the chelators can be included in one or more HA groups, one or more CAM groups, and one or more HOPO groups.

The chelators can include a number of functional groups having metal-coordinating atoms with the functional groups being bonded to a linear scaffold or a branched scaffold. The functional groups and/or substituents described herein may be substituted or unsubstituted. Substituted functional groups and/or substituents can be substituted by one or more hydroxyl groups, one or more alkyl groups having no greater than 10 carbon atoms, one or more amine groups, one or more thiol groups, one or more ester groups, or combinations thereof.

The scaffold can include one or more amine groups. An amine group can include a nitrogen atom bonded to three substituents. In particular embodiments, an amine group can include a nitrogen atom bonded at least one carbon atom of substituent. In various embodiments, an amine group can include a nitrogen atom bonded to at least a first carbon atom of a first substituent and a second carbon atom of a second substituent. In further embodiments, an amine group can include a nitrogen atom bonded to a first carbon atom of a first substituent, a second carbon atom of a second substituent and a third carbon atom of a third substituent. In certain embodiments, an amine group can include a nitrogen atom bonded to one or more hydrogen atoms.

In some embodiments, the scaffold can include one or more amide groups. An amide group can include a nitrogen atom bonded to a carbonyl group and two additional substituents. In various examples, an amide group can include a nitrogen atom bonded to a carbonyl group and a carbon atom of a first additional substituent. In other examples, an amide group can include a nitrogen atom bonded to a carbonyl group and a first carbon atom of a first additional substituent and a second carbon atom of a second additional substituent. In certain embodiments, an amine group can include a nitrogen atom bonded to one or more hydrogen atoms.

In particular embodiments, the scaffold can include one or more amine groups and one or more amide groups. The scaffold can include one or more carbon-based chains bonded between amine groups, a carbon-based chain bonded between amide groups, or one or more carbon-based chains bonded between a combination of one or more amine groups and one or more amide groups. The carbon-based chains can include at least one carbon atom, at least 2 carbon atoms, at least 3 carbon atoms, at least 4 carbon atoms, or at least 5 carbon atoms. In addition, the carbon-based chains can include no greater than 10 carbon atoms, no greater than 9 carbon atoms, no greater than 8 carbon atoms, no greater than 7 carbon atoms, or no greater than 6 carbon atoms. In various embodiments, the carbon-based chains can include from 1 carbon atom to 10 carbon atoms, from 2 carbon atoms to 7 carbon atoms, or from 3 carbon atoms to 6 carbon atoms. In illustrative embodiments, the carbon-based chains can include alkane chains having carbon-carbon single bonds. In some cases, the carbon-based chains can include alkene chains having at least one carbon-carbon double bond. The carbon-based chains can be substituted or unsubstituted.

In particular embodiments, compositions that function as chelators for radionuclides can have the following structure, referred to herein as Structure I:

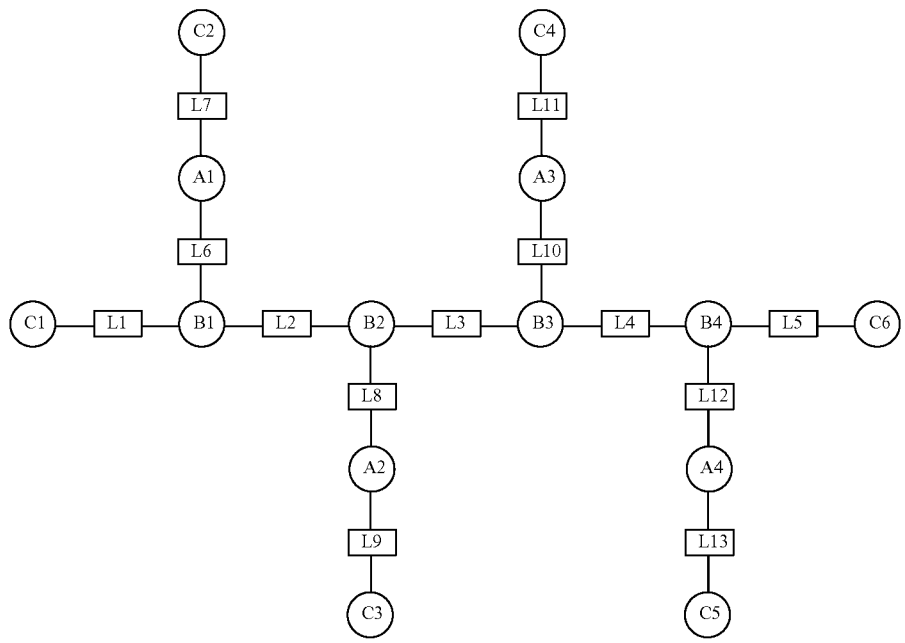

In some examples, A1, A2, A3, and A4 can, individually, include a CAM group, a HOPO group, or a HA group. Additionally, B1, B2, B3, and B4 can, individually, include an amide group or an amine group. Further, at least one of C1, $C_2$, C3, C4, C5, or C6 can, individually, include $NH_2$, C(=O)OH, maleimide, dibromo-maleimide, isothiocyanate, alkyne, or azide. Also, in various examples, at least another one of C1, C2, C3, C4, C5, or C6 can be optional. In particular examples, at least one of L, L2, L3, L4, L5, L6, L7, L8, L9, L10, L11, L12, or L13 can, individually, include H, an alkyl group having no greater than 10 carbon atoms, an alkylamino group having no greater than 10 carbon atoms and no greater than 2 nitrogen atoms; an alkylamido group having no greater than 10 carbon atoms and no greater than 2 nitrogen atoms; an alkyl ether group having no greater than 10 carbon atoms, a hydroxy ester group, or an alkyl ester group having no greater than 10 carbon atoms. In certain examples, at least one of L, L5, L6, L7, L8, L9, L10, L11, L12, or L13 can be optional.

In illustrative examples, at least another one of L2, L3, or L4, can, individually, include an amine group or an amide group. In additional illustrative examples, L, C1, L7, C2, L9, C3, L11, C4, and L13, C5 can be absent, L5 can include an alkyl group having no greater than 5 carbon atoms, and C6 can include NH$_2$, C(=O)OH, maleimide, dibromo-maleimide, isothiocyanate, alkyne, or azide. In further illustrative examples, L2, L3, L4, L6, L8, L10, and L12 can, individually, include an alkyl group having no greater than 5 carbon atoms. Also, A1 can include a CAM group or a 1,2-HOPO group; A2 can include a HA group, A3 can include a HA group, and A4 can include a CAM group, a 1,2-HOPO group, or a HA group. In other illustrative examples, at least one of L2, L3, or L4 includes an alkylamino or alkylamido group.

In various illustrative examples, B1, B2, and B3 can, individually, include an amide group and B4 can include an amino group, L2 and L3 can include an amino group, and L4 can include an alky group having no greater than 5 carbon atoms. Additionally, C1, C2, C3, C4, C5, L1, A1, A2, A3, L, L6, L7, L8, L9, L10, L11, L12, and L13 can be absent; A4 can include a CAM group, a 1,2-HOPO group, or a HA group; and L5 can include an alkyl group having no greater than 5 carbon atoms.

In certain illustrative examples, B1, B2, and B3 can include an amide group and B4 can include an amide group; L2 and L3 can, individually, include an amino group; and L4 includes an alky group having no greater than 5 carbon atoms. Further, C1, C2, C3, C4, C5, A1, A2, A3, L1, L6, L7, L8, L9, L10, L11, and L13 can be absent, L12 can include an amino group, L5 can include an ether group having no greater than 10 carbon atoms, and A4 can include a CAM group, a 1,2-HOPO group, or a HA group.

In particular illustrative examples, C1, C2, C5, C6, L1, L2, L3, L4, L5, L7, L13, B2, and B4 can be absent; B1 and B3 can, individually, include an amide group; L6, L8, L10, and L12 can, individually, include an amino group, A1, A2, A3, and A4 can, individually, include a CAM group, a 1,2-HOPO group, or a HA group; and L9 and L11 can, individually, include an alkyl group having no greater than 5 carbon atoms.

In particular embodiments, compositions that function as chelators for radionuclides can have the following structure, referred to herein as Structure II:

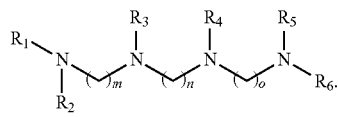

$R_1$, $R_2$, $R_3$, $R_4$, and $R_5$ can, individually, include H, an alkyl group having from 1 to 10 carbon atoms, a CAM group, a HA group, or a 1,2-HOPO group. $R_6$ can include H, an alkyl group having from 1 to 10 carbon atoms, or an alkyl group having from 1 to 10 carbon atoms and substituted by at least one of NH$_2$, C(=O)OH, maleimide, dibromo-maleimide, isothiocyanate, alkyne, or azide. m can be from 1 to 6; n can be from 1 to 6; and o can be from 1 to 6. In particular embodiments, at least one of $R_1$, $R_2$, $R_3$, $R_4$, or $R_5$ can, individually, include a CAM group, a HA group, or a 1,2-HOPO group. In various embodiments, Structure II can include a linear, spermine-based backbone.

In particular embodiments, compositions that function as chelators for radionuclides can have the following structure, referred to herein as Structure III:

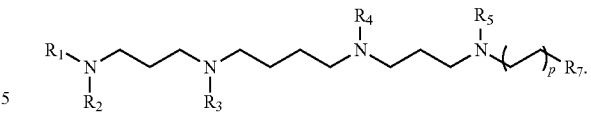

At least one of $R_1$, $R_3$, $R_4$, or $R_5$ can, individually, include a CAM group, a HA group, or a 1,2-HOPO group. Optionally, another one of $R_1$, $R_3$, $R_4$, or $R_5$ can, individually, include H, OH, or an alkyl group having from 1 to 10 carbon atoms. $R_2$ can include H, OH, or an alkyl group including from 1 to 5 carbon atoms. p can be from 0 to 4. $R_7$ can include NH$_2$, C(=O)OH, maleimide, dibromo-maleimide, isothiocyanate, alkyne, or azide. In illustrative embodiments, $R_1$ can include a CAM group or a 1,2-HOPO group, $R_3$ and $R_4$ can, individually, include a HA group, and $R_5$ can include a CAM group, a 1,2-HOPO group, or a HA group.

In particular embodiments, compositions that function as chelators for radionuclides can have the following structure, referred to herein as Structure IV:

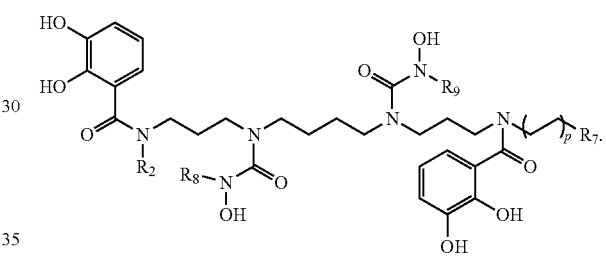

$R_7$ can include NH$_2$, C(=O)OH, maleimide, dibromo-maleimide, isothiocyanate, alkyne, or azide. $R_2$, $R_8$, and $R_9$ can, individually, include H, OH, or an alkyl group including from 1 to 5 carbon atoms. p can be from 0 to 4.

In particular embodiments, compositions that function as chelators for radionuclides can have the following structure, referred to herein as Structure V:

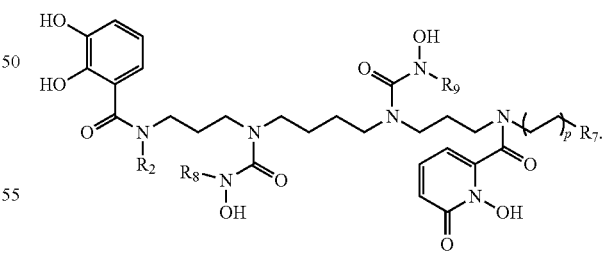

$R_7$ can include NH$_2$, C(=O)OH, maleimide, dibromo-maleimide, isothiocyanate, alkyne, or azide. $R_2$, $R_8$, and $R_9$ can, individually, include H, OH, or an alkyl group including from 1 to 5 carbon atoms. p can be from 0 to 4.

In particular embodiments, compositions that function as chelators for radionuclides can have the following structure, referred to herein as Structure VI:

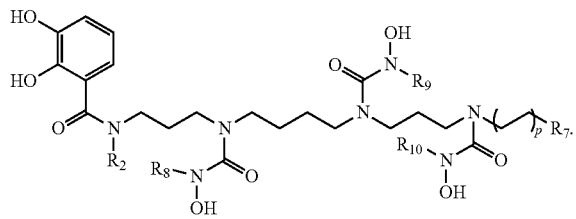

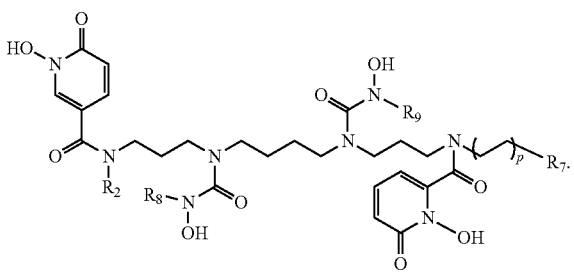

$R_7$ can include $NH_2$, C(=O)OH, maleimide, dibromo-maleimide, isothiocyanate, alkyne, or azide. $R_2$, $R_8$, $R_9$, and $R_{10}$ can, individually, include H, OH, or an alkyl group including from 1 to 5 carbon atoms. p can be from 0 to 4.

In particular embodiments, compositions that function as chelators for radionuclides can have the following structure, referred to herein as Structure VII:

$R_7$ can include $NH_2$, C(=O)OH, maleimide, dibromo-maleimide, isothiocyanate, alkyne, or azide. $R_2$, $R_8$, and $R_9$ can, individually, include H, OH, or an alkyl group including from 1 to 5 carbon atoms. p can be from 0 to 4.

In particular embodiments, compositions that function as chelators for radionuclides can have the following structure, referred to herein as Structure IX:

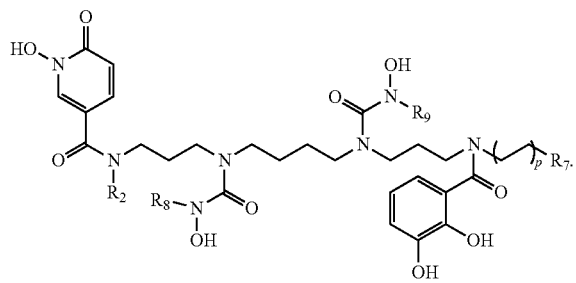

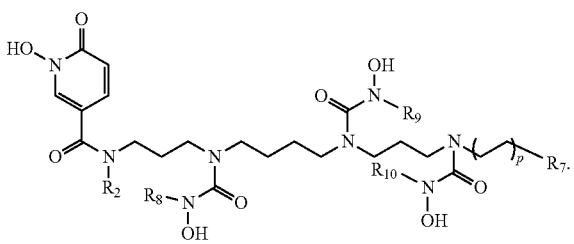

$R_7$ can include $NH_2$, C(=O)OH, maleimide, dibromo-maleimide, isothiocyanate, alkyne, or azide. $R_2$, $R_8$, and $R_9$ can, individually, include H, OH, or an alkyl group including from 1 to 5 carbon atoms. p can be from 0 to 4.

In particular embodiments, compositions that function as chelators for radionuclides can have the following structure, referred to herein as Structure VIII:

$R_7$ can include $NH_2$, C(=O)OH, maleimide, dibromo-maleimide, isothiocyanate, alkyne, or azide. $R_2$, $R_8$, $R_9$, and $R_{10}$ can, individually, include H, OH, or an alkyl group including from 1 to 5 carbon atoms. p can be from 0 to 4.

In particular embodiments, compositions that function as chelators for radionuclides can have the following structure, referred to herein as Structure X:

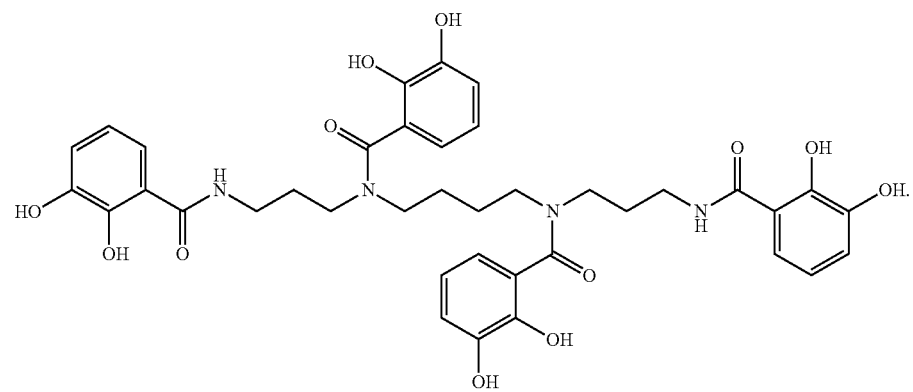 [SMILES: O=C(NCCCN(CCCCN(CCCNC(=O)c1cccc(O)c1O)C(=O)c1cccc(O)c1O)C(=O)c1cccc(O)c1O)c1cccc(O)c1O]

In particular embodiments, compositions that function as chelators for radionuclides can have the following structure, referred to herein as Structure XI:

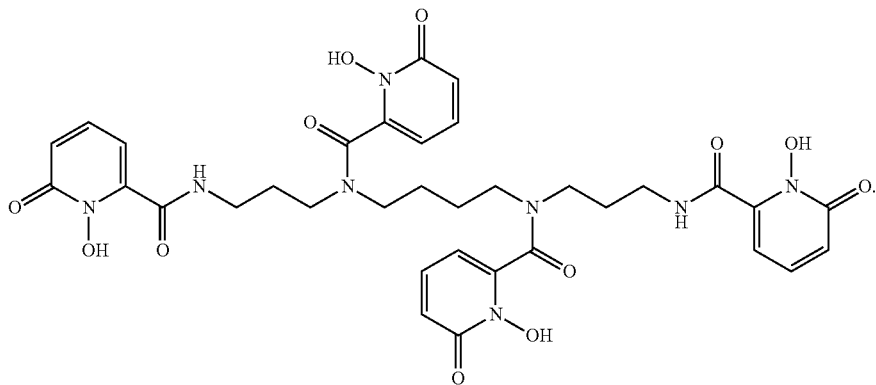 [SMILES: O=C(NCCCN(CCCCN(CCCNC(=O)c1cccc(=O)n1O)C(=O)c1cccc(=O)n1O)C(=O)c1cccc(=O)n1O)c1cccc(=O)n1O]

In particular embodiments, compositions can have a branched backbone rather than the linear, spermine-based backbone of Structures III-XI. In particular embodiments, compositions that function as chelators for radionuclides can have the following structure, referred to herein as Structure XII:

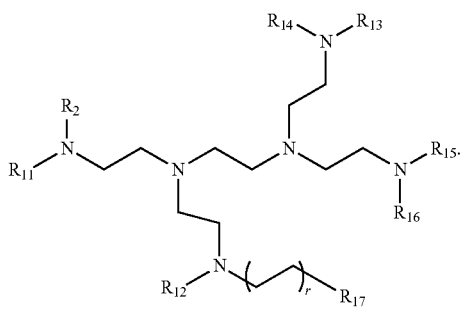

At least one of $R_{11}$, $R_{12}$, $R_{13}$, or $R_{15}$, can, individually, include a CAM group, a HA group, or a 1,2-HOPO group. Optionally, at least another one of $R_{11}$, $R_{12}$, $R_{13}$, or $R_{15}$ can, individually, include H, OH, or an alkyl group having from 1 to 10 carbon atoms. $R_{17}$ can include $NH_2$, $C(=O)OH$, maleimide, dibromo-maleimide, isothiocyanate, alkyne, or azide. r can be from 0 to 6. $R_2$, $R_{14}$, and $R_{16}$ can, individually, include H, OH, or an alkyl group having from 1 to 10 carbon atoms. In illustrative embodiments, $R_{11}$ can include a CAM group or a 1,2-HOPO group, $R_{12}$ and $R_{15}$ can, individually, include a HA group, and $R_{13}$ can include a CAM group, a 1,2-HOPO group, or a HA group.

In particular embodiments, compositions that function as chelators for radionuclides can have the following structure, referred to herein as Structure XIII:

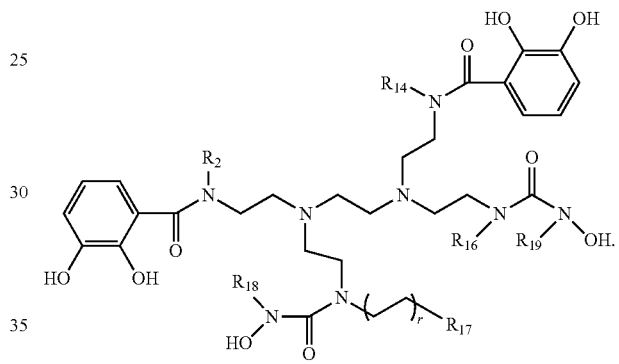

$R_2$, $R_{14}$, $R_{16}$, $R_{18}$, and $R_{19}$ can, individually, include H, OH, or an alkyl group having from 1 to 10 carbon atoms. $R_{17}$ can include $NH_2$, $C(=O)OH$, maleimide, dibromo-maleimide, isothiocyanate, alkyne, or azide. r can be from 0 to 4.

In particular embodiments, compositions that function as chelators for radionuclides can have the following structure, referred to herein as Structure XIV:

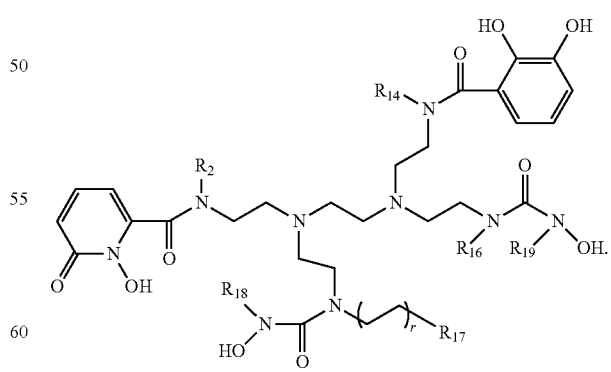

$R_2$, $R_{14}$, $R_{16}$, $R_{18}$, and $R_{19}$ can, individually, include H, OH, or an alkyl group having from 1 to 10 carbon atoms. $R_{17}$ can include $NH_2$, $C(=O)OH$, maleimide, dibromo-maleimide, isothiocyanate, alkyne, or azide. r can be from 0 to 4.

In particular embodiments, compositions that function as chelators for radionuclides can have the following structure, referred to herein as Structure XV:

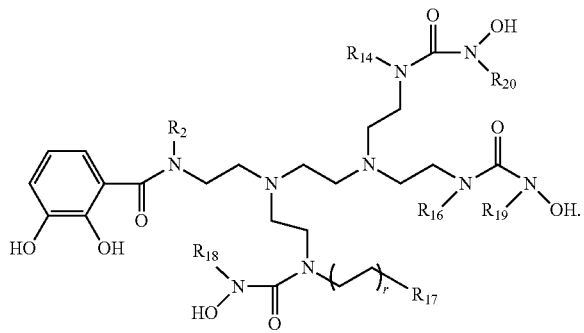

$R_2$, $R_{14}$, $R_{16}$, $R_{18}$, $R_{19}$, and $R_{20}$ can, individually, include H, OH, or an alkyl group having from 1 to 10 carbon atoms. $R_{17}$ can include $NH_2$, C(=O)OH, maleimide, dibromo-maleimide, isothiocyanate, alkyne, or azide. r can be from 0 to 4.

In particular embodiments, compositions that function as chelators for radionuclides can have the following structure, referred to herein as Structure XVI:

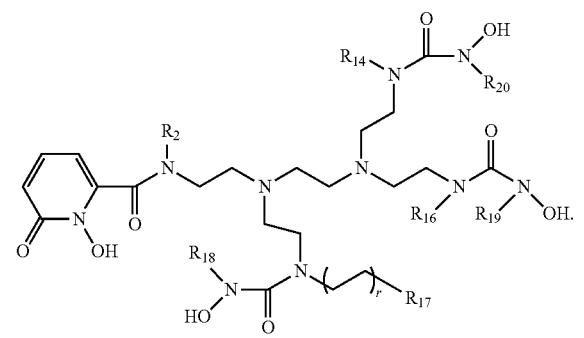

$R_2$, $R_{14}$, $R_{16}$, $R_{18}$, $R_{19}$, and $R_{20}$ can, individually, include H, OH, or an alkyl group having from 1 to 10 carbon atoms. $R_{17}$ can include $NH_2$, C(=O)OH, maleimide, dibromo-maleimide, isothiocyanate, alkyne, or azide. r can be from 0 to 4.

In particular embodiments, compositions that function as chelators for radionuclides can have the following structure, referred to herein as Structure XVII:

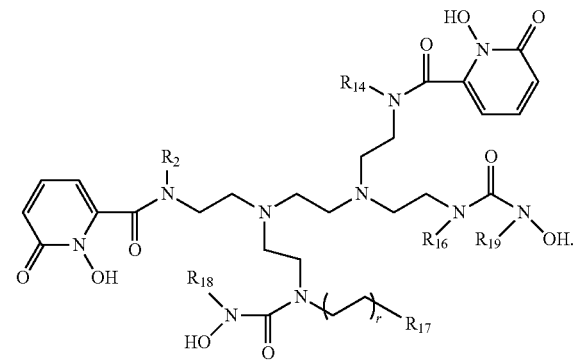

$R_2$, $R_{14}$, $R_{16}$, $R_{18}$, and $R_{19}$ can, individually, include H, OH, or an alkyl group having from 1 to 10 carbon atoms. $R_{17}$ can include $NH_2$, C(=O)OH, maleimide, dibromo-maleimide, isothiocyanate, alkyne, or azide. r can be from 0 to 4.

In particular embodiments, compositions that function as chelators for radionuclides can have the following structure, referred to herein as Structure XVIII:

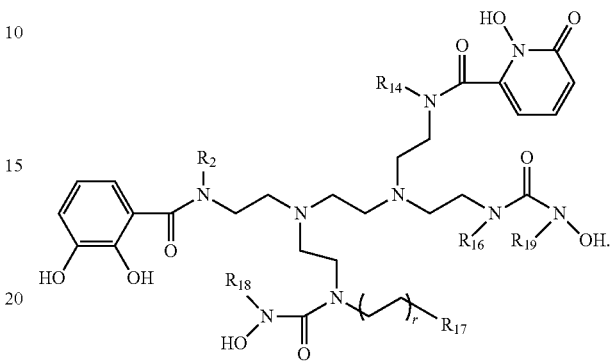

$R_2$, $R_{14}$, $R_{16}$, $R_{18}$, and $R_{19}$ can include H, OH, or an alkyl group having from 1 to 10 carbon atoms. $R_{17}$ can, individually, include $NH_2$, C(=O)OH, maleimide, dibromo-maleimide, isothiocyanate, alkyne, or azide. r can be from 0 to 4.

In particular embodiments, compositions can have a backbone that includes a number of amide groups and a number of amine groups. In some embodiments, the backbone of compositions that function as chelators for radionuclides can be based on Desferrioxamine B. In particular embodiments, compositions that function as chelators can have the following structure, referred to herein as Structure XIX:

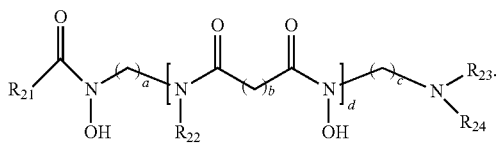

$R_{21}$ and $R_{22}$ can include H, OH, or an alkyl group having from 1 to 10 carbon atoms. $R_{23}$ can include H, OH, an alkyl group having from 1 to 10 carbon atoms, or $(CH_2)_e R_a$, where $R_a$ is $NH_2$, C(=O)OH, maleimide, dibromo-maleimide, isothiocyanate, alkyne, or azide and e is from 1 to 10. $R_{24}$ can include a substituent that includes a CAM group, a 1,2-HOPO group, or a HA group. Optionally, $R_{24}$ can include $NH_2$, C(=O)OH, maleimide, dibromo-maleimide, isothiocyanate, alkyne, or azide. a, b, and c can include from 1 to 10 and d can include from 1 to 4.

In particular embodiments, compositions that function as chelators for radionuclides can have the following structure, referred to herein as Structure XX:

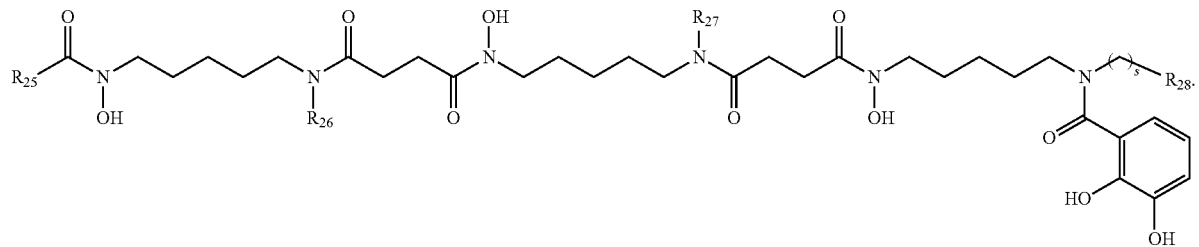

$R_{25}$, $R_{26}$, and $R_{27}$ can, individually, include H, OH, or an alkyl group having from 1 to 10 carbon atoms. $R_{28}$ can include H, an alkyl group having from 1 to 5 carbon atoms, $NH_2$, $C(=O)OH$, maleimide, dibromo-maleimide, isothiocyanate, alkyne, or azide. s can be from 0 to 4.

In particular embodiments, compositions that function as chelators for radionuclides can have the following structure, referred to herein as Structure XXI:

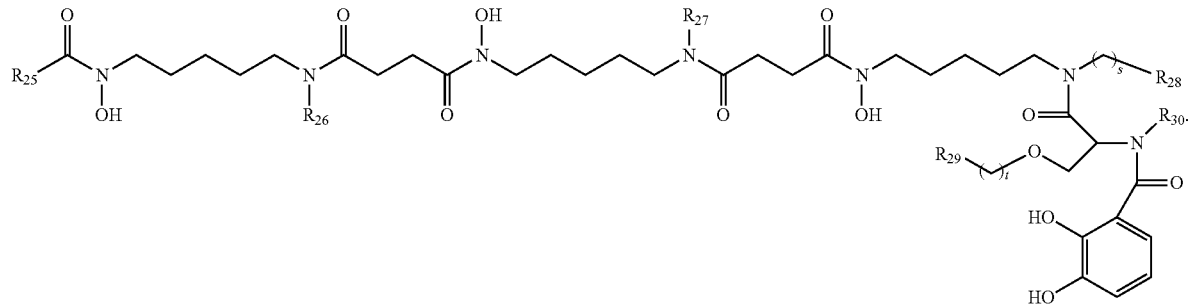

$R_{25}$, $R_{26}$, $R_{27}$, and $R_{30}$ can, individually, include H, OH, or an alkyl group having from 1 to 10 carbon atoms. $R_{28}$ and $R_{29}$ can, individually, include H, an alkyl group having from 1 to 5 carbon atoms, $NH_2$, $C(=O)OH$, maleimide, dibromo-maleimide, isothiocyanate, alkyne, or azide. s can be from 0 to 4. t can be from 0 to 4.

In particular embodiments, compositions that function as chelators for radionuclides can have the following structure, referred to herein as Structure XXII:

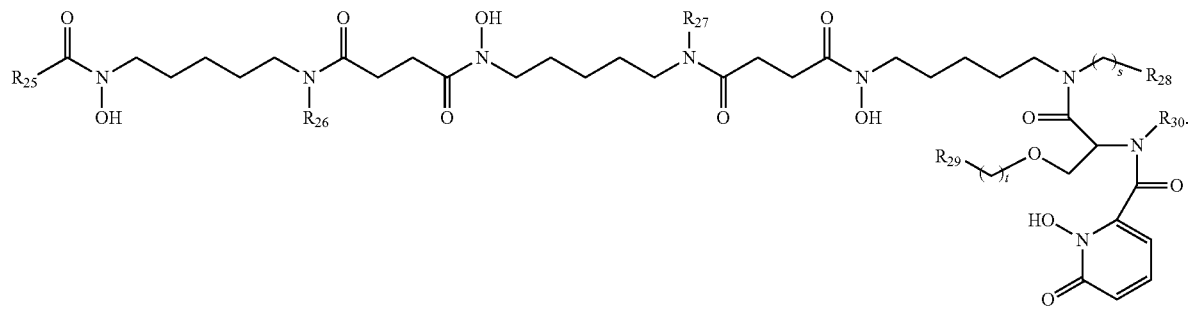

$R_{25}$, $R_{26}$, $R_{27}$, and $R_{30}$ can, individually, include H, OH, or an alkyl group having from 1 to 10 carbon atoms. $R_{28}$ and $R_{29}$ can, individually, include H, an alkyl group having from 1 to 5 carbon atoms, $NH_2$, $C(=O)OH$, maleimide, dibromo-maleimide, isothiocyanate, alkyne, or azide. s can be from 0 to 4. t can be from 0 to 4.

In particular embodiments, compositions that function as chelators for radionuclides can have the following structure, referred to herein as Structure XXIII:

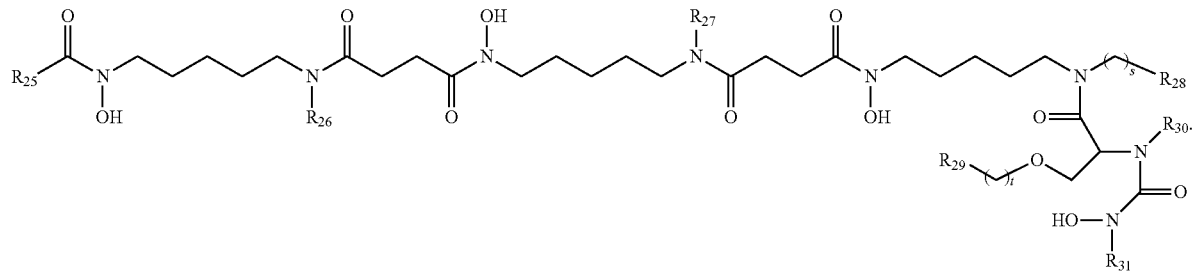

$R_{25}$, $R_{26}$, $R_{27}$, $R_{30}$, and $R_{31}$ can, individually, include H, OH, or an alkyl group having from 1 to 10 carbon atoms. $R_{28}$ and $R_{29}$ can, individually, include H, an alkyl group having from 1 to 5 carbon atoms, $NH_2$, $C(=O)OH$, maleimide, dibromo-maleimide, isothiocyanate, alkyne, or azide. s can be from 0 to 4. t can be from 0 to 4.

In particular embodiments, compositions that function as chelators for radionuclides can have the following structure, referred to herein as Structure XXIV:

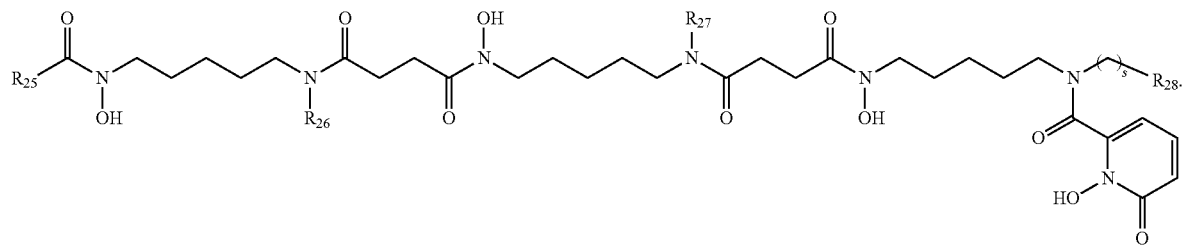

$R_{25}$, $R_{26}$, and $R_{27}$ can, individually, include H, OH, or an alkyl group having from 1 to 10 carbon atoms. $R_{28}$ can include H, an alkyl group having from 1 to 5 carbon atoms, $NH_2$, $C(=O)OH$, maleimide, dibromo-maleimide, isothiocyanate, alkyne, or azide. s can be from 0 to 4.

In particular embodiments, compositions that function as chelators for radionuclides can have the following structure, referred to herein as Structure XXV:

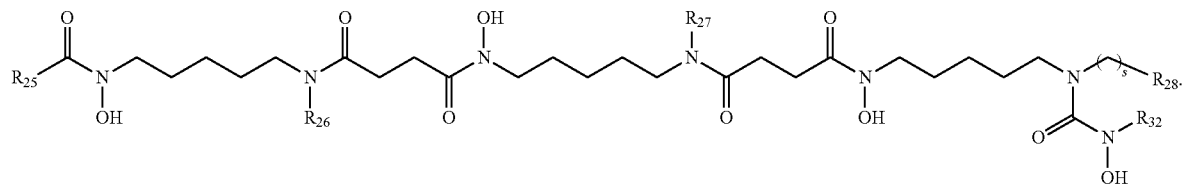

$R_{25}$, $R_{26}$, $R_{27}$, and $R_{32}$ can, individually, include H, OH, or an alkyl group having from 1 to 10 carbon atoms. $R_{28}$ can include H, an alkyl group having from 1 to 5 carbon atoms, $NH_2$, $C(=O)OH$, maleimide, dibromo-maleimide, isothiocyanate, alkyne, or azide. s can be from 0 to 4.

In particular embodiments, compositions can have an amide-based backbone. In particular embodiments, compositions that function as chelators can have the following structure, referred to herein as Structure XXVI:

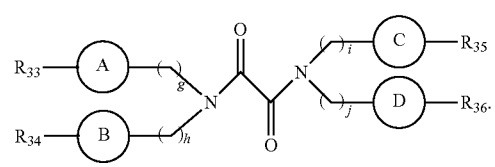

A, B, C, and D can, individually, include one or more amide groups, one or more amine groups, or an alkyl group having from 1 to 10 carbon atoms. $R_{33}$, $R_{34}$, $R_{35}$, and $R_{36}$ can, individually, include a CAM group, a 1,2-HOPO group, or a HA group. g, h, i, and j can, individually, be from 1 to 10.

In particular embodiments, compositions that function as chelators for radionuclides can have the following structure, referred to herein as Structure XXVII:

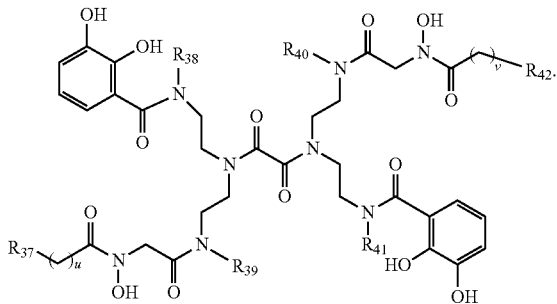

$R_{37}$ and $R_{42}$ can, individually, include H, an alkyl group having from 1 to 5 carbon atoms, $NH_2$, $C(=O)OH$, maleimide, dibromo-maleimide, isothiocyanate, alkyne, or azide. $R_{38}$, $R_{39}$, $R_{40}$, and $R_{41}$ can, individually, include H, OH, or an alkyl group having from 1 to 5 carbon atoms. u and v can, individually, be from 0 to 5.

In particular embodiments, compositions that function as chelators for radionuclides can have the following structure, referred to herein as Structure XXVIII:

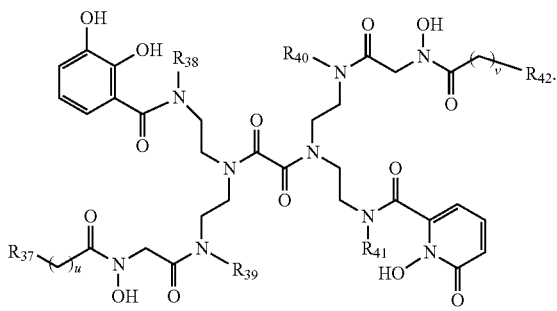

$R_{37}$ and $R_{42}$ can, individually, include H, an alkyl group having from 1 to 5 carbon atoms, $NH_2$, $C(=O)OH$, maleimide, dibromo-maleimide, isothiocyanate, alkyne, or azide. $R_{38}$, $R_{39}$, $R_{40}$, and $R_{41}$ can, individually, include H, OH, or an alkyl group having from 1 to 5 carbon atoms. u and v can, individually, be from 0 to 5.

In particular embodiments, compositions that function as chelators for radionuclides can have the following structure, referred to herein as Structure XXIX:

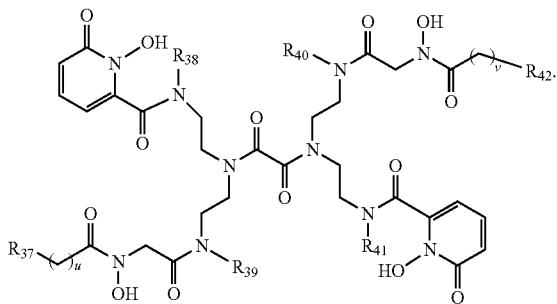

$R_{37}$ and $R_{42}$ can, individually, include H, an alkyl group having from 1 to 5 carbon atoms, $NH_2$, $C(=O)OH$, maleimide, dibromo-maleimide, isothiocyanate, alkyne, or azide. $R_{38}$, $R_{39}$, $R_{40}$, and $R_{41}$ can, individually, include H, OH, or an alkyl group having from 1 to 5 carbon atoms. u and v can, individually, be from 0 to 5.

In particular embodiments, compositions that function as chelators for radionuclides can have the following structure, referred to herein as Structure L:

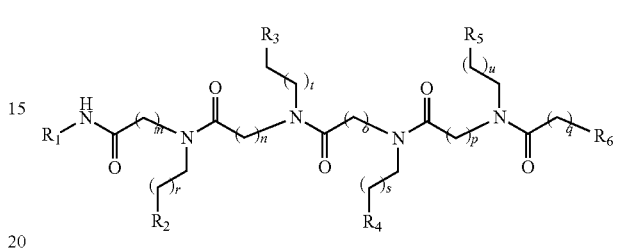

wherein: at least one of $R_1$, $R_2$, $R_3$, $R_4$, $R_5$, individually, comprise a CAM group, a HA group, or a 1,2-HOPO group; at least another one of $R_1$, $R_2$, $R_3$, $R_4$, and $R_5$, individually, comprise H or an alkyl group having from 1 to 10 carbon atoms; $R_6$ comprises (i) H, (ii) an alkyl group having from 1 to 10 carbon atoms, or (iii) an alkyl group having from 1 to 100 carbon atoms and no greater than 2 nitrogen atoms, and substituted by at least one of $NH_2$, $C(=O)OH$, maleimide, dibromo-maleimide, isothiocyanate, alkyne, amide, fluorescent moiety, or azide; m can be from 1 to 6; n can be from 1 to 6; o can be from 1 to 6; p can be from 1 to 6; q can be from 0 to 6; r can be from 1 to 6; s can be from 1 to 6; t can be from 1 to 6.

Figure 38A:
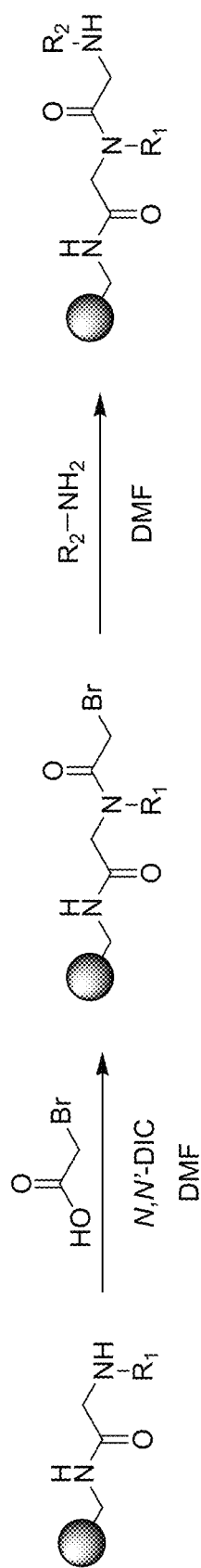
FIG. 38A depicts an embodiment of a general peptoid synthesis.

In some embodiments, the chelator is any one or more of the chelators in any of the figures. In some embodiments, the chelator has a structure as depicted in FIG. 38E. In some embodiments, the chelator is made by any one or more of the flow charts provided in the present figures. In some embodiments, the chelator is a peptoid chelator.

Examples of radioisotopes useful for isolation, collection, enrichment, and/or use etc. include $^{225}Ac$, $^{226}Ac$, $^{228}Ac$, $^{105}Ag$, $^{106}mAg$, $^{110}mAg$, $^{111}Ag$, $^{112}Ag$, $^{113}Ag$, $^{239}Am$, $^{240}Am$, $^{242}Am$, $^{244}Am$, $^{37}Ar$, $^{71}As$, $^{72}As$, $^{73}As$, $^{74}As$, $^{76}As$, $^{77}As$, $^{209}At$, $^{210}At$, $^{191}Au$, $^{192}Au$, $^{193}Au$, $^{194}Au$, $^{195}Au$, $^{196}Au$, $^{196m2}Au$, $^{198}Au$, $^{198}mAu$, $^{199}Au$, $^{200}mAu$, $^{128}Ba$, $^{131}Ba$, $^{133}mBa$, $^{135}mBa$, $^{140}Ba$, $^{7}Be$, $^{203}Bi$, $^{204}Bi$, $^{205}Bi$, $^{206}Bi$, $^{210}Bi$, $^{212}Bi$, $^{243}Bk$, $^{244}Bk$, $^{245}Bk$, $^{246}Bk$, $^{248}mBk$, $^{250}Bk$, $^{76}Br$, $^{77}Br$, $^{80}mBr$, $^{82}Br$, $^{11}C$, $^{14}C$, $^{45}Ca$, $^{47}Ca$, $^{107}Cd$, $^{115}Cd$, $^{11}mCd$, $^{117}mCd$, $^{132}Ce$, $^{133}mCe$, $^{134}Ce$, $^{135}Ce$, $^{137}Ce$, $^{137}mCe$, $^{139}Ce$, $^{141}Ce$, $^{143}Ce$, $^{144}Ce$, $^{246}Cf$, $^{247}Cf$, $^{253}Cf$, $^{254}Cf$, $^{240}Cm$, $^{241}Cm$, $^{242}Cm$, $^{252}Cm$, $^{55}Co$, $^{56}Co$, $^{57}Co$, $^{58}Co$, $^{58}mCo$, $^{60}Co$, $^{48}Cr$, $^{51}Cr$, $^{127}Cs$, $^{129}Cs$, $^{131}Cs$, $^{132}Cs$, $^{136}Cs$, $^{137}Cs$, $^{61}Cu$, $^{62}Cu$, $^{64}Cu$, $^{67}Cu$, $^{153}Dy$, $^{155}Dy$, $^{157}Dy$, $^{159}Dy$, $^{165}Dy$, $^{166}Dy$, $^{160}Er$, $^{161}Er$, $^{165}Er$, $^{169}Er$, $^{171}Er$, $^{172}Er$, $^{250}Es$, $^{251}Es$, $^{253}Es$, $^{254}Es$, $^{254}mEs$, $^{255}Es$, $^{256}mEs$, $^{145}Eu$, $^{146}Eu$, $^{147}Eu$, $^{148}Eu$, $^{149}Eu$, $^{150}mEu$, $^{152}mEu$, $^{156}Eu$, $^{157}Eu$, $^{52}Fe$, $^{59}Fe$, $^{251}Fm$, $^{252}Fm$, $^{253}Fm$, $^{254}Fm$, $^{255}Fm$, $^{257}Fm$, $^{66}Ga$, $^{67}Ga$, $^{68}Ga$, $^{72}Ga$, $^{73}Ga$, $^{146}Gd$, $^{147}Gd$, $^{149}Gd$, $^{151}Gd$, $^{153}Gd$, $^{159}Gd$, $^{68}Ge$, $^{69}Ge$, $^{71}Ge$, $^{77}Ge$, $^{170}H\text{-}f$, $^{171}Hf$, $^{173}Hf$, $^{175}Hf$, $^{179m2}Hf$, $^{180}mHf$, $^{181}Hf$, $^{184}Hf$, $^{192}Hg$, $^{193}Hg$, $^{193}mHg$, $^{195}Hg$, $^{195}mHg$, $^{197}Hg$, $^{197}mHg$, $^{203}Hg$, $^{160}mHo$, $^{166}Ho$, $^{167}Ho$, $^{123}I$, $^{123}I$, $^{124}I$, $^{126}I$, $^{130}I$, $^{132}I$, $^{133}I$, $^{135}I$, $^{109}In$, $^{110}In$, $^{111}In$, $^{114}mIn$, $^{115}mIn$, $^{184}Ir$, $^{185}Ir$, $^{186}Ir$, $^{187}Ir$, $^{188}Ir$, $^{189}Ir$, $^{190}Ir$, $^{190m2}Ir$, $^{192}Ir$, $^{193}mIr$, $^{194}Ir$, $^{194m2}Ir$, $^{195}mIr$, $^{42}K$, $^{43}K$, $^{76}Kr$, $^{79}Kr$, $^{81}mKr$, $^{85}mKr$, $^{132}La$, $^{133}La$, $^{135}La$, $^{140}La$, $^{141}La$, $^{262}Lr$, $^{169}Lu$, $^{170}Lu$, $^{171}Lu$, $^{172}Lu$, $^{174}mLu$, $^{176}mLu$, $^{177}$Lu, $^{177m}$Lu, $^{179}$Lu, $^{257}$Md, $^{258}$Md, $^{260}$Md, $^{28}$Mg, $^{52}$Mn, $^{90}$Mo, $^{93m}$Mo, $^{99}$Mo, $^{13}$N, $^{24}$Na, $^{90}$Nb, $^{91m}$Nb, $^{92m}$Nb, $^{95}$Nb, $^{95m}$Nb, $^{96}$Nb, $^{138}$Nd, $^{139m}$Nd, $^{140}$Nd, $^{147}$Nd, $^{56}$Ni, $^{57}$Ni, $^{66}$Ni, $^{234}$Np, $^{236m}$Np, $^{238}$Np, $^{239}$Np, $^{15}$O, $^{182}$Os, $^{183}$Os, $^{183m}$Os, $^{185}$Os, $^{189m}$Os, $^{191}$Os, $^{191m}$Os, $^{193}$Os, $^{32}$P, $^{33}$P, $^{228}$Pa, $^{229}$Pa, $^{230}$Pa, $^{232}$Pa, $^{233}$Pa, $^{234}$Pa, $^{200}$Pb, $^{201}$Pb, $^{202m}$Pb, $^{203}$Pb, $^{209}$Pb, $^{212}$Pb, $^{100}$Pd, $^{101}$Pd, $^{103}$Pd, $^{109}$Pd, $^{111m}$Pd, $^{112}$Pd, $^{143}$Pm, $^{148}$Pm, $^{148m}$Pm, $^{149}$Pm, $^{151}$Pm, $^{204}$Po, $^{206}$Po, $^{207}$Po, $^{210}$Po, $^{139}$Pr, $^{142}$Pr, $^{143}$Pr, $^{145}$Pr, $^{188}$Pt, $^{189}$Pt, $^{191}$Pt, $^{193m}$Pt, $^{195m}$Pt, $^{197}$Pt, $^{200}$Pt, $^{202}$Pt, $^{234}$Pu, $^{237}$Pu, $^{243}$Pu, $^{245}$Pu, $^{246}$Pu, $^{247}$Pu, $^{223}$Ra, $^{224}$Ra, $^{225}$Ra, $^{81}$Rb, $^{82}$Rb, $^{82m}$Rb, $^{83}$Rb, $^{84}$Rb, $^{86}$Rb, $^{181}$Re, $^{182}$Re, $^{182m}$Re, $^{183}$Re, $^{184}$Re, $^{184m}$Re, $^{186}$Re, $^{188}$Re, $^{189}$Re, $^{190m}$Re, $^{99}$Rh, $^{99m}$Rh, $^{100}$Rh, $^{101m}$Rh, $^{102}$Rh, $^{103m}$Rh, $^{105}$Rh, $^{211}$Rn, $^{222}$Rn, $^{97}$Ru, $^{103}$Ru, $^{105}$Ru, $^{35}$S, $^{118m}$Sb, $^{119}$Sb, $^{120}$Sb, $^{120m}$Sb, $^{122}$Sb, $^{124}$Sb, $^{126}$Sb, $^{127}$Sb, $^{128}$Sb, $^{129}$Sb, $^{43}$Sc, $^{44}$Sc, $^{44m}$Sc, $^{46}$Sc, $^{47}$SC, $^{48}$Sc, $^{72}$Se, $^{73}$Se, $^{75}$Se, $^{153}$Sm, $^{156}$Sm, $^{110}$Sn, $^{113}$Sn, $^{117m}$Sn, $^{119m}$Sn, $^{121}$Sn, $^{123}$Sn, $^{125}$Sn, $^{82}$Sr, $^{83}$Sr, $^{85}$Sr, $^{89}$Sr, $^{91}$Sr, $^{173}$Ta, $^{175}$Ta, $^{176}$Ta, $^{177}$Ta, $^{180}$Ta, $^{182}$Ta, $^{183}$Ta, $^{184}$Ta, $^{149}$Tb, $^{150}$Tb, $^{151}$Tb, $^{152}$Tb, $^{153}$Tb, $^{154}$Tb, $^{154m}$Tb, $^{154m2}$Tb, $^{155}$Tb, $^{156}$Tb, $^{156m}$Tb, $^{156m2}$Tb, $^{160}$Tb, $^{161}$Tb, $^{94}$Tc, $^{95}$Tc, $^{95m}$Tc, $^{96}$Tc, $^{97m}$Tc, $^{99m}$Tc, $^{118}$Te, $^{119}$Te, $^{119m}$Te, $^{121}$Te, $^{121m}$Te, $^{123m}$Te, $^{125m}$Te, $^{127}$Te, $^{127m}$Te, $^{129m}$Te, $^{131m}$Te, $^{132}$Te, $^{227}$Th, $^{231}$Th, $^{234}$Th, $^{45}$Ti, $^{198}$Tl, $^{199}$Tl, $^{200}$Tl, $^{201}$Tl, $^{202}$Tl, $^{204}$Tl, $^{165}$Tm, $^{166}$Tm, $^{167}$Tm, $^{168}$Tm, $^{170}$Tm, $^{172}$Tm, $^{173}$Tm, $^{230}$U, $^{231}$U, $^{237}$U, $^{240}$U, $^{48}$V, $^{178}$W, $^{181}$W, $^{185}$W, $^{187}$W, $^{188}$W, $^{122}$Xe, $^{125}$Xe, $^{127}$Xe, $^{129m}$iXe, $^{131m}$Xe, $^{133}$Xe, $^{133m}$Xe, $^{135}$Xe, $^{85m}$Y, $^{86}$Y, $^{87}$Y, $^{87m}$Y, $^{88}$Y, $^{90}$Y, $^{90m}$Y, $^{91}$Y, $^{92}$Y, $^{93}$Y, $^{166}$Yb, $^{169}$Yb, $^{175}$Yb, $^{62}$Zn, $^{65}$Zn, $^{69m}$Zn, $^{71m}$Zn, $^{72}$Zn, $^{86}$Zr, $^{88}$Zr, $^{89}$Zr, $^{95}$Zr, and $^{97}$Zr. In some embodiments, the following can be used/and/or collected and/or isolated and/or enriched: $^{147}$Sm, $^{227}$Ac, $^{232}$Th, $^{232}$U, $^{233}$U, $^{234}$U, $^{235}$U, $^{236}$U, $^{237}$U, $^{238}$U, $^{237}$Np, $^{238}$Pu, $^{239}$Pu, $^{240}$Pu, $^{242}$Pu, $^{244}$Pu, $^{241}$Am, $^{243}$Am, $^{242}$Cm, $^{243}$Cm, $^{244}$Cm, $^{245}$Cm, $^{246}$Cm, $^{247}$Cm, $^{248}$Cm, $^{247}$Bk, $^{249}$Bk, $^{249}$Cf, $^{252}$Cf.

The term analog (also structural analog or chemical analog) is used to refer to a compound that is structurally similar to another compound but differs with respect to a certain component, such as an atom, a functional group, or a substructure. The term derivative refers to a compound that is obtained from a similar compound or a precursor compound by a chemical reaction. As used herein, analogs and derivatives retain the therapeutic effectiveness of the parent compound (i.e., there is no statistically significant difference in therapeutic activity according to an imaging assay or assessment of clinical improvement) or have improved therapeutic effectiveness as defined elsewhere herein.

Exemplary Embodiments

1. A composition having a structure including:

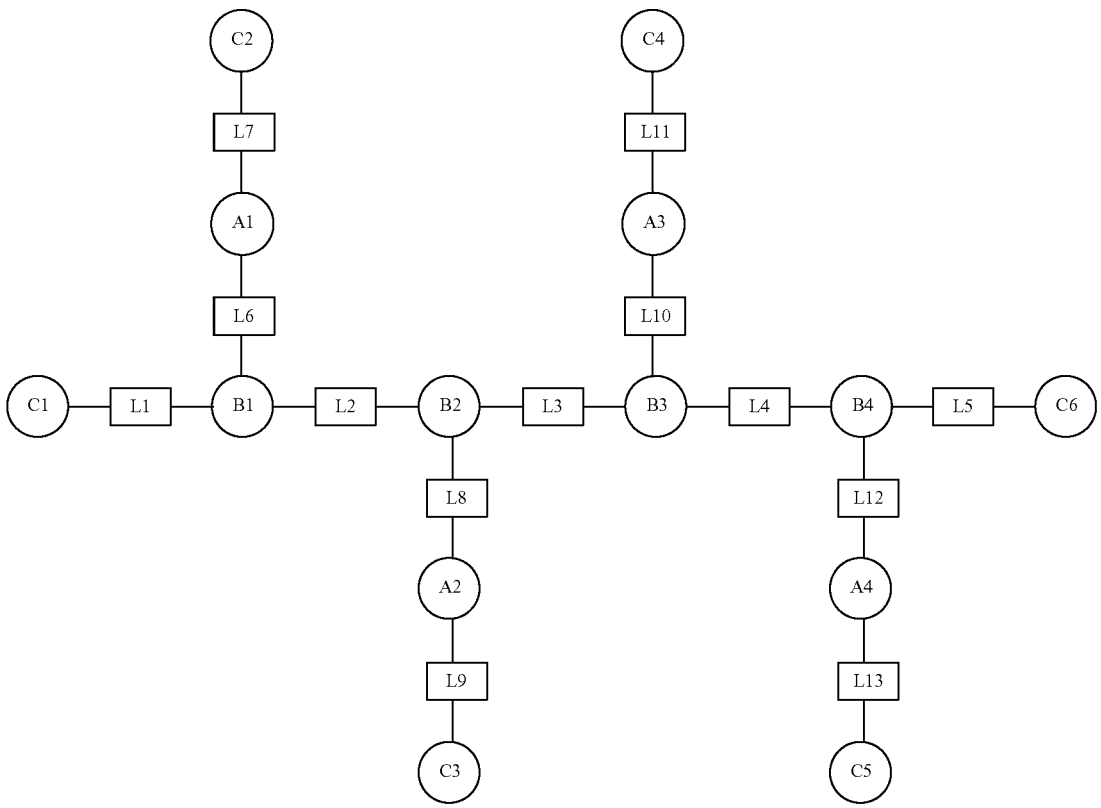

wherein:
(i) A1, A2, A3, and A4, individually, include a CAM group, a 1,2-HOPO group, or a HA group;
(ii) B1, B2, B3, and B4, individually, include an amide group or an amine group;
(iii) at least one of C1, C2, C3, C4, C5, or C6, individually, include $NH_2$, C(=O)OH, maleimide, dibromo-maleimide, isothiocyanate, alkyne, or azide;
(iv) at least another one of C1, C2, C3, C4, C5, or C6 is optional;
(v) at least one of L1, L2, L3, L4, L5, L6, L7, L8, L9, L10, L11, L12, or L13, individually, include H, an alkyl group having no greater than 10 carbon atoms, an alkylamino group having no greater than 10 carbon atoms and no greater than 2 nitrogen atoms; an alkylamido group having no greater than 10 carbon atoms and no greater than 2 nitrogen atoms; an alkyl ether group having no greater than 10 carbon atoms, a hydroxy ester group, or an alkyl ester group having no greater than 10 carbon atoms; and (vi) at least one of L1, L5, L6, L7, L8, L9, L10, L11, L12, or L13 is optional.

2. A composition of embodiment 1, wherein at least another one of L2, L3, or L4, individually, include an amine group or an amide group.

3. A composition of embodiment 1 or embodiment 2, wherein L, C1, L7, C2, L9, C3, L11, C4, and L13, C5 are absent, L5 includes an unsubstituted alkyl group having no greater than 5 carbon atoms, and C6 includes $NH_2$, $C(=O)OH$, maleimide, dibromo-maleimide, isothiocyanate, alkyne, or azide.

4. A composition of embodiment 3, wherein L2, L3, L4, L6, L8, L10, and L12, individually, include an unsubstituted alkyl group having no greater than 5 carbon atoms.

5. A composition of embodiment 4, wherein A1 includes a CAM group or a HOPO group; A2 includes a HA group, A3 includes a HA group, and A4 includes a CAM group, a HOPO group, or a HA group.

6. A composition of any one of embodiments 1-5, wherein at least one of L2, L3, or L4, individually, include an alkylamino or alkylamido group.

7. A composition of embodiment 1, wherein B1, B2, and B3, individually, include an amide group and B4 includes an amino group, L2 and L3 include an amino group, and L4 includes an alky group having no greater than 5 carbon atoms 8. A composition of embodiment 7, wherein:
C1, C2, C3, C4, C5, L1, A1, A2, A3, L, L6, L7, L8, L9, L10, L1, L12, and L13 are absent,
A4 includes a CAM group, a HOPO group, or a HA group; and
L5 includes an alkyl group having no greater than 5 carbon atoms.

9. A composition of embodiment 1, wherein B1, B2, and B3, individually, include an amide group and B4 includes an amide group, L2 and L3, individually, include an amino group, and L4 includes an alky group having no greater than 5 carbon atoms.

10. A composition of embodiment 9, wherein C1, C2, C3, C4, C5, A1, A2, A3, L1, L6, L7, L8, L9, L10, L11, and L13 are absent, L12 includes an amino group, L5 includes an ether group having no greater than 10 carbon atoms, and A4 includes a CAM group, a HOPO group, or a HA group.

11. A composition of embodiment 1, wherein C1, C2, C5, C6, L, L2, L3, L4, L5, L7, L13, B2, and B4 are absent, B1 and B3, individually, include an amide group, L6, L8, L10, and L12, individually, include an amino group, A1, A2, A3, and A4, individually, include a CAM group, a HOPO group, or a HA group, L9 and L11, individually, include an alkyl group having no greater than 5 carbon atoms.

12. A composition, including a structure:

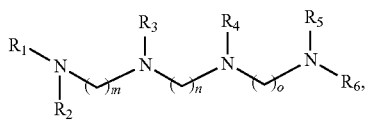

wherein:
at least one of $R_1$, $R_2$, $R_3$, $R_4$, and $R_5$, individually, include a CAM group, a HA group, or a 1,2-HOPO group;
at least another one of $R_1$, $R_2$, $R_3$, $R_4$, and $R_5$, individually, include H or an alkyl group having from 1 to 10 carbon atoms;

$R_6$ includes (i) H, (ii) an alkyl group having from 1 to 10 carbon atoms, or (iii) an alkyl group having from 1 to 10 carbon atoms and substituted by at least one of $NH_2$, $C(=O)OH$, maleimide, dibromo-maleimide, isothiocyanate, alkyne, or azide;
m can be from 1 to 6;
n can be from 1 to 6;
o can be from 1 to 6.

13. A composition of embodiment 12, including a structure:

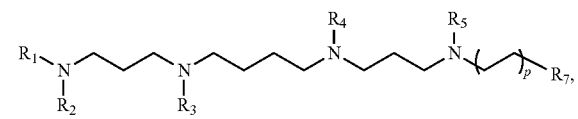

wherein:
at least one of $R_1$, $R_3$, $R_4$, or $R_5$ $R_1$, $R_2$, $R_3$, $R_4$, and $R_5$, individually, include a CAM group, a HA group, or a 1,2-HOPO group;
optionally, another one of $R_1$, $R_3$, $R_4$, or $R_5$ $R_1$, $R_2$, $R_3$, $R_4$, and $R_5$, individually, include H or
an alkyl group having from 1 to 10 carbon atoms;
$R_2$ includes H or an alkyl group including from 1 to 5 carbon atoms;
$R_7$ includes $NH_2$, $C(=O)OH$, maleimide, dibromo-maleimide, isothiocyanate, alkyne, or azide; and
p is from 0 to 4.

14. A composition of embodiment 13, wherein:
$R_1$ includes a CAM group or a 1,2-HOPO group;
$R_3$ and $R_4$, individually, include a HA group; and
$R_5$ includes a CAM group, a 1,2-HOPO group, or a HA group.

15. A composition of embodiment 12, including a structure:

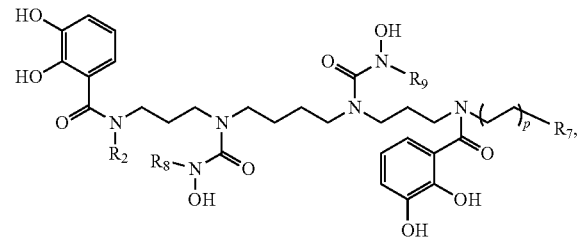

wherein:
$R_7$ includes $NH_2$, $C(=O)OH$, maleimide, dibromo-maleimide, isothiocyanate, alkyne, or azide;
$R_2$, $R_8$, and $R_9$, individually, include H, OH, or an alkyl group including from 1 to 5 carbon atoms; and
p is from 0 to 4.

16. A composition of embodiment 12, including a structure:

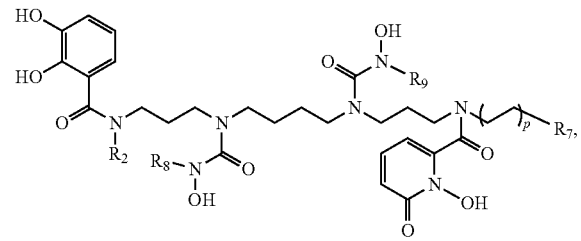

wherein:
$R_7$ includes $NH_2$, $C(=O)OH$, maleimide, dibromo-maleimide, isothiocyanate, alkyne, or azide;

$R_2$, $R_8$, and $R_9$, individually, include H, OH, or an alkyl group including from 1 to 5 carbon atoms; and p is from 0 to 4.

17. A composition of embodiment 12, including a structure:

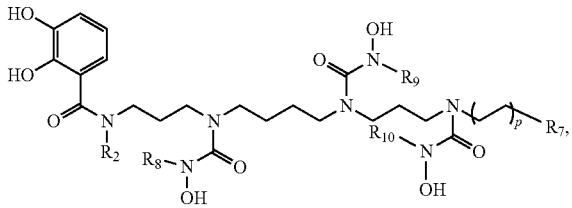

wherein:

$R_7$ includes $NH_2$, C(=O)OH, maleimide, dibromo-maleimide, isothiocyanate, alkyne, or azide;

$R_2$, $R_8$, $R_9$, and $R_{10}$, individually, include H, OH, or an alkyl group including from 1 to 5 carbon atoms; and p is from 0 to 4.

18. A composition of embodiment 12, including a structure:

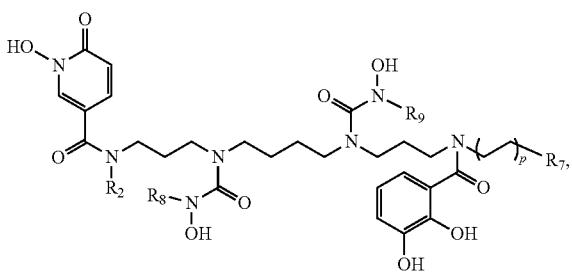

wherein:

$R_7$ includes $NH_2$, C(=O)OH, maleimide, dibromo-maleimide, isothiocyanate, alkyne, or azide;

$R_2$, $R_8$, and $R_9$, individually, include H, OH, or an alkyl group including from 1 to 5 carbon atoms; and p is from 0 to 4.

19. A composition of embodiment 12, including a structure:

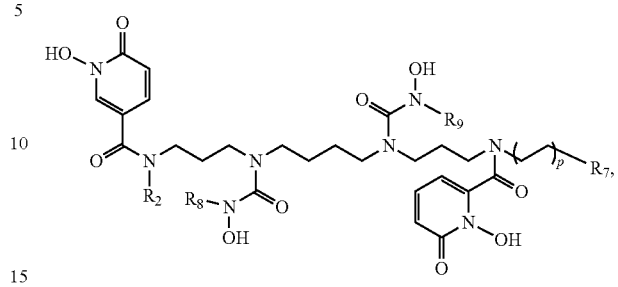

wherein:

$R_7$ includes $NH_2$, C(=O)OH, maleimide, dibromo-maleimide, isothiocyanate, alkyne, or azide;

$R_2$, $R_8$, and $R_9$, individually, include H, OH, or an alkyl group including from 1 to 5 carbon atoms; and p is from 0 to 4.

20. A composition of embodiment 12, including a structure:

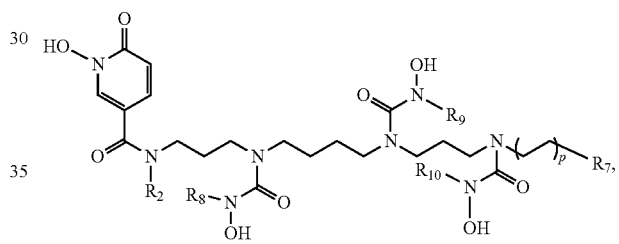

wherein:

$R_7$ includes $NH_2$, C(=O)OH, maleimide, dibromo-maleimide, isothiocyanate, alkyne, or azide;

$R_2$, $R_8$, $R_9$, and $R_{10}$, individually, include H, OH, or an alkyl group including from 1 to 5 carbon atoms; and p is from 0 to 4.

21. A composition of embodiment 12, including a structure:

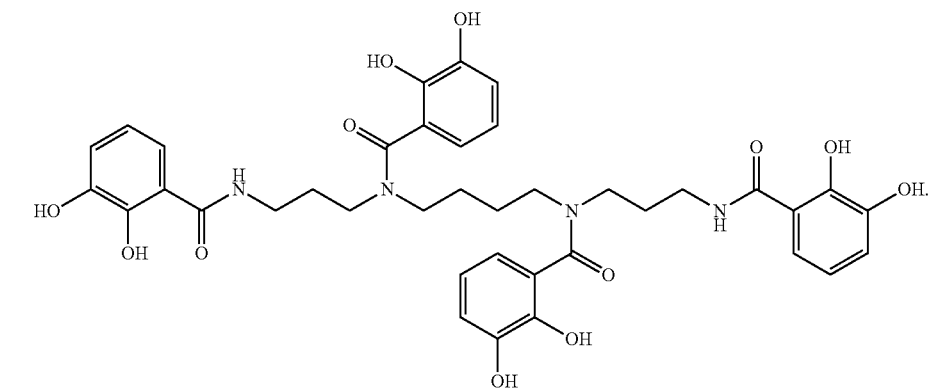 [SMILES: O=C(NCCCN(CCCCN(CCCNC(=O)c1cccc(O)c1O)C(=O)c1cccc(O)c1O)C(=O)c1cccc(O)c1O)c1cccc(O)c1O]

22. A composition of embodiment 12, including a structure:

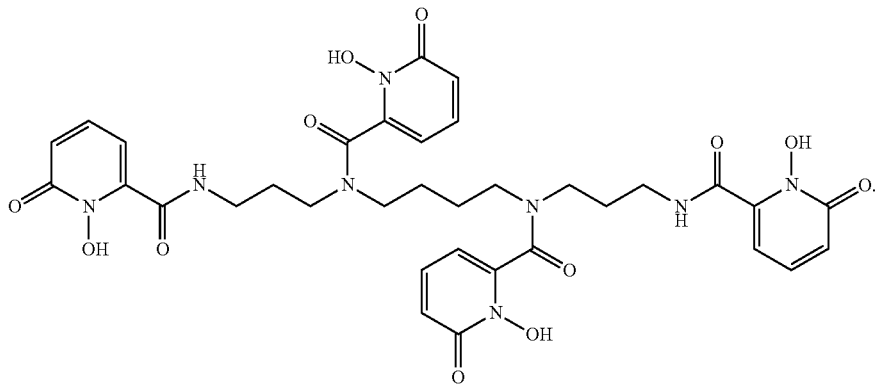 [SMILES: O=C(NCCCN(CCCCN(CCCNC(=O)c1cccc(=O)n1O)C(=O)c1cccc(=O)n1O)C(=O)c1cccc(=O)n1O)c1cccc(=O)n1O]

23. A composition, including a structure:

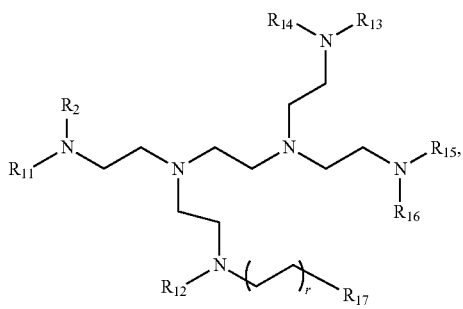

wherein:
at least one of $R_{11}$, $R_{12}$, $R_{13}$, or $R_{15}$, individually, include a CAM group, a HA group, or a 1,2-HOPO group;
optionally, at least another one of $R_{11}$, $R_{12}$, $R_{13}$, or $R_{15}$, individually, include H, OH, or an alkyl group having from 1 to 10 carbon atoms;
$R_{17}$ includes $NH_2$, $C(=O)OH$, maleimide, dibromo-maleimide, isothiocyanate, alkyne, or azide;
$R_2$, $R_{14}$, and $R_{16}$, individually, include H, OH, or an alkyl group having from 1 to 10 carbon atoms; and
r can be from 0 to 6.

24. A composition of embodiment 23, wherein:
$R_{11}$ includes a CAM group or a 1,2-HOPO group;
$R_{12}$ and $R_{15}$, individually, include a HA group; and
$R_{13}$ includes a CAM group, a 1,2-HOPO group, or a HA group.

25. A composition of embodiment 23, including a structure:

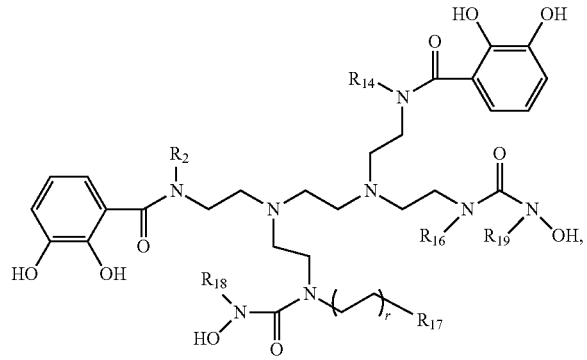

wherein:
$R_2$, $R_{14}$, $R_{16}$, $R_{18}$, and $R_{19}$, individually, include H, OH, or an alkyl group having from 1 to 10 carbon atoms;
$R_{17}$ includes $NH_2$, $C(=O)OH$, maleimide, dibromo-maleimide, isothiocyanate, alkyne, or azide; and
r can be from 0 to 4.

26. A composition of embodiment 23, including a structure:

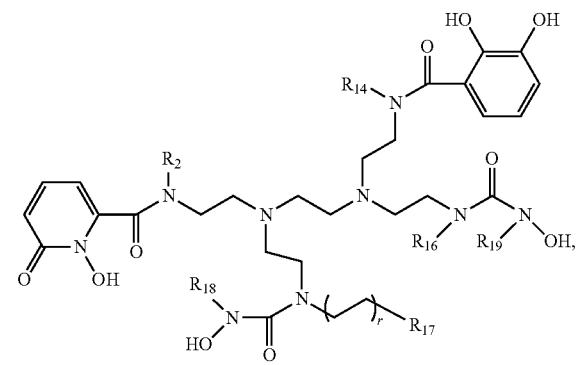

wherein
$R_2$, $R_{14}$, $R_{16}$, $R_{18}$, and $R_{19}$, individually, include H, OH, or an alkyl group having from 1 to 10 carbon atoms;
$R_{17}$ includes $NH_2$, $C(=O)OH$, maleimide, dibromo-maleimide, isothiocyanate, alkyne, or azide; and
r is from 0 to 4.

27. A composition of embodiment 23, including a structure:

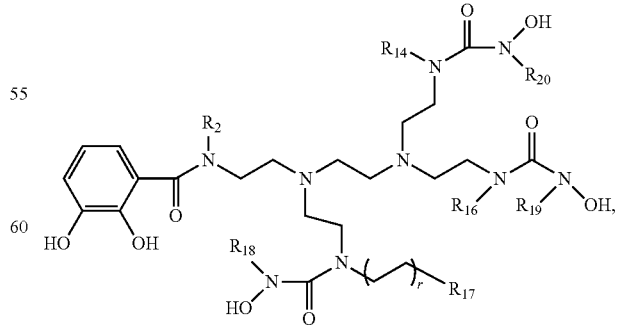

wherein:
$R_2$, $R_{14}$, $R_{16}$, $R_{18}$, $R_{19}$, and $R_{20}$, individually, include H, OH, or an alkyl group having from 1 to 10 carbon atoms;

$R_{17}$ includes $NH_2$, $C(=O)OH$, maleimide, dibromo-maleimide, isothiocyanate, alkyne, or azide; and r can be from 0 to 4.

28. A composition of embodiment 23, including a structure:

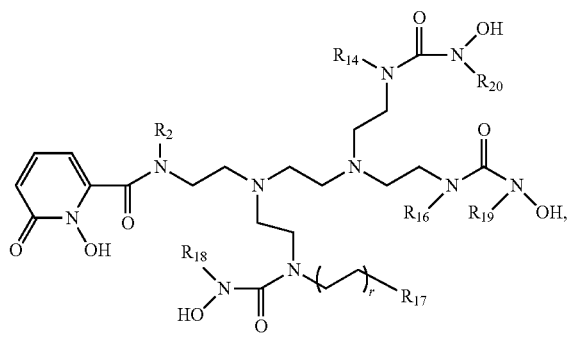

wherein:

$R_2$, $R_{14}$, $R_{16}$, $R_{18}$, $R_{19}$, and $R_{20}$, individually, include H, OH, or an alkyl group having from 1 to 10 carbon atoms;

$R_{17}$ includes $NH_2$, $C(=O)OH$, maleimide, dibromo-maleimide, isothiocyanate, alkyne, or azide; and r can be from 0 to 4.

29. A composition of embodiment 23, including a structure:

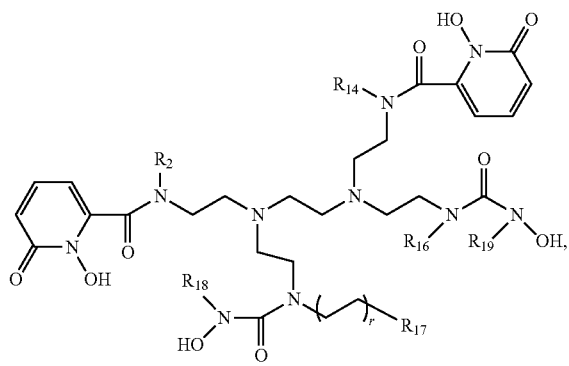

wherein:

$R_2$, $R_{14}$, $R_{16}$, $R_{18}$, and $R_{19}$, individually, include H, OH, or an alkyl group having from 1 to 10 carbon atoms;

$R_{17}$ includes $NH_2$, $C(=O)OH$, maleimide, dibromo-maleimide, isothiocyanate, alkyne, or azide; and r is from 0 to 4.

30. A composition of embodiment 23, including a structure:

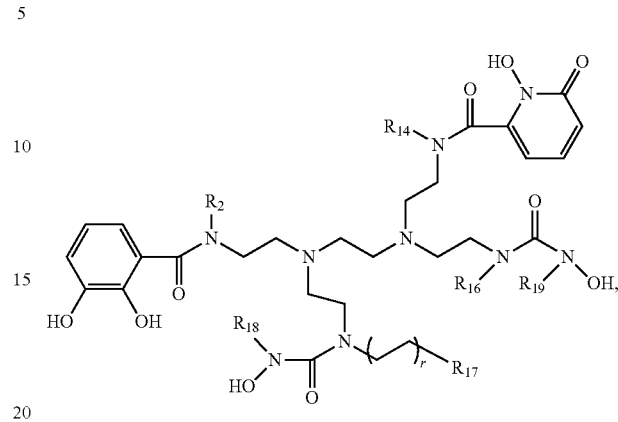

wherein:

$R_2$, $R_{14}$, $R_{16}$, $R_{18}$, and $R_{19}$, individually, include H, OH, or an alkyl group having from 1 to 10 carbon atoms;

$R_{17}$ includes $NH_2$, $C(=O)OH$, maleimide, dibromo-maleimide, isothiocyanate, alkyne, or azide;

r is from 0 to 4.

31. A composition, including a structure:

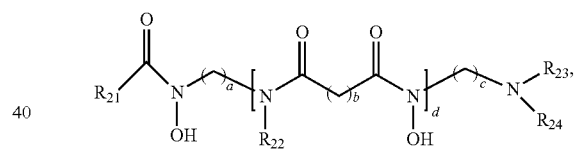

wherein:

$R_{21}$ and $R_{22}$, individually, include H, OH, or an alkyl group having from 1 to 10 carbon atoms;

$R_{23}$ includes H, OH, an alkyl group having from 1 to 10 carbon atoms, or $(CH_2)_e R_a$, where $R_a$ is $NH_2$, $C(=O)OH$, maleimide, dibromo-maleimide, isothiocyanate, alkyne, or azide;

$R_{24}$ includes a substituent having a CAM group, a 1,2-HOPO group, or a HA group;

a, b, and c, individually, are from 1 to 10;

d is from 1 to 4; and e is from 1 to 10.

32. A composition of embodiment 31, wherein $R_{24}$ includes a substituent having $NH_2$, $C(=O)OH$, maleimide, dibromo-maleimide, isothiocyanate, alkyne, or azide.

33. A composition of embodiment 31, including a structure:

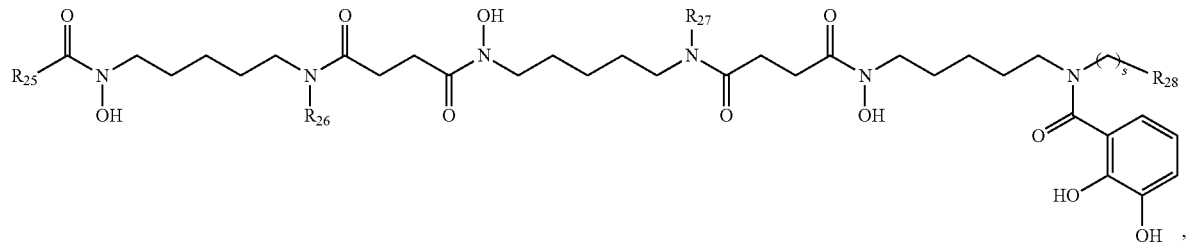

wherein:
$R_{25}$, $R_{26}$, and $R_{27}$, individually, include H, OH, or an alkyl group having from 1 to 10 carbon atoms;
$R_{28}$ includes H, an alkyl group having from 1 to 5 carbon atoms, $NH_2$, $C(=O)OH$, maleimide, dibromo-maleimide, isothiocyanate, alkyne, or azide; and
s is from 0 to 4.

34. A composition of embodiment 31, including a structure:

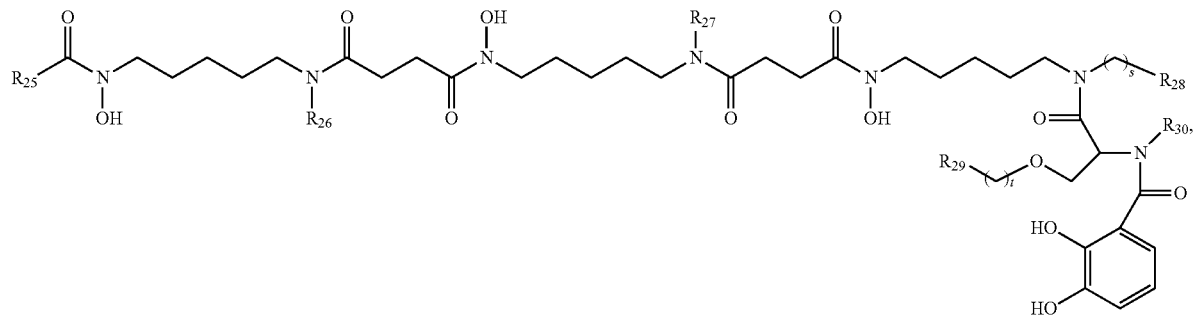

wherein:
$R_{25}$, $R_{26}$, $R_{27}$, and $R_{30}$, individually, include H, OH, or an alkyl group having from 1 to 10 carbon atoms;
$R_{28}$ and $R_{29}$, individually, include H, an alkyl group having from 1 to 5 carbon atoms, $NH_2$, $C(=O)OH$, maleimide, dibromo-maleimide, isothiocyanate, alkyne, or azide;
s is from 0 to 4; and
t is from 0 to 4.

35. A composition of embodiment 31, including a structure:

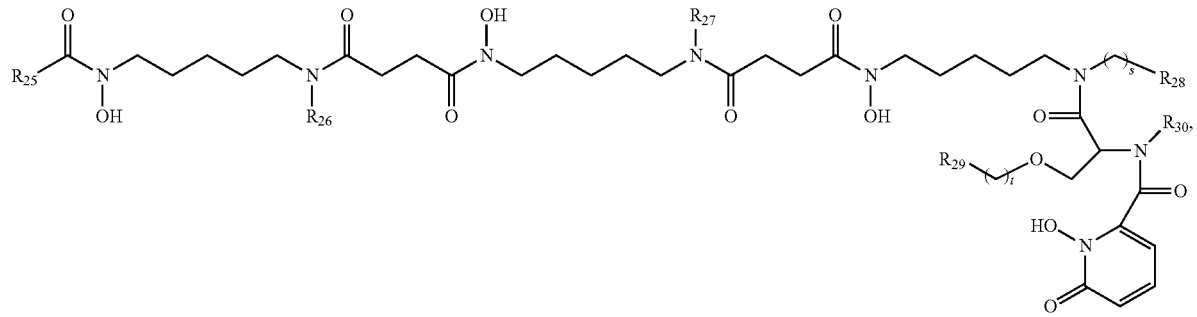

wherein:
$R_{25}$, $R_{26}$, $R_{27}$, and $R_{30}$, individually, include H, OH, or an alkyl group having from 1 to 10 carbon atoms;
$R_{28}$ and $R_{29}$, individually, include H, an alkyl group having from 1 to 5 carbon atoms, $NH_2$, $C(=O)OH$, maleimide, dibromo-maleimide, isothiocyanate, or azide;
s is from 0 to 4; and
t is from 0 to 4.

36. A composition of embodiment 31, including a structure:

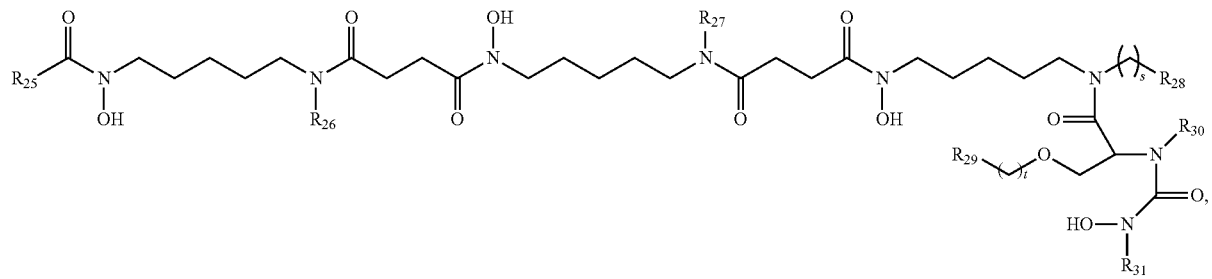

wherein:
$R_{25}$, $R_{26}$, $R_{27}$, $R_{30}$, and $R_{31}$, individually, include H, OH, or an alkyl group having from 1 to 10 carbon atoms;
$R_{28}$ and $R_{29}$, individually, include H, an alkyl group having from 1 to 5 carbon atoms, $NH_2$, C(=O)OH, maleimide, dibromo-maleimide, isothiocyanate, or azide;
s is from 0 to 4; and
t is from 0 to 4.

37. A composition of embodiment 31, including a structure:

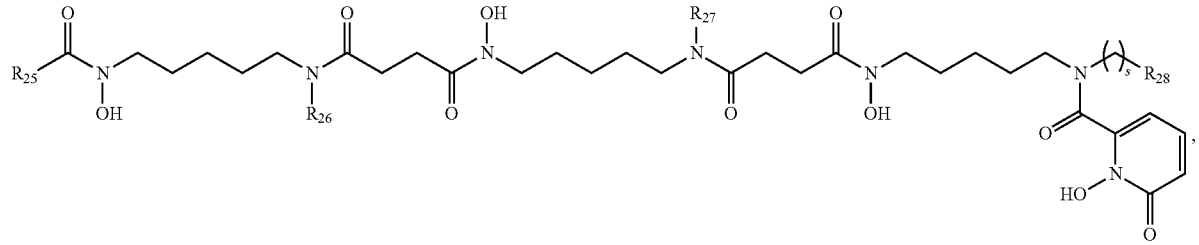

wherein
$R_{25}$, $R_{26}$, and $R_{27}$, individually, include H, OH, or an alkyl group having from 1 to 10 carbon atoms;
$R_{28}$ includes H, an alkyl group having from 1 to 5 carbon atoms, $NH_2$, C(=O)OH, maleimide, dibromo-maleimide, isothiocyanate, alkyne, or azide; and
s is from 0 to 4.

38. A composition of embodiment 31, including a structure:

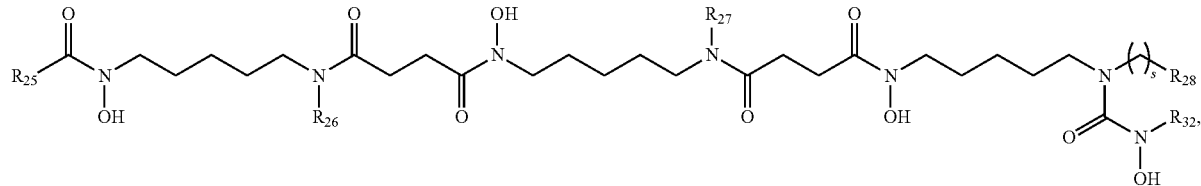

wherein:
$R_{25}$, $R_{26}$, $R_{27}$, and $R_{32}$, individually, include H, OH, or an alkyl group having from 1 to 10 carbon atoms;
$R_{28}$ includes H, an alkyl group having from 1 to 5 carbon atoms, $NH_2$, C(=O)OH, maleimide, dibromo-maleimide, isothiocyanate, alkyne, or azide; and
s is from 0 to 4.

39. A composition, including a structure:

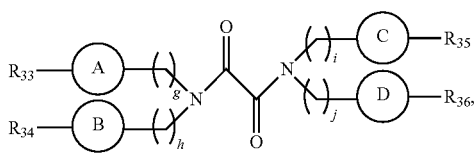

wherein:

A, B, C, and D, individually, include one or more amide groups, one or more amine groups, or an alkyl group having from 1 to 10 carbon atoms;

$R_{33}$, $R_{34}$, $R_{35}$, and $R_{36}$, individually, include a CAM group, a 1,2-HOPO group, or a HA group; and g, h, i, and j, individually, are from 1 to 10.

40. A composition of embodiment 39, including a structure:

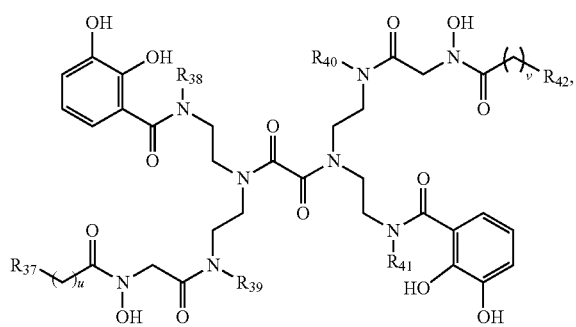

wherein:

$R_{37}$ and $R_{42}$, individually, include H, an alkyl group having from 1 to 5 carbon atoms, $NH_2$, C(=O)OH, maleimide, dibromo-maleimide, isothiocyanate, alkyne, or azide;

$R_{38}$, $R_{39}$, $R_{40}$, and $R_{41}$, individually, include H, OH, or an alkyl group having from 1 to 5 carbon atoms; and u and v, individually, are from 0 to 5.

41. A composition of embodiment 39, including a structure:

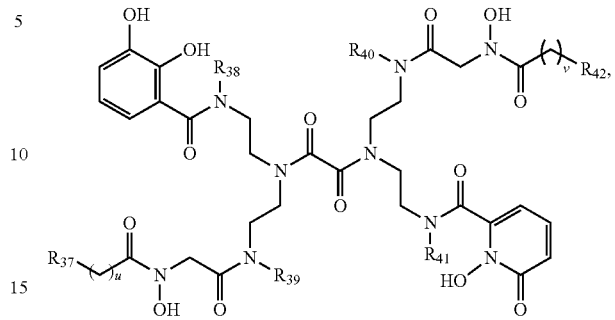

wherein:

$R_{37}$ and $R_{42}$, individually, include H, an alkyl group having from 1 to 5 carbon atoms, $NH_2$, C(=O)OH, maleimide, dibromo-maleimide, isothiocyanate, alkyne, or azide;

$R_{38}$, $R_{39}$, $R_{40}$, and $R_{41}$, individually, include H, OH, or an alkyl group having from 1 to 5 carbon atoms; and u and v, individually, are from 0 to 5.

42. A composition of embodiment 39, including a structure:

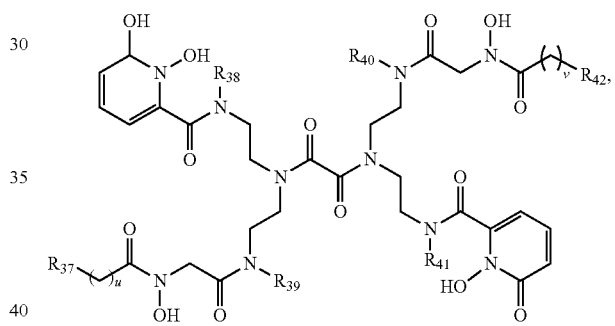

wherein:

$R_{37}$ and $R_{42}$, individually, include H, an alkyl group having from 1 to 5 carbon atoms, $NH_2$, C(=O)OH, maleimide, dibromo-maleimide, isothiocyanate, alkyne, or azide;

$R_{38}$, $R_{39}$, $R_{40}$, and $R_{41}$, individually, include H, OH, or an alkyl group having from 1 to 5 carbon atoms; and u and v, individually, are from 0 to 5.

43. A method of synthesizing a siderophore using dichlorodiphenylmethane.

44. A method of embodiment 43, wherein a siderophore or siderophore-like ligand is synthesized according to the following pathway:

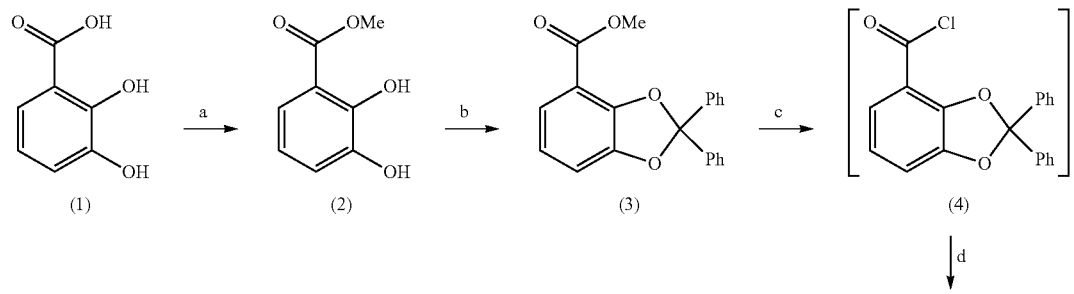

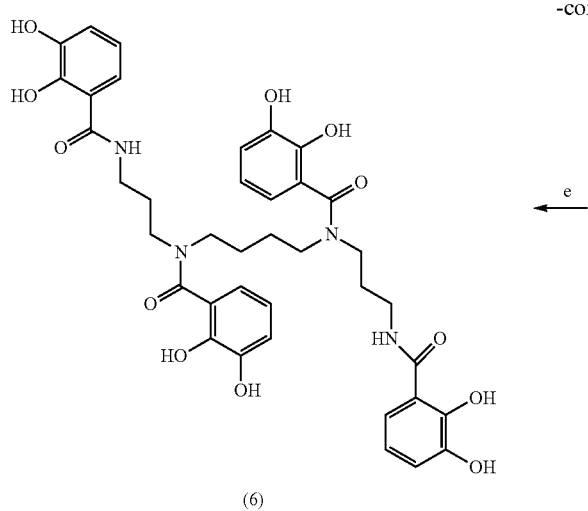

(6)

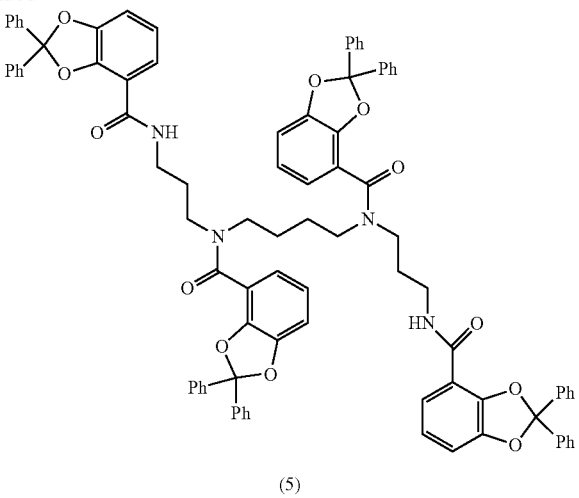

(5)

45. A composition of any one of embodiment s1-42, wherein the metal is a radionuclide.

46. A composition of embodiment 53, wherein the radionuclide includes $^{225}$Ac, $^{226}$Ac, $^{228}$Ac, $^{105}$Ag, $^{106}$mAg, $^{110}$mAg, $^{1}$Ag, $^{112}$Ag, $^{113}$Ag, $^{239}$Am, 240 Am, $^{242}$Am, $^{244}$Am, $^{37}$Ar, $^{71}$As, $^{72}$As, $^{73}$As, $^{74}$As, $^{76}$As, $^{77}$As, $^{209}$At, $^{210}$At, $^{191}$Au, $^{192}$Au, $^{193}$Au, $^{194}$Au, $^{195}$Au, $^{196}$Au, $^{196}$m$^{2}$Au, $^{198}$Au, $^{198}$mAu, $^{199}$Au, $^{200}$mAu, $^{128}$Ba, $^{131}$Ba, $^{133}$mBa, $^{135}$mBa, $^{140}$Ba, $^{7}$Be, $^{203}$Bi, $^{204}$Bi, $^{205}$Bi, $^{206}$Bi, $^{210}$Bi, $^{212}$Bi, $^{243}$Bk, $^{244}$Bk, $^{245}$Bk, $^{246}$Bk, $^{248}$mBk, $^{250}$Bk, $^{76}$Br, $^{77}$Br, $^{80}$mBr, $^{82}$Br, $^{11}$C, $^{14}$C, $^{45}$Ca, $^{47}$Ca, $^{107}$Cd, $^{115}$Cd, $^{11}$mCd, $^{117}$mCd, $^{132}$Ce, $^{133}$mCe, $^{134}$Ce $^{135}$Ce $^{137}$Ce, $^{137}$mCe, $^{139}$Ce, $^{141}$Ce, $^{143}$Ce $^{144}$Ce $^{246}$Cf $^{247}$Cf $^{253}$Cf $^{254}$Cf, $^{240}$Cm, $^{241}$Cm, $^{242}$Cm, $^{252}$Cm, $^{55}$Co, $^{56}$Co, $^{57}$Co, $^{58}$Co, $^{58}$mCo, $^{60}$Co, $^{48}$Cr, $^{51}$Cr, $^{127}$Cs, $^{129}$Cs, $^{131}$Cs, $^{132}$Cs, $^{136}$Cs, $^{137}$Cs, $^{61}$Cu, $^{62}$Cu, $^{64}$Cu, $^{67}$Cu, $^{153}$Dy, $^{155}$Dy, $^{157}$Dy, $^{159}$Dy, $^{165}$Dy, $^{166}$Dy, $^{160}$Er, $^{161}$Er, $^{165}$Er, $^{169}$Er, $^{171}$Er, $^{172}$Er, $^{250}$Es, $^{251}$Es, $^{253}$Es, $^{254}$Es, $^{254}$mEs, $^{255}$Es, $^{256}$mEs, $^{145}$Eu, $^{146}$Eu, $^{147}$Eu, $^{148}$Eu, $^{149}$Eu, $^{150}$mEu, $^{152}$mEu, $^{156}$Eu, $^{157}$Eu, $^{52}$Fe, $^{59}$Fe, $^{251}$Fm, $^{252}$Fm, $^{253}$Fm, $^{254}$Fm, $^{255}$Fm, $^{257}$Fm, $^{66}$Ga, $^{67}$Ga, $^{68}$Ga, $^{72}$Ga, $^{73}$Ga, $^{146}$Gd, $^{147}$Gd, $^{149}$Gd, $^{151}$Gd, $^{153}$Gd, $^{159}$Gd, $^{68}$Ge, $^{69}$Ge, $^{71}$Ge, $^{77}$Ge, $^{170}$1Hf, $^{171}$Hf, $^{173}$Hf, $^{175}$Hf, $^{179}$m$^{2}$Hf, $^{180}$mHf, $^{181}$Hf, $^{184}$Hf, $^{192}$Hg, $^{193}$Hg, $^{193}$mHg, $^{195}$Hg, $^{195}$mHg, $^{197}$Hg, $^{197}$mHg, $^{203}$Hg, $^{160}$mHo, $^{166}$Ho, $^{167}$Ho, $^{123}$I, $^{123}$I, $^{124}$I, $^{126}$I, $^{130}$I, $^{132}$I, $^{133}$I, $^{135}$I, $^{109}$In, $^{110}$In, $^{111}$In, $^{114}$mIn, $^{115}$mIn, $^{184}$Ir, $^{185}$Ir, $^{186}$Ir, $^{187}$Ir, $^{188}$Ir, $^{189}$Ir, $^{190}$Ir, $^{190}$m$^{2}$Ir, $^{192}$Ir, $^{193}$mIr, $^{194}$Ir, $^{194}$m$^{2}$Ir, $^{195}$mIr, $^{42}$K, $^{43}$K, $^{76}$Kr, $^{79}$Kr, $^{81}$mKr, $^{85}$mKr, $^{132}$La, $^{133}$La, $^{135}$La, $^{140}$La, $^{141}$La, $^{262}$Lr, $^{169}$Lu, $^{170}$Lu, $^{171}$Lu, $^{172}$Lu, $^{174}$mLu, $^{176}$mLu, $^{177}$Lu, $^{177}$mLu, $^{179}$Lu, $^{257}$Md, $^{258}$Md, $^{260}$Md, $^{28}$Mg, $^{52}$Mn, $^{90}$Mo, $^{93}$mMo, $^{99}$Mo, $^{13}$N, $^{24}$Na, $^{90}$Nb, $^{91}$mNb, $^{92}$mNb, $^{95}$Nb, $^{95}$mNb, $^{96}$Nb, $^{138}$Nd, $^{139}$mNd, $^{140}$Nd, $^{147}$Nd, $^{56}$Ni, $^{57}$Ni, $^{66}$Ni, $^{234}$Np, $^{236}$mNp, $^{238}$Np, $^{239}$Np, $^{15}$O, $^{182}$Os, $^{183}$Os, $^{183}$mOs, $^{185}$Os, $^{189}$mOs, $^{191}$Os, $^{191}$mOs, $^{193}$Os, $^{32}$P, $^{33}$P, $^{228}$Pa, $^{229}$Pa, $^{230}$Pa, $^{232}$Pa, $^{233}$Pa, $^{234}$Pa, $^{200}$Pb, $^{201}$Pb, $^{202}$mPb, $^{203}$Pb, $^{209}$Pb, $^{212}$Pb, $^{100}$Pd, $^{101}$Pd, $^{103}$Pd, $^{109}$Pd, $^{111}$mPd, $^{112}$Pd, $^{143}$Pm, $^{148}$Pm, $^{148}$mPm, $^{149}$Pm, $^{151}$Pm, $^{204}$Po, $^{206}$Po, $^{207}$Po, $^{210}$Po, $^{139}$Pr, $^{142}$Pr, $^{143}$Pr, $^{145}$Pr, $^{188}$Pt, $^{189}$Pt, $^{191}$Pt, $^{193}$mPt, $^{195}$mPt, $^{197}$Pt, $^{200}$Pt, $^{202}$Pt, $^{234}$Pu, $^{237}$Pu, $^{243}$Pu, $^{245}$Pu, $^{246}$Pu, $^{247}$Pu, $^{223}$Ra, $^{224}$Ra, $^{225}$Ra, $^{81}$Rb, $^{82}$Rb, $^{82}$mRb, $^{83}$Rb, $^{84}$Rb, $^{86}$Rb, $^{181}$Re, $^{182}$Re, $^{182}$mRe, $^{183}$Re, $^{184}$Re, $^{184}$mRe, $^{186}$Re, $^{188}$Re, $^{189}$Re, $^{190}$mRe, $^{99}$Rh, $^{99}$mRh, $^{100}$Rh, $^{101}$mRh, $^{102}$Rh, $^{103}$mRh, $^{105}$Rh, $^{211}$Rn, $^{222}$Rn, $^{97}$Ru, $^{103}$Ru, $^{105}$Ru, $^{35}$S, $^{118}$mSb, $^{119}$Sb, $^{120}$Sb, $^{120}$mSb, $^{122}$Sb, $^{124}$Sb, $^{126}$Sb, $^{127}$Sb, $^{128}$Sb, $^{129}$Sb, $^{43}$Sc, $^{44}$Sc, $^{44}$mSc, $^{46}$Sc, $^{47}$SC, $^{48}$Sc, $^{72}$Se, $^{73}$Se, $^{75}$Se, $^{153}$Sm, $^{156}$Sm, $^{110}$Sn, $^{113}$Sn, $^{117}$mSn, $^{119}$mSn, $^{121}$Sn, $^{123}$Sn, $^{125}$Sn, $^{82}$Sr, $^{83}$Sr, $^{85}$Sr, $^{89}$Sr, $^{91}$Sr, $^{173}$Ta, $^{175}$Ta, $^{176}$Ta, $^{177}$Ta, $^{180}$Ta, $^{182}$Ta, $^{183}$Ta, $^{184}$Ta, $^{149}$Tb, $^{150}$Tb, $^{151}$Tb, $^{152}$Tb, $^{153}$Tb, $^{154}$Tb, $^{154}$mTb, $^{154}$m$^{2}$Tb, $^{155}$Tb, $^{156}$Tb, $^{156}$mTb, $^{156}$m$^{2}$Tb, $^{160}$Tb, $^{161}$Tb, $^{94}$Tc, $^{95}$Tc, $^{95}$mTc, $^{96}$Tc, $^{97}$mTc, $^{99}$mTc, $^{118}$Te, $^{119}$Te, $^{119}$mTe, $^{121}$Te, $^{121}$mTe, $^{123}$mTe, $^{125}$mTe, $^{127}$Te, $^{127}$mTe, $^{129}$mTe, $^{131}$mTe, $^{132}$Te, $^{227}$Th, $^{231}$Th, $^{234}$Th, $^{45}$Ti, $^{198}$Tl, $^{199}$Tl, $^{200}$Tl, $^{201}$Tl, $^{202}$Tl, $^{204}$Tl, $^{165}$Tm, $^{166}$Tm, $^{167}$Tm, $^{168}$Tm, $^{170}$Tm, $^{172}$Tm, $^{173}$Tm, $^{230}$U, $^{231}$U, $^{237}$U, $^{240}$U, $^{48}$V, $^{178}$W, $^{181}$W, $^{185}$W, $^{187}$W, $^{188}$W, $^{122}$Xe, $^{125}$Xe, $^{127}$Xe, $^{129}$miXe, $^{131}$mXe, $^{133}$Xe, $^{133}$mXe, $^{135}$Xe, $^{85}$mY, $^{86}$Y, $^{87}$Y, $^{87}$mY, $^{88}$Y, $^{90}$Y, $^{90}$mY, $^{91}$Y, $^{92}$Y, $^{93}$Y, $^{166}$Yb, $^{169}$Yb, $^{175}$Yb, $^{62}$Zn, $^{65}$Zn, $^{69}$mZn, $^{71}$mZn, $^{72}$Zn, $^{86}$Zr, $^{88}$Zr, $^{89}$Zr, $^{95}$Zr, and $^{97}$Zr.

47. A composition of embodiment 46, wherein the radionuclide includes $^{90}$Y, $^{67}$Cu, $^{213}$Bi, $^{22}$Bi, $^{186}$Re, $^{67}$Cu, $^{90}$Y, $^{213}$Bi, $^{177}$Lu, $^{186}$Re, and/or $^{67}$Ga.

48. A composition of embodiment 46, wherein the radionuclide includes $^{89}$Zr, $^{225}$Ac, and/or $^{227}$Th.

49. A composition of any one of embodiments 1-42, wherein the metal includes a daughter isotope of a radionuclide.

50. A composition of embodiment 49, wherein the daughter isotope of the radionuclide includes $^{89}$Y, $^{18}$O, $^{221}$Fr, $^{213}$Bi, and/or $^{209}$Pb.

51. A composition, comprising a structure:

wherein:

at least one of $R_1$, $R_2$, $R_3$, $R_4$, $R_5$, individually, comprise a CAM group, a HA group, or a 1,2-HOPO group;

at least another one of $R_1$, $R_2$, $R_3$, $R_4$, and $R_5$, individually, comprise H or an alkyl group having from 1 to 10 carbon atoms;

$R_6$ comprises (i) H, (ii) an alkyl group having from 1 to 10 carbon atoms, or (iii) an alkyl group having from 1 to 100 carbon atoms and no greater than 2 nitrogen atoms, and substituted by at least one of $NH_2$, C(=O)OH, maleimide, dibromo-maleimide, isothiocyanate, alkyne, amide or fluorescent moiety or azide;

m can be from 1 to 6;
n can be from 1 to 6;
o can be from 1 to 6;
p can be from 1 to 6;
q can be from 0 to 6;
r can be from 1 to 6;
s can be from 1 to 6; and
t can be from 1 to 6.

In some embodiments, the chelator 3,4,3-LI(1,2-HOPO) is an octadentate, tetraprotic compound including 4 bidentate 1,2-HOPO metal binding units attached onto a spermine ("3,4,3-LI") scaffold, which was recently modified to enable monoclonal antibody attachment and form a bioconjugate chelator that displayed great properties for positron emission tomography (PET) when bound to $^{89}$Zr (Deri, et al., *Bioconjugate Chemistry*, 2015, 26 (12): 2579-2591; Deri, et al., *J. Med. Chem.*, 2014, 57 (11): 4849-4860). Methyl 2,3-dihydroxybenzoate (2). A stirred suspension of 1 (8.06 g, 52.3 mmol) in 100 mL of MeOH was treated with 2.00 ml of concentrated sulfuric acid. The suspension warmed and clarified 2 minutes after the addition. The reaction was equipped with a reflux condenser and was heated to 65° C. overnight. The next morning the conversion was verified by LC-MS and the volatiles were removed under reduced pressure. The crude was partitioned between $H_2O$ (100 mL) and ethyl acetate (100 mL) and the aqueous layer was extracted with ethyl acetate (3×50 mL). The organic extracts were combined, dried over $MgSO_4$, and concentrated under reduced pressure. The crude was passed through a plug of silica using 10% ethyl acetate in hexanes as eluent. The eluent was concentrated under reduced pressure and dried under high vacuum for 2 hours to yield 2 (7.66 g, 45.6 mmol, 88%) as a white solid, the spectral properties of which matched previous reports (Weitl, et al., *J. Am. Chem. Soc.*, 1980, 102 (7): 2289-2293).

Methyl 2,2-diphenylbenzo[d][1,3]dioxole-4-carboxylate (3). Precursor 2 (5.00 g, 29.7 mmol) was mixed with dichlorodiphenylmethane (8.56 mL, 44.6 mol) under an argon atmosphere; the resulting suspension was stirred and heated to 160° C. for 1 hour. The mixture was allowed to cool to room temperature and was diluted with 100 mL of ethyl acetate. The solution was washed with sat. $NaHCO_3$ (30 mL), brine (30 mL), dried over $MgSO_4$, and then concentrated under reduced pressure. The ensuing greyish oil was dissolved in 30 mL of hot MeOH (65° C.) and was slowly cooled to 5° C., which resulted in the formation of white crystals. The crystals were a mixture of 3 and benzophenone that could not be easily separated; the crude product was used as is for the subsequent step.

2,2-diphenylbenzo[d][1,3]dioxole-4-carboxylic acid (4). The mixture from the previous step was dissolved in 100 mL of THF and was treated with 100 mL of 0.9 M LiOH. The emulsion was rapidly stirred and heated to reflux for 5 hours. Conversion was verified by LC-MS and the reaction was cooled to room temperature. The solution was neutralized with 10% v/v aqueous acetic acid and was extracted with ethyl acetate (3×50 mL). The organic extracts were combined, dried over $MgSO_4$, and concentrated under reduced pressure. The crude was chromatographed using 25% ethyl acetate in hexanes as eluent. Volatiles were then removed under reduced pressure followed by high vacuum to yield 4 (7.6 g, 24.06 mmol, 81% over 2 steps) as a white solid, the spectral properties of which matched previous reports (Weitl, et al., *J. Am. Chem. Soc.*, 1980, 102 (7): 2289-2293).

3,4,3-LI(2,2-diphenylbenzo [d][1,3]-2,3-catecholamide) (5). Precursor 4 (746 mg, 2.33 mmol) was suspended in 10 mL of dry toluene under an argon atmosphere and was treated with oxalyl chloride (220 µL, 2.55 mmol). Catalytic N,N-dimethylformamide was added and the suspension was heated to 40° C. The solution was stirred until the evolution of gas ceased and was concentrated on the manifold vacuum at the same temperature. The resulting brown oil was dissolved in 10 mL of dry THF. In a separate container a solution of spermine (118 mg, 0.583 mmol), triethylamine (356 µL, 2.56 mmol), and THF (5 mL) was prepared. The solutions were combined and heated to 50° C. overnight in a sealed flask. The following day the reaction was filtered and concentrated under reduced pressure. The resulting crude oil was chromatographed using 3% MeOH in $CH_2Cl_2$ as eluent. The volatiles were then removed under reduced pressure and dried under vacuum, yielding 5 as a white foam (641 mg, 0.457 mmol, 78% yield). $^1$H NMR (300 MHz, $CDCl_3$) δ 7.88 (1H, t, J=5.7 Hz), 7.66-7.76 (6H, br t), 7.60 (1H, br s), 7.57 (1H, br s), 7.43-7.53 (10H, br s), 7.33-7.40 (4H, br s), 7.19-7.31 (20H, br s), 7.01 (2H, d, J=7.6 Hz), 6.91 (4H, dd, J=12.1 Hz, 8.0 Hz), 6.80 (2H, br s), 6.72 (2H, br s), 3.85 (4H, br s), 3.43 (2H br s), 3.21 (2H, br s), 3.06 (1H, br s), 2.96 (1H, br s), 2.80 (2H, br s), 1.81 (4H, br s), 1.54 (1H, br s), 1.43 (1H, br s), 1.19 (1H, br s), 0.89 (2H, br s). $^{13}$C NMR (75 MHz, $CDCl_3$) δ 167.5, 163.7, 147.3, 147.1, 145.0, 142.8, 139.7, 139.4, 138.9, 129.7, 129.2, 128.4, 128.3, 126.4, 126.3, 126.1, 126.0, 122.3, 122.2, 121.7, 120.4, 118.4, 118.1, 116.0, 111.8, 111.4, 111.3, 109.4, 47.9, 41.8, 36.5, 27.9, 25.5.

3,4,3-LI(CAM) (6). The protected chelator 5 (411 mg, 0.293 mmol) was dissolved in a mixture of 5 mL acetic acid, 0.5 mL $H_2O$, and 0.1 mL concentrated HCl. The solution was stirred in a sealed container at 60° C. overnight. The next day the conversion was confirmed by LC-MS and the volatiles were removed under vacuum. A portion of the crude was purified using reverse-phase prep-HPLC using at 10-*50% MeOH in $H_2O$+0.1% trifluoroacetic acid as eluent. The solvent was removed on a Genevac centrifugal evaporator followed by lyophilization of residual $H_2O$. 6 was obtained as a pure white powder (90% yield). $^1$H NMR (600 MHz, DMSO-$d_6$) δ 12.82 (1H, br s), 12.69 (1H, br s), 9.52 (2H, br s), 9.11 (2H, br s), 8.78 (1H, br s), 8.60 (3H, br s), 7.26 (1H, br s), 7.12 (1H, br s), 6.90 (2H, br s), 6.77 (1H, br s), 6.66 (4H, br s), 6.56 (2H, br s), 6.44 (1H, br s), 2.88-3.52 (12H, overlapping aliphatic signals), 1.16-1.83 (8H, overlapping aliphatic signals); $^{13}$C NMR (125 MHz, MeOD-$d_4$) δ 172.9, 171.5, 150.4, 147.3, 146.6, 125.6, 125.4, 121.0, 119.6, 119.1, 118.8, 118.6, 116.9, 116.6, 47.7, 44.9, 43.2, 37.8, 37.5, 29.3, 28.2, 26.5, 25.5. MS-ESI (m/z) [M+H] Calcd for $C_{38}H_{43}N_4O_{12}$, 747.2878; found 747.2922 and [M−H] Calcd. for $C_{38}H_{41}N_4O_{12}$, 745.2721; found 745.2774.

Another pathway for synthesizing a chelator that includes a carboxyl group for binding with another compound, such as a protein or a dye, can include:

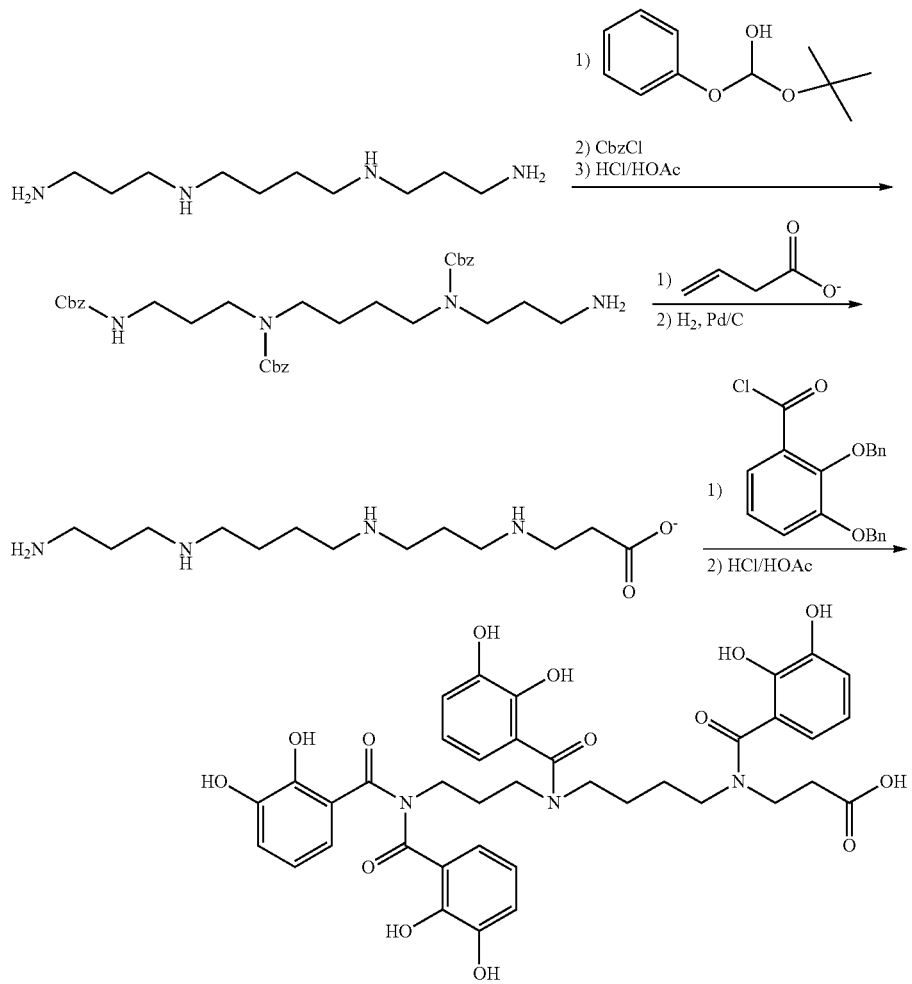

Metal, Chelator Solutions. The trivalent lanthanide Ln(III) working stock solutions were prepared in standardized 0.1 M HCl. A Zr(IV) stock solution was prepared by dissolving $ZrCl_4$ in 3.0 M $H_2SO_4$, to prevent hydrolysis. The metal salt $ZrCl_4$ was handled and stored in a glovebox kept under inert atmosphere. The Zr(IV) stock solution was standardized against EDTA, with xylene orange as the indicator (Welcher, F. J. *The analytical uses of ethylenediamine tetraacetic acid;* 1958). A Th(IV) stock solution was prepared in 0.1 M $H_2SO_4$. Stock solutions (4 mM) of Ent, and 3,4,3-LI(CAM) were prepared by direct dissolution of a weighed portion of chelator in DMSO and aliquots were removed prior to each set of experiments.

Solution Thermodynamics. All titrant solutions were degassed by boiling for 1 h while being purged under Ar. Carbonate-free 0.1 M KOH was prepared from concentrate (J. T Baker Dilut-It) and was standardized by titrating against 0.1 M potassium hydrogen phthalate (99.95%, Sigma Aldrich). Solutions of 0.1 M HCl were similarly prepared and were standardized by titrating against TRIS (99.9%, J. T. Baker). The glass electrode (Metrohm—Micro Combi—response to [H+]) used for the pH measurements was calibrated at 25.0° C. and at an ionic strength of 0.1 M (KCl) before each potentiometric or spectrophotometric titration. The calibration data were analyzed using the program GLEE (Gans & O'Sullivan, *Talanta,* 2000, 51 (1): 33-37) to refine for the E° and slope. All thermodynamic measurements were conducted at 25.0° C., in 0.1 M KCl supporting electrolyte under positive Ar gas pressure. The automated titration system was controlled by an 867 pH Module (Metrohm). Two-milliliter Dosino 800 burets (Metrohm) dosed the titrant (0.1 M KOH or 0.1 M HCl) into the thermostated titration vessel (5-90 mL). UV-visible spectra were acquired with an Ocean Optics USB4000-UV-vis spectrometer equipped with a TP-300 dip probe (Ocean Optics; path length of 10 mm), fiber optics and a DH-2000 light source (deuterium and halogen lamps). The fully automated titration system and the UV-vis spectrophotometer were coordinated by LBNL titration system, a computer program developed in house.

Incremental Spectrophotometric Titrations. This method was used to determine the protonation constants of 3,4,3-LI(CAM) as well as the stability constants of its complexes formed with Eu(III), Zr(IV) and $^{232}$Th(IV). The experimental titration setup is similar to previously described systems (Sturzbecher-Hoehne, et al., *Radiochimica Acta.,* 2013, 101 (6): 359-366). For the 3,4,3-LI(CAM) protonation (and Eu(III)-3,4,3-LI(CAM) complexes), titrations were performed with an initial concentration of 50 μM of 3,4,3-LI (CAM) (and 50 μM of Eu(III)) resulting in absorbance values included between 0 and 1.0 throughout the titration. Typically, 9 mL of a sample containing 3,4,3-LI(CAM) (and Eu(III)) and the supporting electrolyte (KCl/HCl) were incrementally perturbed by addition of 0.025 mL of carbonate-free 0.1 M KOH followed by a time delay of 80 s. Buffering of the solution was ensured by the addition of 10 mM of HEPES, 10 mM of CHES and 10 mM of MES. Between 130 and 250 data points were collected per titration, each data point including a pH measurement and a UV-Vis spectrum (250-450 nm) over the pH range 1.5 to 12.0. All spectra were corrected for dilution before data fitting. The entire procedure (electrode calibrate, titration and data treatment) was performed independently five times for the protonation constants and four times for the Eu(III)-3,4,3-LI(CAM) complexes. For the Zr(IV) and Th(IV) complexes, titrations were performed similarly but in the presence of DTPA to avoid the formation of metal hydroxides at low pH, before the uptake by 3,4,3-LI(CAM). For each metal, three titrations were performed independently in the presence of 1.1 to 40 equivalents of DTPA. Examples of titrations are displayed in the Supporting Information.

Data Treatment. Thermodynamic constants and spectral deconvolution were refined using the nonlinear least-squares fitting program HypSpec (Gans, et al., *Talanta*, 1996, 43 (10): 1739-1753). All equilibrium constants were defined as cumulative formation constants, $\beta_{mlh}$ according to Equation (1), where the metal and chelator are designated as M and L, respectively. All metal and chelator concentrations were held at estimated values determined from the volume of standardized stock solutions. All species formed with 3,4,3-LI(CAM) were considered to have significant absorbance to be observed in the UV-vis spectra and were therefore included in the refinement process. The refinements of the overall formation constants 3 included in each case with previously determined chelator protonation constants and the metal hydrolysis products, whose equilibrium constants were fixed to the literature values (Smith, et al., NIST standard reference database 46. NIST Critically selected stability constants of metal complexes database ver 2004, 2) The speciation diagrams were calculated using the modeling program Hyss (Alderighi, et al., *Coordination Chemistry Reviews*, 1999, 184 (1): 311-318). Errors on log $\beta_{mlh}$ and $pK_a$ values presented in this Example correspond to the standard deviation observed over the n replicates (n=3 to 5) of the entire procedure (electrode calibrate, titration and data treatment).

3,4,3-LI(CAM) was synthesized from readily available building blocks. The new preparation moves away from using harsh reaction conditions by using the protected diphenylmethylene acetal derivative (5), which greatly simplifies purification of the final product.

Affinity of 3,4,3-LI(CAM) Toward 3+ and 4+ Metals. A comprehensive solution thermodynamic analysis was performed to characterize the affinity of 3,4,3-LI(CAM) for trivalent and tetravalent metals and the effect of substituting 1,2-HOPO for CAM binding units on the octadentate spermine scaffold. The protonation constants of 3,4,3-LI(CAM) were determined by spectrophotometric titrations, and eight protonation equilibria were assigned to sequential removal of two protons from each of the four CAM units. Previous studies of Ent and other CAM-containing synthetic analogs established that the protonation constants ($pK_{a1}$-$pK_{a4}$) of the meta-hydroxyl oxygen atoms are well separated from the ortho-hydroxyl oxygen atoms ($pK_{a5}$-$pK_{a8}$) (Loomis & Raymond, *Inorganic Chemistry*, 1991, 30 (5): 906-911). The last four $pK_a$ values are most relevant to metal binding as moieties corresponding to these values have to be deprotonated at physiological pH in order to bind the metal ions. The overall acidity of 3,4,3-LI(CAM) can be defined as $\Sigma pK_{a5-8}$=45.4 versus 3,4,3-LI(1,2-HOPO)'s 21.2 (Abergel, et al., *Inorganic chemistry* 2009, 48 (23): 10868-10870) with lower values representing higher acidity. 3,4,3-LI(CAM) is therefore less prone to bind hard Lewis acids at low pH than its 1,2-HOPO analog, due to competition between metal uptake and protonation of the CAM moieties.

Incremental spectrophotometric titrations were then carried out to determine the formation of $Eu^{III}$, $Zr^{IV}$ or $Th^{IV}$ complexes with 3,4,3-LI(CAM). Because of the very short half-life of $^{225}Ac$ and the scarce availability of the longer-lived $^{227}Ac$, $Eu^{III}$ was used here as a non-radioactive Ln surrogate for $Ac^{III}$. Based on previous solution thermodynamic studies of $Ln^{III}$ complexes of 3,4,3-LI(1,2-HOPO) and other common polyaminocarboxylate chelators, 15 it is reasonable to expect similar stability constants for $Eu^{III}$ and $Ac^{III}$ complexes of 3,4,3-LI(CAM). The CAM octadentate chelator showed a very high affinity for both 3+ and 4+ ions. The stability constants of $[Eu-3,4,3-LI(CAM)]^{5-}$, $[Th-3,4,3-LI(CAM)]^{4-}$ and $[Zr-3,4,3-LI(CAM)]^{4-}$ are several orders of magnitude higher than those of their 1,2-HOPO counterparts, with log β110 values of 29.7, 47.7 and 57.3, respectively. Consequently, 3,4,3-LI(CAM) is one of the strongest chelators ever reported for the chelation of both trivalent and tetravalent f-elements. For comparison, a cyclic octadentate terephthalamide derivative was recently designed to bind Th4+ in vivo and showed an unprecedented affinity for Th4+ with a log β110 (ThL4-) value of 53.7 (Pham, et al., *J. Am. Chem. Soc.*, 2014, 136 (25): 9106-9115). To inspect the pH dependency of metal complex formation, speciation diagrams were calculated for 3,4,3-LI(CAM) in the presence of 1 equivalent of Eu(III), Zr(IV) or Th(IV). Both Zr(IV) and Th(IV) complexes start forming at around pH 3, with the mono and fully deprotonated species, $[MIVLH]^{3-}$ and $[MIVL]^{4-}$, being predominant at physiological pH (7.4). This behavior departs from that of 3,4,3-LI(1,2-HOPO), with which 4+ metal complexes are formed even under very acidic conditions (pH<0) (Deblonde, et al., *Inorganic chemistry*, 2013, 52 (15); 8805-8811; Sturzbecher-Hoehne, et al., *Inorganic chemistry*, 2015, 54 (7): 3462-3468). For Eu(III), complexation by 3,4,3-LI(CAM) starts at pH 5 and the mono-protonated complex, $[Eu^{III}LH]^{4-}$, is the only species present at pH 7.4. Similar to what is observed with 4+ metals, the pH at which Eu(III)-3,4,3-LI(CAM) complexes start forming is higher than in the case of Eu(III)-3,4,3-LI (1,2-HOPO) species that already appear at pH 1 under those same conditions (Abergel, et al., *Inorganic chemistry*, 2009, 48 (23): 10868-10870). Additional embodiments of various chelators are shown in FIG. 38A, which depicts an embodiment of a general peptoid synthesis. Submonomer units are generally depicted as "R" group, and can be metal chelating units substituted with an available primary amine. These submonomer units can be used to prepare the peptoids on Rink Amide resin employing standard coupling chemistry. An unlimited number of submonomer units can be added, with each submonomer unit providing 1, 2, 3, or more metal chelating atoms such as oxygen, nitrogen, or sulfur donors. Peptoid structures formed with one, two, three, four, or five submonomer CAM- or HOPO-based units will result in bidentate, tetradentate, hexadentate, Octadentate, or pentadentate ligands. Unless noted otherwise, all synthetic aspects may be carried out in fritted polypropylene syringes, which allowed for recovery of submonomer for re-use. Synthesis can include: 1. Adding 100-150 mg of Rink amide resin to a fritted syringe. Swelling the resin by adding 2 mL of DMF and rock for 30 minutes. Ejecting the solution to isolate the swelled resin. 2. Adding 1 mL of 20% 4-methylpiperidine in DMF (v/v) to deprotect the Fmoc group. Agitating for 2 minutes, draining, and repeating for 12 minutes. 3. Rinsing the resin with DMF (2 mL, 5 times for 1 minute). 4. Bromoacetylation. Premixing 0.8 M bromoacetic acid in DMF with 0.8 M N,N-diisopropylcarbodiimide (DIC), 2 mL total solution with 0.4 M of each reagent. Drawing the solution into the syringe, agitating for 5 minutes, and rinsing (2 mL DMF 5×1 minute). 5. Displacement. Drawing in 1.5 mL of submonomer solution (0.2 M in DMF), agitating for 1 hour at 45° C., then rinsing (DMF 5×1 minute). 6. Repeating bromoacetylation and displacement until synthesis is finished. Washing with DCM (2 mL 3×1 minute) after last DMF wash and drying resin by pulling the plunger out and applying a gentle vacuum onto the syringe needle.

Figure 38B:
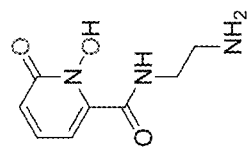
FIG. 38B depicts an embodiment of a general peptoid synthesis.
Figure 38B:
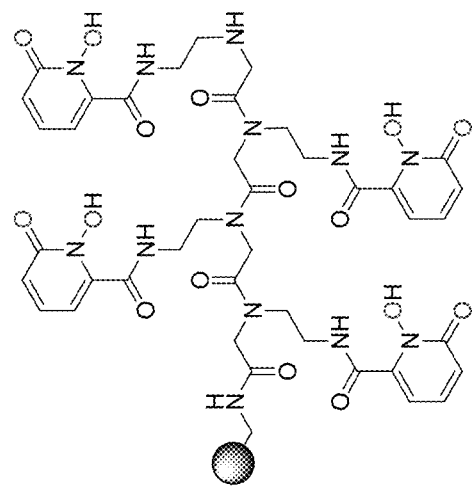
Figure 38C:
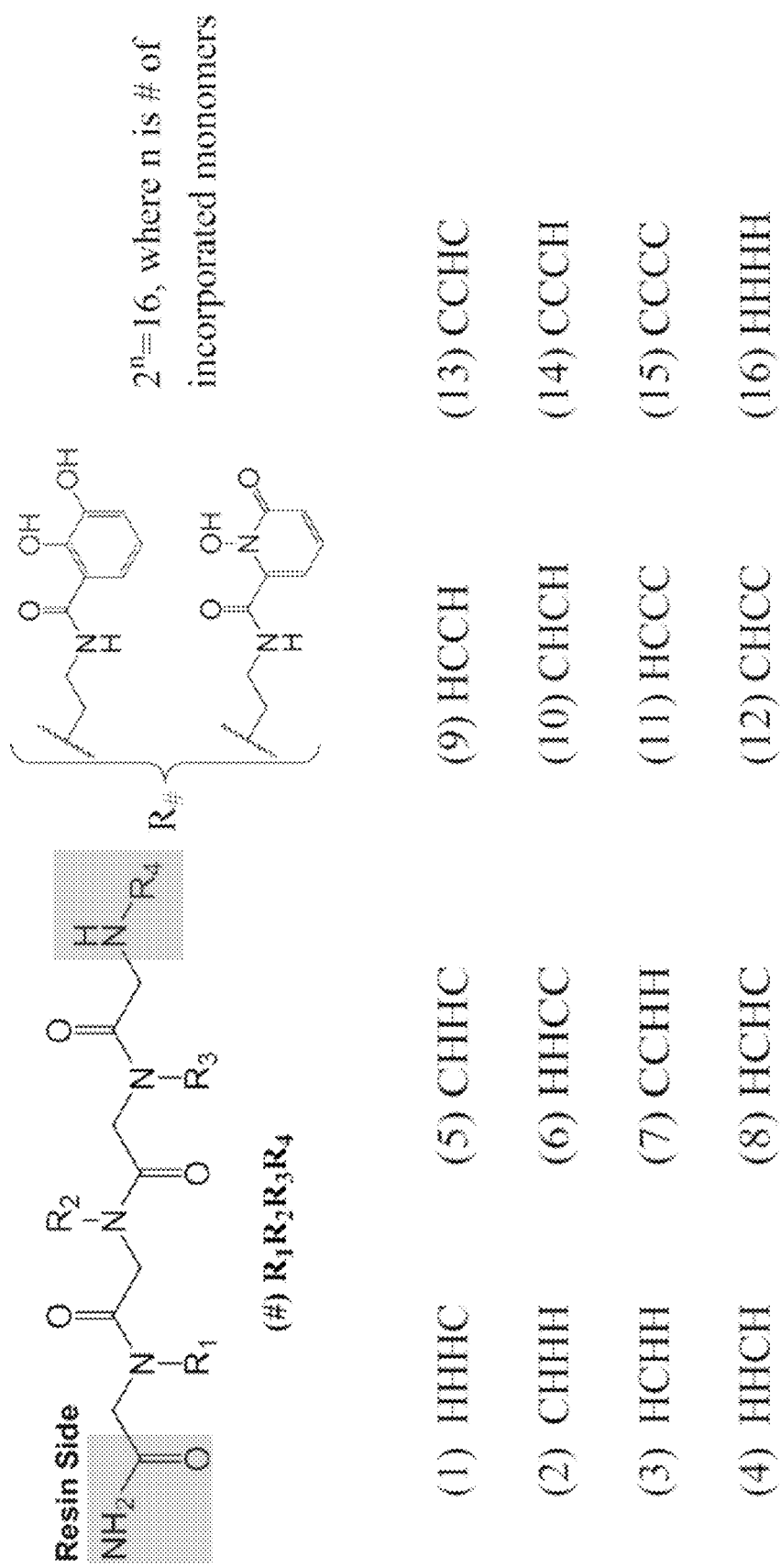
FIG. 38C depicts some embodiments of a general peptoid synthesis.

FIG. 38B depicts an embodiment of a general peptoid synthesis, where only one same submonomer unit is used throughout four coupling steps. The submonomer unit comprises a 1,2-HOPO chelating functionality linked to a primary amine through an ethylene bridge to allow for coupling to the peptoid scaffold. The resulting peptoid ligand is octadentate, with four HOPO chelating units available for metal binding. In some embodiments, different units can be added for different functionality, such as to allow cross-linking or other functions. FIG. 38C depicts an embodiment of a general peptoid synthesis where two different submonomer units are used throughout four coupling steps. The submonomer units comprise either a 1,2-HOPO or CAM chelating functionality linked to a primary amine through an ethylene bridge to allow for coupling to the peptoid scaffold. The combinatorial nature of peptoid synthesis provides a unique opportunity to control binding moiety sequence. The modularity of the scaffold allows for the preparation of up to 16 possible tetrapeptoid, octadentate ligands, with zero, one, two, three, or four HOPO or CAM chelating units available for metal binding. "H" and "C" are defined in FIG. 38D. The option of this approach allows for the generation of a wide variety of resulting chelators.

Figure 38D:
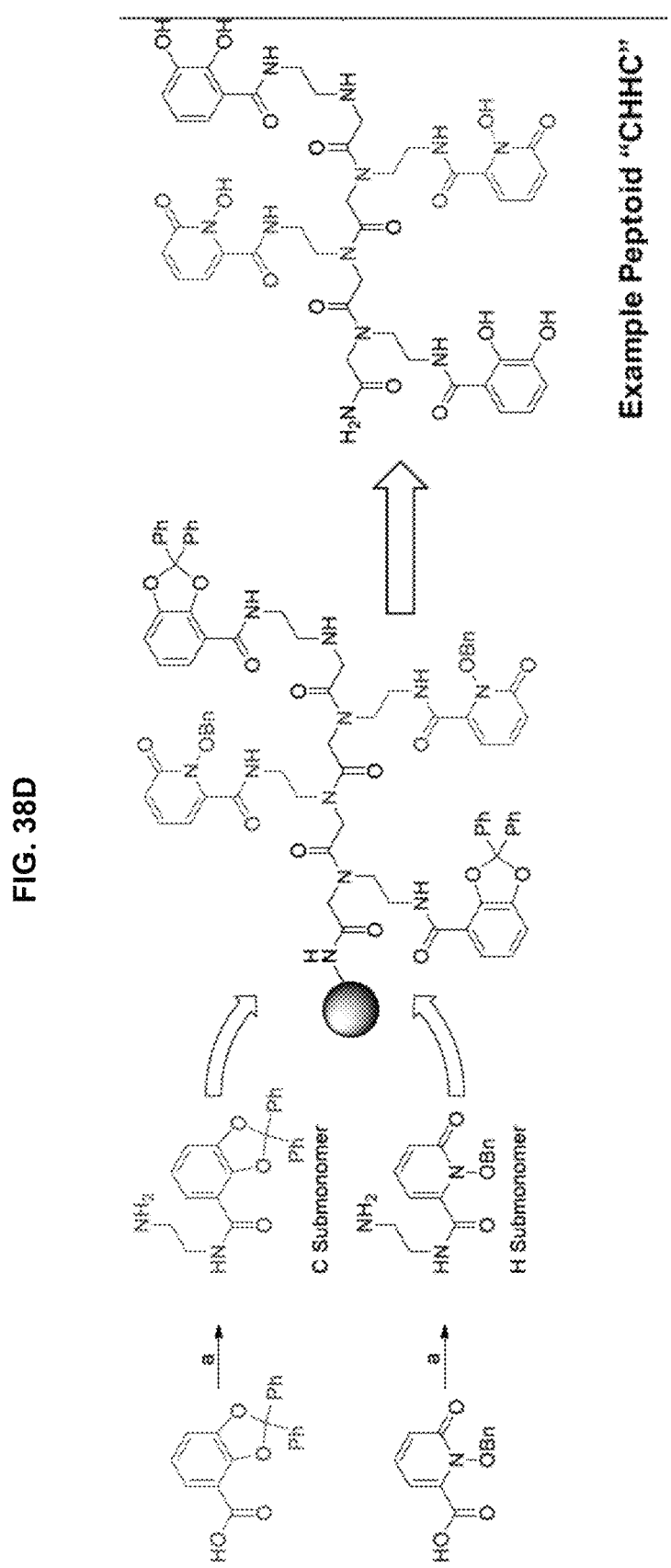
FIG. 38D depicts some embodiments of a general peptoid synthesis.
Figure 38E:
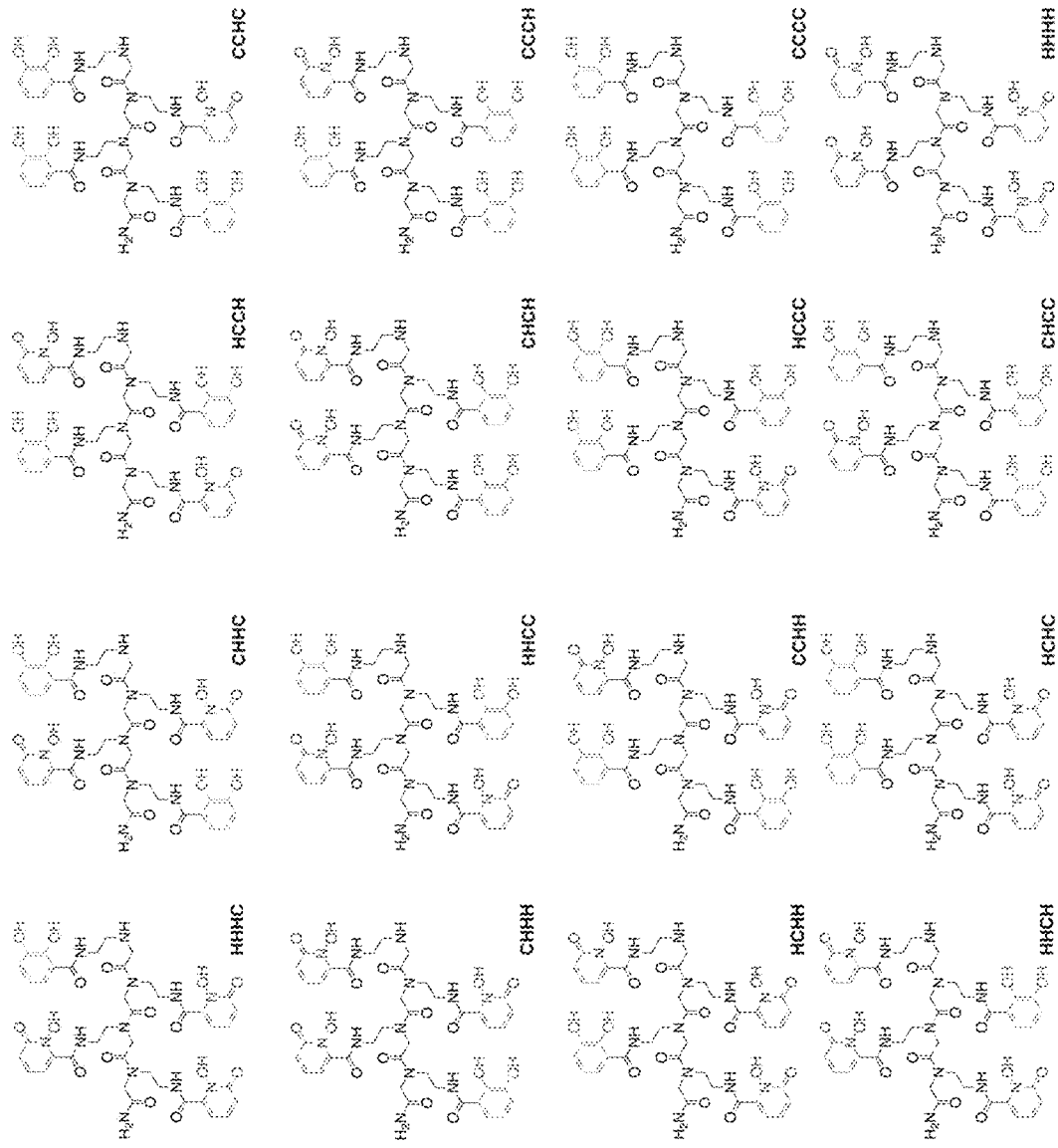
FIG. 38E depicts some embodiments of a combination of products obtained from a general peptoid synthesis scheme.

FIG. 38D depicts an embodiment of a general peptoid synthesis, where two different submonomer units are each used throughout two coupling steps. The submonomer units can comprise a 1,2-HOPO or CAM chelating functionality linked to a primary amine through an ethylene bridge to allow for coupling to the peptoid scaffold. The particular embodiment depicts the "CHHC" peptoid ligand, which incorporates directionally from the rink amide resin a CAM, two HOPO, and a CAM chelating units available for metal binding.

FIG. 38E depicts an embodiment of the 16 products obtained from a general peptoid synthesis, where two different submonomer units are used throughout four coupling steps. The submonomer units comprise a 1,2-HOPO or CAM chelating functionality linked to a primary amine through an ethylene bridge to allow for coupling to the peptoid scaffold. The modularity of the scaffold allows for the preparation of up to 16 possible tetrapeptoid, octadentate ligands, with zero, one, two, three, or four HOPO or CAM chelating units available for metal binding.

Figure 38F:
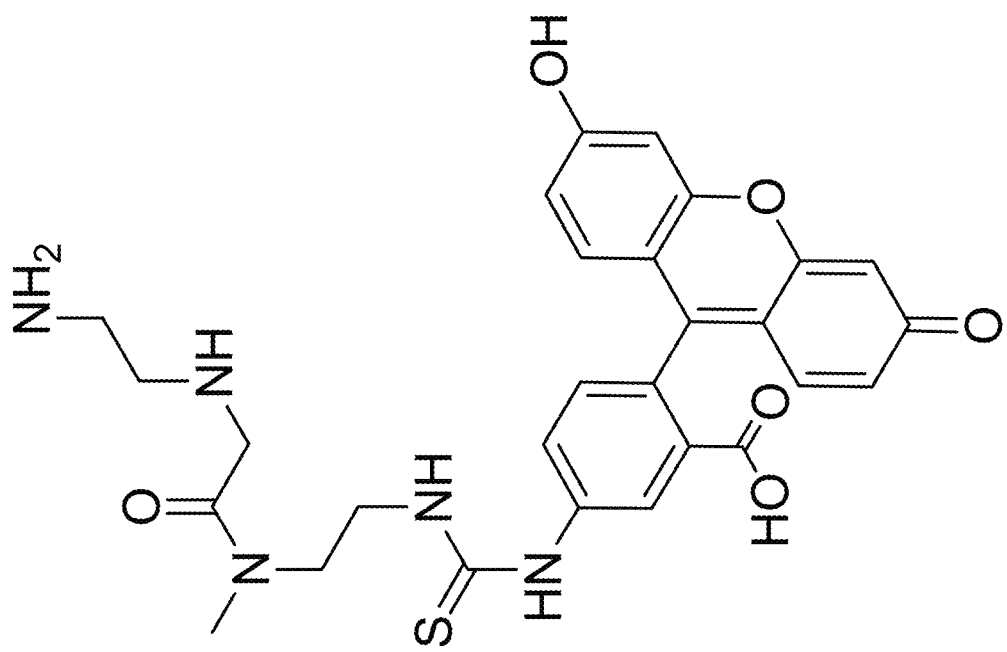
FIG. 38F depicts some embodiments of a fluorescent tag.

FIG. 38F depicts an embodiment of an organic fluorophore, FITC, that can be used as a fluorescent tag. The tag, similarly to the majority of well-characterized commercially-available fluorophores, can be incorporated onto the peptoid structures through standard amine coupling conditions, using its available primary-amine-reactive isothiocyanate functionality.

Figure 39A:
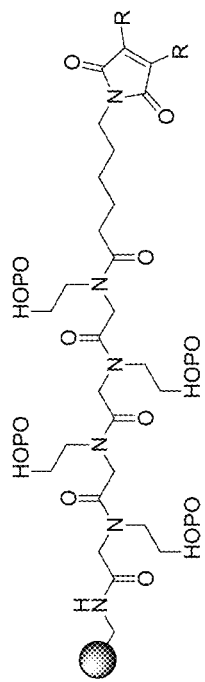
FIG. 39A depicts some embodiments of a conjugation pathway.
Figure 39A:
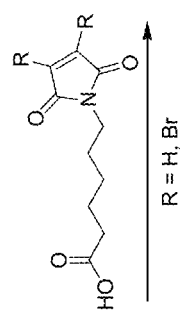
Figure 39A:
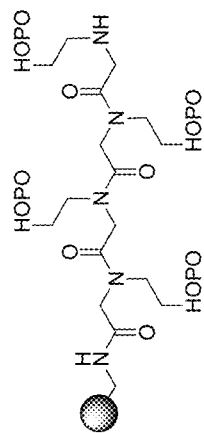

FIG. 39A depicts an embodiment of a conjugation pathway for attachment to biologically-relevant targeting molecules, solid resins, or nanoparticles, that contain thiol reactive sites (such as those in cysteine residues). A maleimide or dibromo-maleimide functionality can be attached to the peptoid ligands through standard amide coupling conditions as a subsequent step following the addition of the last chelating submonomer. This embodiment specifically depicts the functionalization of the available peptoid secondary amine by a carboxylic group linked to maleimide or di-bromomaleimide groups through an alkyl chain. In this case, the alkyl chain comprises 5 carbons, but its length can vary from 2 to 10 carbon atoms.

Figure 39B:
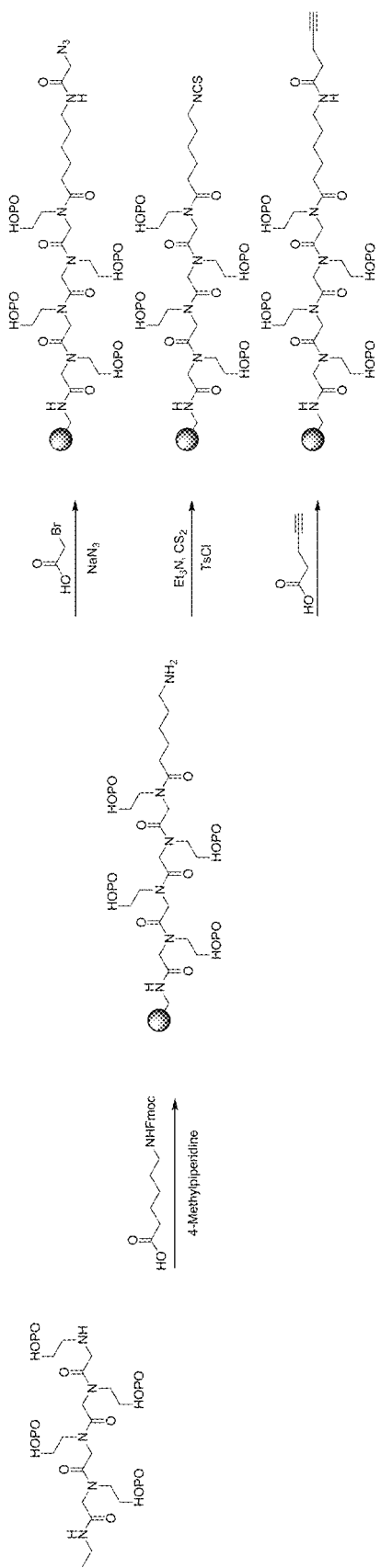
FIG. 39B depicts some embodiments of a conjugation pathway.

FIG. 39B depicts an embodiment of conjugation pathways that use click chemistry methods for attachment to biologically-relevant targeting molecules, solid resins, or nanoparticles. A functionality comprising of isothiocyanate, azide, or alkyne, can be attached to the peptoid ligands through standard amide coupling conditions as a subsequent step following the addition of the last chelating submonomer. This embodiment specifically depicts the addition of an available peptoid primary amine linked to the scaffold through an alkyl chain and its subsequent reaction to form the isothiocyanate, azide, or alkyne moiety. In this case, the alkyl chain comprises 5 carbons, but its length can vary from 2 to 10 carbon atoms.

Figure 40A:
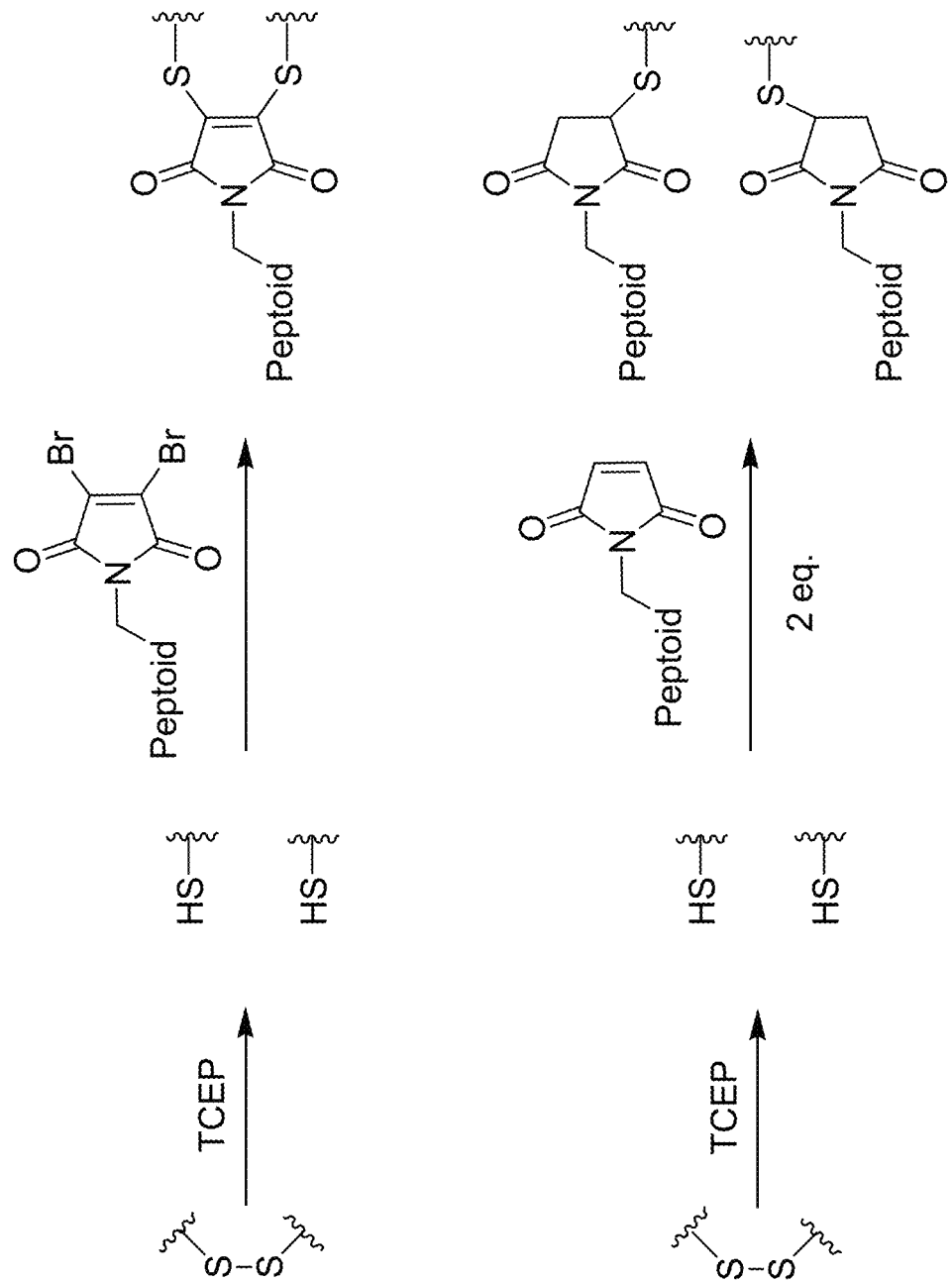
FIG. 40A depicts reaction schemes for conjugation.

FIG. 40A depicts reaction schemes for the conjugation of maleimide- or dibromomaleimide-substituted peptoids to the disulfide bridges available on antibodies. Reduction of the disulfide bridges results in the formation of thiol functionalities on the targeting antibodies, which then readily react with the substituted peptoid.

Figure 40B:
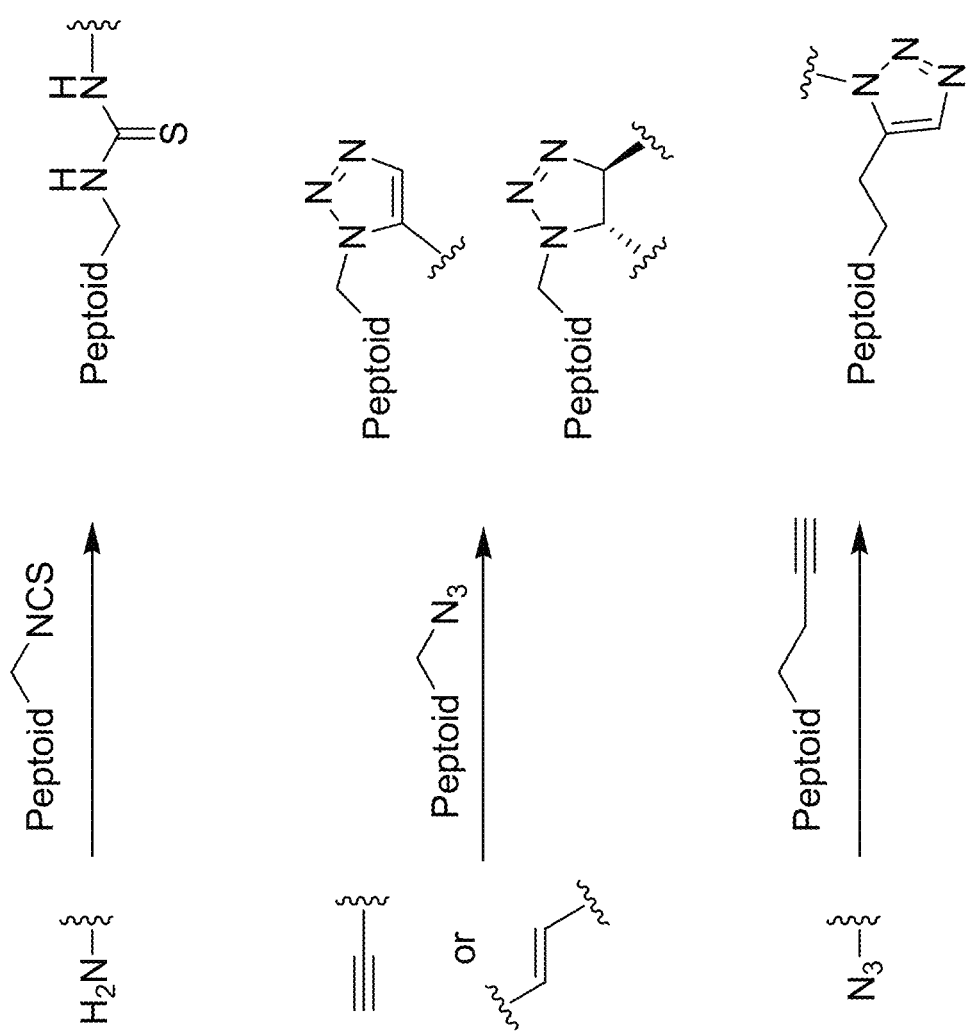
FIG. 40B depicts reaction schemes for a conjugation.

FIG. 40B depicts the reaction schemes for the conjugation of isothiocyanate- or azide-substituted peptoids to antibody substitutions sites through standard click chemistry methods.

Figure 40C:
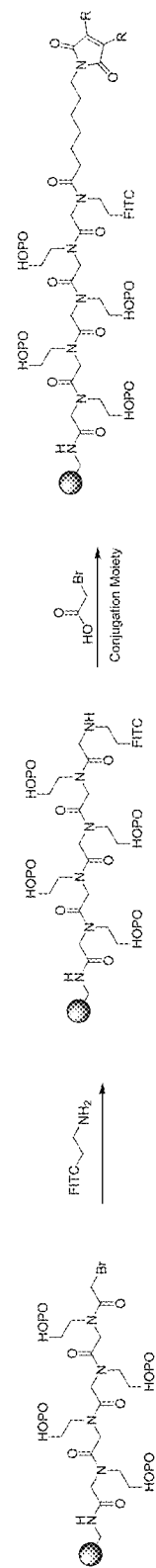
FIG. 40C depicts some embodiments of a fluorescent tag incorporation.

FIG. 40C depicts some embodiments of a fluorescent tag incorporation. A fluorophore can be attached to the peptoid ligands through standard amide coupling conditions as a subsequent step following the addition of the last chelating submonomer. This embodiment specifically depicts the functionalization of the peptoid through additional bromo-acetylation and displacement steps with the FITC fluorophore that is substituted with a primary amine through an alkyl chain. In this case, the alkyl chain comprises 2 carbons, but its length can vary from 2 to 10 carbon atoms. Any fluorophore can be used in some embodiments.

Ultra-Selective Ligand-Driven Separation of Metal Cations

Isotope production has been the cornerstone of many research fields and applications throughout the last century (NSAC Isotopes Subcommittee. *Meeting isotope needs and capturing opportunities for the future: the* 2015 *long range plan for the DOE-NP isotope program.* 1-160 (US DOE, 2015)) and relies largely on separation science. Contemporary examples illustrating the primary importance of separations include radionuclide purification for use in radiopharmaceuticals (Hagemann, U. B. et al. In Vitro and In Vivo Efficacy of a Novel CD33-Targeted Thorium-227 Conjugate for the Treatment of Acute Myeloid Leukemia. *Mol. Cancer Therapeutics* 15, 2422-2431 (2016)) or in radioactive thermoelectric generators that are vital to space exploration (Witze, A. Nuclear power: Desperately seeking plutonium. *Nature News* 515, 484-486 (2014)). The development of efficient separation methods is also critical for forensics analysis, recycling of ageing weapon materials, fabrication of nuclear fuels (Veliscek-Carolan, J. Separation of actinides from spent nuclear fuel: A review. *J. Hazard.*

Mater. 318, 266-281 (2016)), production of radiotracers for research (Roberto, J. B. et al. Actinide targets for the synthesis of super-heavy elements. *Nucl. Phys. A* 944, 99-116 (2015)), as well as manufacturing of high-purity actinide targets for the discovery of new elements (Oganessian, Y. T. et al. Experimental studies of the 249 Bk+48 Ca reaction including decay properties and excitation function for isotopes of element 117, and discovery of the new isotope 277 Mt. *Phys. Rev.* C 87, (2013)). Regardless of the application, product purity must be as high as possible, which requires highly efficient and cost-effective separation methods. Radionuclide production through either target irradiation ($^{225}$Ac, $^{177}$Lu, $^{90/86}$Y, $^{89}$Zr, $^{47/44}$Sc, $^{238}$PU, $^{248}$Cm, $^{249}$Bk, $^{249/252}$Cf, etc.) or milking from long-lived sources ($^{227}$Ac→$^{227}$Th→$^{223}$Ra, $^{241}$Pu→$^{241}$Am, $^{233}$U→$^{229}$Th→$^{225}$Ra→$^{225}$Ac, $^{232}$Th→$^{212}$Pb, etc.) involves the handling of mixtures of metal ions where major impurities are often neighboring elements in the periodic table. In most cases, the ratio between the valuable element and impurities is extremely high (a few µg diluted in multi-g targets), rendering purification very challenging, albeit critical for the availability of the coveted isotope.

Most chemical purifications rely on chromatographic separations or liquid-liquid extraction methods or both, depending on the process scale and the desired specifications. These bi-phasic techniques are based on intrinsic interactions between metal ions and organic molecules dissolved in an organic diluent (liquid-liquid extraction) or grafted onto a solid matrix (chromatography). Ideally, these organic molecules (hereafter "extractants") are amenable to transfer ions of interest from one phase to another in a selective manner relative to impurities. Extractant performance is typically not predictable and not always transposable from one separation system to another. In fact, predicting the efficiency and metal selectivity of a given process formulation (aqueous phase, diluent, and extractant) is a scientific challenge with numerous correlated variables (Beltrami, D. et al. Recovery of Uranium from Wet Phosphoric Acid by Solvent Extraction Processes. *Chem. Rev.* 114, 12002-12023 (2014); Leydier, A. et al. Recovery of uranium (VI) from concentrated phosphoric acid using bifunctional reagents. *Hydrometallurgy* 171, 262-266 (2017)) such as metal speciation in the aqueous phase, metal-extractant compound speciation in the organic phase, free extractant speciation, influence of the diluent, loading capacity of the organic phase, etc. Most extractants currently used in hydrometallurgy can potentially co-extract multiple elements depending on chemical conditions (acidity, extractant concentration, phase ratio . . . ) (Zhu, Z.-X., Sasaki, Y., Suzuki, H., Suzuki, S. & Kimura, T. Cumulative study on solvent extraction of elements by N,N,N',N'-tetraoctyl-3-oxapentanediamide (TODGA) from nitric acid into n-dodecane. *Anal. Chim. Acta* 527, 163-168 (2004); Horwitz, E. P. & Bloomquist, C. A. A. Chemical separations for super-heavy element searches in irradiated uranium targets. *J. Inorg. Nucl. Chem.* 37, 425-434 (1975); Cary, S. K. et al. Advancing Understanding of the +4 Metal Extractant Thenoyltrifluoroacetonate (TTA−); Synthesis and Structure of $M^{IV}$ TTA$_4$ ($M^{IV}$=Zr, Hf, Ce, Th, U, Np, Pu) and $M_{III}$ (TTA)$_4$_($M_{III}$=Ce, Nd, Sm, Yb). *Inorg. Chem.* 57, 3782-3797 (2018)). Separation selectivity is only achieved by finely tuning those chemical conditions and operational conditions for these processes are generally highly constrained, with many required steps to reach desired purities.

Metal ion separations are critical to numerous fields, including nuclear medicine, waste recycling, space exploration, and fundamental research. Nonetheless, operational conditions and performance are limited, imposing compromises between recovery, purity, and cost. Siderophore-inspired ligands show unprecedented charge-based selectivity and compatibility with harsh industry conditions, affording excellent separation efficiency, robustness and process control.

In order to overcome these challenges, in some embodiments, a class of hydroxypyridinone (HOPO) chelators was investigated for its high metal-binding selectivity and applicability to separation needs. In some embodiments, these molecules exhibit a unique combination of properties long sought in separation science: i) water-solubility, ii) structures consisting of solely H, C, N, and O atoms, iii) ability to control metal oxidation states without additional redox-active species iv) extremely high charge-based selectivity, and v) high metal-ligand complex stability even in strong acid (up to 10 M H+).

In some embodiments, using the model octadentate HOPO chelator, 3,4,3-LI(1,2-HOPO) (hereafter "343HOPO"), and taking advantage of these unprecedented characteristics, highly efficient and robust chemical separation processes were developed for three strategic examples: the purification of $^{225}$Ac, Pu-isotopes, and $^{249}$Bk.

In some embodiments, provided herein is a general separation strategy on three distinct systems, for Ac (Example 20), Pu (Example 21 and Example 22), and Bk (Example 23 and Example 24) purification.

In some embodiments, separation factors (SF) obtained with model compound 3,4,3-LI(1,2-HOPO) are orders of magnitude higher than with any other ligand currently employed: $10^6$ between Ac and relevant metal impurities (Example 20), and over $10^8$ for redox-free Pu purification against uranyl ions and trivalent actinides or fission products (Example 21 and Example 22). In some embodiments, a one-step separation method (SF>$3\times10^6$ and radiopurity>99.999%) enables the isolation of Bk from adjacent actinides and fission products (Example 23 and Example 24). Without being limited by any particular theory, the approach offers a paradigm change for the production of strategic elements.

In some embodiments, the purification systems described herein can be applied to any metal. In some embodiments, the purification systems described herein can be applied to any divalent, trivant, and/or tertravelanet metal.

In some embodiments, the purification systems described in Examples 20-24 can be applied to any metal. In some embodiments, the purification systems described in Examples 20-24 can be applied to any divalent, trivant, and/or tertravelanet metal.

In some embodiments, the separation factor for any of the purification sysmtes described herein ranges from about 1000 to about 1,000,000,000. In some embodiments, the separation factor for any of the purification sysmtes described herein is about 500, 1,000, 5,000, 10,000, 50,000, 100,000, 500,000, 1,000,000, 5,000,000, 10,000,000, 50,000,000, 100,000,000, 500,000,000 or 1,000,000,000 or a value within a range difned by any two of the aforementioned values.

In some embodiments, the separation factor for the purification sysmtes described in Examples 20-24 ranges from about 1000 to about 1,000,000,000. In some embodiments, the separation factor for any of the purification sysmtes described herein is about 500, 1,000, 5,000, 10,000, 50,000, 100,000, 500,000, 1,000,000, 5,000,000, 10,000,000, 50,000,000, 100,000,000, 500,000,000 or 1,000,000,000 or a value within a range difned by any two of the aforementioned values.

EXAMPLES

The following examples are non-limiting and other exemplary variants as contemplated by one of ordinary skill in the art are acceptable.

Example 1

HDEHP was 95% pure and received from Merck and dissolved in kerosene to form an organic stock solution of 0.5 M HDEHP. Sodium nitrate (99%) was purchased from Alfa Aesar and dissolved in Milli-Q water to form a stock of 5.168 M. Gd(III) chloride hexahydrate was purchased from Aldrich at a purity of 99.999% and dissolved in 0.1 M nitric acid to for a 5.0 mM stock solution. Nitric acid was purchased from BDH at 70% concentration. Racemic sodium lactate was purchased from Sigma Aldrich at a purity of 99%. Stock solutions of DTPA (98%, Tokyo Chemical Industry) were made by dissolving the solid acid in water and adjusting the pH to 5.4 by 37% NaOH. 3,4,3-LI(1,2-HOPO) was prepared by Synthetech, Inc using previously reported proceduresii, 12. The HOPO monomer, 98% pure and purchased from Tokyo Chemical Industry, was dissolved in Milli-Q water. One mCi of 225-Ac(NO$_3$)$_3$ dissolved in 50 µL of 50 mM HCl was received from Oak Ridge National Lab at a purity of 99%. 326.85 µCi of Gd-153 was received from Oak Ridge National Laboratory and dissolved in 1.0 M HCl. CmCl$_3$ used for the experiments was 95.78% 248-Cm, 4.12% 246-Cm, 0.06% Cm-245, 0.02% Cm-244/Cm-247 by isotopic distribution.

All liquid-liquid extractions were conducted using a 1:1 organic to aqueous phase ratio for a total volume of 1 mL. Samples were pH adjusted by HNO$_3$ and prepared for a final concentration of 1.0 M sodium lactate, 40 mM of hold-back reagent (160 mM in the case of the HOPO monomer), and 2.0 M Na$^+$. The concentration of the trivalent f-element was dependent on the availability and radioactivity of the isotopes. The organic phase consisted of 0.5 M HDEHP in kerosene. All samples were incubated in a thermostatic shaker held at 28° C. and rocked at 280 rpm for 90 minutes. To ensure complete phase separation, samples were left overnight at room temperature to equilibrate. Radioactive samples were analyzed by liquid scintillation counting (LSC). The analytical protocol consisted of diluting 10 uL of radioactive sample into 10 mL of Ultima Gold™. Ultima Gold™ is a commercially available analytical reagent commonly used for LSC. The resulting analytical samples were shaken for 10 min prior to counting on a Perkin-Elmer Packard Tri-Carb instrument (model B4430).

Data was analyzed by the distribution ratio ($D_m$), separation factor ($SF_{m1/m2}$) and extraction percentage (% Extraction) as defined by Equations (6), (7) and (8), respectively. Equation (8) uses concentrations of the metal in each phase since the aqueous: organic ratio was 1. Both the organic and aqueous phases were analyzed after liquid-liquid extraction and phase separation. These calculation methods rely on the assumptions that no metal (M) is lost to sorption or precipitation and that no volume variation occurred during the mass transfer between the aqueous and organic phases.

$$D_m = \frac{[M]_{f.org}}{[M]_{f.aq}} = \frac{[M]_{i.aq} - [M]_{f.aq}}{[M]_{f.aq}} \quad (6)$$

$$SF_{m1/m2} = \frac{D_{m1}}{D_{m2}} \quad (7)$$

$$\% \text{ Extraction} = \frac{[M]_{f.org}}{[M]_{i.aq}} = \frac{[M]_{i.aq} - [M]_{f.aq}}{[M]_{i.aq}} = 1 - \frac{[M]_{f.org}}{[M]_{i.aq}} \quad (8)$$

The results are shown in FIGS. 11 and 12.

Example 2

Series of liquid-liquid extraction experiments were first performed with the radionuclide actinium-225. Actinium is the lightest element of the actinide series and its chemistry was expected to be similar to that of americium and curium because the three elements exhibit the same oxidation state in solution: Ac(III), Am(III), and Cm(III) but with ionic radii of 1.26 Å, 1.115 Å, and 1.11 Å,$_7$ respectively. The main difference among Ac, Am and Cm is that the only isotopes of actinium available for bulk chemistry (Ac-225 and Ac-227) are short-lived isotopes ($t_{1/2}$=9.95 days and 21.8 years, respectively) whereas long-lived isotopes of americium and curium are available for research purposes ($t_{1/2}$=7, 388 years for Am-243 and 3.5×10$_5$ years for Cm-248). The practical consequence is that samples of Ac-225 are far more radioactive that the corresponding Am-243 and Cm-248 samples. So far, no data have been published on the behavior of actinium in the TALSPEAK process.

The behavior of Ac(III) was probed during liquid-liquid extraction conditions similar to that of TALSPEAK and compare it to Am(III) and Gd(III). Gd(III) was used as a surrogate for Eu(III) and was expected to behave similarly based on the similarity in ionic radii of 1.08 Å and 1.09 Å for Gd(III) and Eu(III), respectively.$_7$ Graphs summarizing the extraction of Ac, Am, and Gd are shown in FIG. 8 and FIG. 26 for DTPA and 3,4,3-LI(1,2-HOPO), respectively.

FIG. 8 shows the extraction profile of Ac(III)-225, Am(III)-243, and Gd(III) (with [Gd(III)-153]=0.21 nM) with DTPA as the hold-back reagent. [Ac(III)-225]=0.4 nM, [Gd(III)]=500 µM, [Am(III)-243]=40.4 nM. Selective extraction of Gd(III) at pH 3-4 was observed, just as expected for this system under TALSPEAK conditions. FIG. 26 shows extraction profile of Ac(III)-225, Am(III)-243, and Gd(III) (with [Gd(III)-153]=0.21 nM) with 3,4,3-LI(1,2-HOPO) as the hold-back reagent. [Ac(III)-225]=0.4 nM, [Gd(III)Total]=500 µM, [Am(III)-243]=40.4 nM. In this case, evidence for the selective extraction of Ac(III) over Gd(III) and Am(III)-243 was seen.

The separation factors of Ac(III)/M(III) (M=Am, Gd) are compared for DTPA and 3,4,3-LI(1,2-HOPO) in TABLE 2. A comparison of the behavior between Am and Gd for 3,4,3-LI(1,2-HOPO) is provided in FIG. 19, which shows the extraction profile for Gd(III) and Am(III) along with the separation factor are plotted at various pH. Selective extraction for Gd(III) was observed at pH 1-2.5.

Example 3

Figure 18:
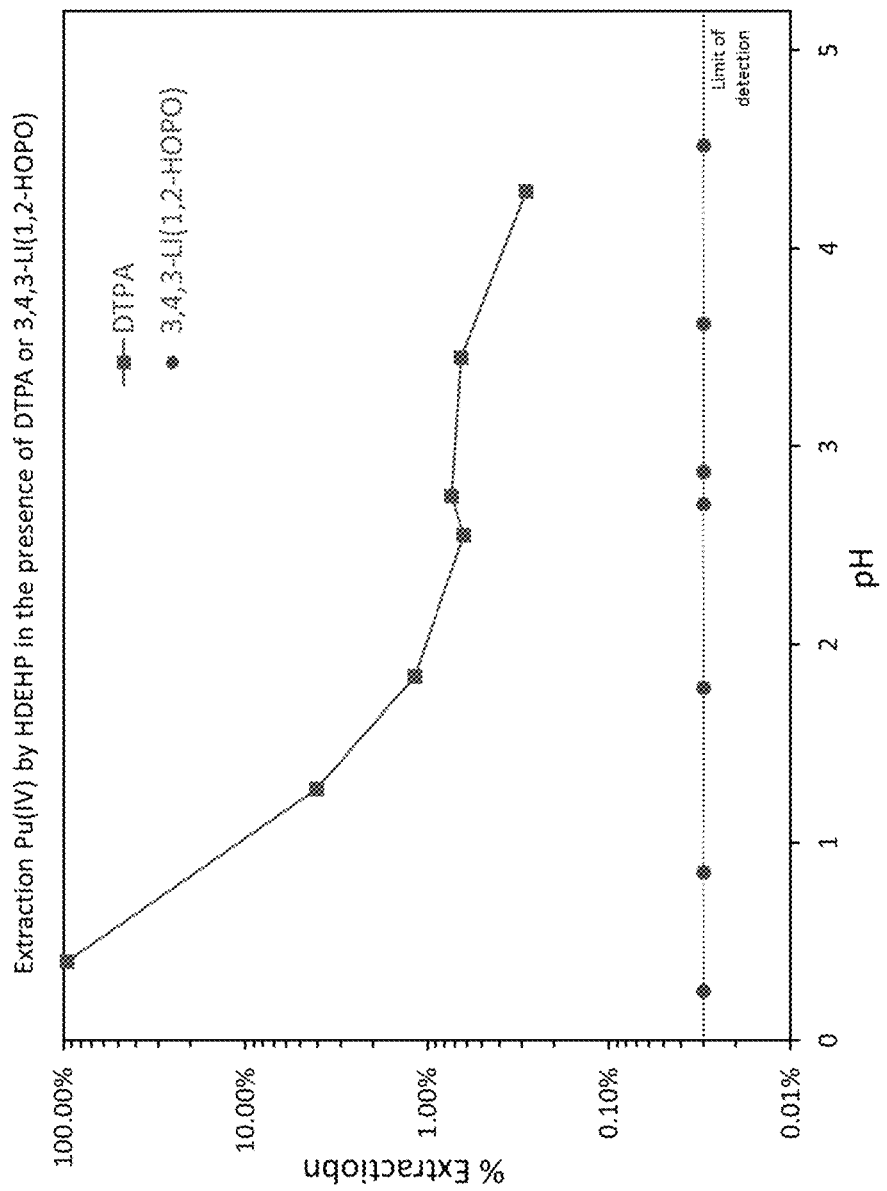
FIG. 18 shows percentage of extraction of plutonium(IV) as a function of pH. For clarity, a logarithm scale is used on the Y-axis.

FIG. 18 shows that, in the presence of 3,4,3-LI(1,2-HOPO), the extraction capacity of HDEHP is totally suppressed and that no Pu$^{4+}$ is transferred into the organic phase. Literally no activity was detected in the organic phase after extraction meaning that the [Pu(IV)3,4,3-LI(1,2-HOPO)] is too stable to be challenged by HDEHP. FIG. 18 shows percentage of extraction of plutonium(IV) as a function of pH, i.e., extraction yields obtained for tetravalent plutonium ions from nitric media in the presence of 3,4,3-LI(1,2-HOPO). The extractant used in this example was HDEHP since this commercially available molecule is very common in the nuclear chemistry field and in hydrometallurgy processes. See, K. L. Nash, The Chemistry of TALSPEAK: A Review of the Science, Solvent Extr. Ion Exch. 33 (2015) 1-55. doi:10.1080/07366299.2014.985912. Similar experiments were also performed with DTPA instead of 3,4,3-LI(1,2-HOPO) since DTPA is often taken as a reference chelator for actinide ions. Note that the plutonium(IV) case was studied here because it is a good chemical surrogate for thorium(IV) and because of the availability of Pu-242 in our laboratory. Pu-242 ($t_{1/2}$=3.7×10$^5$ y) was also more convenient to analyze by liquid scintillation counting than the natural and long-lived isotope of thorium (Th-232; $t_{1/2}$=1.4×10$^{10}$ y).

A value of 0.03% was plotted on FIG. 18, which corresponds to our instrumental detection limit under the tested conditions, but this extraction yield has to be taken as an upper limit for Pu$^{4+}$.

In contrast, when DTPA is present in the aqueous phase, Pu$^{4+}$ ions are extracted with an increase in the extraction yield from 0.30 to 95.2% when the pH decreases from 4.2 to 0.4 due to the release of Pu$^{4+}$ by DTPA (FIG. 18). These results clearly show that DTPA cannot be used to hold-back Pu$^{4+}$ in the aqueous phase.

In the case of 3,4,3-LI(1,2-HOPO), the ligand affords a total sequestration of Pu$^{4+}$ in the aqueous phase. Based on the solution thermodynamics data (FIG. 20), a similar behavior is expected in the case of the other tetravalent ions such as Zr$^{4+}$, Ce$^{4+}$, and Th$^{4+}$.

Figure 23:
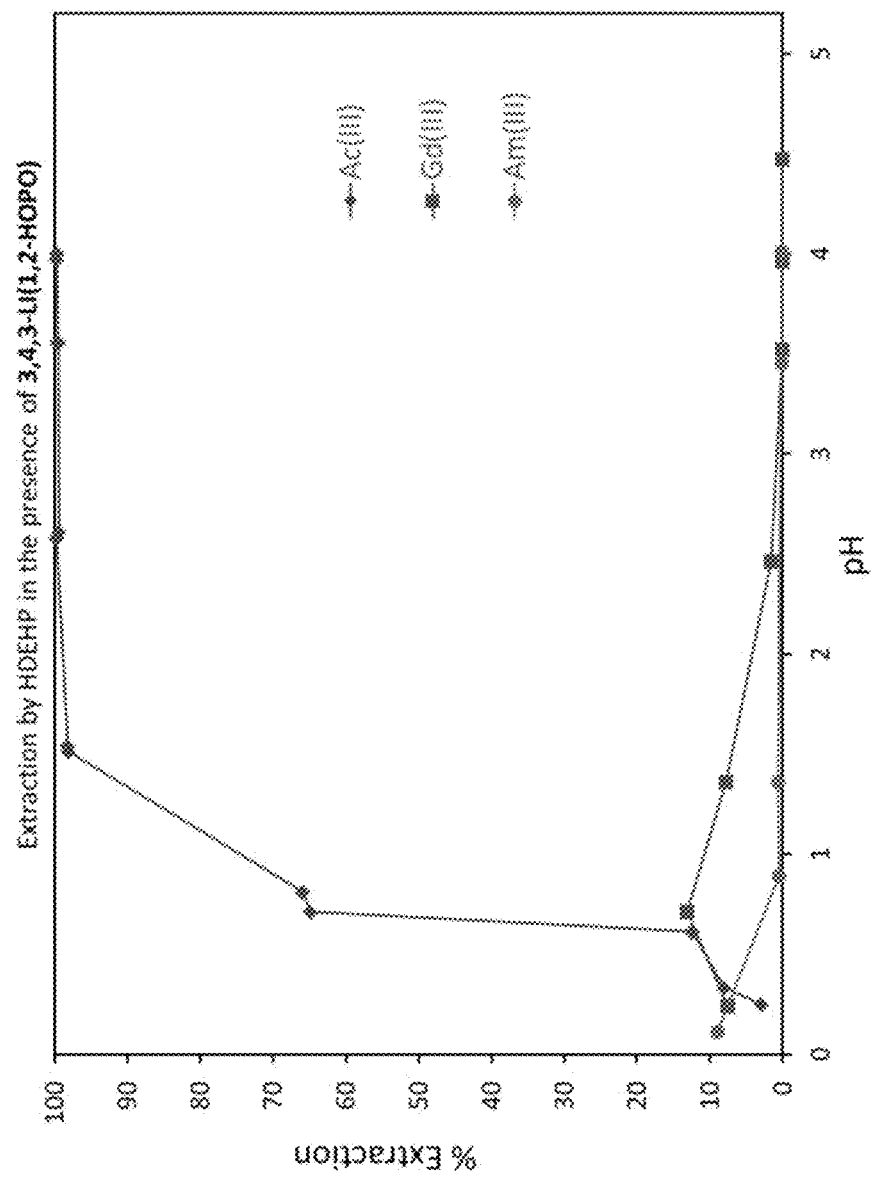
FIG. 23 shows percentage of extraction as a function of pH for trivalent actinium, americium and, gadolinium ions (Ac(III)-225, Am(III)-243, and Gd(III)-153, respectively) in the presence of 3,4,3-LI(1,2-HOPO) as hold-back reagent.

In FIG. 23, aqueous phase: [ligand]=40 mM, buffer sodium lactate/sodium nitrate. Organic phase: [HDEHP]= 0.5 M, kerosene diluent. T=25° C. O/A=1, one contact. Initial metal concentrations: [Ac-225]=0.4 nM, [Am-243]= 40.4 nM, or [Gd]=500 µM (spiked with Gd-153 for LSC measurements). For actinium, data acquired in the absence or presence of 500 µM of Eu(III) did not show any significant influence on the extraction yields.

FIG. 23 shows percentage of extraction as a function of pH for trivalent actinium, americium and, gadolinium ions in the presence of 3,4,3-LI(1,2-HOPO), i.e., extraction yields obtained for the trivalent ions Ac$^{3+}$, Gd$^{3+}$ and, Am$^{3+}$ using 3,4,3-LI(1,2-HOPO) and chemical conditions similar to those described above for Pu$^{4+}$. The equation for release from the ligand is given by Equation (4) main phase transfer equation for trivalent ions and HDEHP is given by Equation (5). See, K. L. Nash, The Chemistry of TALSPEAK: A Review of the Science, Solvent Extr. Ion Exch. 33 (2015) 1-55. doi:10.1080/07366299.2014.985912. At pH below 1, low extraction yields are obtained due the protonation of HDEHP which competes with the extraction of the trivalent ions. See, K. L. Nash, The Chemistry of TALSPEAK: A Review of the Science, Solvent Extr. Ion Exch. 33 (2015) 1-55. doi:10.1080/07366299.2014.985912; K. V. Lohithakshan, P. Patil, S. K. Aggarwal, Solvent extraction studies of plutonium(IV) and americium(III) in room temperature ionic liquid (RTIL) by di-2-ethyl hexyl phosphoric acid (HDEHP) as extractant, J. Radioanal. Nucl. Chem. 301 (2014) 153-157. doi:10.1007/s10967-014-3119-9. This behavior is specific to the extractant HDEHP and is not a limitation to the present invention. Other extractants that work at low pH values, such as the tertiaryalkyl amines or alkylphophates, could be used in lieu of HDEHP.

Equation (4) (release from the ligand):

(4)

Equation (5) (extraction):

(5)

When 3,4,3-LI(1,2-HOPO) is present and for a pH higher than 1, Am$^{3+}$ and Gd$^{3+}$ ions are retained in the aqueous phase. This behavior was expected from the solution thermodynamic data in FIG. 20. A slight extraction of Gd$^{3+}$ ions is observed in the pH range 1-2 due to the release of Gd$^{3+}$ ions by 3,4,3-LI(1,2-HOPO). No extraction is observed for Am$^{3+}$ which is in line with the higher stability of the Am$^{3+}$ complex (See, M. Sturzbecher-Hoehne, P. Yang, A. D'Aldo, R. J. Abergel, Intramolecular sensitization of americium luminescence in solution: shining light on short-lived forbidden 5f transitions, Dalton Trans. (2016). doi:10.1039/C6DT00328A) when compared to the Gd$^{3+}$ complex (See, M. Sturzbecher-Hoehne, C. Ng Pak Leung, A. D'Aléo, B. Kullgren, A.-L. Prigent, D. K. Shuh, K. N. Raymond, R. J. Abergel, 3,4,3-LI(1,2-HOPO): In vitro formation of highly stable lanthanide complexes translates into efficacious in vivo europium decorporation, Dalton Trans. 40 (2011) 8340. doi:10.1039/cldt10840a). In the case of actinium, a quantitative extraction is observed at pH higher than 1.5 suggesting that the 3,4,3-LI(1,2-HOPO) complex of Ac$^{3+}$ is not stable enough to compete with the extraction by HDEHP (Equation (5)). This distinct behavior for Ac$^{3+}$ represents a powerful leverage for separation methods.

Combining the results in FIG. 18 and FIG. 23, it is clear that actinium can be selectively extracted from a mixture of trivalent lanthanide, trivalent actinide and, tetravalent ions when using 3,4,3-LI(1,2-HOPO) as a hold-back reagent. A one-step process would afford a direct and very selective extraction of actinium.

Example 4

Figure 16:
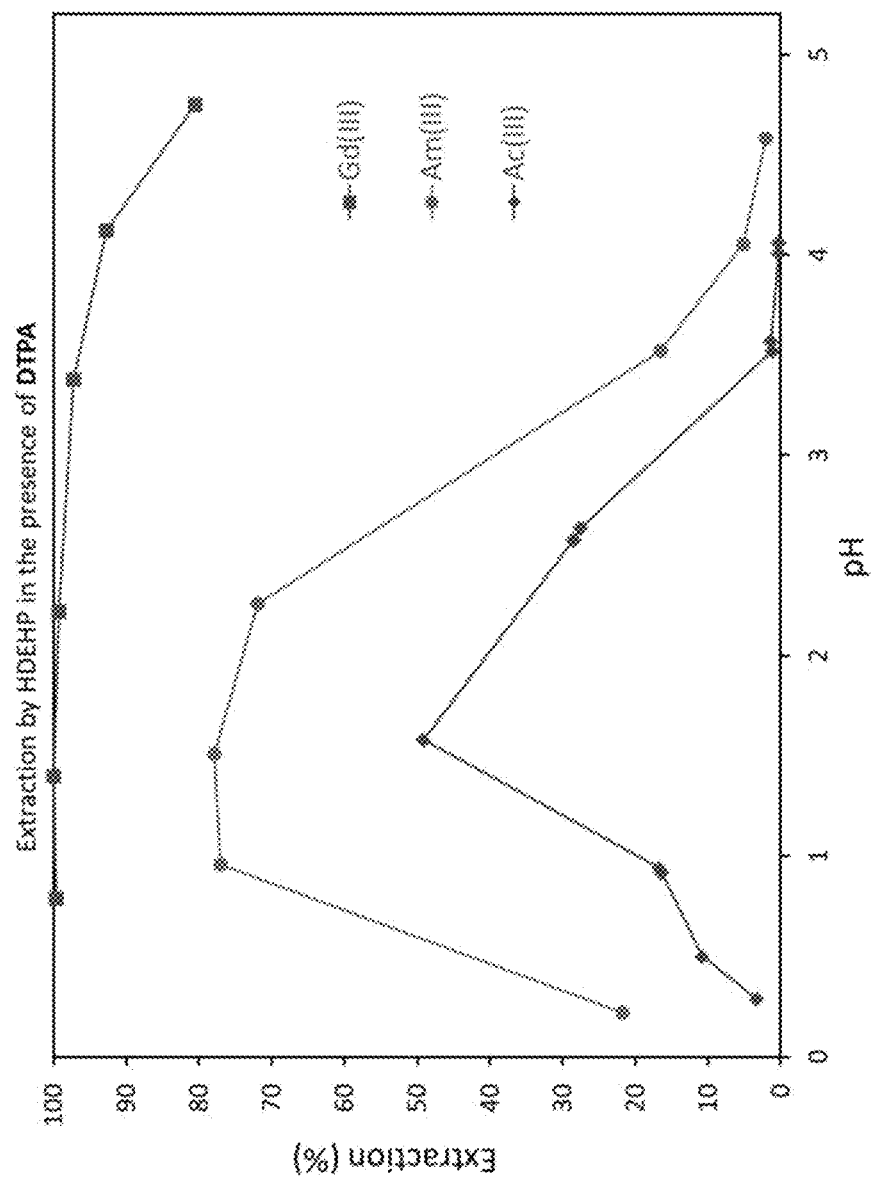
FIG. 16 shows percentage of extraction as a function of pH for trivalent Ac, Am and, Gd ions in the presence of DTPA as hold-back reagent.

The specificity of the 3,4,3-LI(1,2-HOPO) chelator for actinium was demonstrated. Similar experiments were performed for the DTPA ligand and the trivalent metal ions. FIG. 16 shows that DTPA is not strong enough to scavenge Ac$^{3+}$, Gd$^{3+}$ or Am$^{3+}$ ions in the aqueous phase. In FIG. 16 aqueous phase: [ligand]=40 mM, buffer sodium lactate/sodium nitrate. Organic phase: [HDEHP]=0.5 M, kerosene diluent. T=25° C. O/A=1, one contact. Initial metal concentrations: [Ac-225]=0.4 nM, [Am-243]=40.4 nM, or [Gd]= 500 µM (spiked with Gd-153 for LSC measurements). For actinium, data was acquired in the absence or presence of 500 µM of Eu(III) did not show any significant influence on the extraction yields. Therefore, actinium cannot be purified from a mixture of Ac$^{3+}$, Ln$^{3+}$ and An$^{3+}$ when using DTPA as a hold-back reagent because the metals would be partially extracted at the same time. The extraction yields for Ac$^{3+}$ are also not quantitative (under the conditions tested) and would lead to a partial recovery of Ac isotopes. Chelators of the DTPA family (i.e. carboxylic acids) that are commonly used in separation processes, such as EDTA, NTA and, DOTA, are likely to exhibit a similar non-selectivity toward actinium. For comparison purposes, the separation factors that would be obtained with the method proposed here are plotted in FIG. 17.

Figure 17:
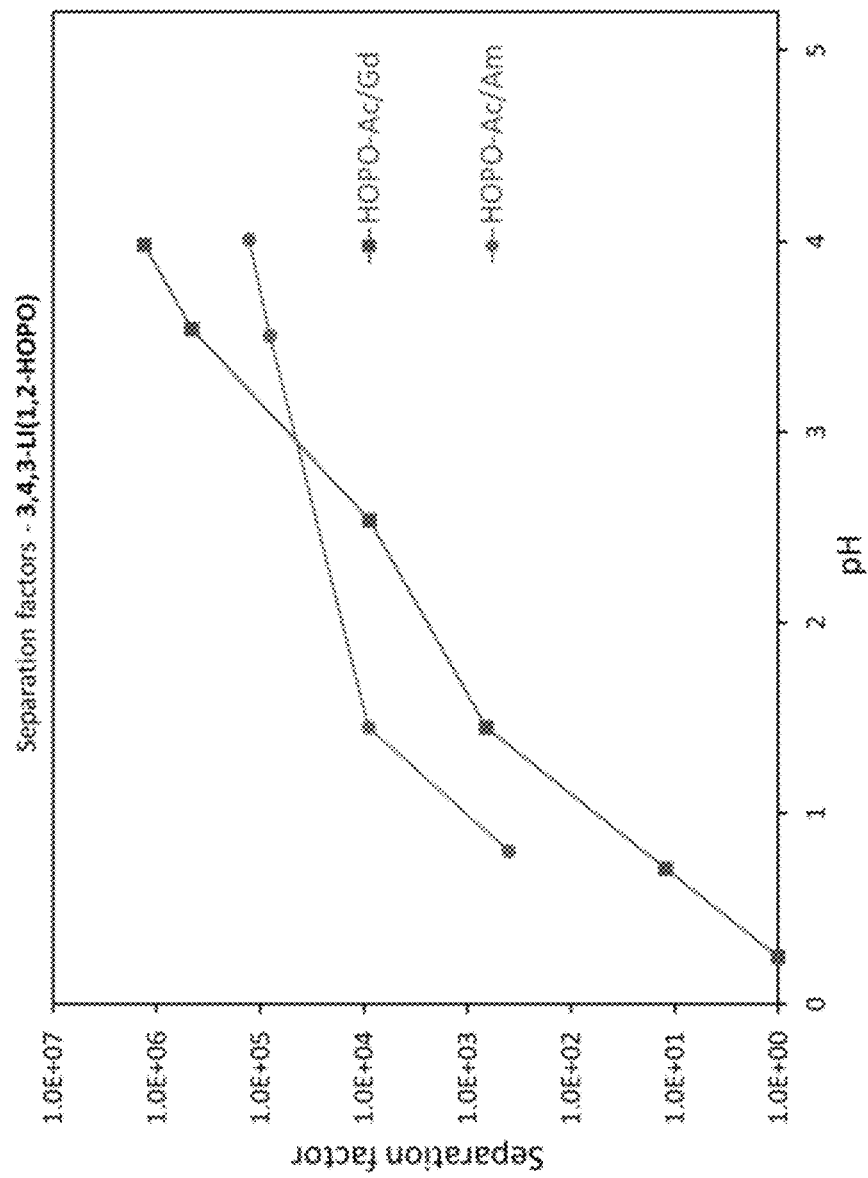
FIG. 17 shows calculated separation factors (Ac/Gd and Ac/Am) for a 1-step extraction using 3,4,3-LI(1,2-HOPO) as a hold-back reagent.

In FIG. 17, aqueous phase: [ligand]=40 mM, buffer sodium lactate/sodium nitrate, organic phase: [HDEHP]=0.5 M, kerosene diluent. T=25° C. O/A=1, one contact. Initial metal concentrations: [Ac-225]=0.4 nM, [Am-243]=40.4 nM, or [Gd]=500 µM (spiked with Gd-153 for LSC measurements). Separation factor=ratio $M_1/M_2$ in the final organic phase/ratio M1/M2 in the initial aqueous phase.

In FIG. 18, aqueous phase: [ligand]=40 mM, buffer sodium lactate/sodium nitrate, organic phase: [HDEHP]=0.5

M, kerosene diluent. T=25° C. O/A=1, one contact. Initial metal concentrations: [Pu-242]=5 µM. Phases analyzed after one contact. Contact time: 30 min. Limit of detection: 0.03% of the initial Pu-242 activity. Data for separation of tetravalent metal ions from trivalent metal ions using 3,4,3-LI(1,2-HOPO) as a hold-back reagent for tetravalent metal ions are shown in TABLE 0.1.

TABLE 0.1

Percentage of extraction of plutonium(IV) by HDEHP as a function of pH and using either diethylenetriaminepentaacetic acid (DTPA) or 3,4,3-LI(1,2-HOPO) as hold-back reagent

| Hold-back reagent | pH | Activity in organic phase (cpm) | Activity in aqueous phase (cpm) | % Extraction |
|---|---|---|---|---|
| DTPA | 0.40 | 4181 | 209 | 95.24% |
|  | 1.27 | 110 | 2585 | 4.08% |
|  | 1.84 | 35 | 2951 | 1.17% |
|  | 2.55 | 19 | 2995 | 0.63% |
|  | 2.75 | 23 | 3121 | 0.73% |
|  | 3.45 | 22 | 3379 | 0.65% |
|  | 4.29 | 10 | 3491 | 0.29% |
| 3,4,3-LI(1,2-HOPO) | 0.25 | 0 | 2791 | 0.00% |
|  | 0.85 | 0 | 3325 | 0.00% |
|  | 1.78 | 0 | 3310 | 0.00% |
|  | 2.71 | 0 | 3219 | 0.00% |
|  | 2.87 | 0 | 3339 | 0.00% |
|  | 3.62 | 0 | 3185 | 0.00% |
|  | 4.52 | 0 | 2896 | 0.00% |

Very high separation factors could be obtained between actinium and the lanthanides or actinides, after only 1 extraction step. The separation factors $Ac^{3+}/Pu^{4+}$ were not calculated since the extraction yield of $Pu^{4+}$ is null (FIG. 18) in the presence of 3,4,3-LI(1,2-HOPO), meaning a virtually infinite separation factor.

Thus, in some embodiments, the proposed method combines two essential features: (i) quantitative extraction for actinium, and (ii) a very high decontamination capability.

For DTPA extractions, the expected behavior of the system with selective extraction of Gd(III) at pH 3-4 under TALSPEAK conditions was observed. Below pH ~1.5 (FIG. 21), retention of Ac(III) and Am(III) in the aqueous phase was observed and corresponding to Equation (2), where the equilibrium lies to the left. Protonation of the extractant in the organic phase prevents metal complexation and does not necessarily indicate DTPA binding. In the speciation diagram in FIG. 8, free metal or nitrate complexes are expected to be present below pH 1. As pH increases in the extraction samples, the selectivity of DTPA begins to emerge with preferential binding to the Ac(III) and Am(III), while Gd(III) is extracted by HDEHP. Additionally, a high pH dependence of the process in the 2.5-3.5 pH range was observed and this can be attributed to the shift from the protonated metal complex to the proton independent complex, as modeled in FIG. 8.

Extraction of Gd(III) was above 90% until after pH 4, while for Ac(III) (49%) and Am(III) (78%) maximum metal extraction is around pH 1.5 and decreases to less than 10% at pH 4. Above pH 3.5, a decrease in extraction of Gd(III) is observed, hence the decrease in selectivity for the current TALSPEAK model.

Metals with larger ionic radii was expected to form weaker complexes relative to smaller metals. Therefore, higher retention of Am(III) (1.115 Å) relative to Ac(III) (1.26 Å) in the aqueous phase. However, the reverse was observed.

(2)

Based on the speciation diagram for 3,4,3-LI(1,2-HOPO) in FIG. 26, metal complexation was expected to persist even at low pH. However, the complete extraction of Ac(III) above pH 1.5 (FIG. 28) was unexpected and indicated relatively weak binding of Ac(III) by the HOPO chelator compared to DTPA.

Without being bound any particular theory, upon examining the structures of DTPA and 3,4,3-LI(1,2-HOPO), an argument can be made for the relative cavity limitations when binding metals. Each of the chelating moieties in 3,4,3-LI(1,2-HOPO) is bidentate and the ligand scaffold is not directly involved in metal binding. On the other hand, DTPA chelates through the three nitrogen atoms in the diethylenetriamine backbone and the five carboxylic acid groups, potentially giving it more flexibility in the size of metal it can chelate. 3,4,3-LI(1,2-HOPO) may be limited by the length of the scaffold and chelate a metal as large as Ac(III) less efficiently than a more flexible ligand like DTPA.

In FIG. 28, a striking contrast in the behavior of Ac(III) and Gd(III)/Am(III) was observed, where complete retention of Gd(III) and Am(III) is seen above pH 2.5. TABLE 2 helps accentuate the difference in the selective extraction of Ac(III) when using 3,4,3-LI(1,2-HOPO) and DTPA.

TABLE 2

Comparison of the separation factors for Ac(III)/M(III) (M = Am, Gd) for 3,4,3-LI(1,2-HOPO) and DTPA at various pH.

| pH* | HOPO | DTPA |
|---|---|---|
| $SF_{Ac/Gd}$ | | |
| 0.8 | $1.23 * 10$ | $<10^{-3}$ |
| 1.5 | $6.55 * 10^2$ | $<10^{-3}$ |
| 3.5 | $4.61 * 10^5$ | $<10^{-3}$ |
| 4.0 | $1.33 * 10^6$ | $<10^{-3}$ |
| $SF_{Ac/Am}$ | | |
| 0.9 | $3.99 * 10^2$ | $5.83 * 10^{-2}$ |
| 1.5 | $9.06 * 10^3$ | $2.70 * 10^{-1}$ |
| 3.5 | $8.13 * 10^4$ | $6.86 * 10^{-2}$ |
| 4.0 | $1.28 * 10^5$ | $1.11 * 10^{-1}$ |

The data in TABLE 2 show that Ac extraction is more selective when using 3,4,3-LI(1,2-HOPO) and the selectivity increases with increasing pH. pH values are ±0.1.

In some embodiments, DTPA conferred no selectivity between Ac and Gd(III)/Am(III), whereas with 3,4,3-LI(1,2-HOPO) selective extraction of Ac(III) was observed.

Figure 19:
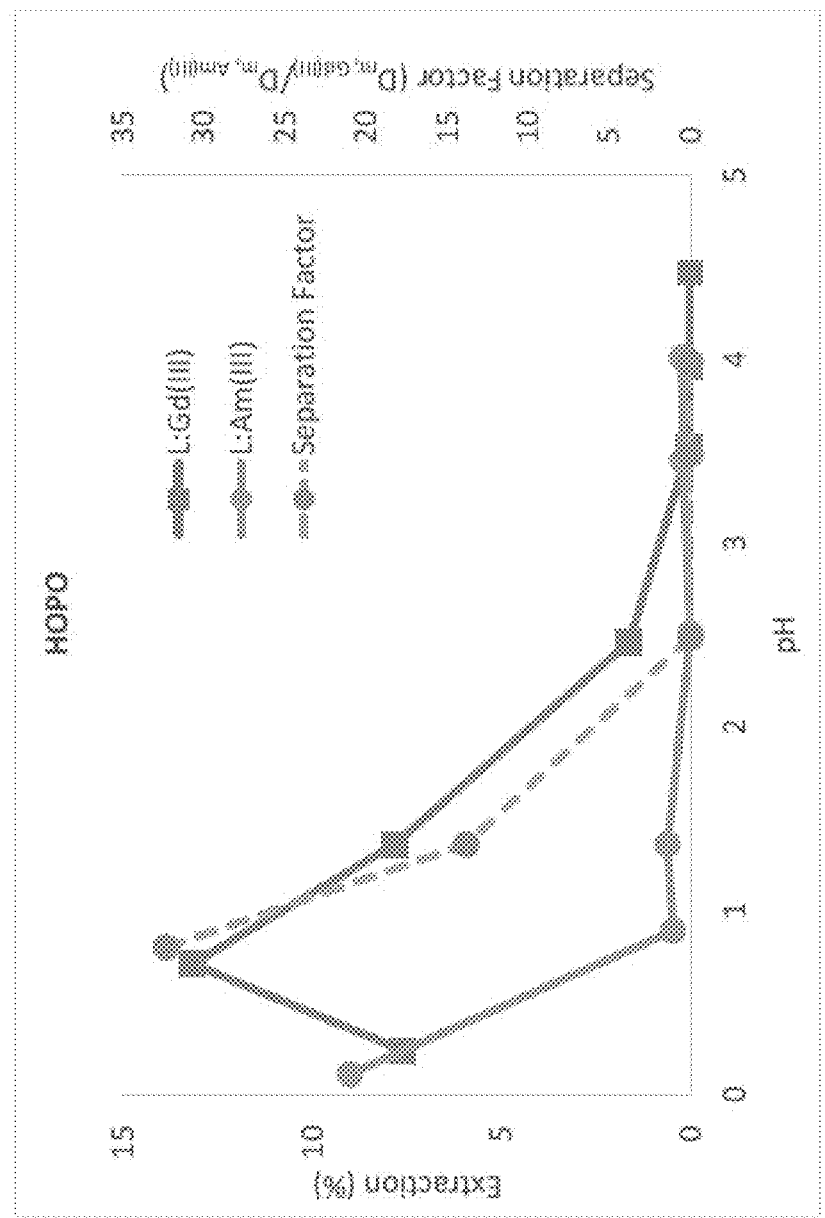
FIG. 19 shows extraction profile for Gd(III) and Am(III) along with the separation factor plotted at various pH with 3,4,3-LI(1,2-HOPO) as hold-back reagent.

As previously mentioned, 3,4,3-LI(1,2-HOPO) was expected to form complexes at lower pH and a DTPA-like extraction profile shifted to lower pH regions was expected. Low extraction of Gd(III) and Am(III) (FIG. 19) was observed even at pH below 1, and slight increase at pH slightly above 1, where the latter corresponds to the deprotonation of HDEHP and extraction of the metal as in Equation (2). FIG. 19 shows selective extraction for Gd(III) is observed at pH 1-2.5.

As in the DTPA system, higher affinity to metals at higher pH was observed and reached almost complete extraction above pH 2.5. The equilibria of the process are described by Equation (3), where the protonated complex is the primary species in solution. Gd(III) selective extraction over Am(III) is seen at pH 1-2.5 and albeit a small difference under the current conditions it serves as evidence for selective extraction of Gd(III).

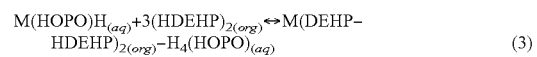

(3)

Example 5

Figure 27:
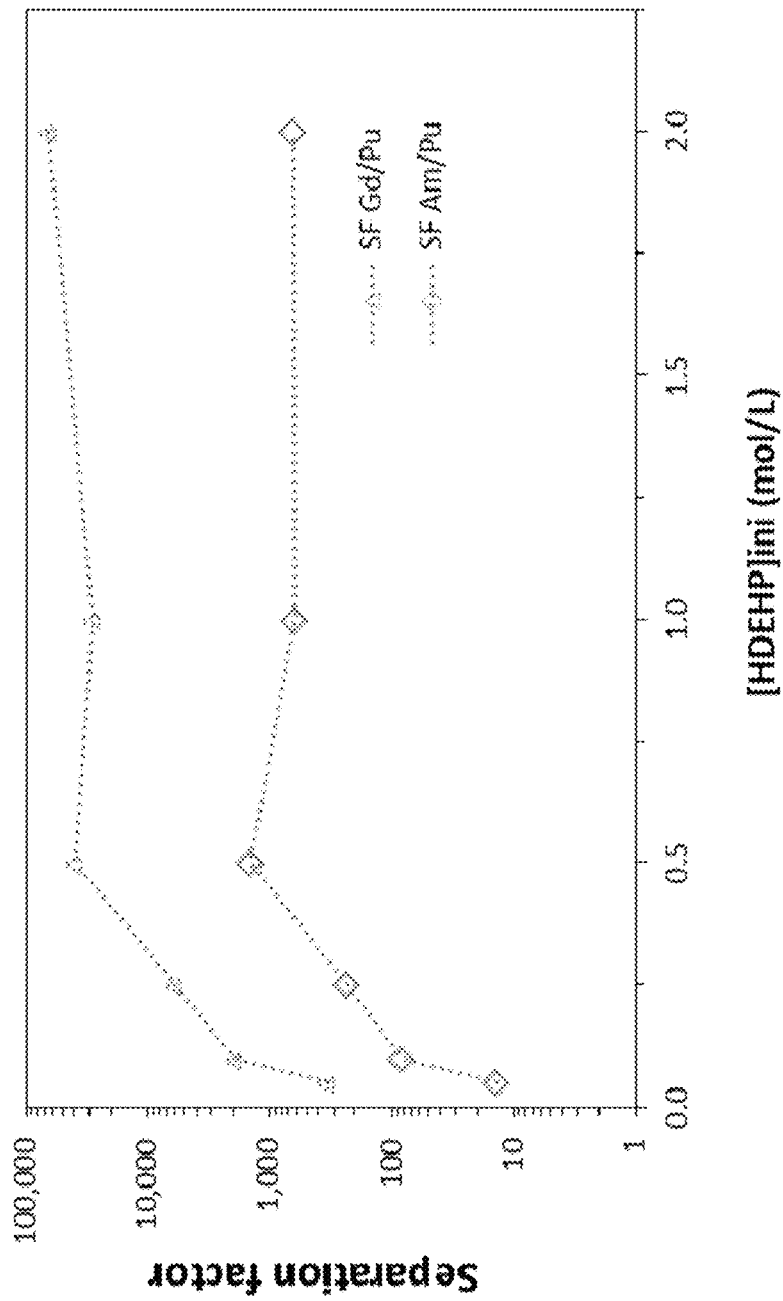
FIG. 27 shows corresponding separation factors for FIG. 26.

FIG. 26 and FIG. 27 show data related to separation of tetravalent metal ions from trivalent metal ions using a HOPO chelator as a hold-back reagent for tetravalent metal ions.

FIG. 26 shows percentage of extraction of plutonium(IV), americium(III), and gadolinium(III) by HDEHP at constant pH and using 3,4,3-LI(1,2-HOPO) as hold-back reagent. In FIG. 26, aqueous phase: [ligand]=1 mM, buffer 0.1 M $HNO_3$/1.9 M $NaNO_3$. Organic phase: HDEHP diluted in kerosene. [HDEHP]=0.05, 0.10, 0.25, 0.50, 1.0, or 2.0 M. T=25° C. Volume organic phase/Volume aqueous phase=1. Initial metal concentrations: [Pu-242]=10 µM, [Am-243]=0.25 µM, or [Gd-153]=0.16 nM. Phases analyzed after one contact. Contact time: 30 min.

FIG. 27 shows corresponding separation factors: SF $M_1/M_2$=Ratio [M1]/[M2] in the final organic phase/Ratio [M1]/[M2] in the initial aqueous solution. The separation factor values given here must been seen as lower limit since the extraction of Pu(IV) is near zero. Data for FIG. 26 and FIG. 27 are shown in TABLE 0.2

FIG. 28 shows data related to separation of trivalent actinides from trivalent lanthanides using 3,4,3-LI(1,2-HOPO) in the aqueous phase and a non-selective extractant in the organic phase. FIG. 28 shows percentage of extraction of americium(III), and gadolinium(III) by HDEHP at constant pH and using 3,4,3-LI(1,2-HOPO) as hold-back reagent. In FIG. 28, aqueous phase: [ligand]=1 mM, buffer 0.1 M $HNO_3$/1.9 M $NaNO_3$. Organic phase: HDEHP diluted in kerosene. [HDEHP]=0.05, 0.10, 0.25, 0.50, 1.0, or 2.0 M. T=25° C. Volume organic phase/Volume aqueous phase=1. Initial metal concentrations: [Am-243]=0.25 µM, or [Gd-153]=0.16 nM. Phases analyzed after one contact. Contact time: 30 min. Corresponding separation factors (SF) are given on the right Y-axis. SF Gd/Am=Ratio [Gd]/[Am] in the final organic phase/Ratio [Gd]/[Am] in the initial aqueous solution. Data for FIG. 28 are shown in TABLE 0.2

Example 6

Metal ions can be separated in an extraction. One first provides an aqueous solution that comprises a first metal ion ($M^{4+}$) and a second metal ion ($M^{3+}$). The solution is at a pH of between 0 and 1. One then adds a HOPO chelator (3,4,3-LI(1,2-HOPO)) to the aqueous solution. One then performs an extraction against the aqueous solution using an organic solution, wherein the HOPO chelator functions as a holdback agent to selectively keep the first metal ion in the aqueous solution. This allows the second metal ion to go into an organic phase during the extraction. One then decants the organic solution, keeping the first metal ion in the aqueous phase. One can then optionally release the first metal ion from the chelator by further lowering the pH. Optionally, a non-specific extractant can be used to assist in moving the M3+ metal ions to the organic phase.

Example 7

Metal ions can be separated in an extraction. One first provides an aqueous solution that comprises a first metal ion ($M^{3+}$) and a second metal ion ($M^{3+}$). The solution is at a pH of between 0 and 1. One then adds a HOPO chelator (3,4,3-LI(1,2-HOPO)) to the aqueous solution. The first metal ion has a stronger affinity for the HOPO chelator than the second metal ion does. One then performs an extraction against the aqueous solution using an organic solution, wherein the HOPO chelator functions as a holdback agent to selectively keep the first metal ion in the aqueous solution. This allows for more of the second metal ion to go into an organic phase during the extraction. One then decants the organic solution, keeping the first metal ion in the aqueous phase. One can then optionally release the first metal ion from the chelator by further lowering the pH. Optionally, a non-specific extractant can be used to assist in moving the M3+ metal ions to the organic phase.

Example 8

A method of processing spent nuclear fuel is provided. It involves obtaining spent nuclear fuel that comprises $Pu^{4+}$ and dissolving the metal in an acidic medium at a pH of less than 2. One then contacts the dissolved spent nuclear fuel with a spermine-based octadentate ligand and an organic phase to generate a mixture (and agitating the mixture such

TABLE 0.2

|  | Concentration HDEHP | Activity in organic phase (cpm) | Activity in aqueous phase (cpm) | % Extraction | SF $Gd^{3+}$/$Am^{3+}$ | SF $Gd^{3+}$/$Pu^{4+}$ | SF $Am^{3+}$/$Pu^{4+}$ |
|---|---|---|---|---|---|---|---|
| $^{243}$Americium(III) | 0.05 | 5 | 2326 | 0.21% | 24.1 | | |
| | 0.10 | 30 | 2237 | 1.32% | 23.3 | | |
| | 0.25 | 246 | 2195 | 10.08% | 25.3 | | |
| | 0.50 | 735 | 1693 | 30.27% | 27.0 | | |
| | 1.00 | 1296 | 1297 | 49.98% | 45.6 | | |
| | 2.00 | 1277 | 952 | 57.29% | 99.8 | | |
| $^{153}$Gadolinium(III) | 0.05 | 2505 | 48361 | 4.92% | | 331 | |
| | 0.10 | 12170 | 38983 | 23.79% | | 1948 | |
| | 0.25 | 40716 | 14376 | 73.91% | | 5976 | |
| | 0.50 | 51171 | 4362 | 92.15% | | 39182 | |
| | 1.00 | 55033 | 1207 | 97.85% | | 28460 | |
| | 2.00 | 56084 | 419 | 99.26% | | 64723 | |
| $^{242}$Plutonium(IV) | 0.05 | 1 | 6382 | 0.02% | | | 14 |
| | 0.10 | 1 | 6241 | 0.02% | | | 84 |
| | 0.25 | 3 | 6330 | 0.05% | | | 236 |
| | 0.50 | 2 | 6680 | 0.03% | | | 1450 |
| | 1.00 | 10 | 6242 | 0.16% | | | 624 |
| | 2.00 | 13 | 6286 | 0.21% | | | 649 |

*SF = separation factor;
cpm = count per minute that the organic and aqueous phases mix). One then separates an aqueous phase enriched for $Pu^{4+}$ from the mixture by decanting. The organic phase will contain various $M^{3+}$ and/or $M^{2+}$ metal ions. Optionally, a non-specific extractant can be used to assist in moving the $M^{3+}/M^{2+}$ metal ions to the organic phase.

Example 8

A method for enriching a metal ion is provided. One contacts a first aqueous phase with an organic phase to generate a mixture (e.g., during an extraction). The first aqueous phase comprises a plurality of metal ions (both $M^{3+}$ and $M^{4+}$) and a spermine-based octadentate ligand (e.g., a HOPO chelator). The aqueous phase has an acidic pH of less than 1. One then separates from the mixture a second aqueous phase. The second aqueous phase is only different from the first in that it is, relatively enriched (or has a greater purity) for a $M^{4+}$ metal ion of the plurality of metal ions. The organic phase will be enriched for the $M^{3+}$ metal ions. Optionally, a non-specific extractant can be used to assist in moving the $M^{3+}$ metal ions to the organic phase.

Example 9

A method of preparing a medical isotope is provided. The method involves obtaining a metallic precursor dissolved under an acidic condition. The metallic precursor comprises a medical isotope ($M^{4+}$ or $M^{3+}$), while the precursor is a mixture of various metal ions ($M^{4+}$ and $M^{3+}$ or different $M^{3+}$). One then contacts the dissolved metallic precursor with a spermine-based octadentate ligand (e.g., 3,4,3-LI(1,2-HOPO)) and an organic phase to generate a mixture. One then separates the medical isotope from the one or more metal ions in the dissolved metallic precursor based on an interaction between the octadentate ligand and the medical isotope. The metal that has a higher affinity for the HOPO ligand will remain in the aqueous phase while the metal with a lower affinity (that is not chelated) can be moved to the organic phase via a non-specific extractant. The desired medial isotope will then be in one or the other of the aqueous phase or the organic phase.

Example 10

A method of separating metal ions for nuclear forensics is provided. The method includes obtaining a sample derived from a nuclear material, wherein the sample comprises $UO_2^{2+}$, $Pu^{4+}$, and $Np^{4+}$. One then contacts the sample with a spermine-based octadentate ligand (e.g., 3,4,3-LI(1,2-HOPO)) to generate a first mixture. The first mixture has an acidic pH of 1 or lower. One then separates $UO_2^{2+}$ from $Pu^{4+}$ and $Np^{4+}$ in the mixture based on an interaction between the 3,4,3-LI(1,2-HOPO) and $Pu^{4+}$, and $Np^{4+}$. A non-specific extractant can be used to assist in moving the $UO_2^{2+}$ to the organic phase. This results in altering the first mixture to form a second mixture comprising the $Pu^{4+}$ and $Np^{4+}$ (but it is still the aqueous phase). One can then chromatographically separate $Pu^{4+}$ from $Np^{4+}$ in the second mixture.

Example 11

A method of separating metal ions is provided. The method involves contacting a liquid composition comprising a plurality of metal ions with a spermine-based octadentate ligand (e.g., 3,4,3-LI(1,2-HOPO)) to generate a mixture, under conditions sufficient to form a metal ion-ligand complex comprising a metal ion of the plurality of metal ions. One then separates a first fraction of the mixture enriched for the metal ion-ligand complex from a second fraction depleted for the metal ion-ligand complex. The first fraction of the mixture has an acidic pH of less than 1 and will include the 3,4,3-LI(1,2-HOPO) and any metal chelated thereto. A non-specific extractant can be used to assist in moving any unchelated metal ions to the organic phase. The plurality of metal ions are selected from the group consisting of: a p-, d- or f-block element of period 5 or greater, a group 3 element, or a group 4 element.

Example 12

Experimental Procedures

General Considerations.

Chemicals were obtained from commercial suppliers and were used as received unless stated otherwise. $^1$H NMR spectra were recorded on Bruker instruments; $^{13}$C NMR spectra were recorded on Bruker instruments with tetramethylsilane as an internal reference. SilicaFlash G60 (particle size 60-200 am) was used for flash column chromatography. LC-MS was performed on an Agilent LC/MS system consisting of an Agilent 1200 binary LC pump, a temperature-controlled autosampler, a PDA UV detector, and a 6530 Accurate Mass Q-TOF mass spectrometer (Wilmington, Del., USA). The mass spectrometer was equipped with a JetStream® ESI probe operating at atmospheric pressure. The ESI source parameter settings were: mass range m/z 100-1200, gas temperature 350° C., gas flow 10 L/min, nebulizer 50 psi, sheath gas temperature 400° C., sheath gas flow 12 L/min, capillary voltage (Vcap) 3500 V, nozzle voltage 500 V, fragmentor 200 V, skimmer 65 V, octopole RF (OCT 1 RF Vpp) 750 V. Reverse phase preparatory HPLC was performed on a Varian ProStar system with a Vydac C18 column. HRMS and MS-MS were obtained on a Waters Xevo G2 Qtof mass spectrometer, leucine encephalin lockspray with mass correction was used for HRMS.

Example 13—Synthetic Procedures—Submonomer

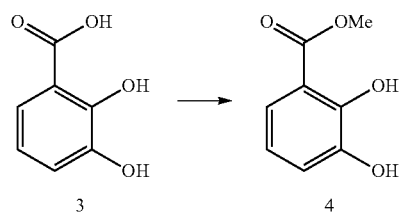 [SMILES: O=C(O)c1cccc(O)c1O ; COC(=O)c1cccc(O)c1O]

Methyl 2,3-dihydroxybenzoate, 4. A stirred suspension of 3 (8.06 g, 52.3 mmol) in 100 ml of methanol was treated with 2.00 ml of concentrated sulfuric acid. The suspension warmed and clarified 2 minutes after the addition. The reaction was equipped with a reflux condenser and was heated to 65° C. overnight. The next morning the conversion was verified by LC-MS and the volatiles were removed under reduced pressure. The crude was partitioned between water (100 ml) and ethyl acetate (100 ml) and the aqueous layer was extracted with ethyl acetate (3×50 ml). The organic extracts were combined, dried over $MgSO_4$, and concentrated under reduced pressure. The crude was passed through a plug of silica using 10% ethyl acetate in hexanes as eluent. The eluent was concentrated under reduced pressure and dried under high vacuum for 2 hours to yield 4 (7.66 g, 45.6 mmol, 88%) as a white solid, the spectral properties of which matched previous reports.[1]

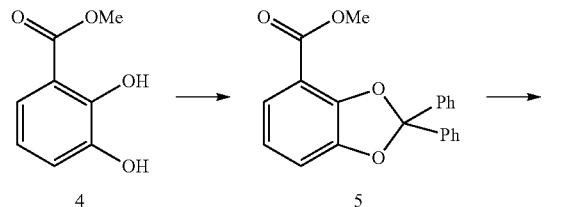

Methyl 2,2-diphenylbenzo[d][1,3]dioxole-4-carboxylate, 5. 4 (5.00 g, 29.7 mmol) was mixed with dichlorodiphenylmethane (8.56 ml, 44.6 mmol) under an argon atmosphere, the resulting suspension was stirred and heated to 160° C. for 1 hour. The mixture was allowed to cool to room temperature and was diluted with 100 ml of ethyl acetate. The solution was washed with sat. NaHCO$_3$(30 mL) then brine (30 mL), dried over MgSO$_4$, then concentrated under reduced pressure. The ensuing greyish oil was dissolved in 30 mL of hot methanol (65° C.) and was slowly cooled to 5° C., which resulted in the formation of white crystals. The crystals were a mixture of 5 and benzophenone dimethyl acetal that could not be easily separated; product was used as is for the subsequent step.

2,2-diphenylbenzo[d][1,3]dioxole-4-carboxylic acid, 6. The mixture from the previous step was dissolved in 100 mL of THF and was treated with 100 mL of 0.9 M LiOH. The emulsion was rapidly stirred and heated to reflux for 5 hours. Conversion was verified by LC-MS and the reaction was cooled to room temperature. The solution was neutralized with 10% v/v aqueous acetic acid and was extracted with ethyl acetate (3×50 mL). The organic extracts were combined, dried over MgSO$_4$, and concentrated under reduced pressure. The crude was chromatographed using 25% ethyl acetate in hexanes as eluent. Volatiles were then removed under reduced pressure followed by high vacuum to yield 6 (7.6 g, 24 mmol, 81% over 2 steps) as a white solid, the spectral properties of which matched previous reports.[1]

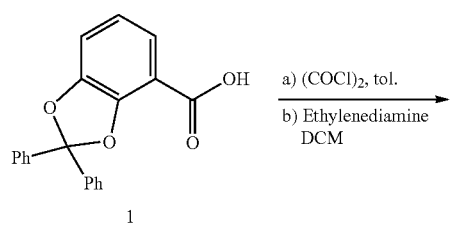

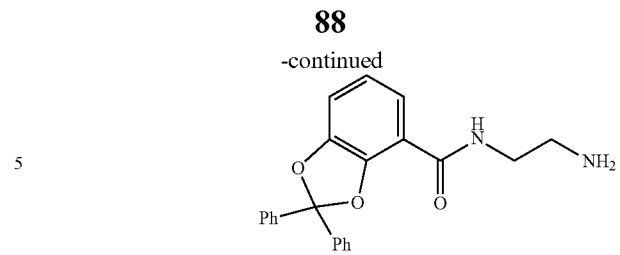

"CAM Submonomer, 2." 1(3.84 g, 12.1 mmol) was suspended in 30 mL of toluene under an argon atmosphere. Oxalyl chloride (1.14 mL, 13.3 mmol) was then added followed by a catalytic amount of N,N-dimethylformamide. The suspension was heated to 40° C. and was stirred until it became clear and the evolution of gas has ceased (~1 hour). The volatiles were then removed under reduced pressure and the resulting white solid was dissolved in dry dichloromethane. A separate 1 L roundbottom flask outfitted with an addition funnel was charged with ethylenediamine (8 mL, 120 mmol) and 50 mL dry dichloromethane; the resulting solution was cooled to 0° C. using an ice bath. The aforementioned solution of acyl chloride was transferred into the addition funnel and was diluted with dichloromethane to a total volume of 700 mL. The acyl chloride solution was then added into the vigorously stirred ethylenediamine over 1.5 hours at 0° C. Following the addition, the reaction solution was transferred into a separatory funnel and was washed with 0.5 M NaOH in 50% saturated aq. NaCl (50 mL×2). The organic phase was dried over MgSO$_4$ and was concentrated on a rotary evaporator yielding the crude. The crude was purified using silica column chromatography (5→10% MeOH in DCM with 1% Et$_3$N, R$_f$=0.35 in 10% MeOH in DCM). The desired fractions were combined, concentrated under reduced pressure, and dried under vacuum yielding the CAM submonomer as a sticky yellow oil (3.49 g, 9.68 mmol, 80% yield). $^1$H NMR (300 MHz, CDCl$_3$) δ 7.64 (1H, br s, NH), 7.56-7.61 (5H, m, ArH), 7.37-7.42 (6H, m, ArH), 7.01 (1H, dd, J=7.7, 1.4 Hz, ArH), 6.94 (1H, t, J=7.9 Hz, ArH), 3.56 (2H, q, J=6.0 Hz, NHC$\underline{H}_2$), 2.97 (2H, t, J=6.0 Hz, NH$_2$C$\underline{H}_2$), 2.75 (2H, s, NH$_2$). $^{13}$C NMR (75 MHz, CDCl$_3$) δ 163.7, 147.2, 144.7, 139.4, 129.5, 128.4, 126.2, 122.4, 122.0, 118.0, 116.0, 111.6, 42.3, 41.5. HRMS-ESI (m/z) [M+H] Calcd. For C$_{22}$H$_{20}$N$_2$O$_3$+H, 361.1563; found, 361.1581.

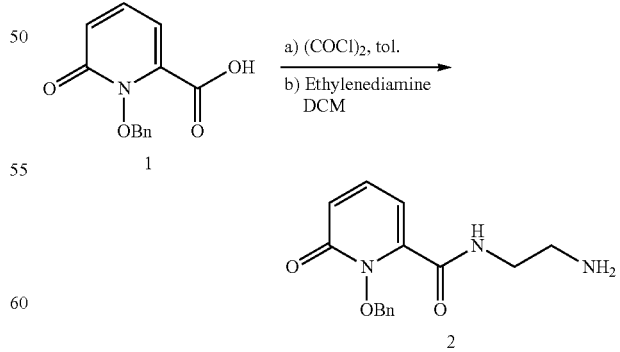

"HOPO Submonomer, 3." 3 was synthesized in an identical fashion to 2 above, using 1-benzyloxy-6-carboxy-2 (1H) pyridinone (J. Labelled Cpd. Radiopharm. 2001, 44, 13-19, CAS 210366-15-7, US Patent U.S. Pat. No. 6,846, 915) as the starting material. The crude product was purified using silica column chromatography (10% NH$_4$OH (10%) in MeOH) in DCM, R$_f$=0.08). The desired fractions were combined, concentrated under reduced pressure, and dried under vacuum yielding the HOPO submonomer 3 as a sticky yellow oil in ~80% yield). $^1$H NMR (300 MHz, CDCl$_3$) δ 7.40-7.48 (3H, m, ArH), 7.35-7.38 (3H, m, ArH and NH), 7.24-7.29 (1H, m, ArH), 6.66 (1H, dd, J=9.0, 1.5 Hz, CHCHCH), 6.45 (1H, dd, J=6.9, 1.8 Hz, CHCHCH), 5.29 (2H, s, CH$_2$Ph), 3.36 (2H, q, J=6.0 Hz, NHCH$_2$), 2.80 (2H, t, J=6.0 Hz, NH$_2$CH$_2$). $^{13}$C NMR (75 MHz, CDCl$_3$) δ 160.3, 158.5, 142.5, 138.0, 133.2, 130.1, 129.4, 128.6, 124.0, 106.4, 79.3, 77.4, 77.0, 76.6, 42.7, 40.7. Calcd. For C$_{15}$H$_{17}$N$_3$O$_3$+H, 288.1328; found, 288.1361.

Example 14—Synthesis of Peptoids

Unless noted otherwise, all steps were carried out in fritted polypropylene syringes, which allowed for recovery of submonomer for re-use. Automatic peptoid synthesis was not an option for this work due to difficulty of sub-monomer preparation.
1. Add 100-150 mg of Rink amide resin to a fritted syringe. Swell the resin by adding 2 mL of DMF and rock for 30 minutes. Eject the solution to isolate the swelled resin.
2. Add 1 mL of 20% 4-methylpiperidine in DMF (v/v) to deprotect the Fmoc group. Agitate for 2 minutes, drain, and repeat for 12 minutes.
3. Rinse the resin with DMF (2 mL, 5 times for 1 minute)
4. Bromoacetylation. Premix 0.8 M bromoacetic acid in DMF with 0.8 M N,N-diisopropylcarbodiimide (DIC), 2 mL total solution with 0.4 M of each reagent. Draw the solution into the syringe, agitate for 5 minutes, and rinse (2 mL DMF 5×1 minute).
5. Displacement. Draw in 1.5 mL of submonomer solution (0.2 M in DMF), agitate for 1 hour at 45° C., then rinse (2 mL DMF 5×1 minute).
6. Repeat bromoacetylation and displacement until synthesis is finished. Wash with DCM (2 mL 3×1 minute) after last DMF wash and dry resin by pulling the plunger out and applying a gentle vacuum onto the syringe needle.

Example 15—Deprotection, Cleavage, and Purification

Dry resin (100-150 mg) was placed into a scintillation vial and was swollen in 9 mL of DCM by shaking for 30 minutes. 1 mL of 1.0 M BBr$_3$ in hexanes was added via a syringe, the vial was capped and shaken for 60 minutes ensuring that all of the resin was thoroughly submerged; this removes benzyl protecting groups from HOPO units. The solvent was carefully removed with a glass pipette and the resin was washed with DCM (2 mL) methanol (2×2 mL) followed by DCM (2×2 mL). The peptoid was then cleaved from resin by treatment with cleavage cocktail for 60 minutes (the treatment also deprotects CAM units). The cleavage cocktail (95% trifluoroacetic acid, 2.5% water, 2.5% triethylsilane) was filtered from resin and a small aliquot was removed and diluted with methanol for LC-MS analysis (1→30% MeCN in H$_2$O over 20 minutes, both with 0.1% formic acid); the resin was washed of TFA traces and discarded. Most LC-MS analyses showed a relatively clean desired compound; iron complexes were sometimes seen, which we believe came from stainless steel components of the instrument. Volatiles were then removed from the filtrate using a vacuum pump. The resulting residue was dissolved in 90/10 acetic acid/water (0.5-1 mL) and the resulting clear solution was stirred at 42° C. and treated with water in 0.5 mL increments. The solution turned turbid upon addition of water and slowly clarified with continued stirring (5-15 min between additions). A total of ~2.5 mL of water was added, at which point the solution remained turbid even with prolonged stirring.

The turbid solution was taken up into a syringe and injected onto reverse-phase prep-HPLC through a 0.45 μm filter in no more than 2.0 mL batches (~2 injections per peptoid).

Example 16—Reversed-Phase Preparative HPLC Method

| Time (min) | % Acetonitrile (with 0.1% TFA) | % Water (with 0.1% TFA) | Flow (ml/min) |
|---|---|---|---|
| 0 | 5 | 95 | 10 |
| 5 | 5 | 95 | 10 |
| 25 | 20 | 80 | 15 |
| 70 | 40 | 20 | 15 |
| 75 | 90 | 10 | 15 |
| 80 | 5 | 95 | 15 |
| 85 | 5 | 95 | 15 |

Most peptoids had peak maxima between 20 and 40 minutes, methods were typically terminated once the target material was collected. The column was flushed with 50/50 solvent composition for 5 minutes and equilibrated to initial condition for at least 20 minutes before every injection; insufficient equilibration leads to low column loading and very low yields. Peptoids with higher CAM compositions tended to be less polar and thus came out later than HOPO-heavy analogs.

Figure 41:
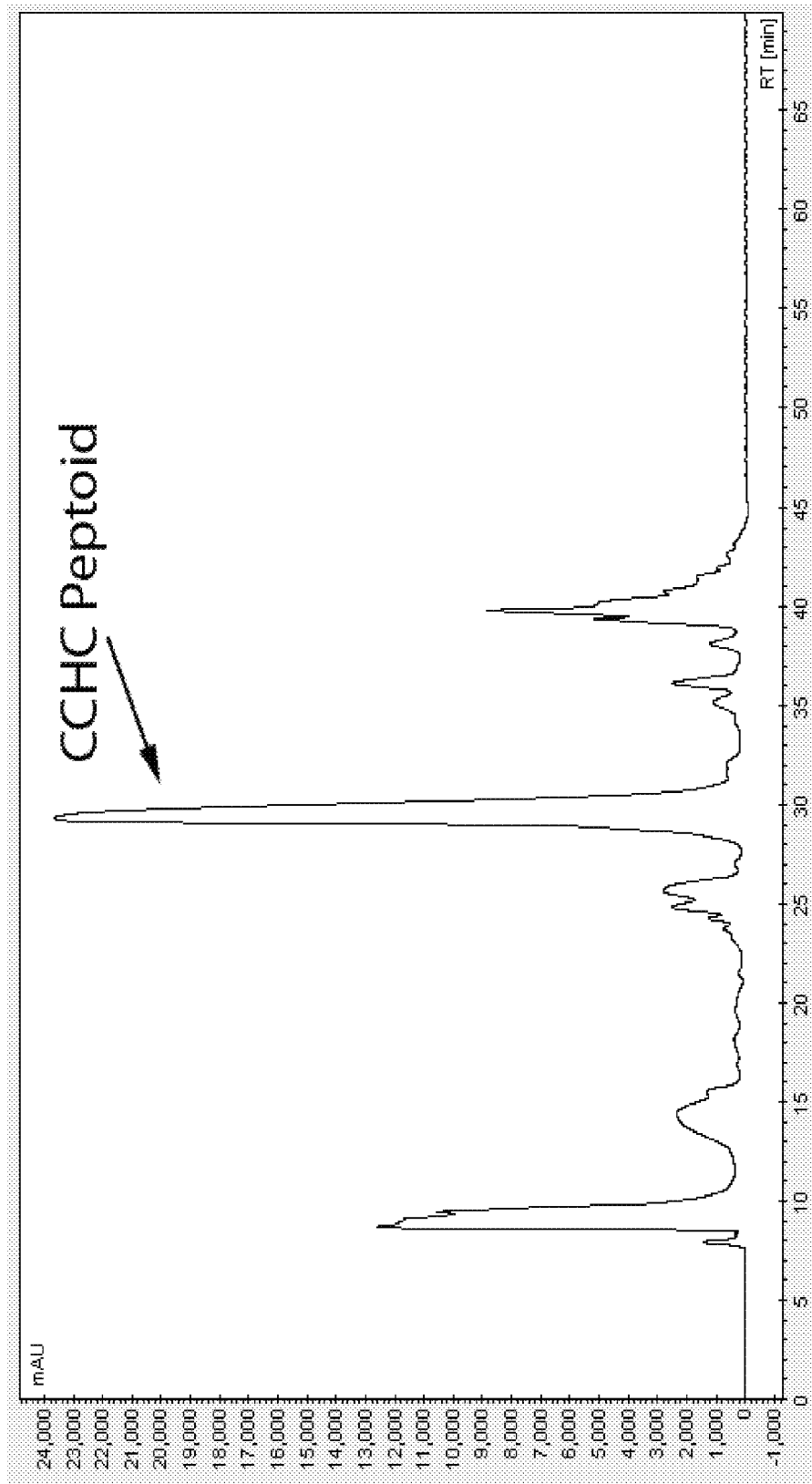
FIG. 41 depicts a representative reversed-phase HPLC trace

A representative reversed-phase preparative HPLC trace is presented in FIG. 41.

Example 17→Peptoid LC-MS of Purified Peptoids

LC traces of peptoids A@320. Ion counts along the entire peak including shoulders were used to generate mass spectra. Spectra were obtained in negative mode on Agilent 6530 mass spectrometer.

Figure 42A:
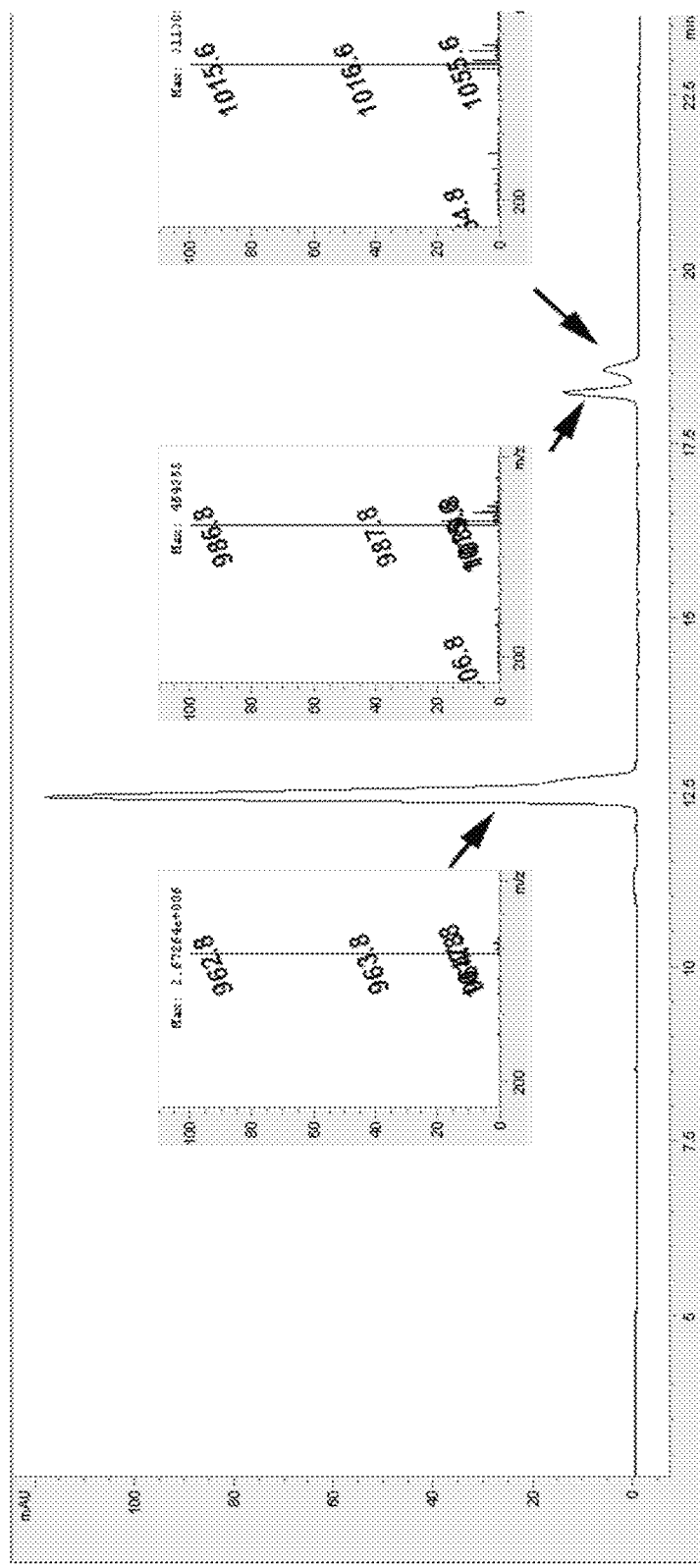
FIG. 42A depicts the mass spectra (HHHC Peptoid. MS1: free peptoid, MS2: peptoid-Na, MS3: peptoid-Fe and peptoid-Fe—K.
Figure 42B:
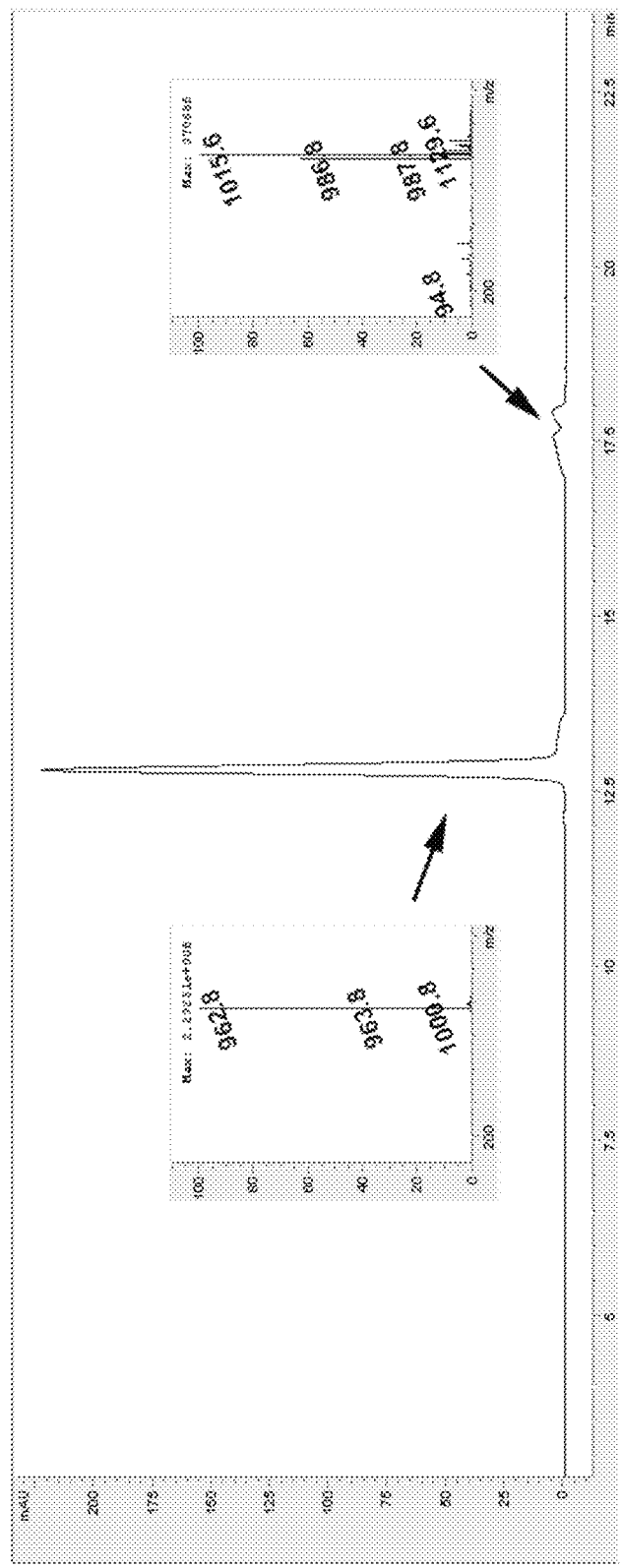
FIG. 42B depicts the mass spectra for CHHH Peptoid. MS1: free peptoid and peptoid-K, MS2: peptoid-Na, peptoid-Fe, and possible impurity.
Figure 42C:
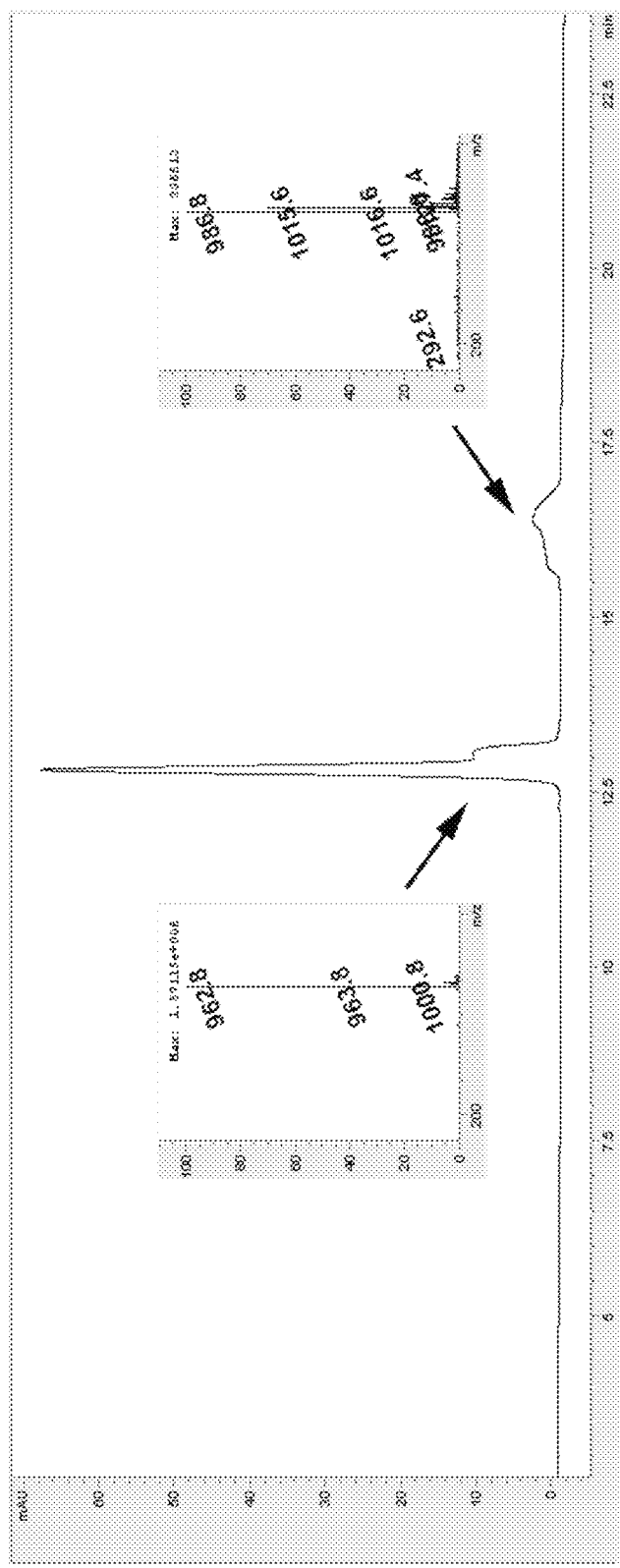
FIG. 42C depicts the mass spectra for HCHH Peptoid. MS1: free peptoid and peptoid-K, MS2: peptoid-Na, peptoid-Fe.
Figure 42D:
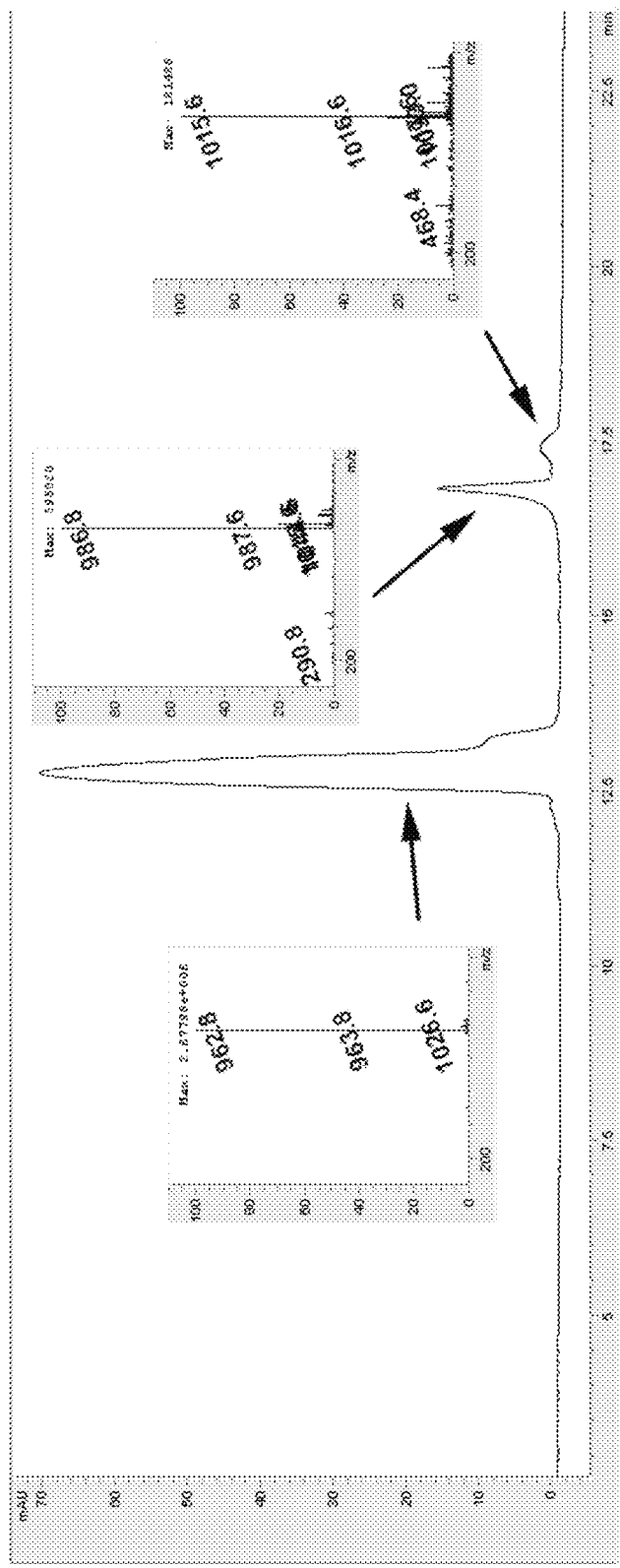
FIG. 42D depicts the mass spectra for HHCH Peptoid. MS1: free peptoid and possible impurity, MS2: peptoid-Na, MS3: Peptoid-Fe.
Figure 42E:
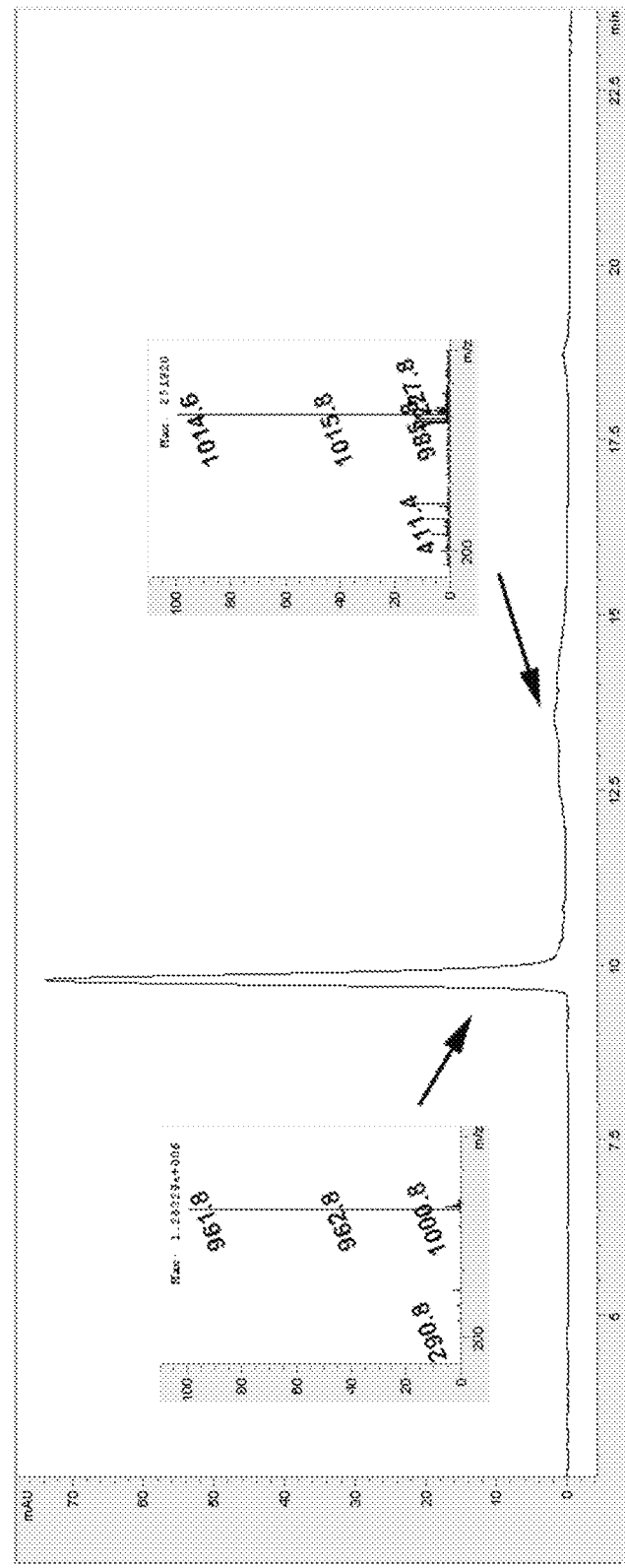
FIG. 42E depicts the mass spectra for CHHC Peptoid. MS1: free peptoid only and peptoid-K, MS2: peptoid-Na and peptoid-Fe.
Figure 42F:
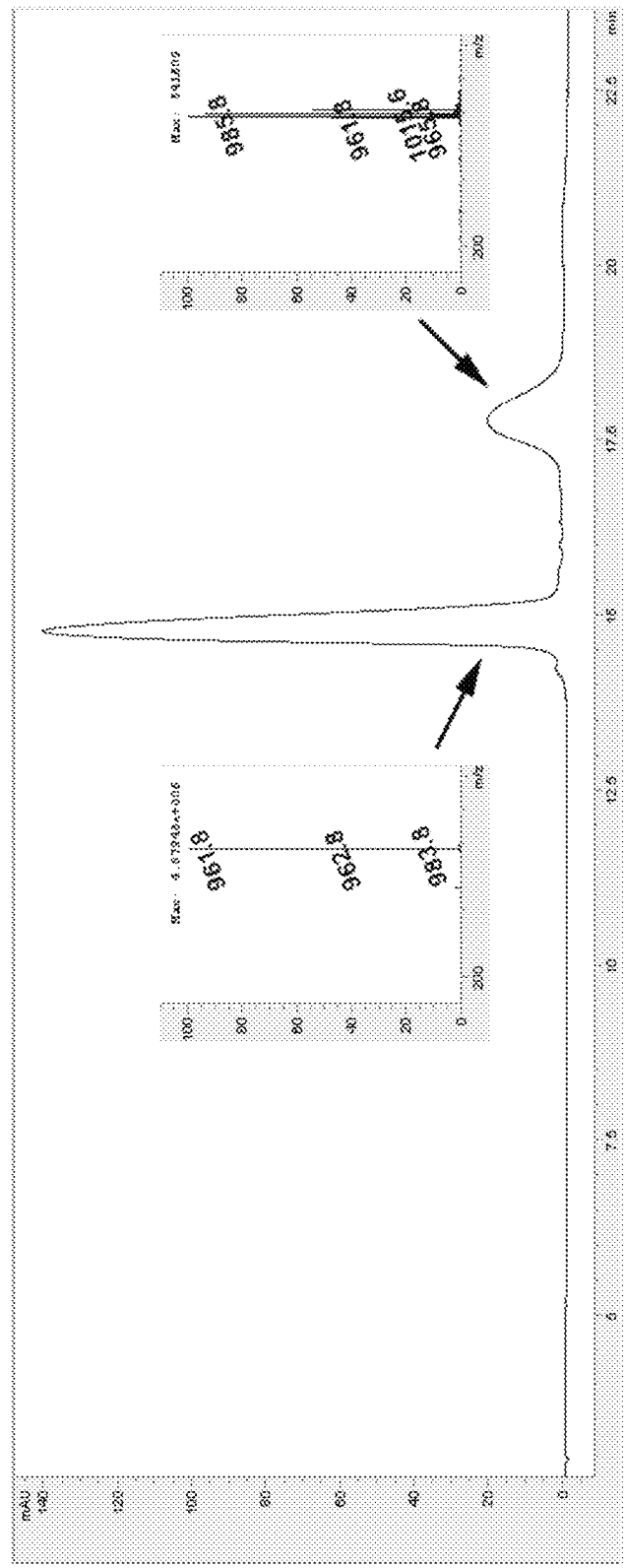
FIG. 42F depicts the mass spectra for HHCC Peptoid. MS1: free peptoid and peptoid-Na, MS2: peptoid-Na, free peptoid, and peptoid-Fe.
Figure 42G:
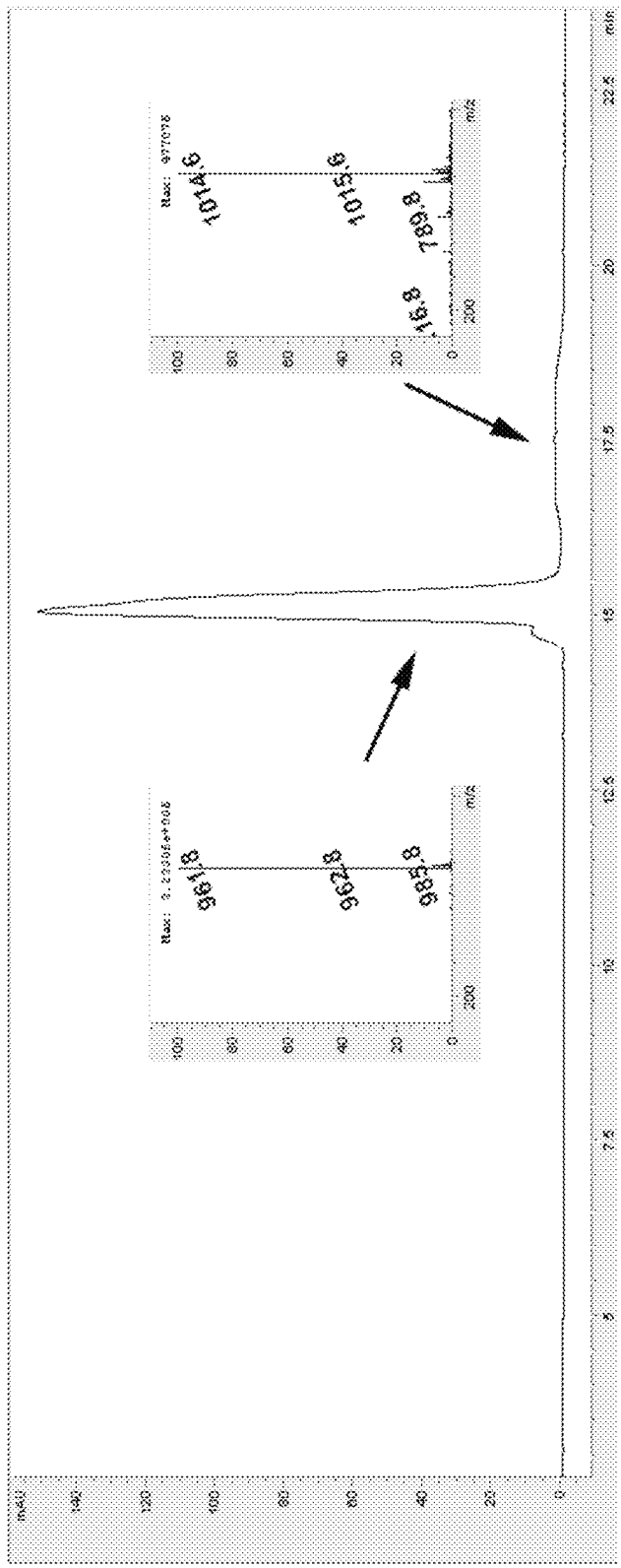
FIG. 42G depicts the mass spectra for CCHH Peptoid. MS1: free peptoid and peptoid-Na, MS2: Peptoid-Fe and possible trimer.
Figure 42H:
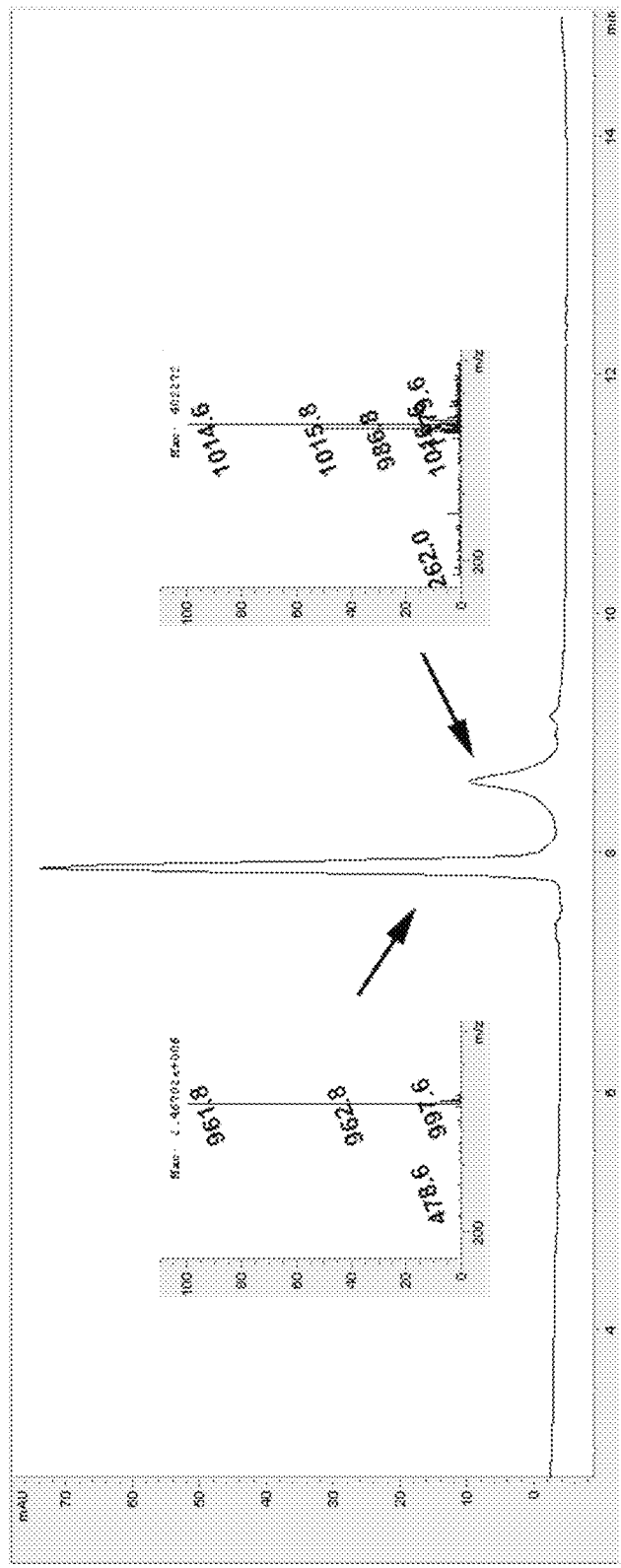
FIG. 42H depicts the mass spectra for HCHC Peptoid. MS1: free peptoid, MS2: peptoid-Fe and peptoid-Na.
Figure 42I:
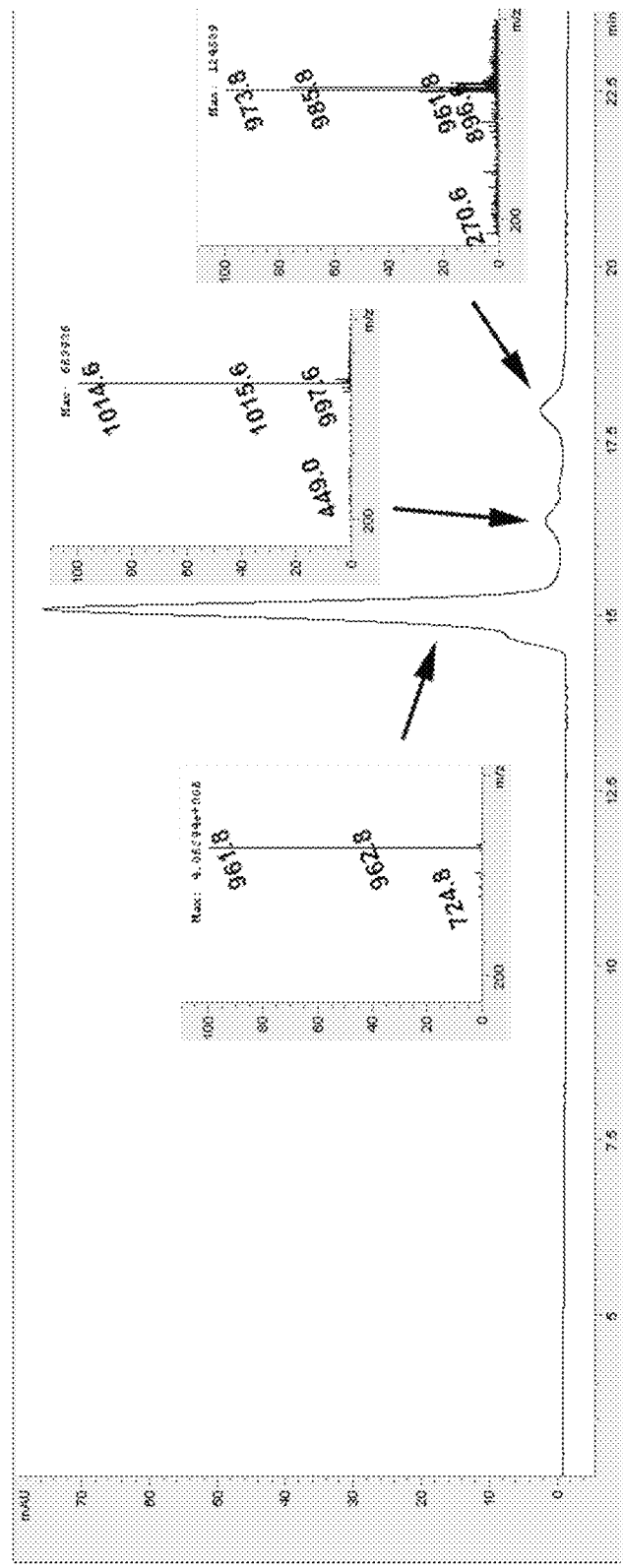
FIG. 42I depicts the mass spectra for HCCH Peptoid. MS1: free peptoid and small amount trimer, MS2: peptoid-Fe, MS3: peptoid-Na and possible fragments.
Figure 42J:
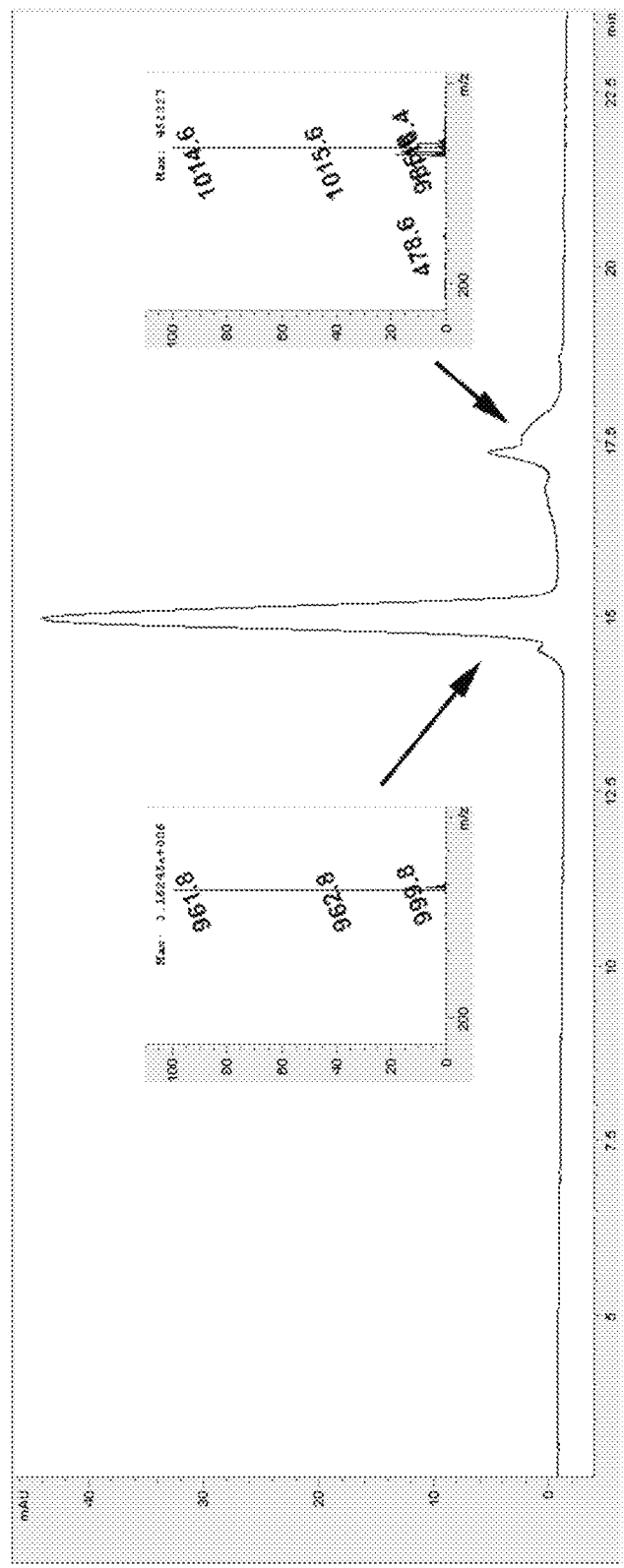
FIG. 42J depicts the mass spectra for CHCH Peptoid. MS1: free peptoid and peptoid-K, MS2: peptoid-Fe.
Figure 42K:
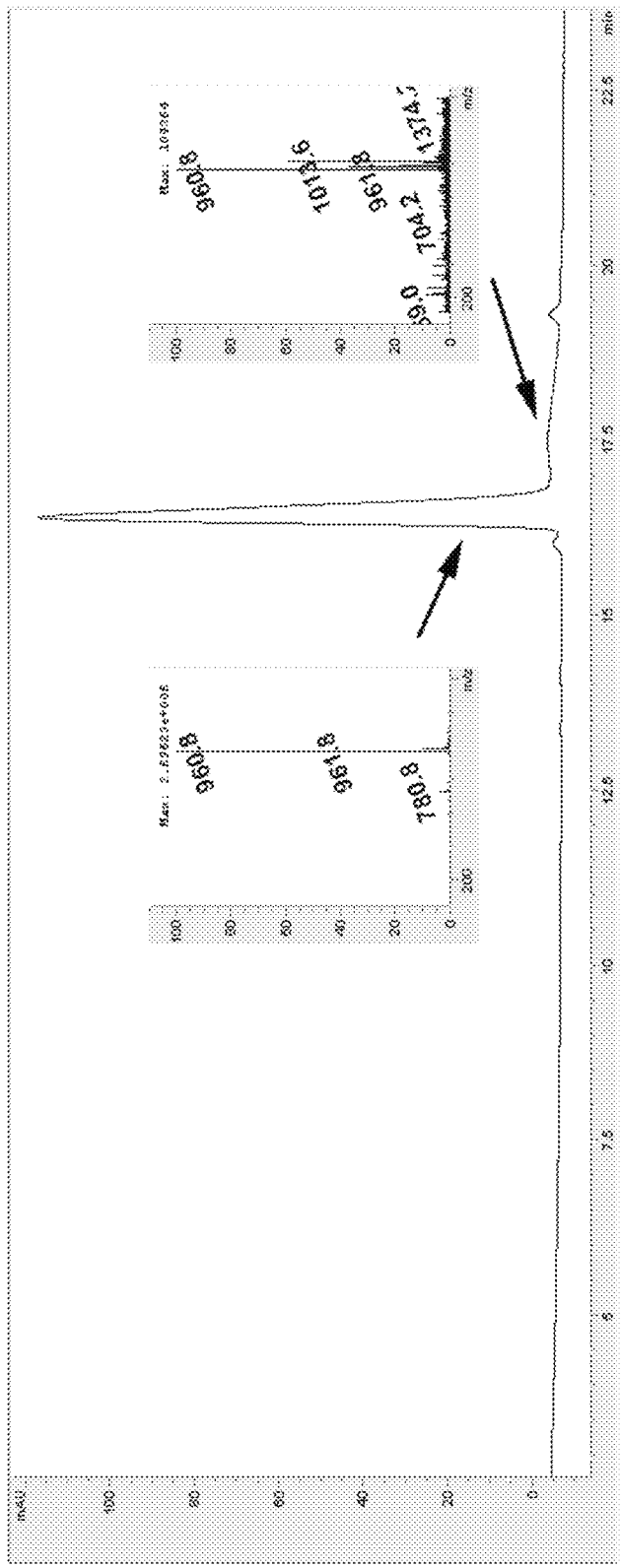
FIG. 42K depicts the mass spectra for HCCC Peptoid. MS1: free peptoid and trimer-Fe trace, MS2: free peptoid and peptoid-Fe.
Figure 42L:
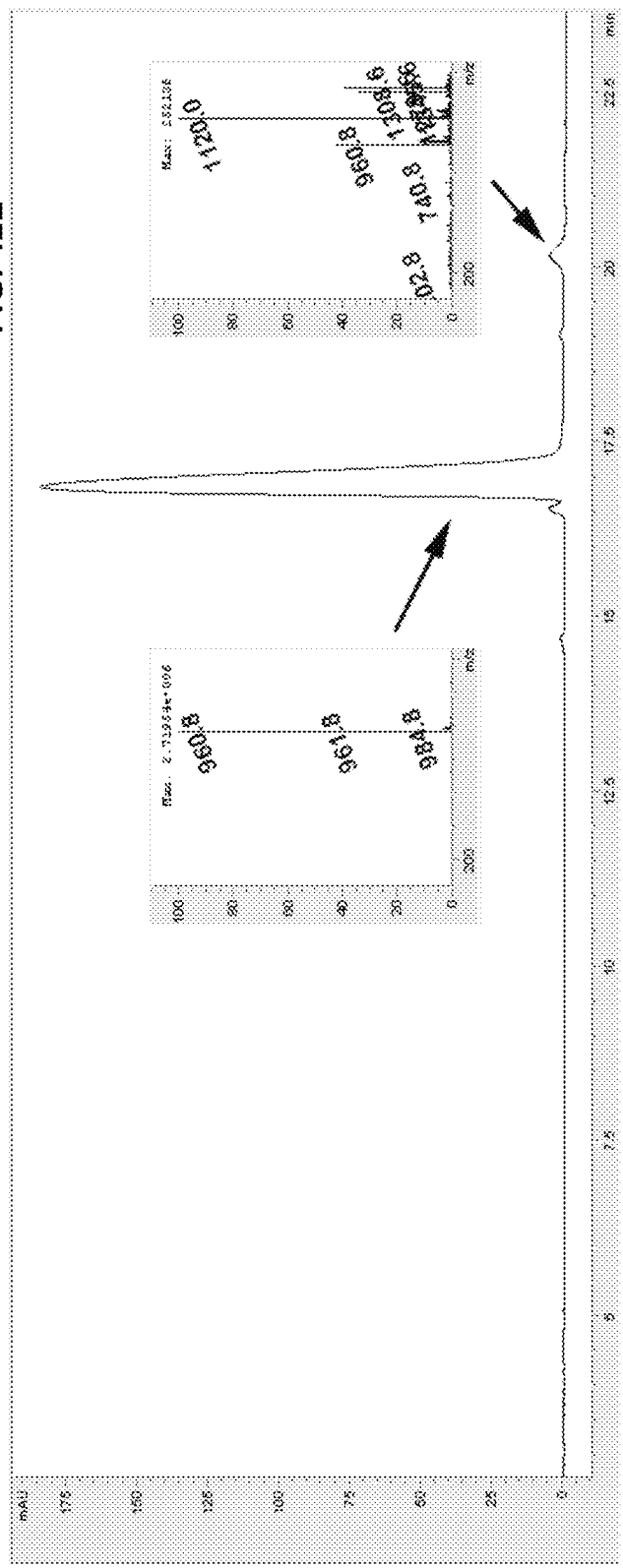
FIG. 42L depicts the mass spectra for CHCC Peptoid. MS1: free peptoid and peptoid-Na, MS2: free peptoid and unidentified masses.
Figure 42M:
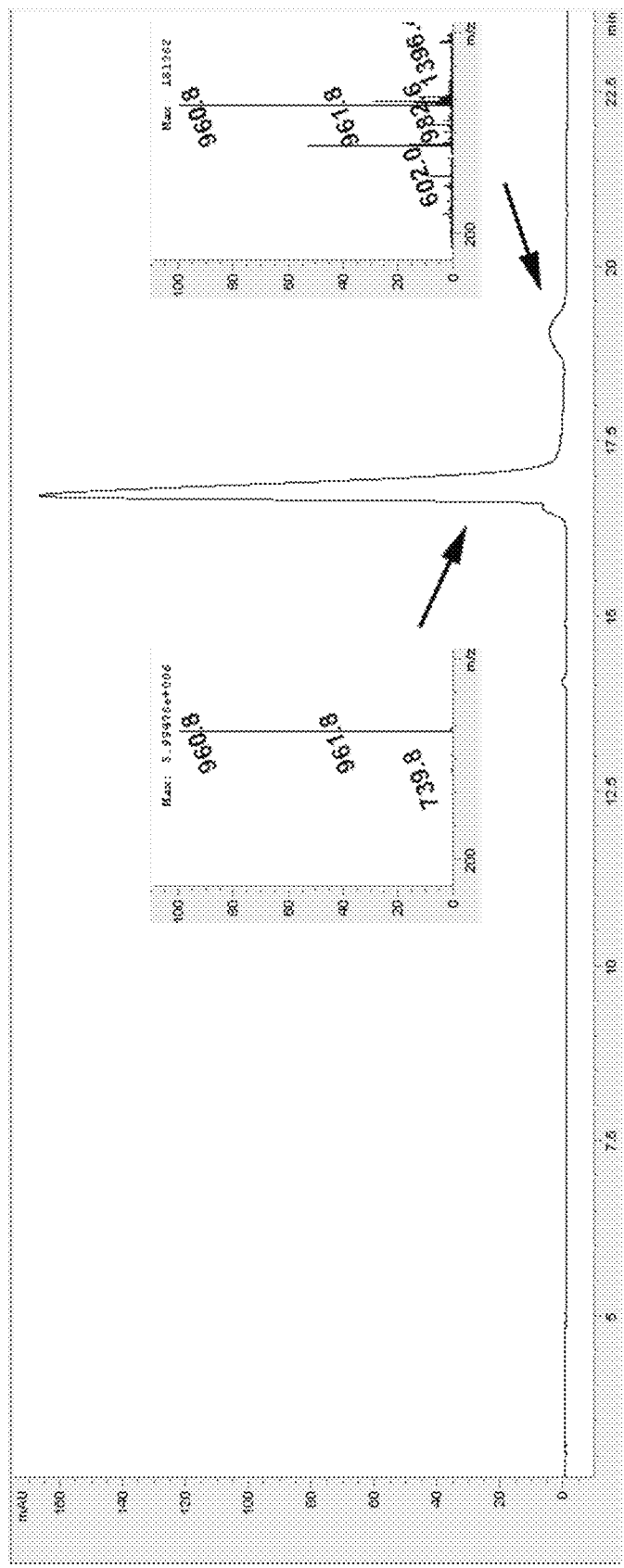
FIG. 42M depicts the mass spectra for CCHC Peptoid. MS1: free peptoid, MS2: free peptoid and peptoid-Na.
Figure 42N:
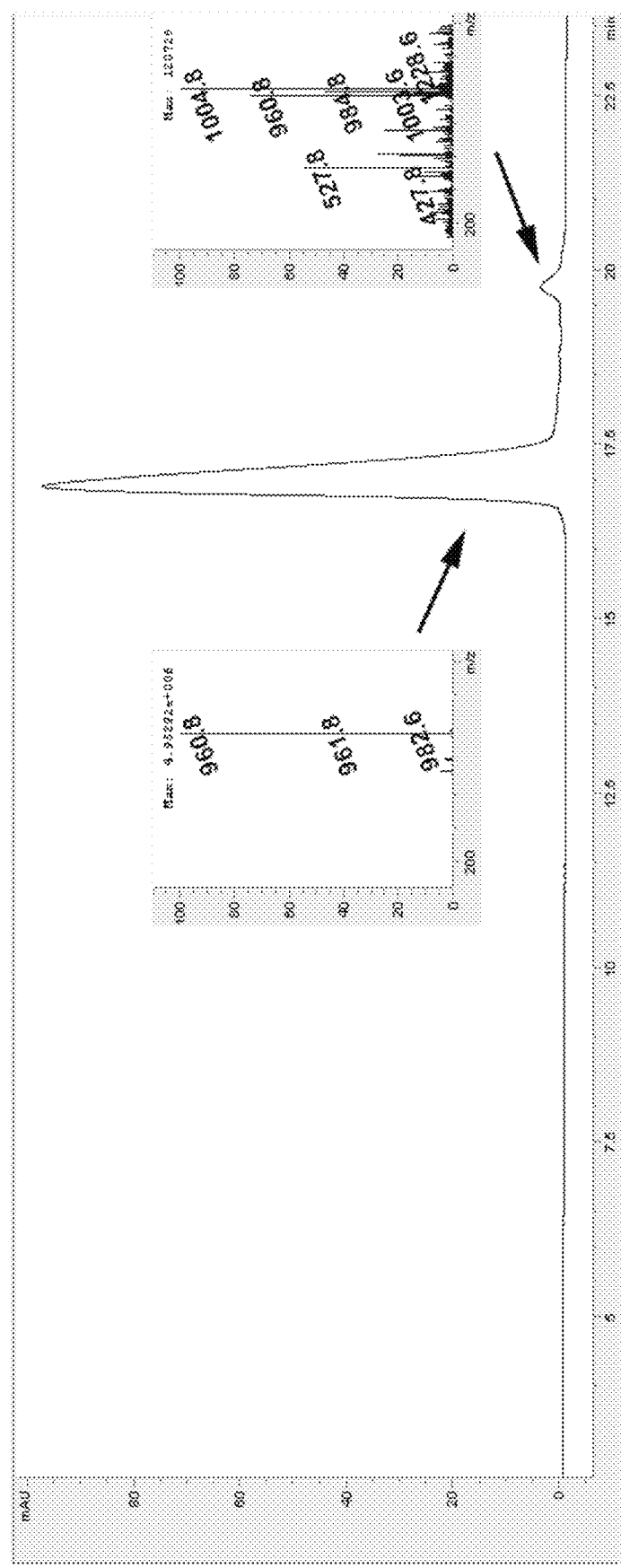
FIG. 42N depicts the mass spectra for CCCH Peptoid. MS1: free peptoid and peptoid-Na, MS2: free peptoid and peptoid-K/Na.
Figure 42O:
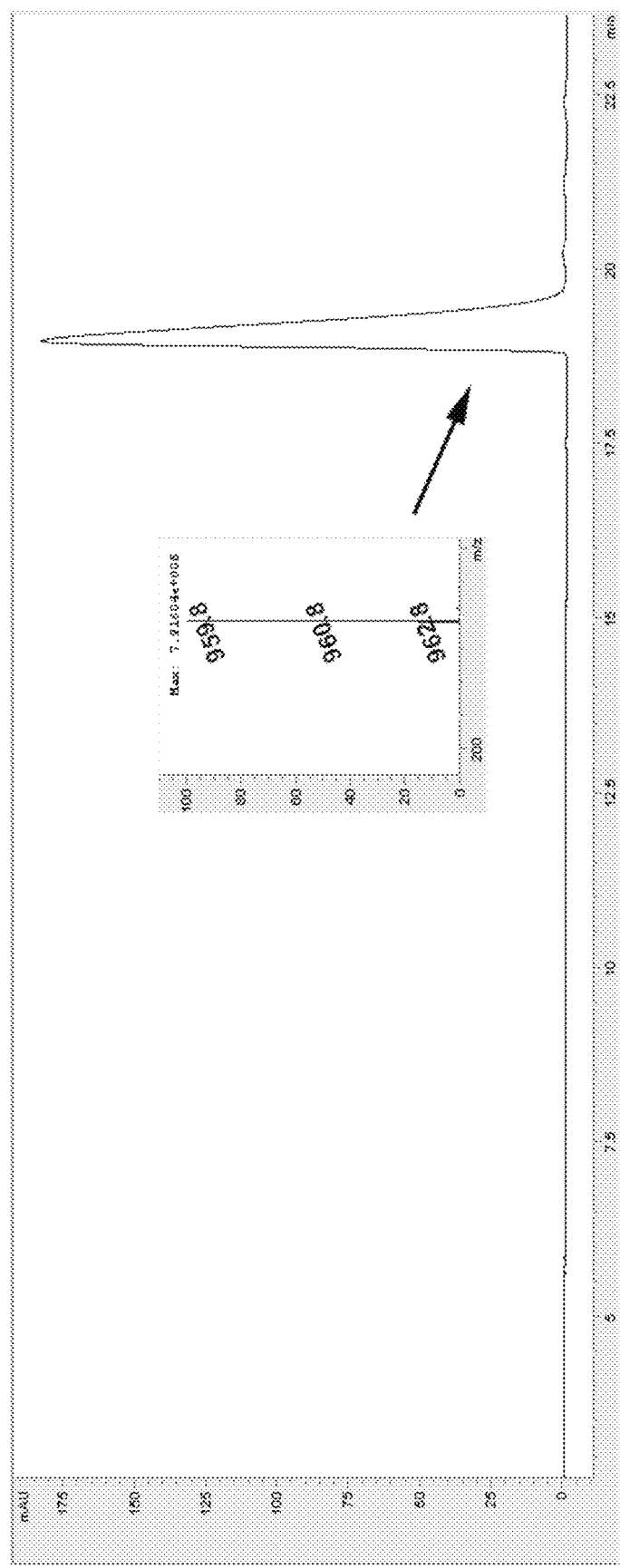
FIG. 42O depicts the mass spectra for CCCH Peptoid. MS1: free peptoid and peptoid-Na, MS2: free peptoid and peptoid-K/Na.
Figure 42P:
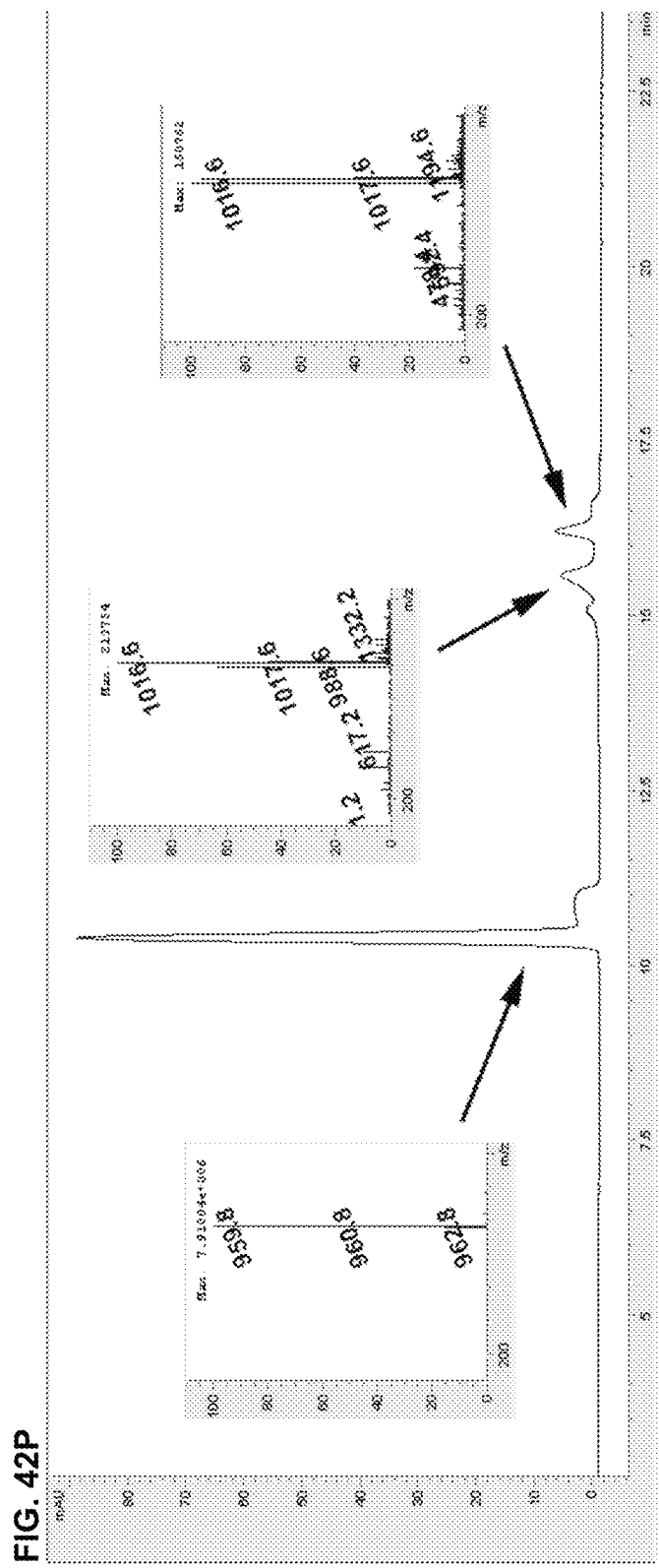
FIG. 42P is the mass spectra for HHHH Peptoid. MS1: free peptoid, MS2: peptoid-Fe/Na, MS3: Peptoid-Fe—Na.

MS labels from left to right and are shown in FIG. 42A (HHHC Peptoid. MS1: free peptoid, MS2: peptoid-Na, MS3: peptoid-Fe and peptoid-Fe—K. FIG. 42B is the mass spectra for CHHH Peptoid. MS1: free peptoid and peptoid-K, MS2: peptoid-Na, peptoid-Fe, and possible impurity. FIG. 42C is the mass spectra for HCHH Peptoid. MS1: free peptoid and peptoid-K, MS2: peptoid-Na, peptoid-Fe. FIG. 42D is the mass spectra for HHCH Peptoid. MS1: free peptoid and possible impurity, MS2: peptoid-Na, MS3: Peptoid-Fe. FIG. 42E is the mass spectra for CHHC Peptoid. MS1: free peptoid only and peptoid-K, MS2: peptoid-Na and peptoid-Fe. FIG. 42F is the mass spectra for HHCC Peptoid. MS1: free peptoid and peptoid-Na, MS2: peptoid-Na, free peptoid, and peptoid-Fe. FIG. 42G is the mass spectra for CCHH Peptoid. MS1: free peptoid and peptoid-Na, MS2: Peptoid-Fe and possible trimer. FIG. 42H is the mass spectra for HCHC Peptoid. MS1: free peptoid, MS2: peptoid-Fe and peptoid-Na. FIG. 42I is the mass spectra for HCCH Peptoid. MS1: free peptoid and small amount trimer, MS2: peptoid-Fe, MS3: peptoid-Na and possible fragments. FIG. 42J is the mass spectra for CHCH Peptoid. MS1: free peptoid and peptoid-K, MS2: peptoid-Fe. FIG. 42K is the mass spectra for HCCC Peptoid. MS1: free peptoid and trimer-Fe trace, MS2: free peptoid and peptoid-Fe. FIG. 42L is the mass spectra for CHCC Peptoid. MS1: free peptoid and peptoid-Na, MS2: free peptoid and unidentified masses. FIG. 42M is the mass spectra for CCHC Peptoid. MS1: free peptoid, MS2: free peptoid and peptoid-Na. FIG. 42N is the mass spectra for CCCH Peptoid. MS1: free peptoid and peptoid-Na, MS2: free peptoid and peptoid-K/Na. FIG. 42O is the mass spectra for CCCH Peptoid. MS1: free peptoid and peptoid-Na, MS2: free peptoid and peptoid-K/Na. FIG. 42P is the mass spectra for HHHH Peptoid. MS1: free peptoid, MS2: peptoid-Fe/Na, MS3: Peptoid-Fe—Na.

Example 18—High Resolution Mass Spectrometry Data

Figure 43A:
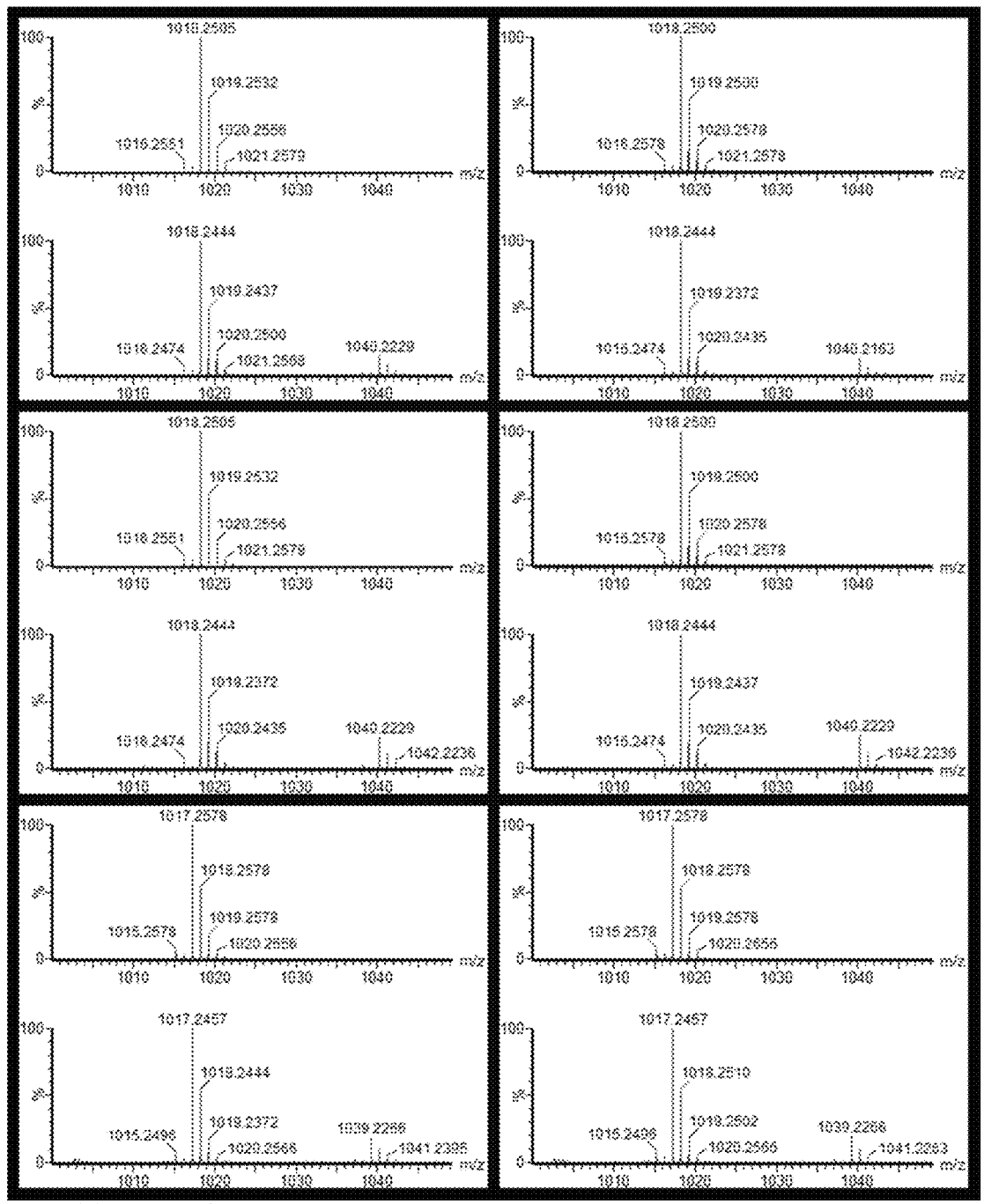
FIGS. 43A-43C depict the spectra that were obtained in negative mode. All peptoids are 1:1 $Fe^{3+}$ complexes except for CCCC and HHHH. Top spectrum is calculated and bottom is obtained.
Figure 43B:
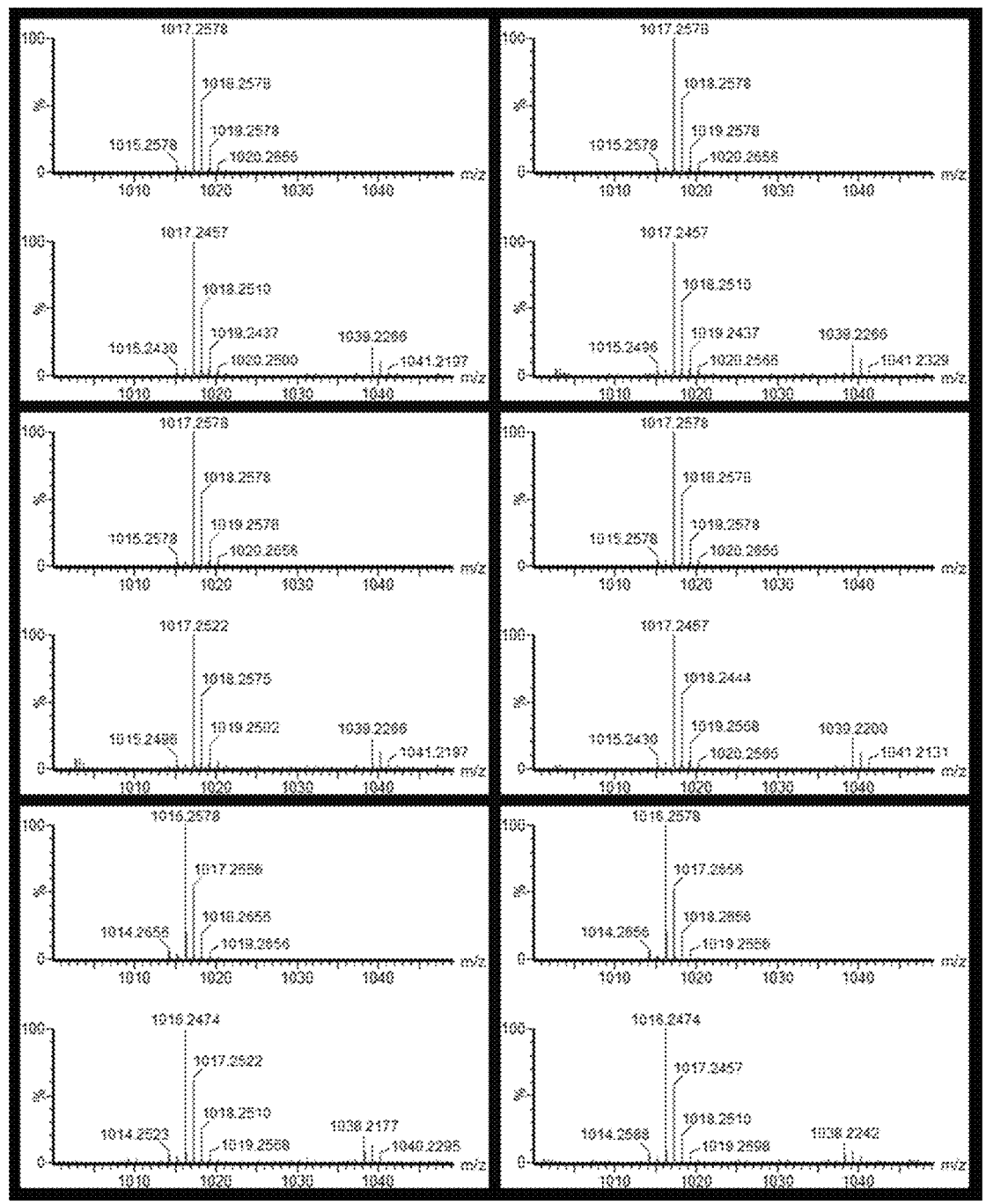
Figure 43C:
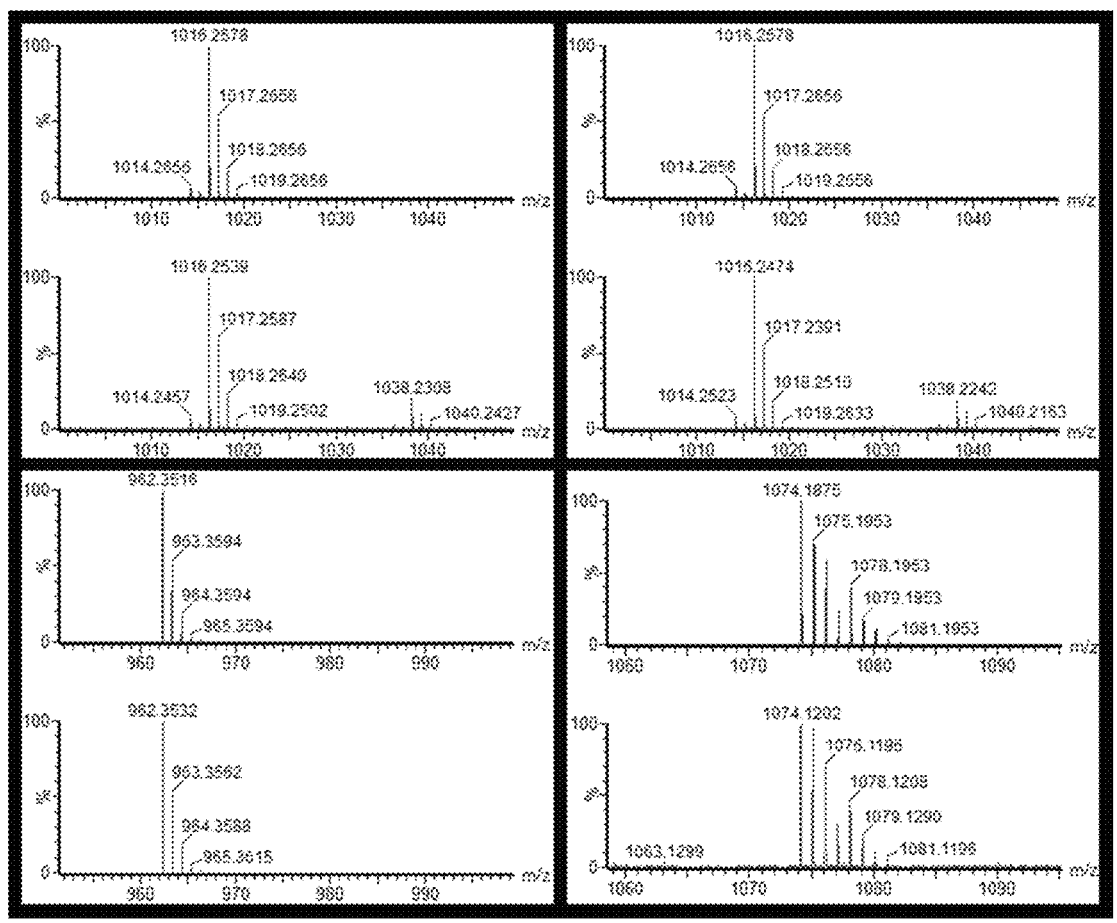

FIGS. 43A-43C depict the spectra that were obtained in negative mode. All peptoids are 1:1 $Fe^{3+}$ complexes except for CCCC and HHHH. Top spectrum is calculated and bottom is obtained.

Example 19—TOF MSMS of Select Peptoids

Figure 44:
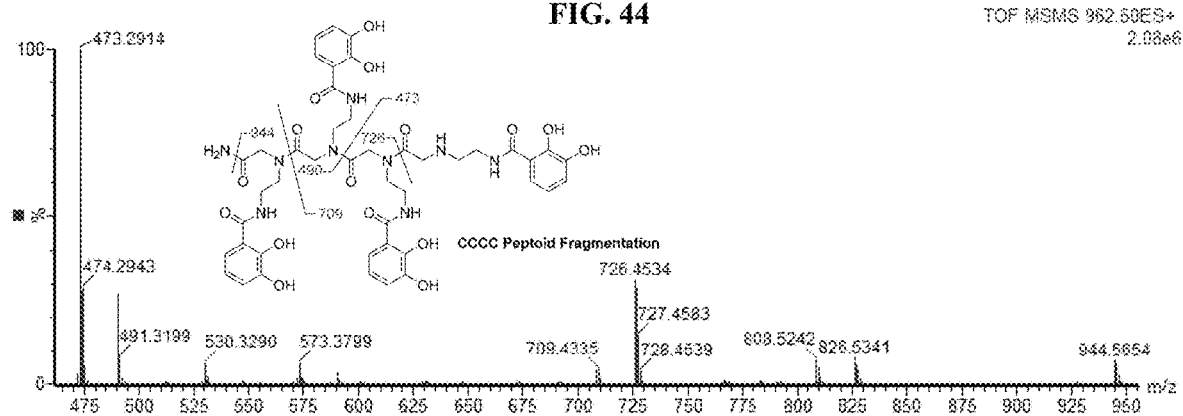
FIG. 44 depicts the TOF MSMS of select peptoids.
Figure 44:
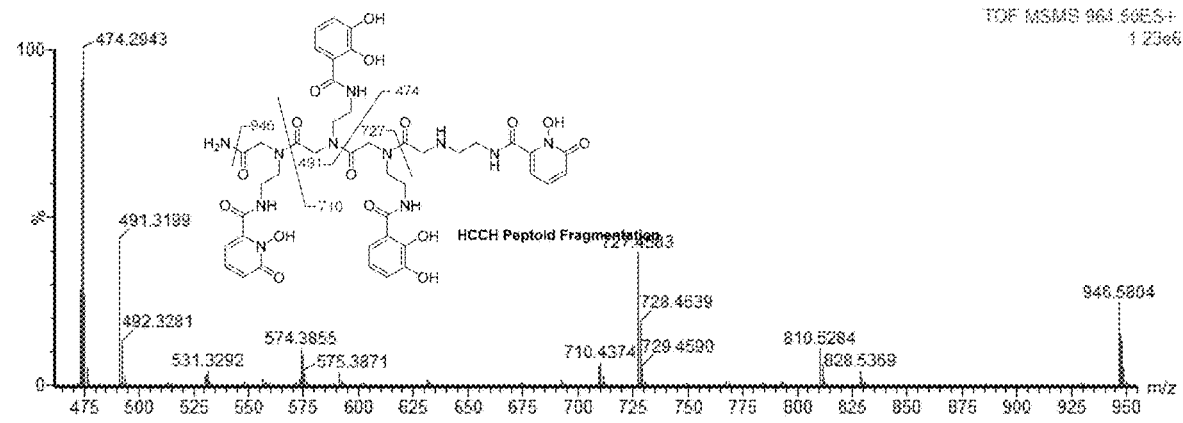
Figure 44:
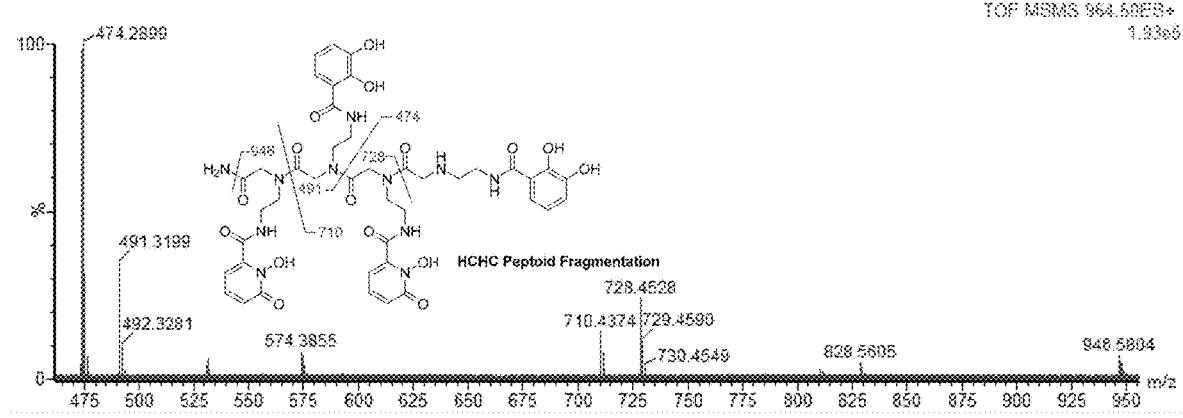
Figure 45A:
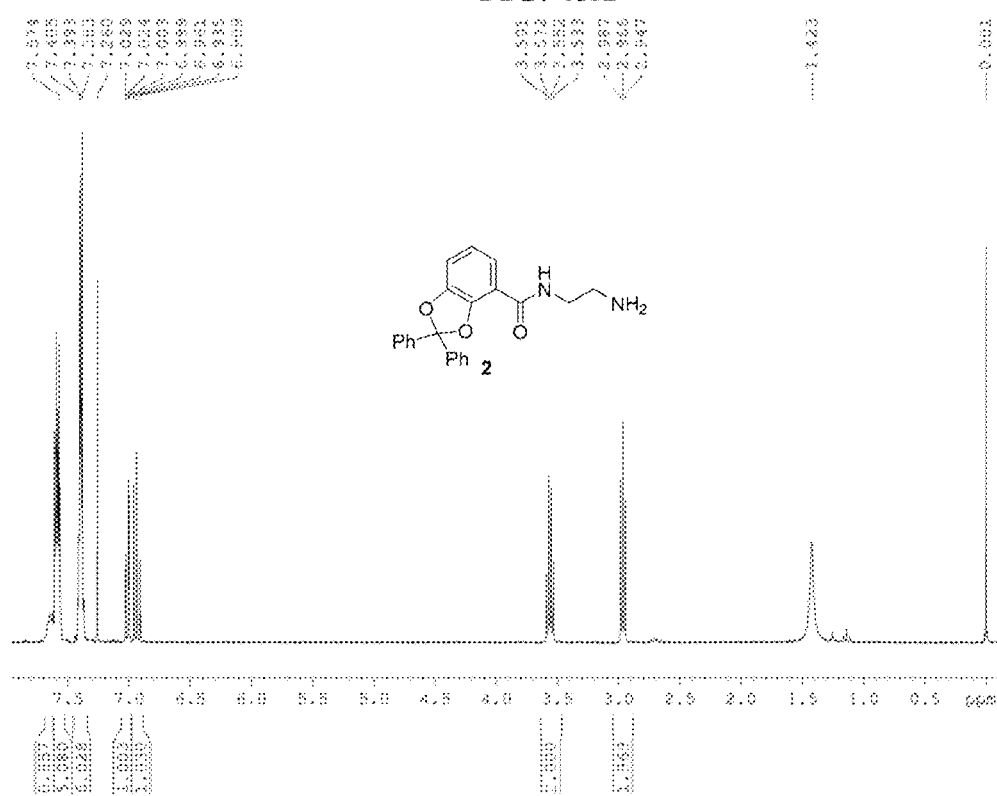
FIGS. 45A-45D depict NMR results of select peptoids.
Figure 45B:
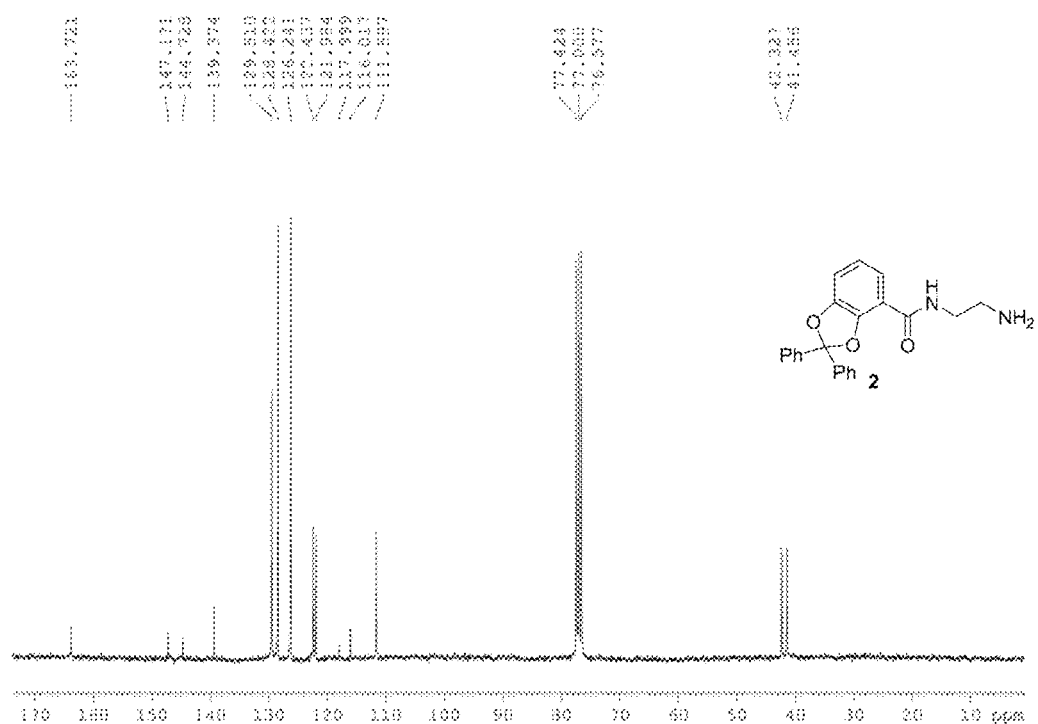
Figure 45C:
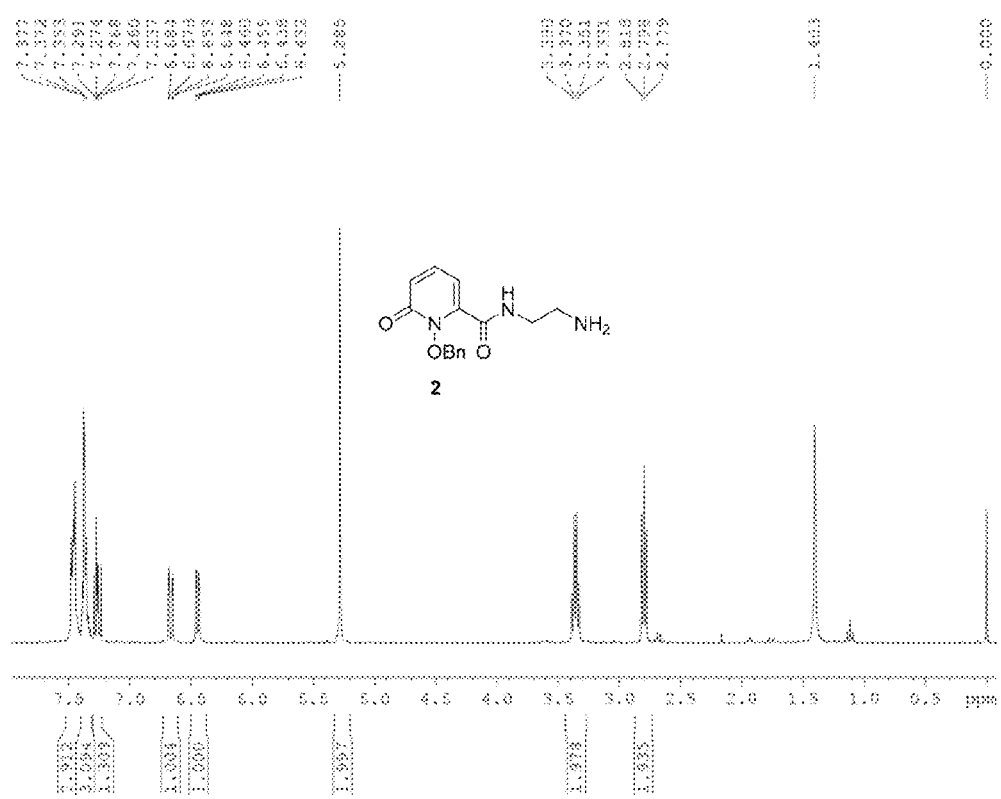
Figure 45D:
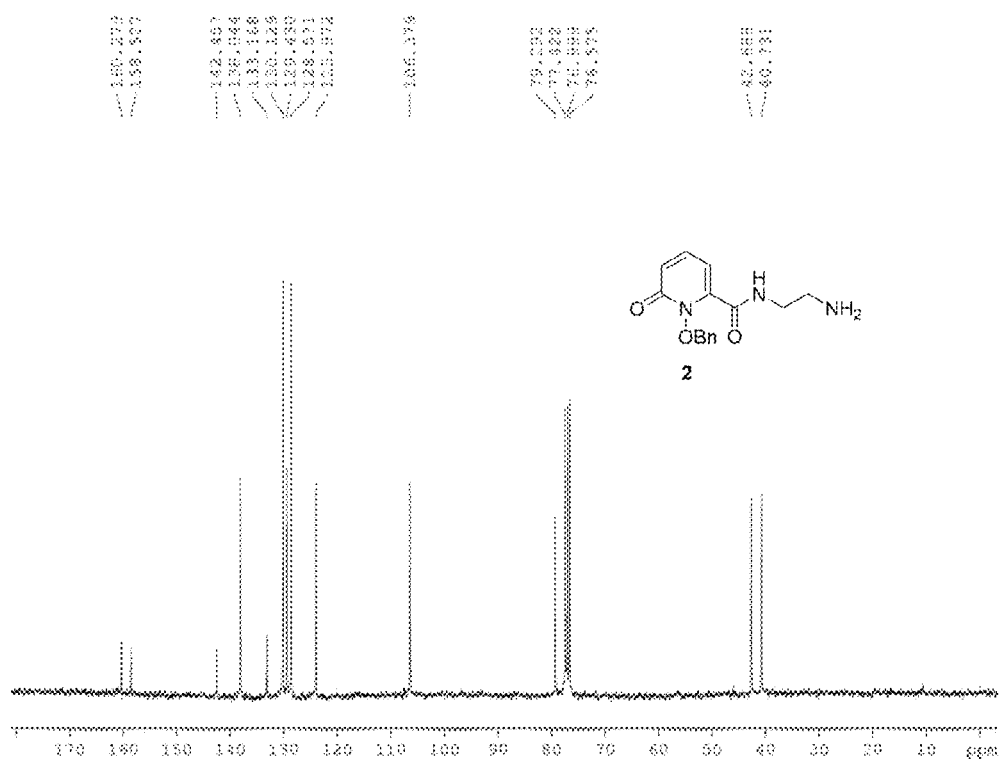

FIG. 44 depicts the positive mode, fragmentation of molecular ion, masses of interest. Differences in peptoids are illustrated based on both composition and sequence. H and C units differ by a mass of 1 amu. FIGS. 45A-45D depict the NMR results.

Example 20—Choice of Aqueous Chelator as Hold-Back Reagent

Figure 46A:
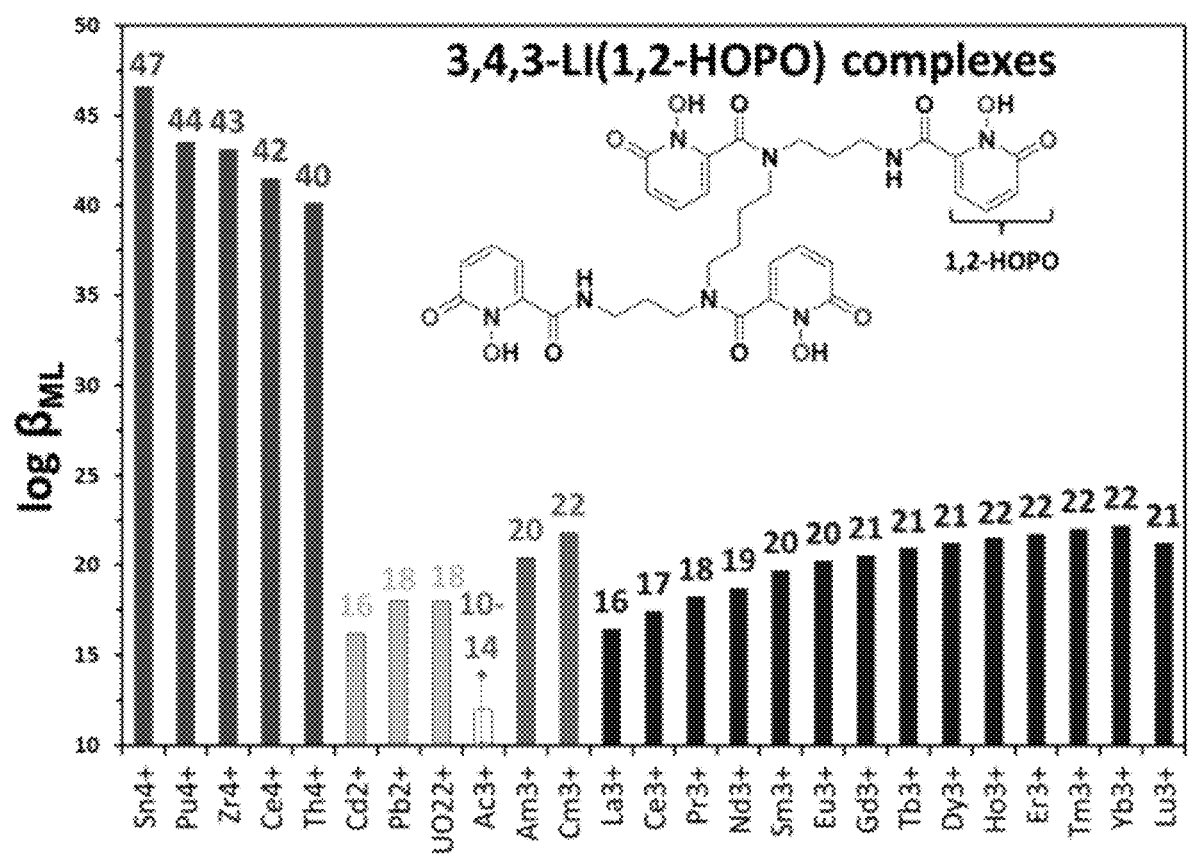
FIG. 46A shows stability constants ($\log/f_{ML}$) of 343HOPO complexes with tetravalent cations ($Sn^{4+}$, $Pu^{4+}$, $Ce^{4+}$, $Th^{4+}$), divalent ions ($Cd^{2+}$, $Pb^{2+}$, $UO_2^{2+}$), trivalent actinides ($Ac^{3+}$, $Am^{3+}$, $Cm^{3+}$), and trivalent lanthanides ($La^{3+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$). The value plotted for $Ac^{3+}$ is an estimate based on its ionic radius.
Figure 46B:
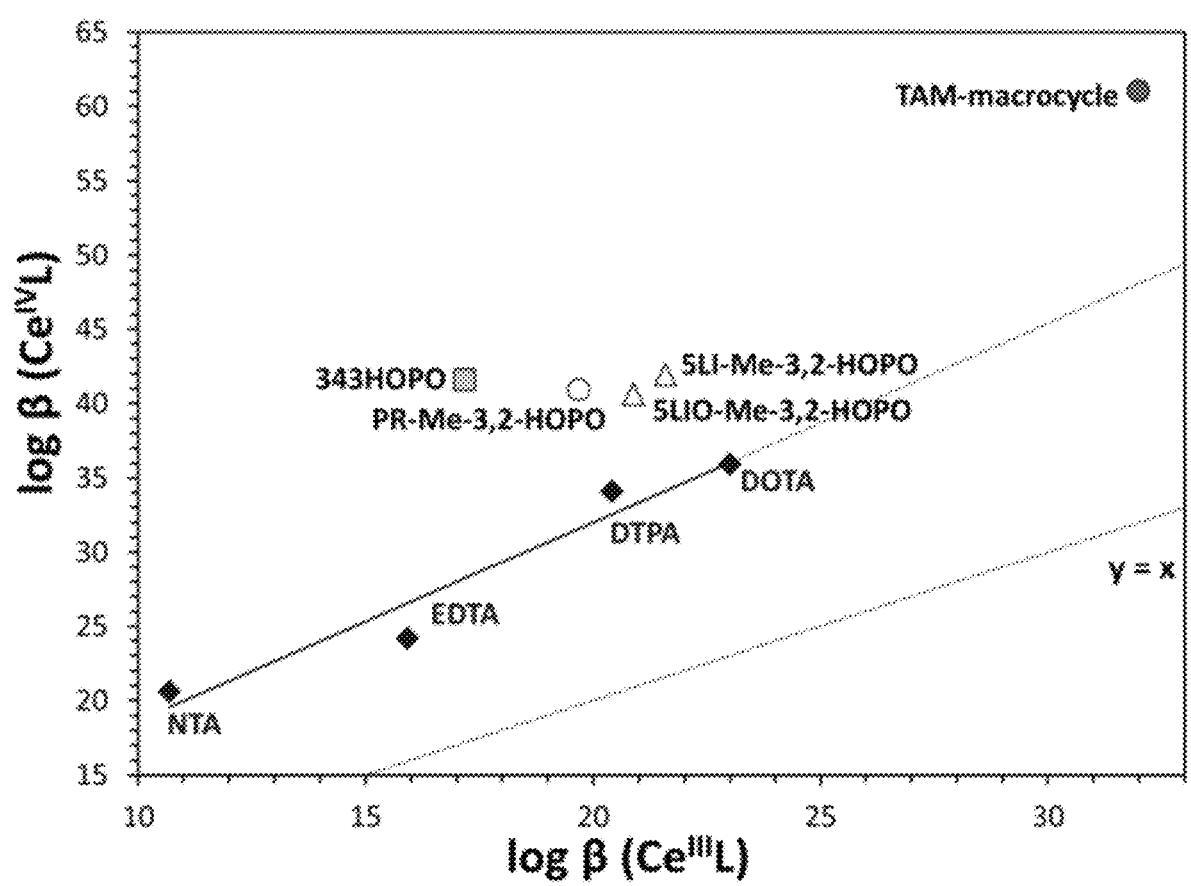
FIG. 46B shows selectivity comparisons for $Ce^{4+}/Ce^{3+}$ with HOPO and CAM ligands and classical chelators used in separations.
Figure 46C:
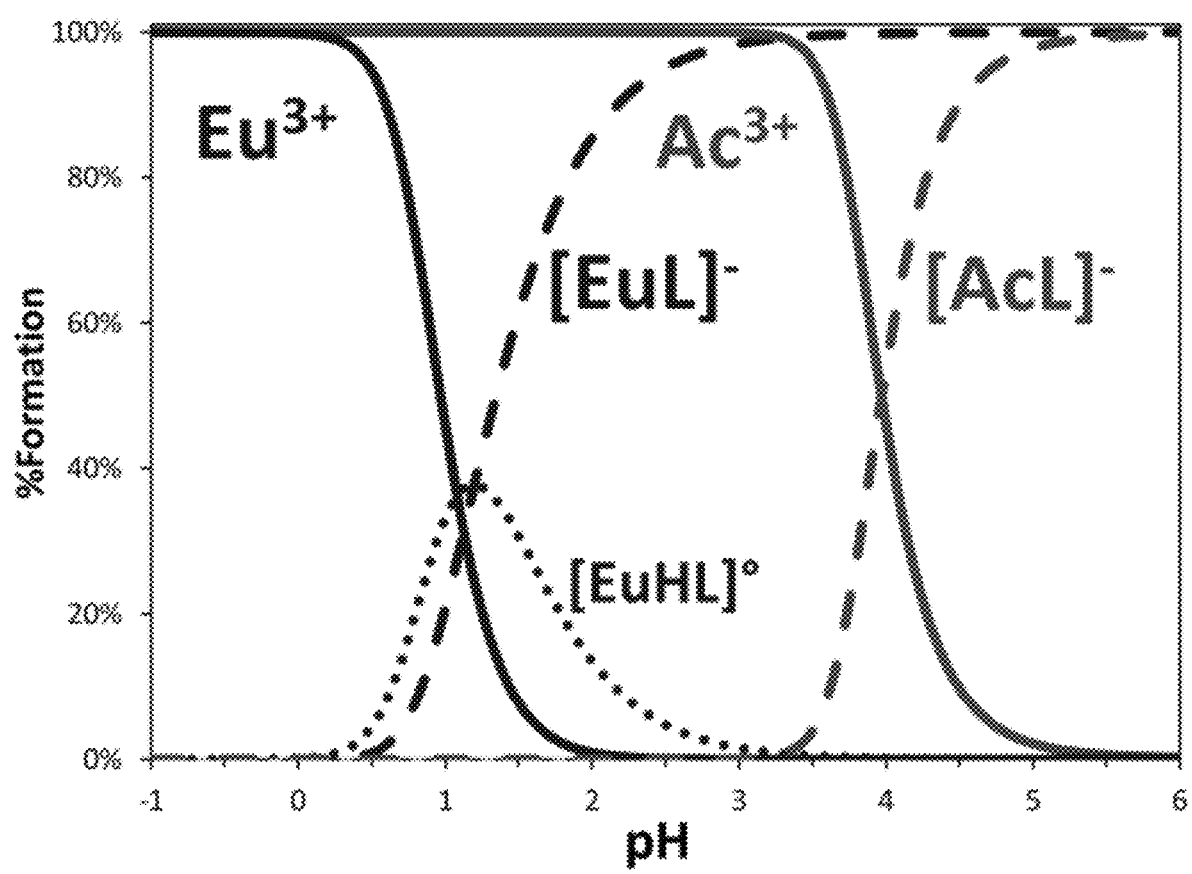
FIG. 46C shows embodiments of metal speciation diagrams for 343HOPO solutions containing $Ac^{3+}$ or $Eu^{3+}$ [Chelator]/[Metal]=1 mol/mol. L=Ligand. Solid lines: free metal. Dotted lines: 343HOPO complexes.
Figure 46D:
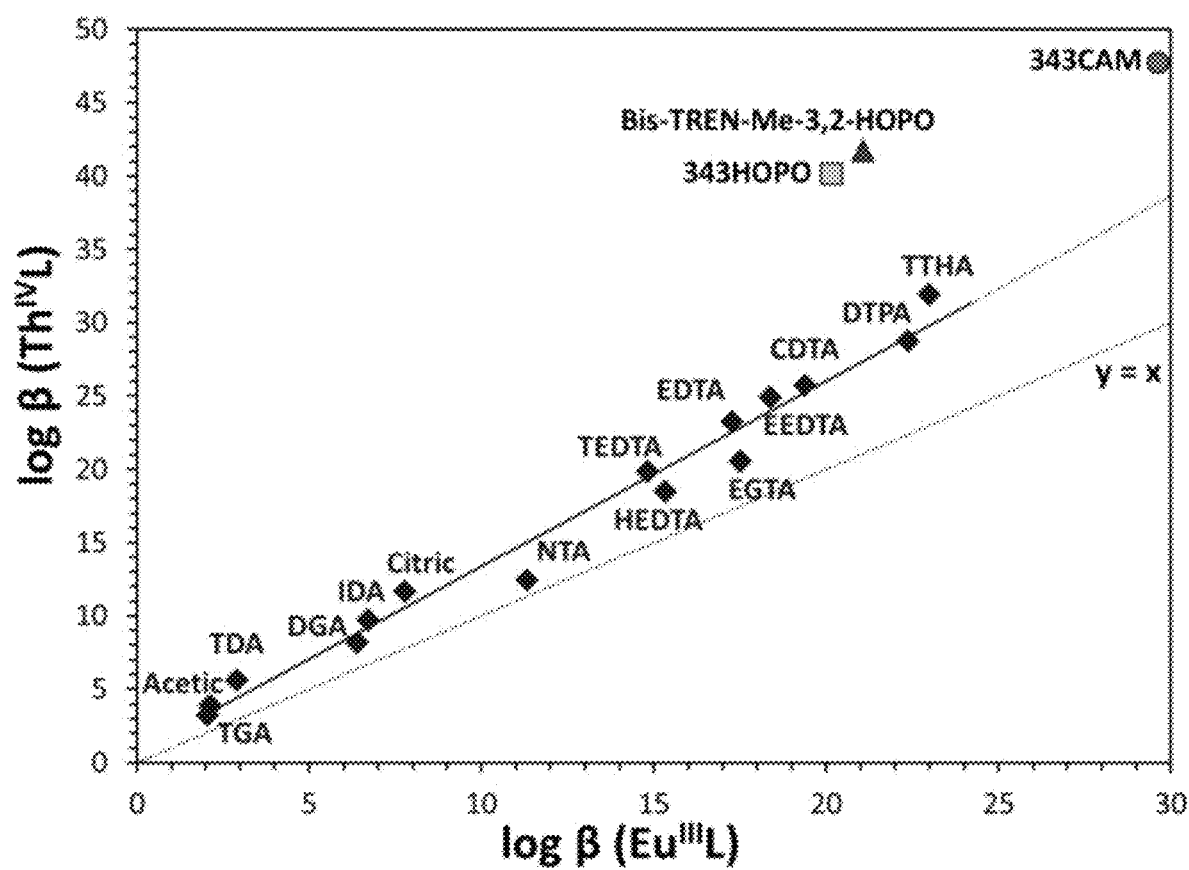
FIG. 46D shows selectivity comparisons for $Th^{4+}/Eu^{3+}$ with HOPO and CAM ligands and classical chelators used in separations.
Figure 46E:
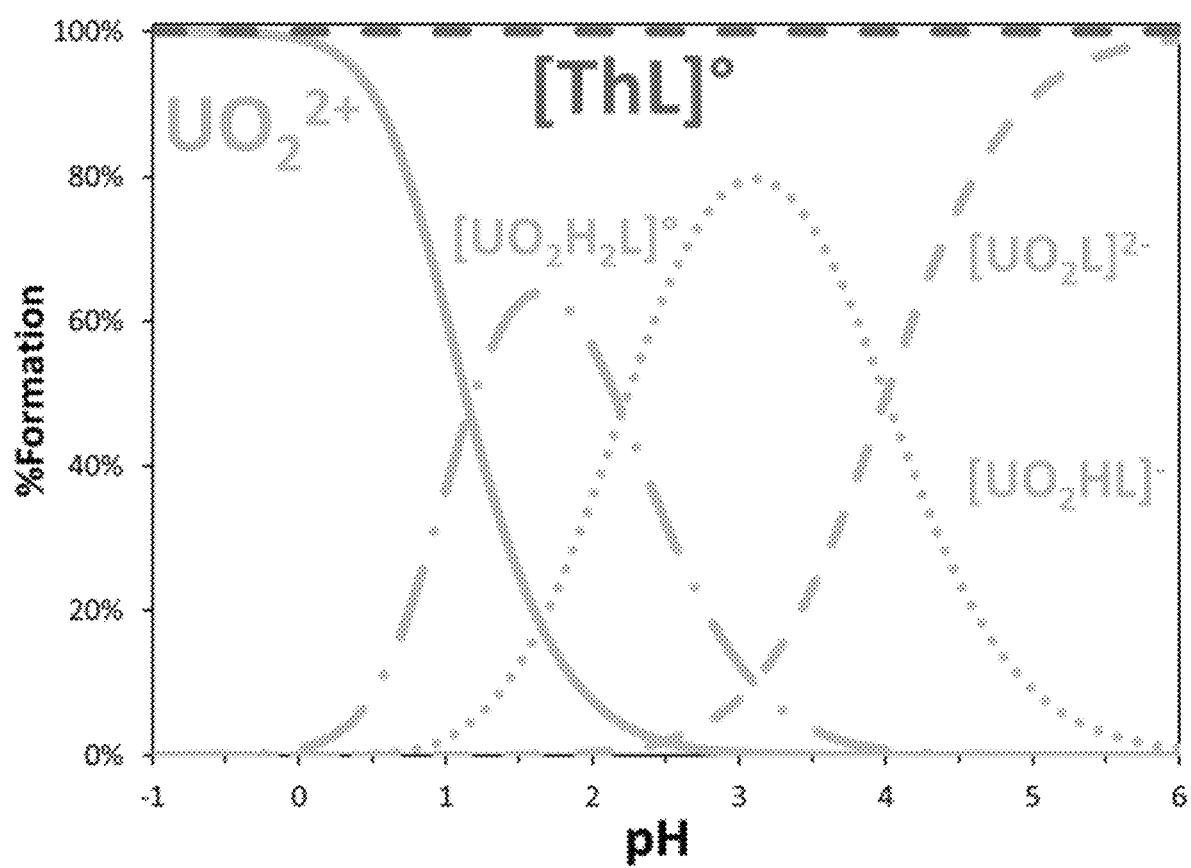
FIG. 46E shows embodiments of metal speciation diagrams for 343HOPO solutions containing $UO_2^{2+}$ or $Th^{4+}$. [Chelator]/[Metal]=1 mol/mol. L=Ligand. Solid lines: free metal. Dotted lines: 343HOPO complexes.
Figure 46F:
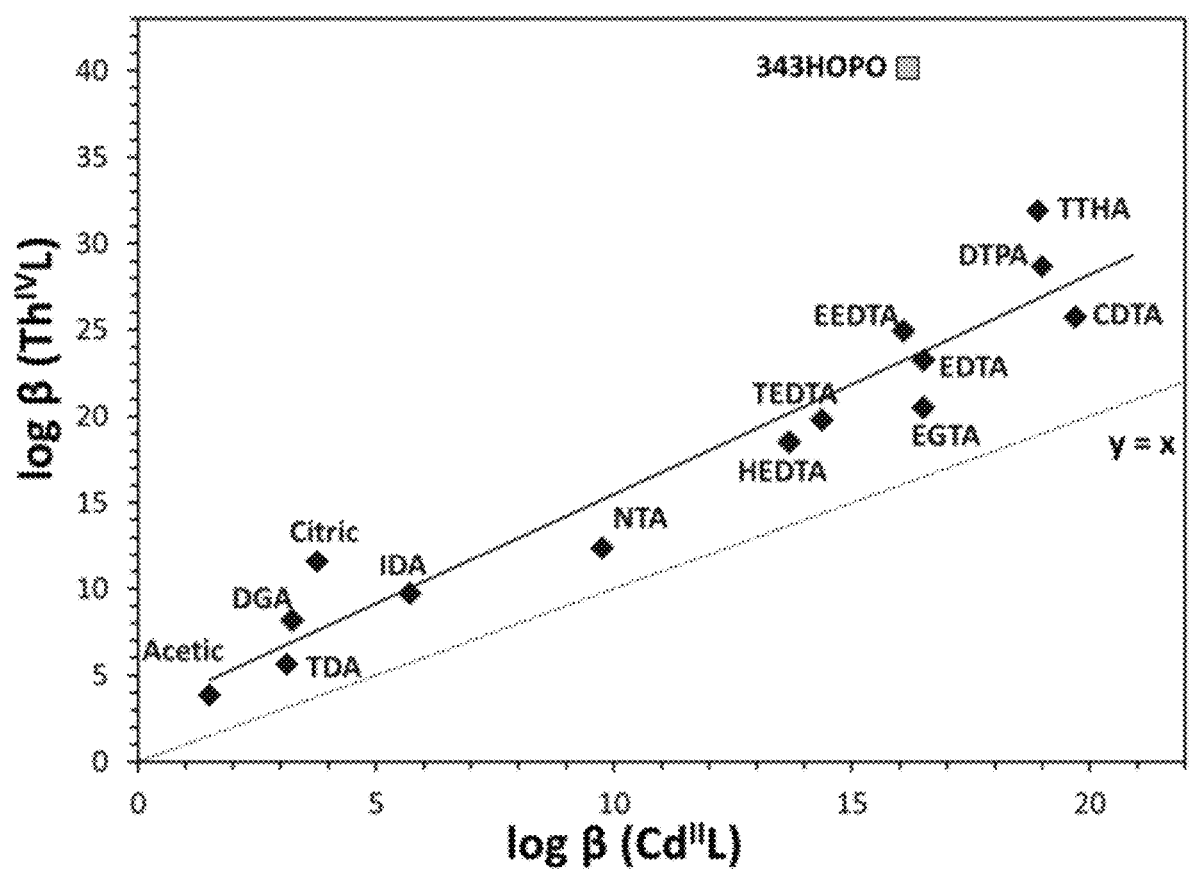
FIG. 46F shows selectivity comparisons for $Th^{4+}/Cd^{2+}$ with HOPO and CAM ligands and classical chelators used in separations.
Figure 48:
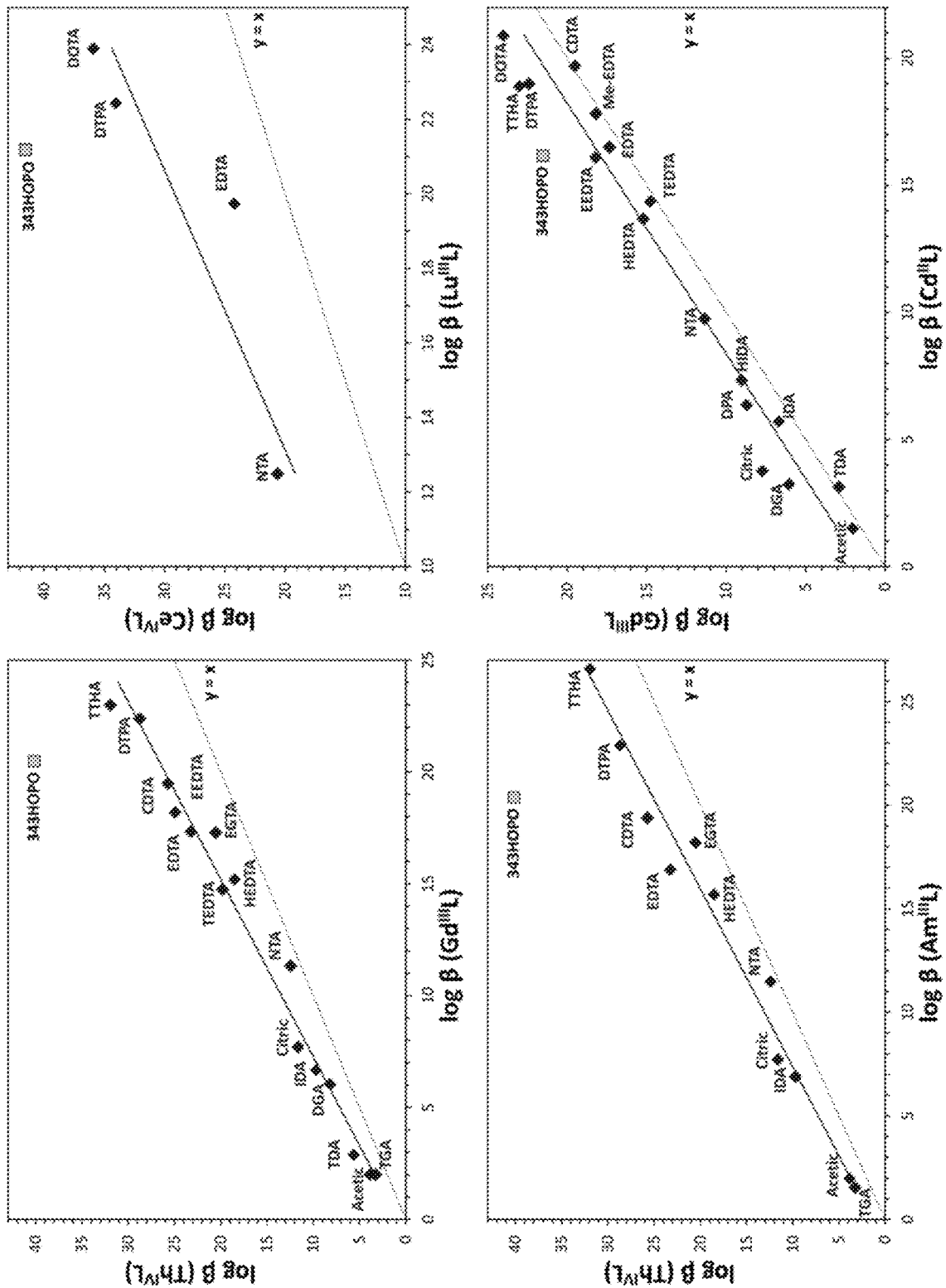
FIG. 48 shows additional comparisons of ligand selectivity between $Th^{4+}$ and $Gd^{3+}$, $Ce^{4+}$ and $Lu^{4+}$, $Th^{4+}$ and $Am^{3+}$ as well as $Gd^{3+}$ and $Cd^{2+}$.

Numerous drug development studies (Abergel, R. J. et al. Biomimetic actinide chelators: an update on the preclinical development of the orally active hydroxypyridonate decorporation agents 3,4,3-LI(1,2-HOPO) and 5-LIO(Me-3,2-HOPO). *Health Phys.* 99, 401-407 (2010); Gorden, A. E. V., Xu, J., Raymond, K. N. & Durbin, P. Rational Design of Sequestering Agents for Plutonium and Other Actinides. *Chem. Rev.* 103, 4207-4282 (2003); Deri, M. A. et al. p-SCN-Bn-HOPO: A Superior Bifunctional Chelator for 89Zr ImmunoPET. *Bioconj. Chem.* 26, 2579-2591 (2015)) have focused on synthetic "siderophore-inspired" compounds because of their ability to form stable, and sometimes luminescent, complexes with metal ions of interest for medical imaging, radionuclide decontamination, and cancer treatments. While this class of ligands, encompassing HOPO and catecholamide (CAM) derivatives, has been known for decades, it had never been studied in details for separation applications. In fact, a few exceptions aside, most of these chelators have only been studied with a single cation, such as $Gd^{3+}$, $Th^{4+}$, or $Pu^{4+}$, impairing broader evaluation of their metal-metal selectivity. The chemistry of some HOPO ligands was recently extended across the periodic table, highlighting their outstanding selectivity, and large superiority over polyaminocarboxylate chelators (IDA, EDTA, DTPA, etc.), typically encountered in separations (FIGS. 46A-46F). Stability constants (log $\beta_{ML}$) were calculated as described in Sturzbecher-Hoehne, M., Kullgren, B., Jarvis, E. E., An, D. D. & Abergel, R. J. Highly Luminescent and Stable Hydroxypyridinonate Complexes: A Step Towards New Curium Decontamination Strategies. *Chem. Eur. J.* 20, 9962-9968 (2014); Sturzbecher-Hoehne, M., Yang, P., D'Aldo, A. & Abergel, R. J. Intramolecular sensitization of americium luminescence in solution: shining light on short-lived forbidden 5f transitions. *Dalton Trans.* 45, 9912-9919 (2016); Deblonde, G. J.-P., Lohrey, T. D., An, D. D. & Abergel, R. J. Toxic heavy metal—Pb, Cd, Sn—complexation by the octadentate hydroxypyridinonate ligand archetype 3,4,3-LI(1,2-HOPO). *New J. Chem.* 42, 7649-7658 (2018). For tetradentate ligands 5-LIO-Me-3,2-HOPO and 5-LI-Me-3,2-HOPO, the $\beta_{ML2}$ value was used (FIGS. 46B, 46D, and 46F). For bidentate PR-Me-3,2-HOPO, the $\beta_{ML4}$ value was used (FIGS. 46B, 46D, and 46F). The line y=x corresponded to no selectivity (FIGS. 46B, 46D, and 46F). Additional selectivity comparisons are given in FIG. 48, which shows Additional comparisons of ligand selectivity between $Th^{4+}$ and $Gd^{3+}$, $Ce^{4+}$ and $Lu^{4+}$, $Th^{4+}$ and $Am^{3+}$ as well as $Gd^{3+}$ and $Cd^{2+}$. TABLE 4 shows the full names of the ligands. The line y=x corresponds to no selectivity (FIGS. 46B, 46D, and 46F). Log β values were taken from the National Institute of Standards and Technologies database (NIST46—NIST Critically Selected Stability Constants of Metal Complexes: Version 8.0). Full ligand names and structures are given in TABLE 4.

TABLE 4

List of ligands and extractants mentioned in this study.

| Abbreviation<br>Compound name | Ligand formula |
|---|---|
| TBP<br>n-tributyl phosphate | (structure shown) |
| HDEHP<br>Bis(2-ethylhexyl) phosphate.<br>Also known as D2EHPA or DEHPA. | (structure shown) |

TABLE 4-continued

List of ligands and extractants mentioned in this study.

| Abbreviation<br>Compound name | Ligand formula |
|---|---|
| TODGA<br>N,N,N',N'-tetraoctyl diglycolamide | |
| 343HOPO<br>3,4,3-LI(1,2-HOPO) | |
| 343CAM<br>3,4,3-LI-CAM | |
| Bis-TREN-Me-3,2-HOPO | |

TABLE 4-continued
List of ligands and extractants mentioned in this study.
| Abbreviation<br>Compound name | Ligand formula |
|---|---|
| 5LIO-Me-3,2-HOPO | 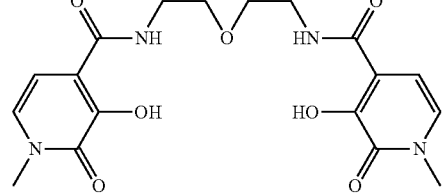 |
| 5LI-Me-3,2-HOPO | 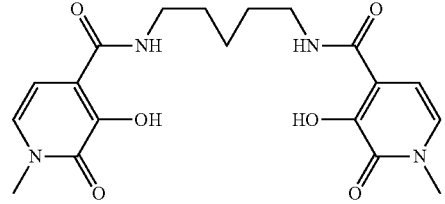 [SMILES: Cn1ccc(C(=O)NCCOCCNC(=O)c2ccn(C)c(=O)c2O)c(O)c1=O] |
| Acetic<br>Acetic acid | 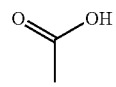 |
| CDTA<br>Trans-1,2-cyclohexanediamine-<br>N,N,N',N'-tetraacetic acid | 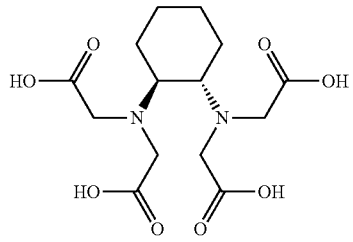 [SMILES: O=C(O)CN(CC(=O)O)[C@H]1CCCC[C@@H]1N(CC(=O)O)CC(=O)O] |
| Citric<br>Citric acid | 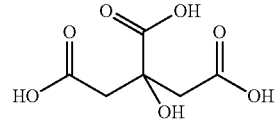 [SMILES: O=C(O)CC(O)(CC(=O)O)C(=O)O] |
| DGA<br>Diglycolic acid | 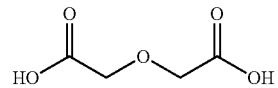 |
| DOTA<br>1,4,7,10-Tetraazacyclododecane-<br>1,4,7,10-tetraacetic acid | 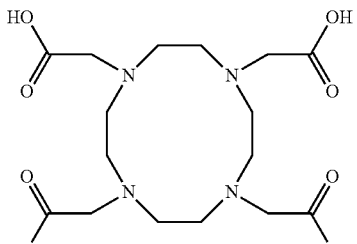 |
| DPA<br>Dipicolinic acid | 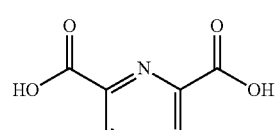 |

TABLE 4-continued

List of ligands and extractants mentioned in this study.

| Abbreviation<br>Compound name | Ligand formula |
|---|---|
| DTPA<br>Diethylenetriaminepentaacetic acid | |
| EDTA<br>Ethylenediaminetetraacetic acid | |
| EEDTA<br>2,2',2'',2'''-[Oxybis(2,1-ethanediylnitrilo)]tetraacetic acid.<br>Also known as "BAETA" | |
| EGTA<br>Ethylene glycol tetraacetic acid | |
| IDA<br>Iminodiacetic acid | |
| HEDTA<br>Hydroxyethylethylenediamine-triacetic acid | |

TABLE 4-continued

List of ligands and extractants mentioned in this study.

| Abbreviation<br>Compound name | Ligand formula |
|---|---|
| Me-EDTA<br>Propylenediamine-N,N,N',N'-tetraacetic acid<br>Also known as "PDTA". | |
| NTA<br>Nitrilotriacetic acid | |
| TAM-macrocycle | |
| TDA<br>Thiodiacetic acid | |
| TEDTA<br>2,2',2'',2'''-[Sulfanediylbis(2,1-ethanediylnitrilo)]tetraacetic acid | |
| TGA<br>Thioglycolic acid | |

TABLE 4-continued

List of ligands and extractants mentioned in this study.

| Abbreviation Compound name | Ligand formula |
|---|---|
| TTHA Triethylenetetramine-N,N,N',N'',N''',N'''-hexaacetic acid | (structure shown) |

Figure 47:
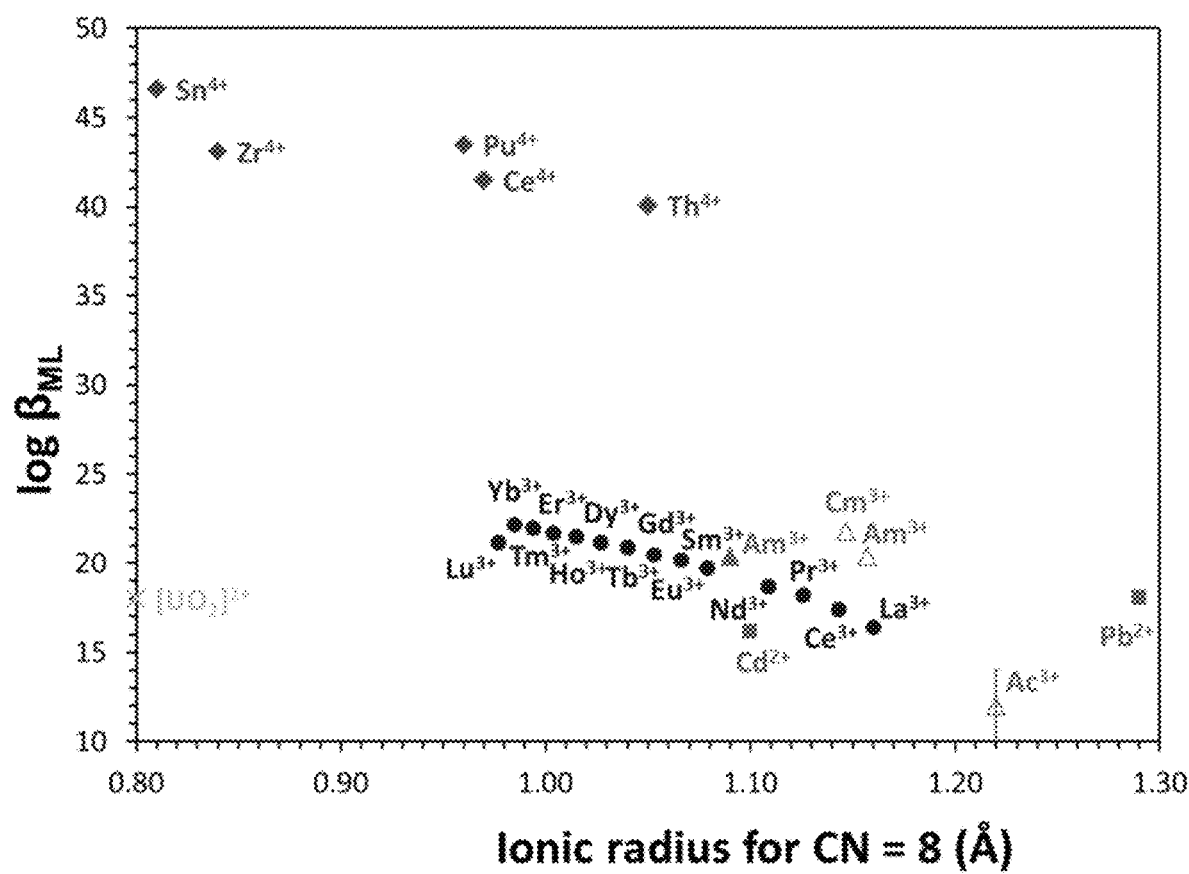
FIG. 47 shows stability constants of the complexes of 343HOPO against the ionic radius of the metal ions (for a coordination number, CN, of 8).

A comparison of metal complex formation constants for the octadentate 343HOPO shows striking differences between tetravalent species and corresponding divalent or trivalent ones. FIG. 47 shows stability constants of the complexes of 343HOPO against the ionic radius of the metal ions (for a coordination number, CN, of 8). Ionic radius values were taken from Shannon (1976) and Lundberg and Persson (2016). Since no ionic radius value for a CN of 8 has been published for $Ac^{3+}$, and $Cm^{3+}$, ionic radius values for a CN of 9 were used and plotted for comparison purposes (empty symbols). The uranyl ion is arbitrary placed at 0.8 Å for comparison. The observed selectivity seems mainly charge-based and only slightly dependent on the ionic radius of the cations (FIG. 47), although some selectivity is noted across the trivalent lanthanide and actinide series. 343HOPO outperforms any known chelator in terms of charge-specific selectivity and, in particular, for the binding of tetravalent ions. As such, the $Ce^{4+}/Ce^{3+}$ selectivity of 343HOPO is about 15 orders of magnitude higher than what could be expected from a carboxylate ligand. Extreme selectivity is also observed even for ions of similar size such as in the $Th^{4+}/Am^{3+}$, $Th^{4+}/Gd^{3+}$, $Ce^{4+}/Lu^{3+}$, or $Th^{4+}/Cd^{2+}$ pairs (FIGS. 46A-46F, and 48). As shown in FIGS. 46A-46F, a handful of other molecules from the same family (octadentate 3,4,3-LI-CAM, Bis-TREN-Me-3,2-HOPO, and TAM-macrocycle; tetradentate 5LI-Me-3,2-HOPO, 5LIO-Me-3,2-HOPO; and bidentate PR-Me-3,2-HOPO) (Captain, I. et al. Engineered Recognition of Tetravalent Zirconium and Thorium by Chelator-Protein Systems: Toward Flexible Radiotherapy and Imaging Platforms. Inorg. Chem. 55, 11930-11936 (2016); Xu, J., Radkov, E., Ziegler, M. & Raymond, K. N. Plutonium(IV) Sequestration: Structural and Thermodynamic Evaluation of the Extraordinarily Stable Cerium (IV) Hydroxypyridinonate Complexes[1]. Inorg. Chem. 39, 4156-4164 (2000); Deblonde, G. J.-P. et al. Solution Thermodynamics and Kinetics of Metal Complexation with a Hydroxypyridinone Chelator Designed for Thorium-227 Targeted Alpha Therapy. Inorg. Chem. (2018). doi:10.1021/acs.inorgchem.8b02430; Pham, T. A. et al. A Macrocyclic Chelator That Selectively Binds Ln4+ over Ln3+ by a Factor of 1029. Inorg. Chem. 55, 9989-10002 (2016)) exhibited known solution thermodynamic properties that matched those of 343HOPO but none of the chelators typically used for separation methods were nearly as selective. Many additional HOPO and CAM ligands have been designed (Gorden, A. E. V., Xu, J., Raymond, K. N. & Durbin, P. Rational Design of Sequestering Agents for Plutonium and Other Actinides. Chem. Rev. 103, 4207-4282 (2003)) and previously reported octadentate 1,2-HOPO (D'Aléo, A., Moore, E. G., Xu, J., Daumann, L. J. & Raymond, K. N. Optimization of the Sensitization Process and Stability of Octadentate Eu(III) 1,2-HOPO Complexes. Inorg. Chem. 54, 6807-6820 (2015)), mixed 3,4,3-LI(1,2-HOPO/Me-3,2-HOPO) (Xu, J. et al. Synthesis and Initial Evaluation for In Vivo Chelation of Pu(IV) of a Mixed Octadentate Spermine-Based Ligand Containing 4-Carbamoyl-3-hydroxy-1-methyl-2(1H)-pyridinone and 6-Carbamoyl-1-hydroxy-2 (1H)-pyridinone. J. Med. Chem. 45, 3963-3971 (2002)), and DFO/1,2-HOPO (Deblonde, G. J.-P., Sturzbecher-Hoehne, M. & Abergel, R. J. Solution Thermodynamic Stability of Complexes Formed with the Octadentate Hydroxypyridinonate Ligand 3,4,3-LI(1,2-HOPO): A Critical Feature for Efficient Chelation of Lanthanide(IV) and Actinide(IV) Ions. Inorg. Chem. 52, 8805-8811 (2013)) structures would certainly make excellent candidates for charge-based selectivity; however, their chelation properties have so far only been investigated with either $Eu^{3+}$, $Zr^{4+}$, or $Pu^{4+}$. Due to its current kg-scale availability and established solution thermodynamics, 343HOPO was used here as a model case. Without being limited by any particular theory, 343HOPO was not initially designed for separation applications and its performance should not be considered as the upper limit for a separation strategy that could be extended to an entire molecular family.

The selectivity of 343HOPO for tetravalent ions was so high that it was expected to form complexes even under very acidic conditions (experimentally observed (Deblonde, G. J.-P., Lohrey, T. D., An, D. D. & Abergel, R. J. Toxic heavy metal—Pb, Cd, Sn—complexation by the octadentate hydroxypyridinonate ligand archetype 3,4,3-LI(1,2-HOPO). New J. Chem. 42, 7649-7658 (2018)) in 3 M HCl for $Sn^{4+}$), whereas it should release trivalent (Sturzbecher-Hoehne, M. et al. 3,4,3-LI(1,2-HOPO): In vitro formation of highly stable lanthanide complexes translates into efficacious in vivo europium decorporation. Dalton Trans. 40, 8340 (2011)) and divalent (Deblonde, G. J.-P., Lohrey, T. D., An, D. D. & Abergel, R. J. Toxic heavy metal—Pb, Cd, Sn—complexation by the octadentate hydroxypyridinonate ligand archetype 3,4,3-LI(1,2-HOPO). New J. Chem. 42, 7649-7658 (2018); Sturzbecher-Hoehne, M., Deblonde, G. J.-P. & Abergel, R. J. Solution thermodynamic evaluation of hydroxypyridinonate chelators 3,4,3-LI(1,2-HOPO) and 5-LIO(Me-3,2-HOPO) for UO2(VI) and Th(IV) decorporation. Radiochim. Acta 101, 359-366 (2013)) ions completely below pH~2 (FIGS. 46A-46F). Without being limited by any particular theory, to our knowledge, no other reported class of ligands exhibits such behavior. The clear metal discrimination afforded by 343HOPO (bound $M^{4+}$ versus free $M^{3+/2+/1+}$) can therefore be leveraged as a chemical switch to isolate charged ions, a needed tool when separating $Ac^{3+}/Th^{4+}$ or $Pu^{4+}/Am^{3+}$ mixtures. If such an ultra-selective complexant is present in the aqueous phase, overall process selectivity is expected to be decoupled from extractant selectivity, since a system containing 343HOPO in the aqueous phase and a completely non-selective extractant in the organic phase will still result in highly efficient separation. Such ligand-driven performance enables more flexible solvent formulation and operational process conditions. It will also spare the cumbersome development of new extractants and can be applied to a variety of $M^{x+}/M^{y+}$ pairs, as demonstrated below.

Example 21—Actinium Purification

Figure 49A:
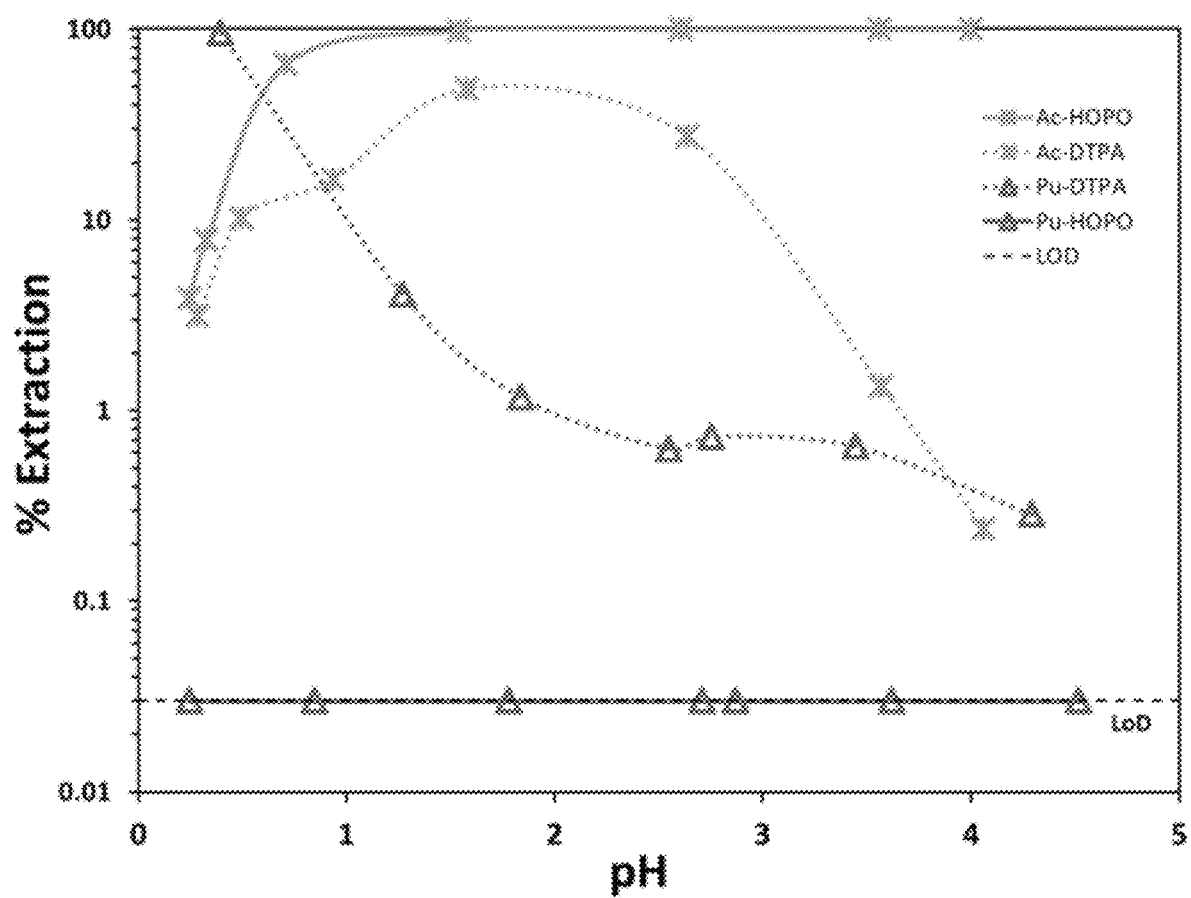
FIG. 49A shows extraction yield of $Ac^{3+}$ (stars) and $Pu^{4+}$ (triangles) by 0.5 M HDEHP as a function of pH, in the presence of DTPA (dotted lines) or 343HOPO (solid lines). A logarithmic scale is used due to the low extraction yields of $Pu^{4+}$.
Figure 49B:
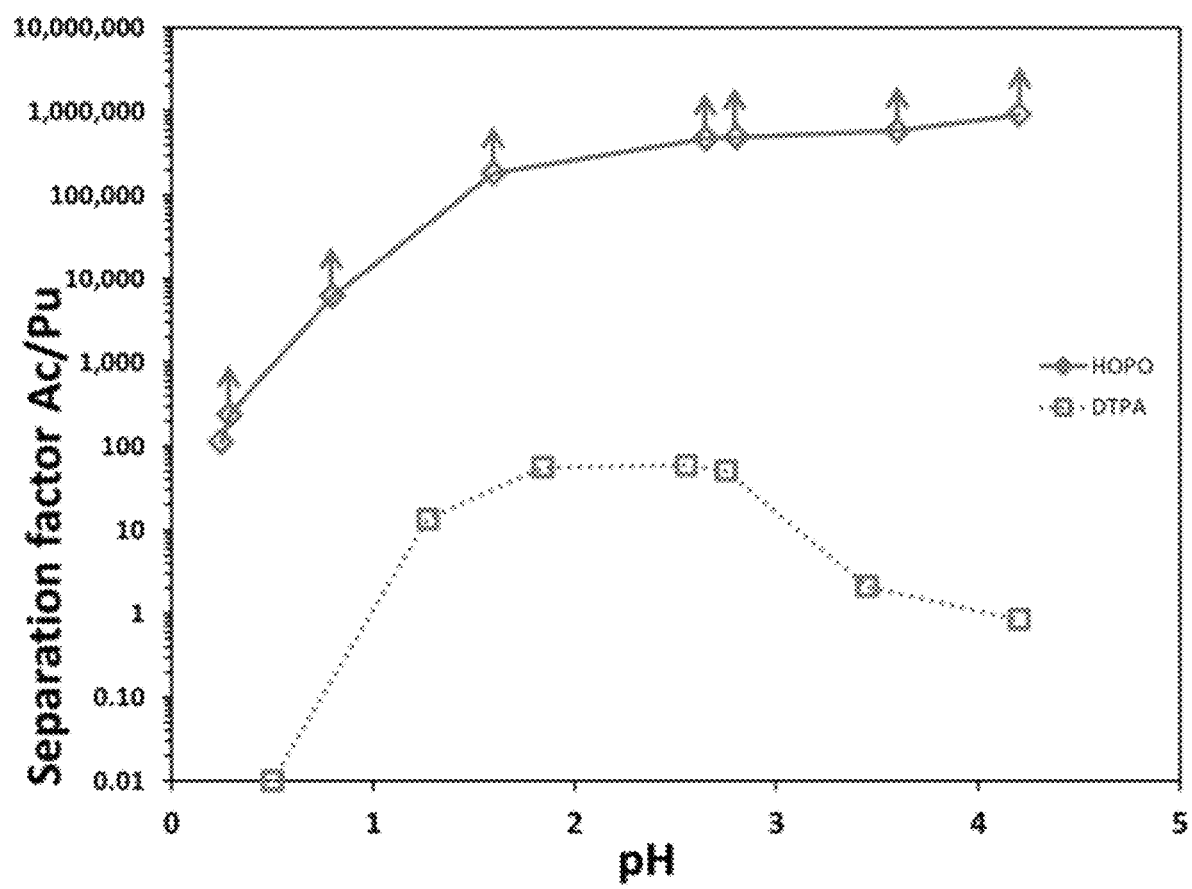
FIG. 49B shows corresponding separation factors for FIG. 49A. Aqueous phase: 40 mM of chelator in sodium lactate/sodium nitrate buffer (I=2 M). $V_{org}/V_{aq}$=1. T=25° C. LoD=Limit of detection. Data points with arrows are lower limits.
Figure 50A:
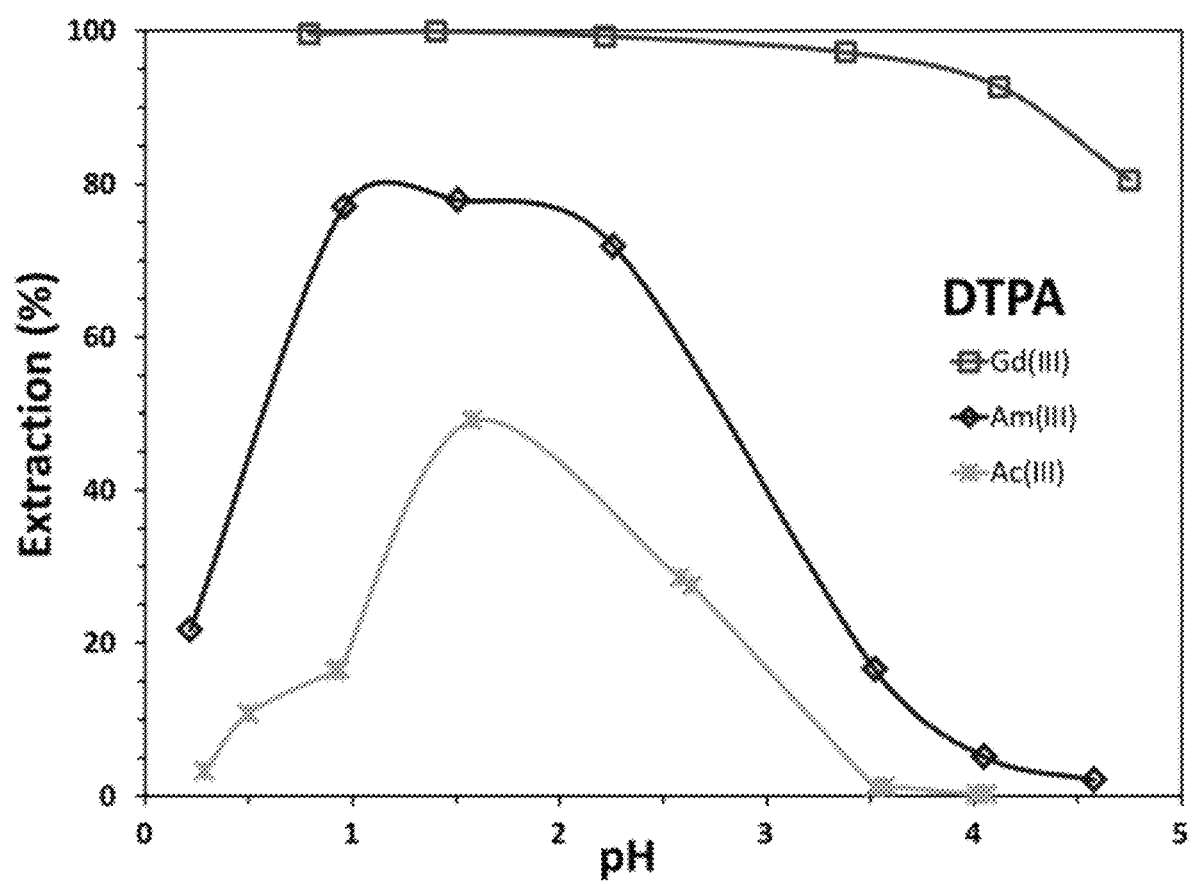
FIG. 50A shows extraction yield of trivalent Ac (stars), Gd (squares), and Am (circles) by 0.5 M HDEHP as a function of pH, in the presence of DTPA. A logarithmic scale was used due to the low extraction yields of $Pu^{4+}$.
Figure 50B:
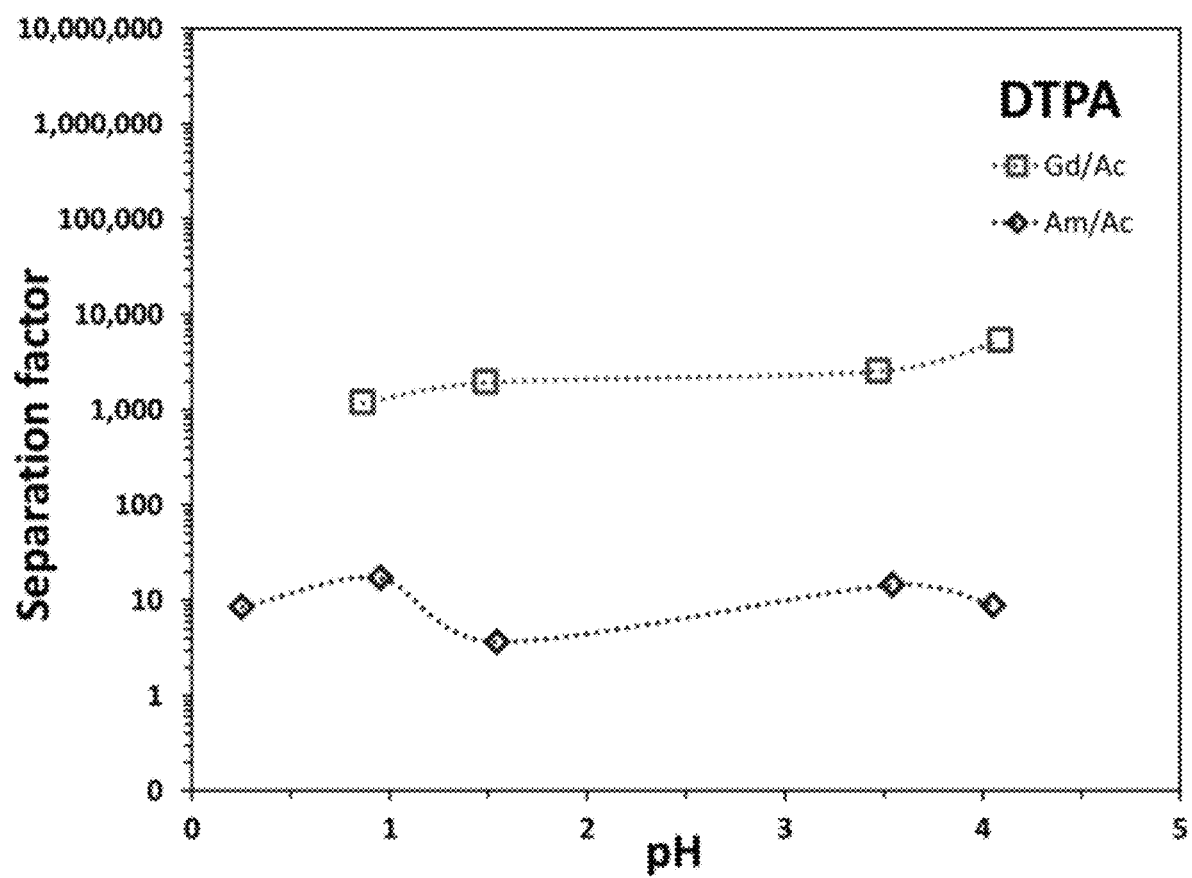
FIG. 50B shows the corresponding separation factors in the presence of DTPA for FIG. 50A. Aqueous phase: 40 mM of chelator in sodium lactate/sodium nitrate buffer (I=2 M). $V_{org}/V_{aq}$=1, one contact. T=25° C. Data points with arrows are lower limits.
Figure 50C:
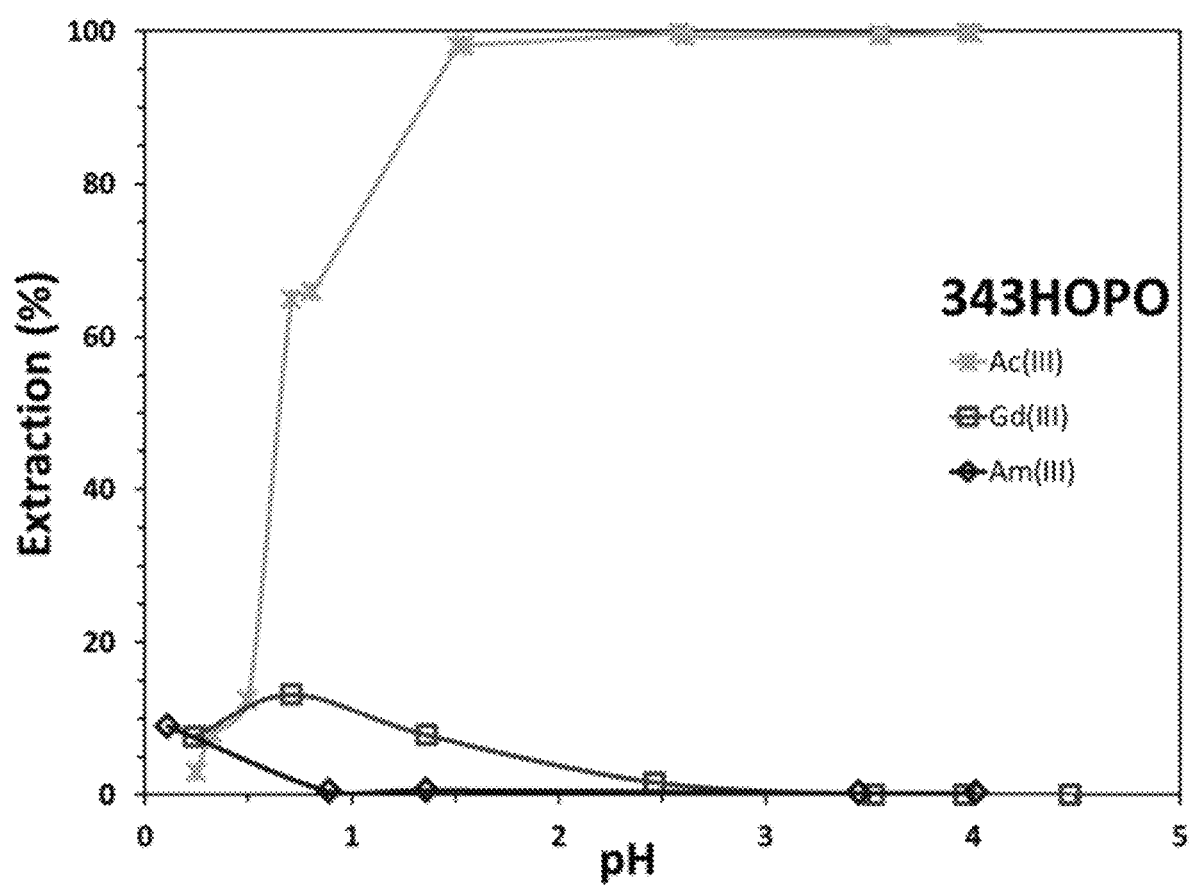
FIG. 50C shows extraction yield of trivalent Ac (stars), Gd (squares), and Am (circles) by 0.5 M HDEHP as a function of pH, in the presence of 343HOPO. A logarithmic scale was used due to the low extraction yields of $Pu^{4+}$.
Figure 50D:
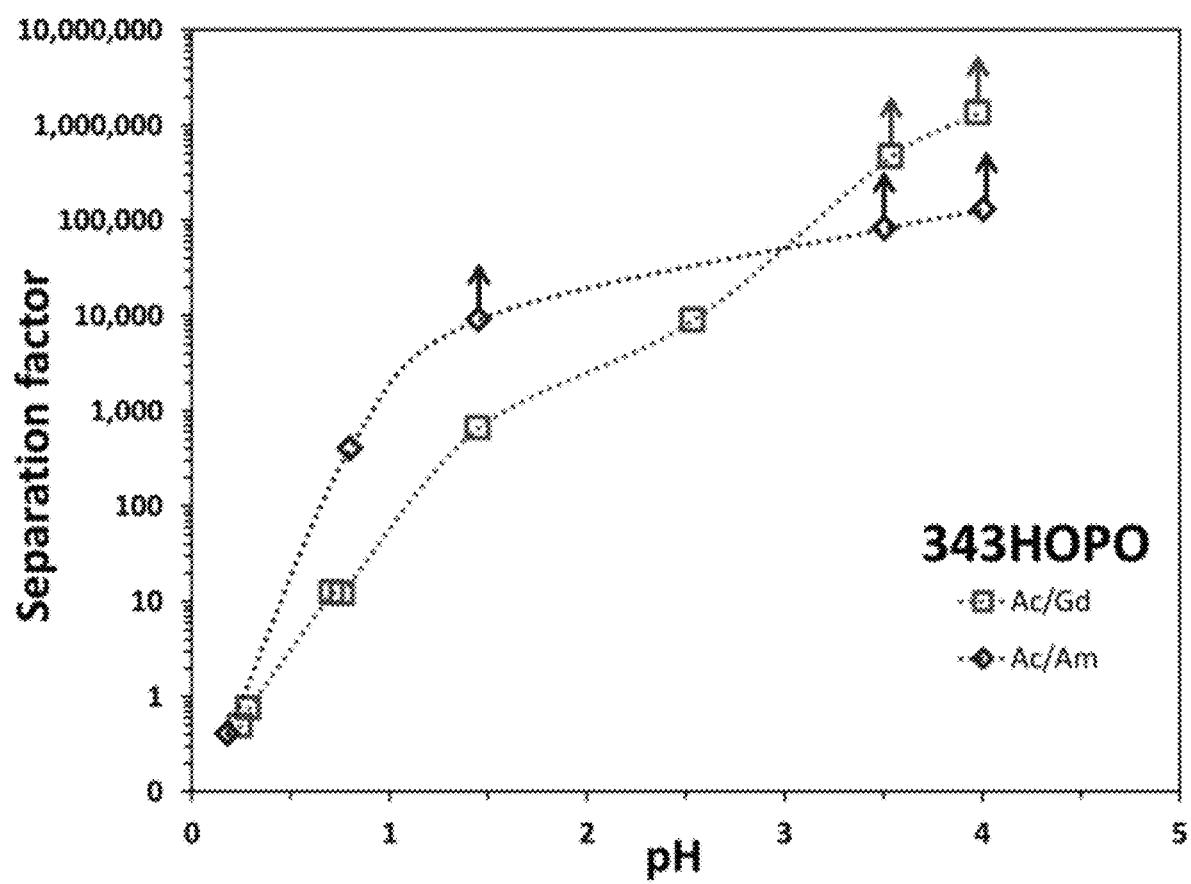
FIG. 50D shows the corresponding separation factors in the presence of 343HOPO for FIG. 50C. Aqueous phase: 40 mM of chelator in sodium lactate/sodium nitrate buffer (I=2 M). $V_{org}/V_{aq}$=1, one contact. T=25° C. Data points with arrows are lower limits.

While there is great interest in using $^{225}Ac$ for targeted alpha therapy (Wilson, J. J. et al. Evaluation of nitrogen-rich macrocyclic ligands for the chelation of therapeutic bismuth radioisotopes. *Nucl. Med. Biol.* 42, 428-438 (2015); Ferrier, M. G. et al. Synthesis and Characterization of the Actinium Aquo Ion. *ACS Cent. Sci.* 3, 176-185 (2017)), the development of $^{225}Ac$-based pharmaceuticals is still hindered by low isotope availability relative to potential market needs (NSAC Isotopes Subcommittee. *Meeting isotope needs and capturing opportunities for the future: the 2015 long range plan for the DOE-NP isotope program.* 1-160 (US DOE, 2015)). Furthermore, Ac chemistry is largely unexplored since i) $Ac^{3+}$ being the biggest trivalent ion of the periodic table (Ferrier, M. G. et al. Synthesis and Characterization of the Actinium Aquo Ion. *ACS Cent. Sci.* 3, 176-185 (2017); Lundberg, D. & Persson, I. The size of actinoid(III) ions—structural analysis vs. common misinterpretations. *Coord. Chem. Rev.* 318, 131-134 (2016)), there is no adequate surrogate to study its chemistry, and ii) its highly-radioactive longest-lived isotope ($^{227}Ac$, $t_{1/2}$=21.8 yr) is available in only g amounts. Both $^{227}Ac$ decay and $^{225}Ac$ production yield mixtures of $Ac^{3+}$, $Th^{4+}$, $Ra^{2+}$, and trivalent lanthanides. The ratio between unwanted elements and Ac is typically very high and purification options are limited (Radchenko, V. et al. Application of ion exchange and extraction chromatography to the separation of actinium from proton-irradiated thorium metal for analytical purposes. *J. Chromat. A* 1380, 55-63 (2015)). 343HOPO exhibits very low affinity toward $Ac^{3+}$ compared with other trivalent ions and has extremely high affinity for tetravalent ions, providing a straightforward tool to selectively isolate Ac. FIG. 49A shows the $Ac^{3+}$ and $Pu^{4+}$ extraction yields by HDEHP (extractant widely used in hydrometallurgy, also known as D2EHPA) (Nash, K. L. The Chemistry of TALSPEAK: A Review of the Science. *Solv. Extract. Ion Exchange* 33, 1-55 (2015); Braley, J. C., Grimes, T. S. & Nash, K. L. Alternatives to HDEHP and DTPA for Simplified TALSPEAK Separations. *Ind. Eng. Chem. Res.* 51, 629-638 (2012)) in the presence of 343HOPO at different pH values. Full $Ac^{3+}$ extraction in the organic layer was achieved, while scavenging $Pu^{4+}$ (a surrogate for $Th^{4+}$) in the aqueous layer. Similar experiments in the presence of reference aqueous chelator DTPA, also used in the so-called TALSPEAK process (Nash, K. L. The Chemistry of TALSPEAK: A Review of the Science. *Solv. Extract. Ion Exchange* 33, 1-55 (2015)), showed partial extraction of both isotopes and no practical separation or recovery. After only a single step and despite a large initial Pu/Ac ratio (~10,000 mol/mol), $SF_{Ac/Pu}$ values reached at least 1,000, 000 in the presence of 343HOPO, combined with recovery yields of up to 99.70% for Ac in the organic phase and higher than 99.97% for Pu in the aqueous phase (FIG. 49B). In comparison, DTPA $SF_{Ac/Pu}$ values were between 1 and 100, the typical selectivity range observed in hydrometallurgical processes, with less than 50% Ac recovery (FIG. 49B). Separation of Ac from trivalent impurities was also investigated.

Figure 51:
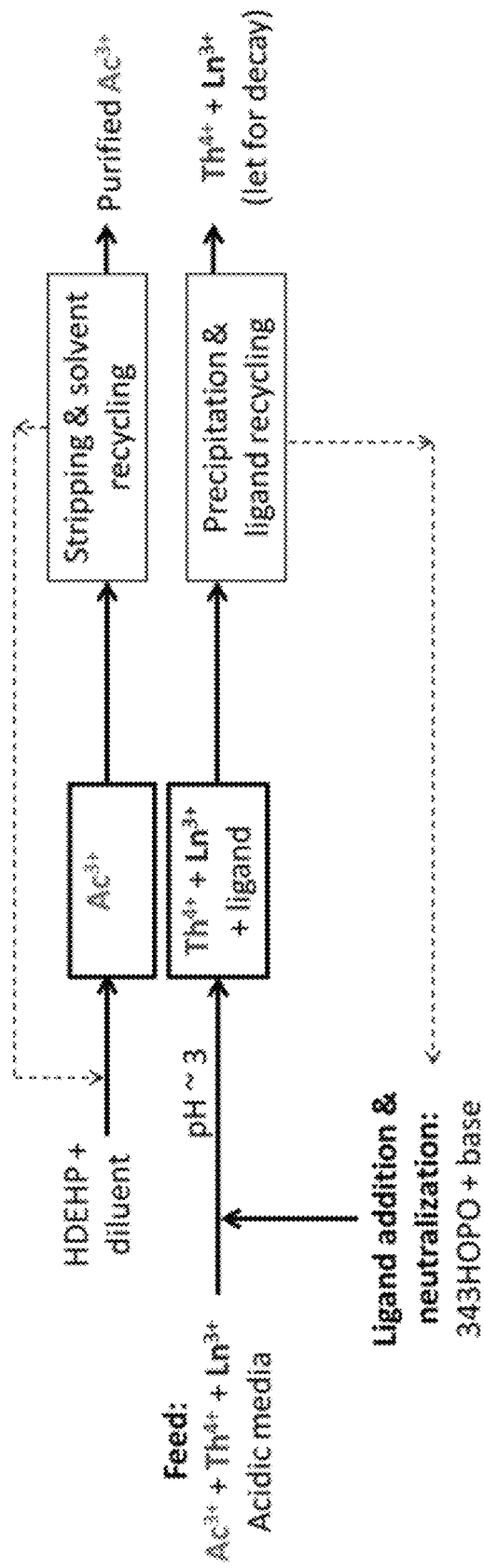
FIG. 51 shows an embodiment of a general process flowsheet proposed for the purification of actinium isotopes using 343HOPO and HDEHP.

FIG. 50A-FIG. 50D displays $Ac^{3+}$, $Am^{3+}$, and $Gd^{3+}$ extraction profiles in both HDEHP/343HOPO-$HNO_3$ and HDEHP/DTPA-$HNO_3$ systems. Significant discrimination was observed for $Ac^{3+}$ against $Am^{3+}$ and $Gd^{3+}$, with $SF_{Ac/Am}$ and $SF_{Ac/Gd}$ reaching 130,000 and 1,300,000, respectively. In the DTPA case, $SF_{Am/Ac}$ and $SF_{Gd/Ac}$ values were below 10 and 5,300, respectively, and Ac recovery was low. A process flowsheet for $^{225}Ac$ purification using the 343HOPO-HDEHP combination is shown in FIG. 51.

Example 22—Plutonium Purification (1)

Since the 1940's, worldwide Pu inventory has evolved from almost 0 to ~2,500,000 kg due to anthropogenic activities (Glaser, A. & Mian, Z. Fissile Material Stocks and Production, 2008. *Bull. Atom. Sci.* 65, 35-47 (2009); Zhao, P. et al. Plutonium(IV) and (V) Sorption to Goethite at Sub-Femtomolar to Micromolar Concentrations: Redox Transformations and Surface Precipitation. *Environ. Sci. Technol.* 50, 6948-6956 (2016)), and is estimated to increase by 70,000 kg/yr (Albright, D. & Kramer, K. Stockpiles still growing. *Bull. Atom. Sci.* 60, 14-16 (2004)) based on civilian nuclear power generation forecasts. Pu materials must be properly safeguarded throughout their lifespan, which necessitates advanced nuclear forensic controls and reprocessing activities. In this context, isolation of Pu from minor actinide and fission product impurities is essential. The standard PUREX (Plutonium Uranium Redox EXtraction) liquid-liquid extraction process ( ) Herbst, R. S., Baron, P. & Nilsson, M. 6—Standard and advanced separation: PUREX processes for nuclear fuel reprocessing. in *Advanced Separation Techniques for Nuclear Fuel Reprocessing and Radioactive Waste Treatment* (eds. Nash, K. L. & Lumetta, G. J.) 141-175 (Woodhead Publishing, 2011). doi:10.1533/9780857092274.2.141 allows recovering and separating Pu and U from minor actinides and fission products. PUREX operates in concentrated $HNO_3$ media and includes two critical steps: i) $UO_2^{2+}$ and $Pu^{4+}$ co-extraction into the organic phase (30% TBP in diluent) while leaving trivalent ions in the aqueous phase, and ii) reductive back-extraction of Pu as $Pu^{3+}$ while leaving $UO_2^{2+}$ in the organic phase. The latter is indispensable for U/Pu separation because of TBP's lack of selectivity between tetravalent and actinyl species. While reduction of $Pu^{4+}$ to $Pu^{3+}$ is achieved by addition of strong reducing agents into the liquid-liquid extraction batteries, (Paviet-Hartmann, P., Riddle, C., Campbell, K. & Mausolf, E. Overview of reductants utilized in nuclear fuel reprocessing/recycling. in 79-86 (2013)) $Pu^{3+}$ is inherently unstable, and this redox component creates constraints in the reactive TBP-nitric medium (reduction of $HNO_3$ to $HNO_2$ and formation of potentially explosive compounds such as $HN_3$).

Figure 52:
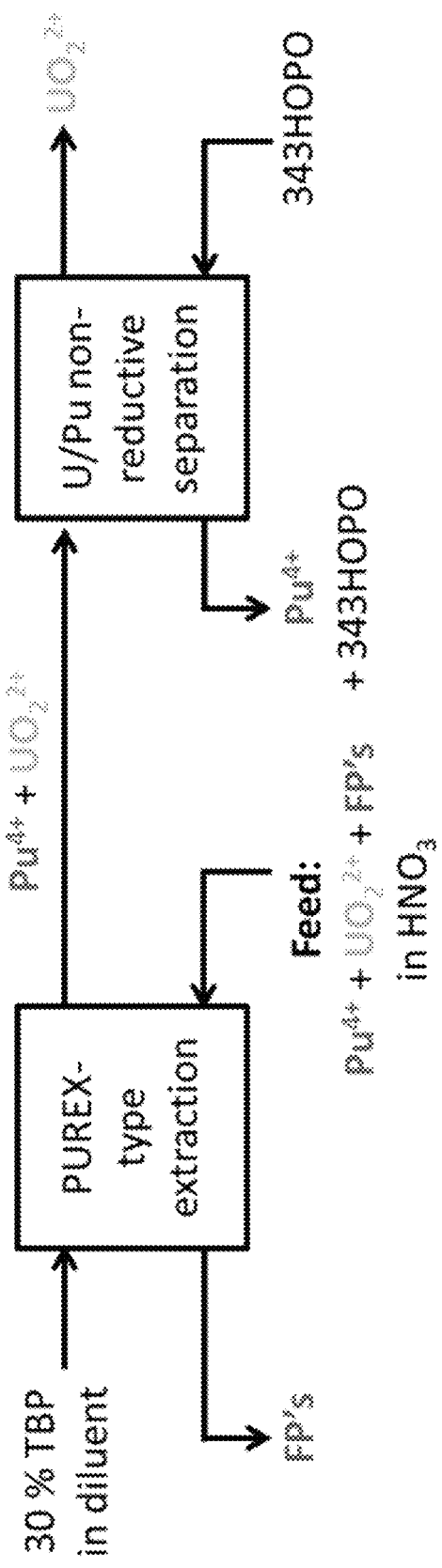
FIG. 52 shows an embodiment of a conceptual flowsheet for the modification of the PUREX method allowing the recovery and separation of uranyl and $Pu^{4+}$ ions without using a reductive striping step for Pu. FP=Fission product.
Figure 53A:
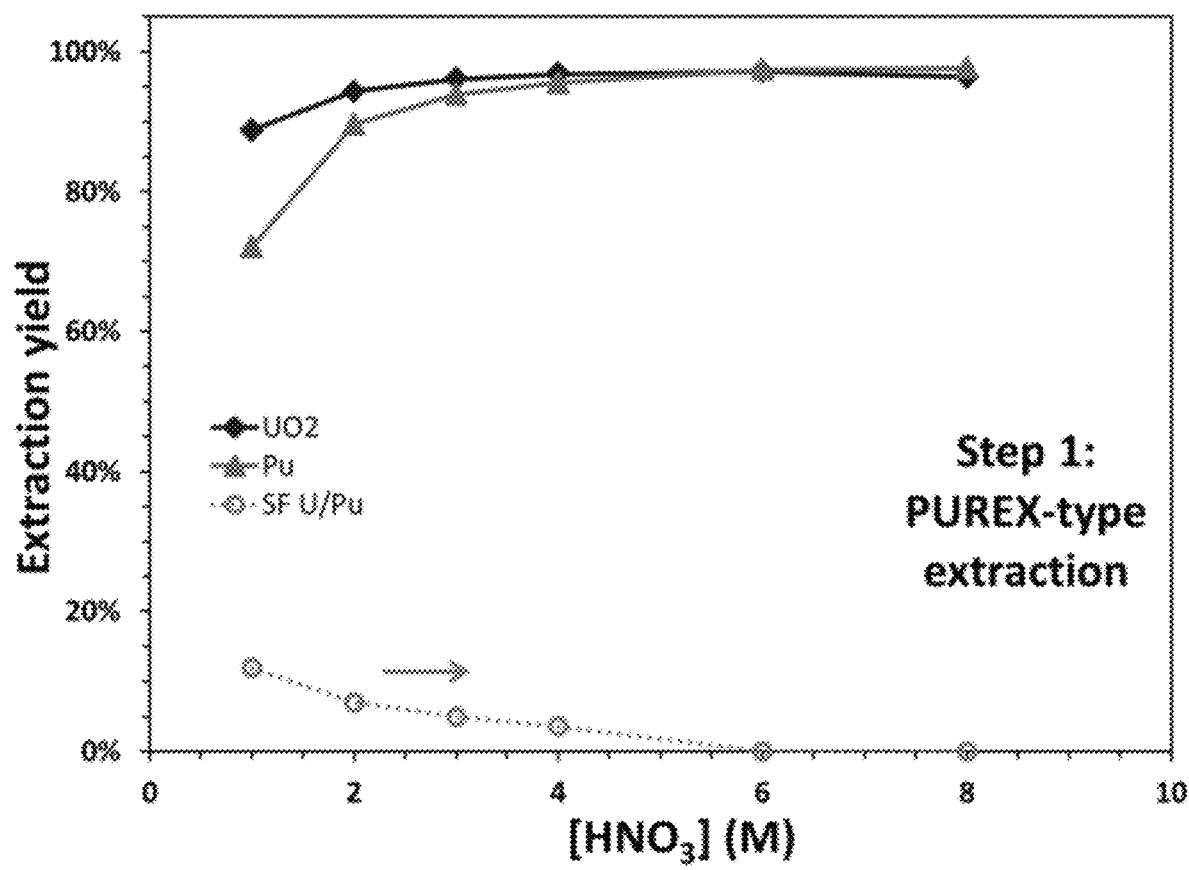
FIG. 53A shows extraction of $Pu^{4+}$ (triangles) and $UO_2^{2+}$ (diamonds) under typical PUREX conditions. Dotted lines: separation factor U/Pu. Organic phase: 30% TBP in kerosene.
Figure 53B:
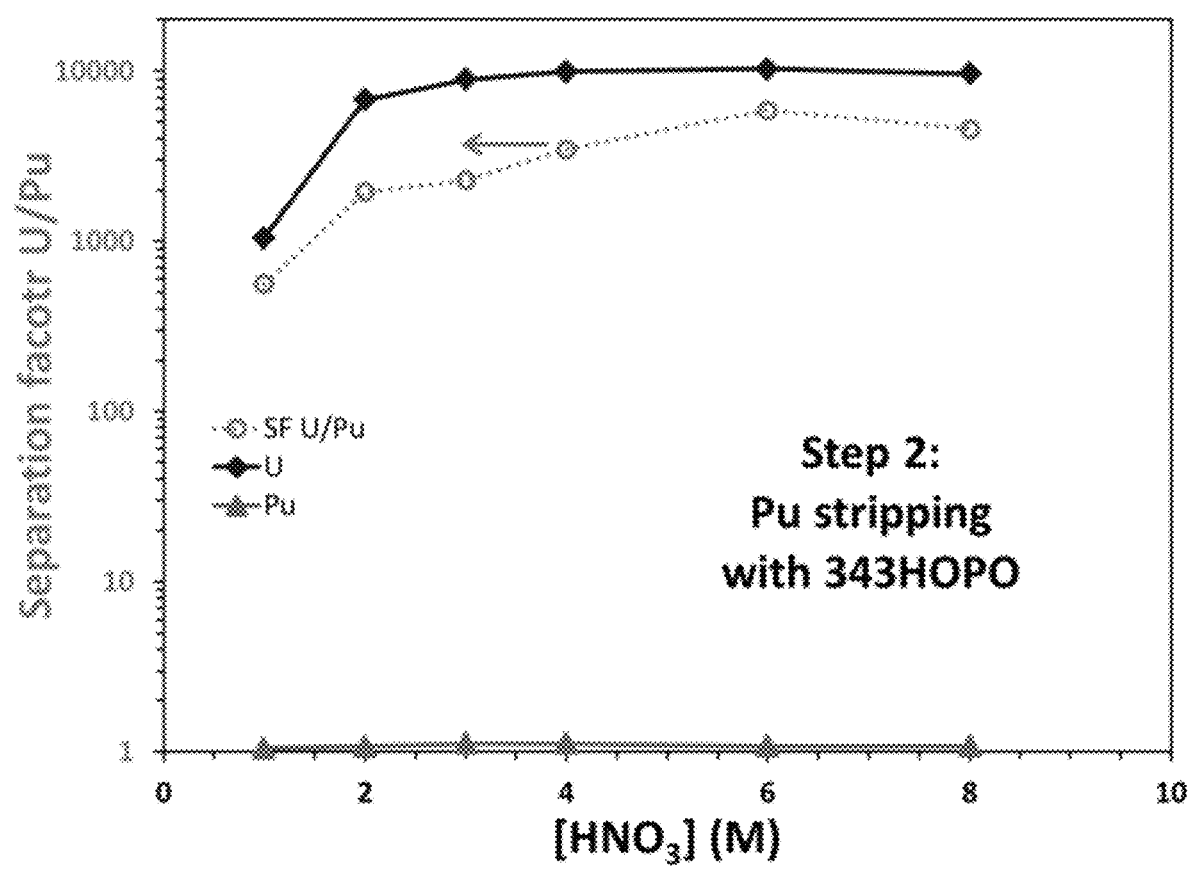
FIG. 53B shows back-extraction $Pu^{4+}$ (triangles) and $UO_2^{2+}$ (diamonds) in the presence of 1 mM 343HOPO (B). Dotted lines: separation factor U/Pu. Organic phase: 30% TBP in kerosene.
Figure 53C:
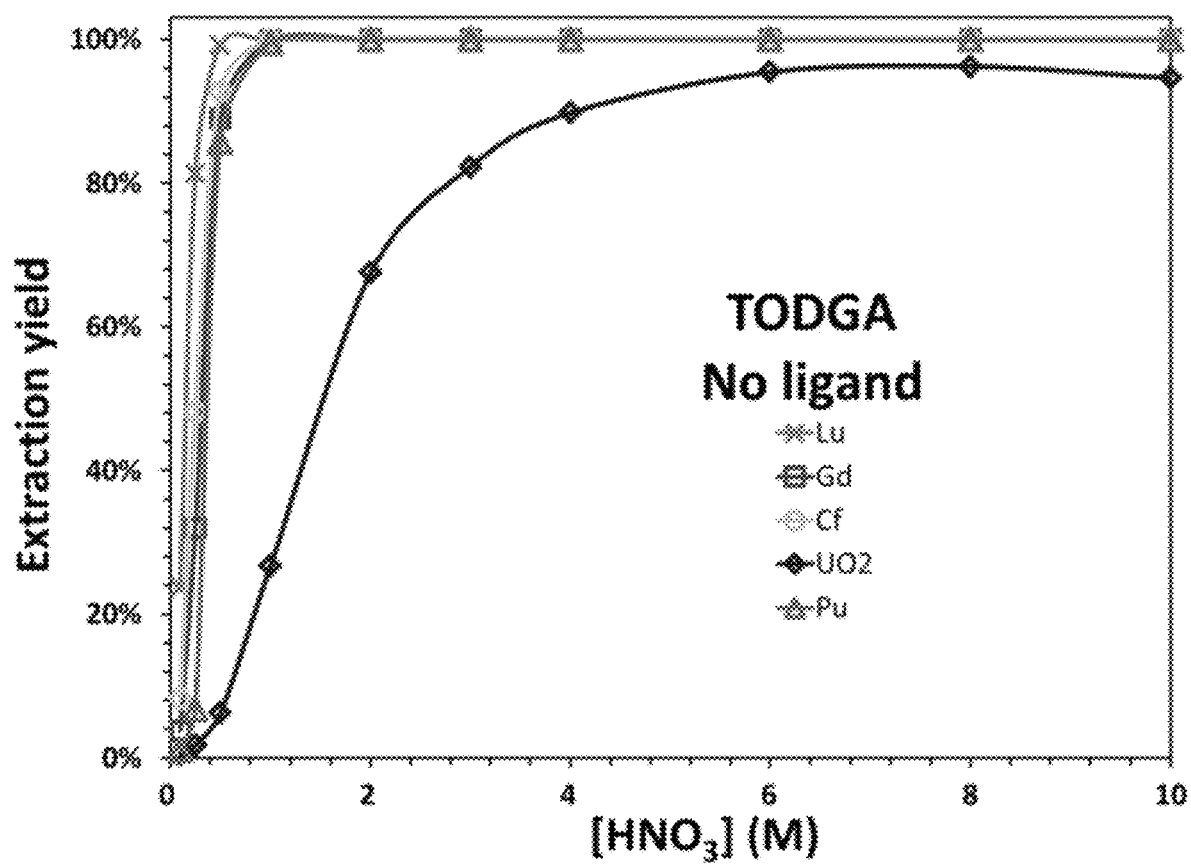
FIG. 53C shows the extraction yields of $Gd^{3+}$ (squares), $Lu^{3+}$ (crosses), $Cf^{3+}$ (circles), $UO_2^{2+}$, and $Pu^{4+}$ by TODGA in the absence of 1 mM 343HOPO.
Figure 53D:
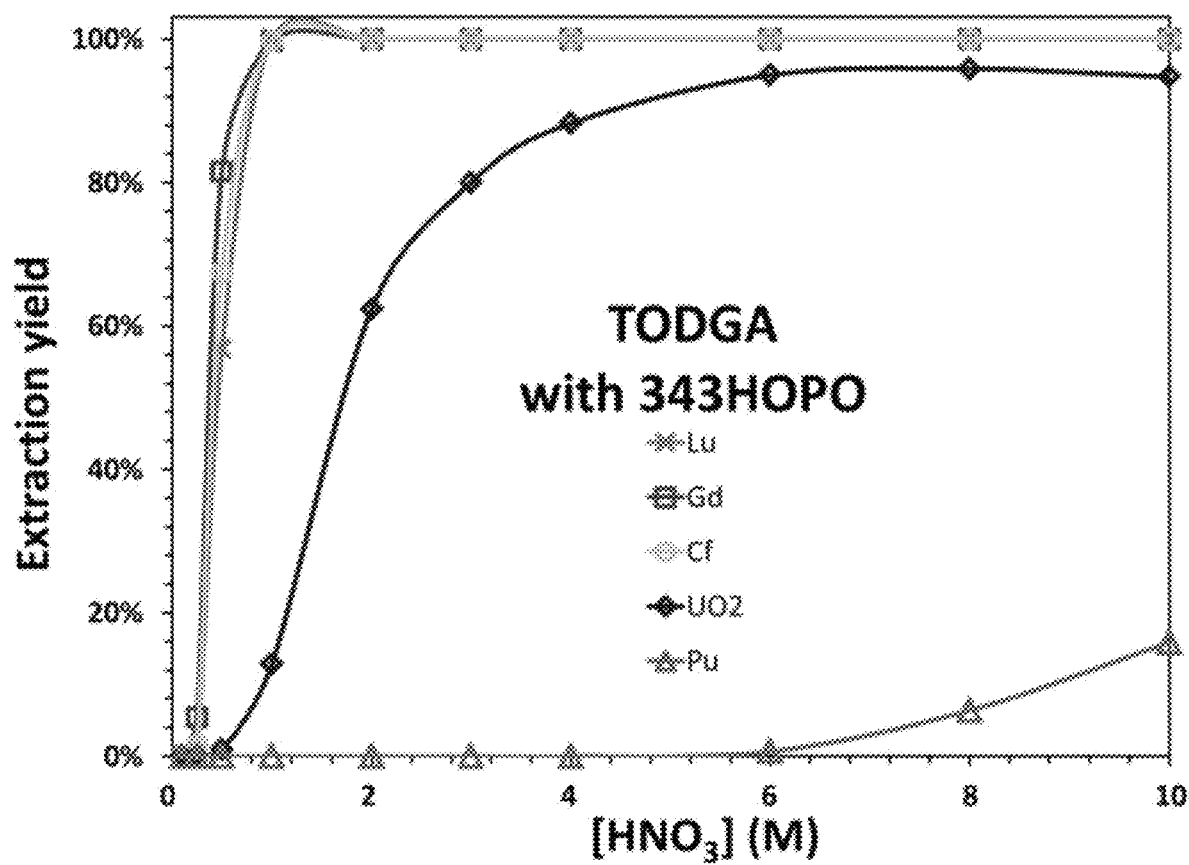
FIG. 53D shows the extraction yields of $Gd^{3+}$ (squares), $Lu^{3+}$ (crosses), $Cf^{3+}$ (circles), $UO_2^{2+}$, and $Pu^{4+}$ by TODGA in the presence of 1 mM 343HOPO.
Figure 53E:
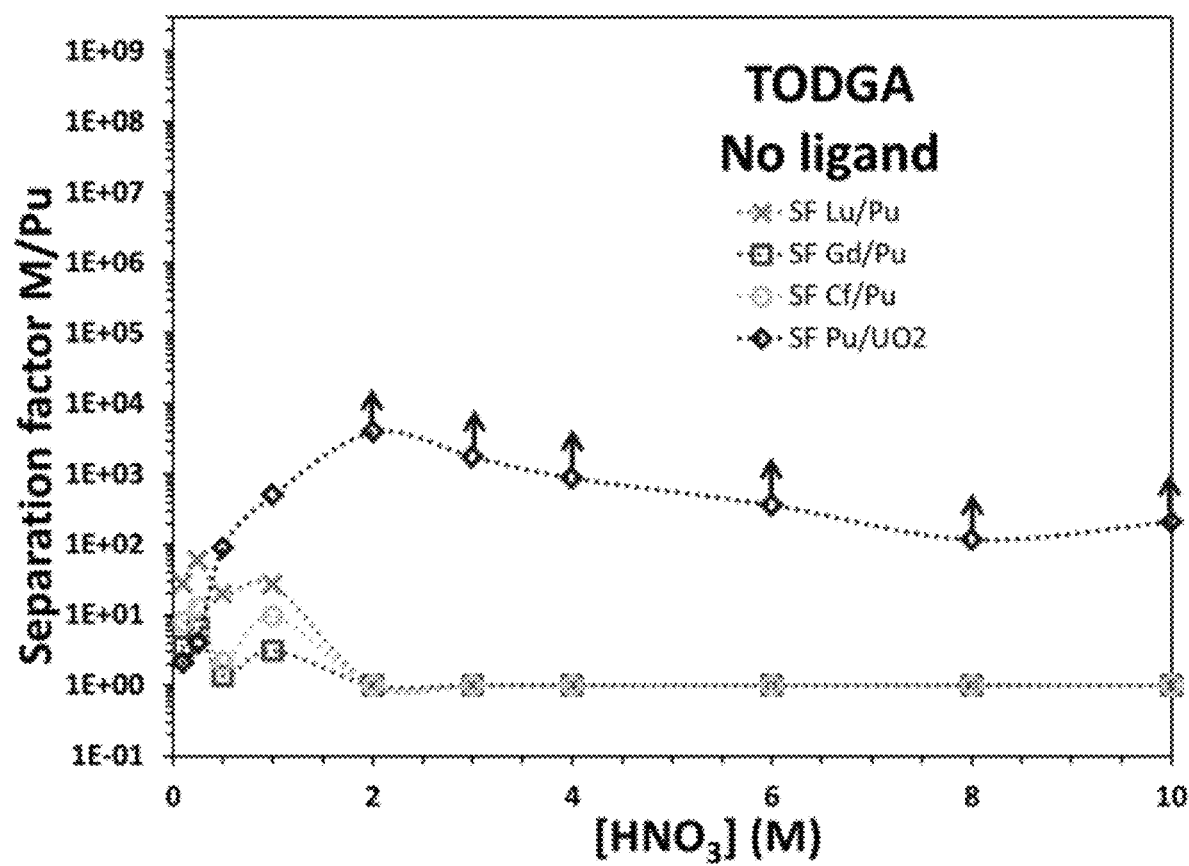
FIG. 53E shows the corresponding separation factor for FIG. 53C. Organic phase: 0.1 M TODGA in kerosene. Aqueous solvent: $HNO_3$. T=25° C. O/A=1, one contact. Points with arrows are lower limits.
Figure 53F:
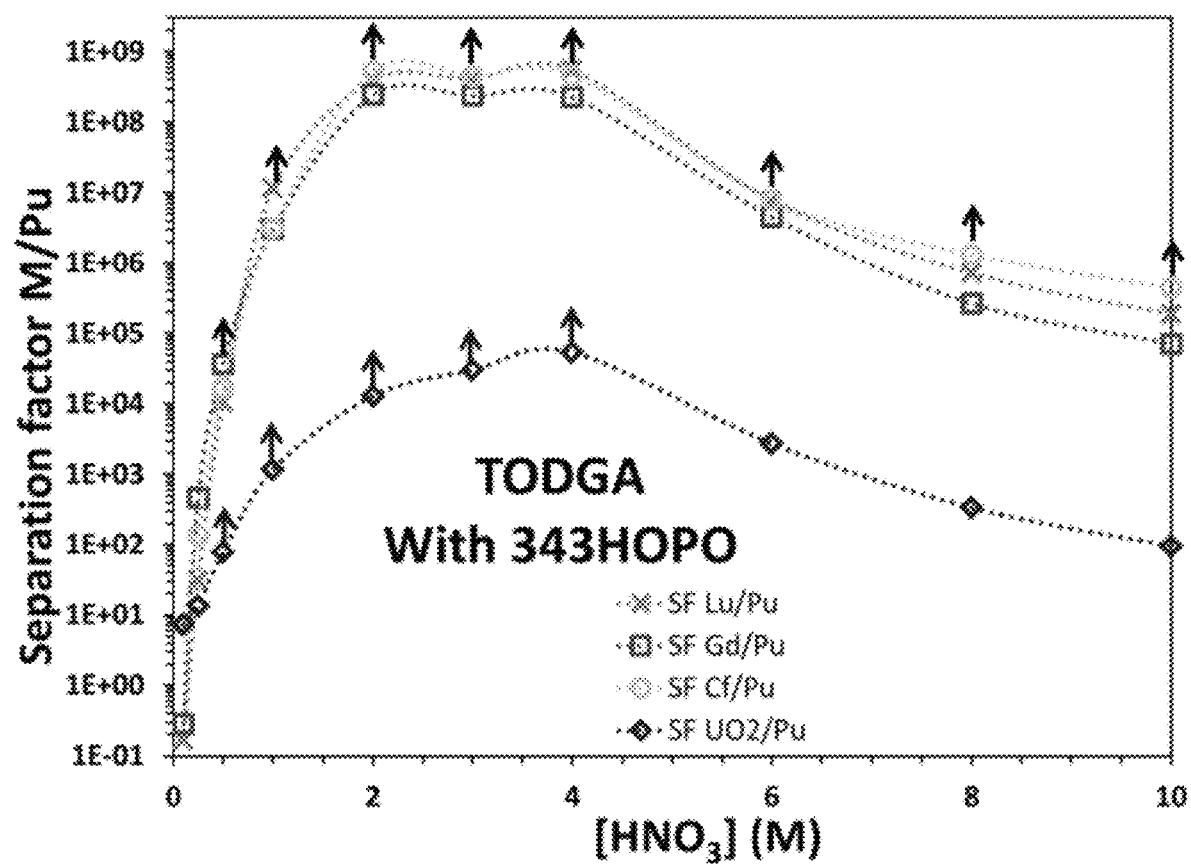
FIG. 53F shows the corresponding separation factor for FIG. 53D. Organic phase: 0.1 M TODGA in kerosene. Aqueous solvent: $HNO_3$. T=25° C. O/A=1, one contact. Points with arrows are lower limits.

A simple but effective modification of PUREX was investigated for non-reductive separation of Pu and U (FIG. 52).

FIGS. 53A-53F show that $Pu^{4+}$ and $UO_2^{2+}$ extraction behaviors under typical PUREX conditions are expectedly very similar, with quantitative extraction of both elements and $SF_{U/Pu}$ values below 3. After co-extraction of U and Pu by TBP, the unprecedented chelation properties of 343HOPO at high acidity and its charge-based selectivity can be leveraged to selectively strip $Pu^{4+}$ from the organic phase. Efficient U/Pu separation was observed in the presence of 343HOPO (FIGS. 53A-53F) by selective chelation of $Pu^{4+}$, without significant interactions with $UO_2^{2+}$ over a broad range of acidity (up to 8 M $HNO_3$) and $SF_{U/Pu}$ values as high as 5,800. The use of 343HOPO-type chelators could afford straightforward and efficient separation methods for the purification of U and Pu, and so, without using any redox-active chemical or non-volatile contaminant. This method also leads to very flexible process control, as demonstrated by the broad acidity range under which 343HOPO selectively scavenges $Pu^{4+}$.

Example 23—Plutonium Purification (2)

Figure 54:
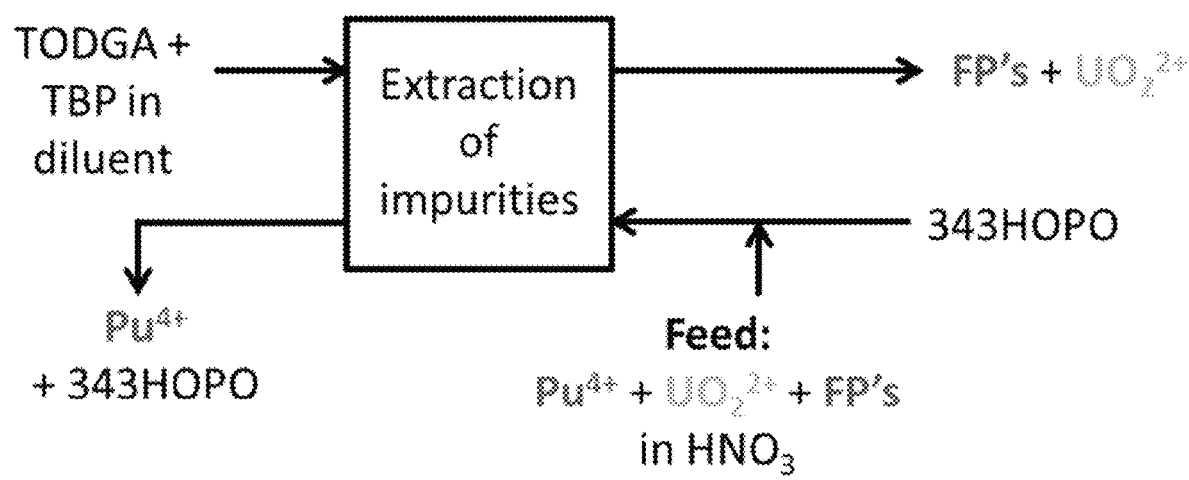
FIG. 54 shows an embodiment of a flowsheet for the flash and redox-free purification of Pu from uranyl and fission products (FP).

Another route, using TODGA as extractant, was explored for the purification of Pu not only from divalent ions but also from trivalent metals. TODGA is from the diglycolamide family used for resins separations (Whittaker, D. et al. Applications of Diglycolamide Based Solvent Extraction Processes in Spent Nuclear Fuel Reprocessing, Part 1: TODGA. *Solv. Extract. Ion Exchange* 36, 223-256 (2018); Modolo, G., Asp, H., Schreinemachers, C. & Vijgen, H. Recovery of actinides and lanthanides from high-level liquid waste by extraction chromatography using TODGA+TBP impregnated resins. *Radiochim. Acta* 95, (2007)), and is currently investigated for next-generation nuclear waste treatment processes such as EURO-GANEX (Zhu, Z.-X., Sasaki, Y., Suzuki, H., Suzuki, S. & Kimura, T. Cumulative study on solvent extraction of elements by N,N,N',N'-tetraoctyl-3-oxapentanediamide (TODGA) from nitric acid into n-dodecane. *Anal. Chim. Acta* 527, 163-168 (2004); Carrott, M. et al. Distribution of plutonium, americium and interfering fission products between nitric acid and a mixed organic phase of TODGA and DMDOHEMA in kerosene, and implications for the design of the "EURO-GANEX" process. *Hydrometallurgy* 152, 139-148 (2015); Modolo, G., Asp, H., Schreinemachers, C. & Vijgen, H. Development of a TODGA based Process for Partitioning of Actinides from a PUREX Raffinate Part I: Batch Extraction Optimization Studies and Stability Tests. Solv. *Extract. Ion Exchange* 25, 703-721 (2007)). TODGA is effective at extracting trivalent lanthanides and actinides from concentrated nitric media but its selectivity towards other ions, such as $Pu^{4+}$, is very low. Very high yields were observed for the extraction of $Gd^{3+}$, $Lu^{3+}$, $UO_2^{2+}$, $Pu^{4+}$, and $Cf^{3+}$ from $HNO_3$ (>99.5% if $HNO_3>1$ M), emphasizing the lack of potential for practical separation (FIG. 4). In the presence of 343HOPO, $Pu^{4+}$ is selectively held-back in the aqueous phase whereas the extraction behaviors of trivalent actinides, lanthanides, and uranyl are not impacted, offering a direct avenue for Pu recovery. SF values between the trivalent ions and $Pu^{4+}$ are above 450,000,000 (LoD reached) whereas $SF_{U/Pu}$ values are around 50,000. $SF_{U/Pu}$ values are limited by the relatively low distribution factors of uranyl (Du<30) when using TODGA, as observed here and elsewhere (Zhu, Z.-X., Sasaki, Y., Suzuki, H., Suzuki, S. & Kimura, T. Cumulative study on solvent extraction of elements by N,N,N',N'-tetraoctyl-3-oxapentanediamide (TODGA) from nitric acid into n-dodecane. *Anal. Chim. Acta* 527, 163-168 (2004)). Combining the high affinity of TODGA for trivalent lanthanides and actinides with the high affinity of TBP for uranyl and the selectivity of 343HOPO for Pu, a redox-free process was devised for the flash-recovery and purification of Pu from materials containing Pu, uranyl, minor actinides, and fission products (FIG. 54).

Example 24—Berkelium Purification (1)

Bk and Cf are of particular interest due to their use as targets for the production of super-heavy elements, such as elements 117 (tennessine, named after a $^{249}$Bk target manufactured at ORNL, Tennessee) (Öhrström, L. & Reedijk, J. Names and symbols of the elements with atomic numbers 113, 115, 117 and 118 (IUPAC Recommendations 2016). *Pure Appl. Chem.* 88, (2016)) and 118 (oganesson, produced from $^{249}$Cf) (Oganessian, Y. T. et al. *Results from the First 249Cf+48Ca Experiment.* 11 (Lawrence Livermore National Laboratory, 02/0302003)). $^{252}$Cf is also a strategic isotope for oil and gas exploration as well as quality control of nuclear reactors (NSAC Isotopes Subcommittee. *Meeting isotope needs and capturing opportunities for the future: the 2015 long range plan for the DOE-NP isotope program.* 1-160 (US DOE, 2015)). Bk and Cf are produced via prolonged neutron irradiation of Am/Cm targets, yielding mixtures of actinides from Am to Fm and some fission products (Roberto, J. B. et al. Actinide targets for the synthesis of super-heavy elements. *Nucl. Phys. A* 944, 99-116 (2015)). These transplutonium elements have traditionally displayed very similar chemistries as they exhibit the +III oxidation state in solution and have almost identical ionic radii (Deblonde, G. J.-P. et al. Spectroscopic and Computational Characterization of Diethylenetriaminepentaacetic Acid/Transplutonium Chelates: Evidencing Heterogeneity in the Heavy Actinide(III) Series. *Angew. Chem. Int. Ed.* 57, 4521-4526 (2018)). To separate $Cf^{3+}$ from $Bk^{3+}$, $Bk^{3+}$ can eventually be oxidized to $Bk^{4+}$ under harsh conditions (heating combined with excess $NaBrO_3$ in 8 M $HNO_3$) but it is unstable, which adds another level of complications to the eventual separation scheme. Only one process in the world, performed at ORNL, is currently amenable to produce and purify isotopes of Bk and Cf. Purification campaigns for mg amounts of $^{249}$Bk take several months (Roberto, J. B. et al. Actinide targets for the synthesis of super-heavy elements. *Nucl. Phys. A* 944, 99-116 (2015); Du, M., Tan, R. & Boll, R. Applications of MP-1 anion exchange resin and Eichrom LN resin in berkelium-249 purification. *J. Radioanal. Nucl. Chem.* 318, 619-629 (2018)) and result in relatively limited purification factors. The Bk isolation process (Roberto, J. B. et al. Actinide targets for the synthesis of super-heavy elements. *Nucl. Phys. A* 944, 99-116 (2015)) comprises about 25 steps, with a purification factor for the entire procedure (product of SF values from all steps) of ~$10^7$.

Figure 55:
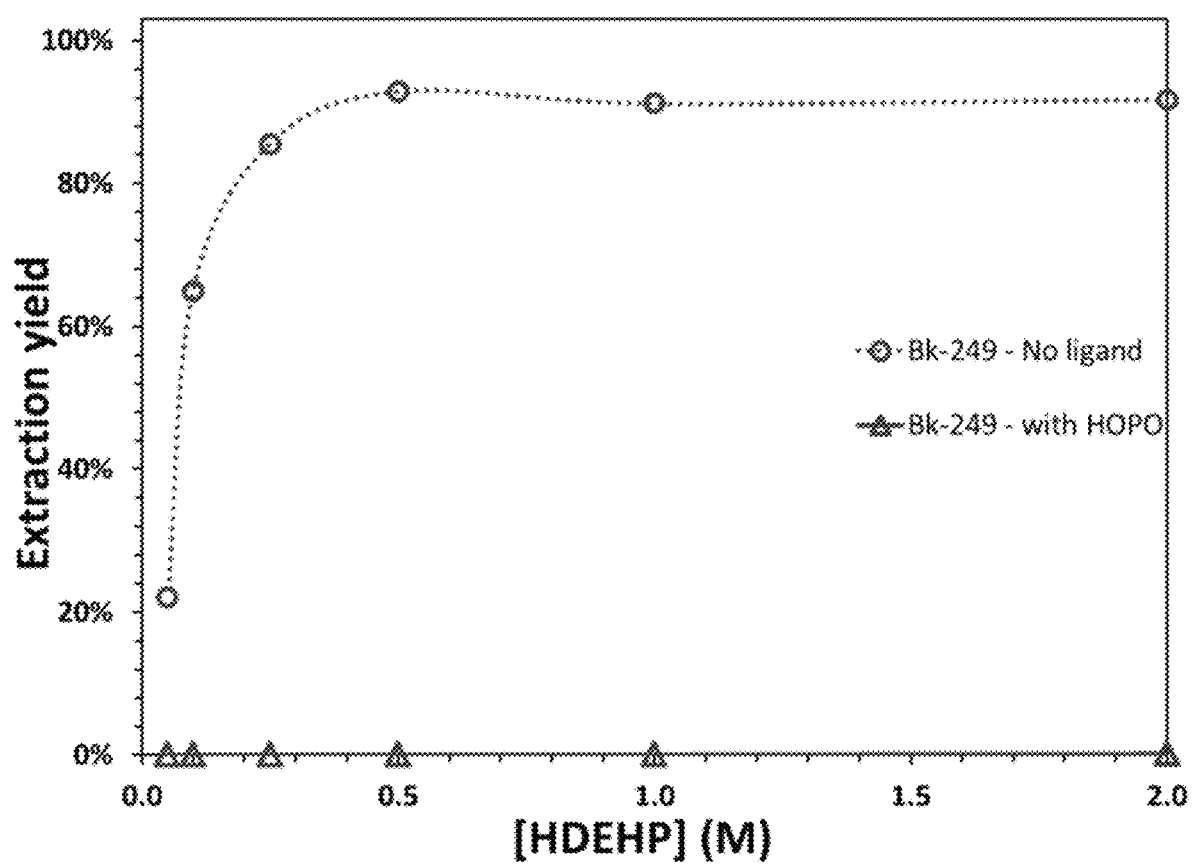
FIG. 55 shows an embodiment of an extraction profile of $^{249}$Bk by HDEHP in the absence (dotted line) or presence (solid line) of 343HOPO. Aqueous phase: 0 or 1 mM 343HOPO in 0.1 M $HNO_3$ and 1.9 M $NaNO_3$. Organic phase: HDEHP in kerosene. O/A=1. T=25° C. One contact.
Figure 56:
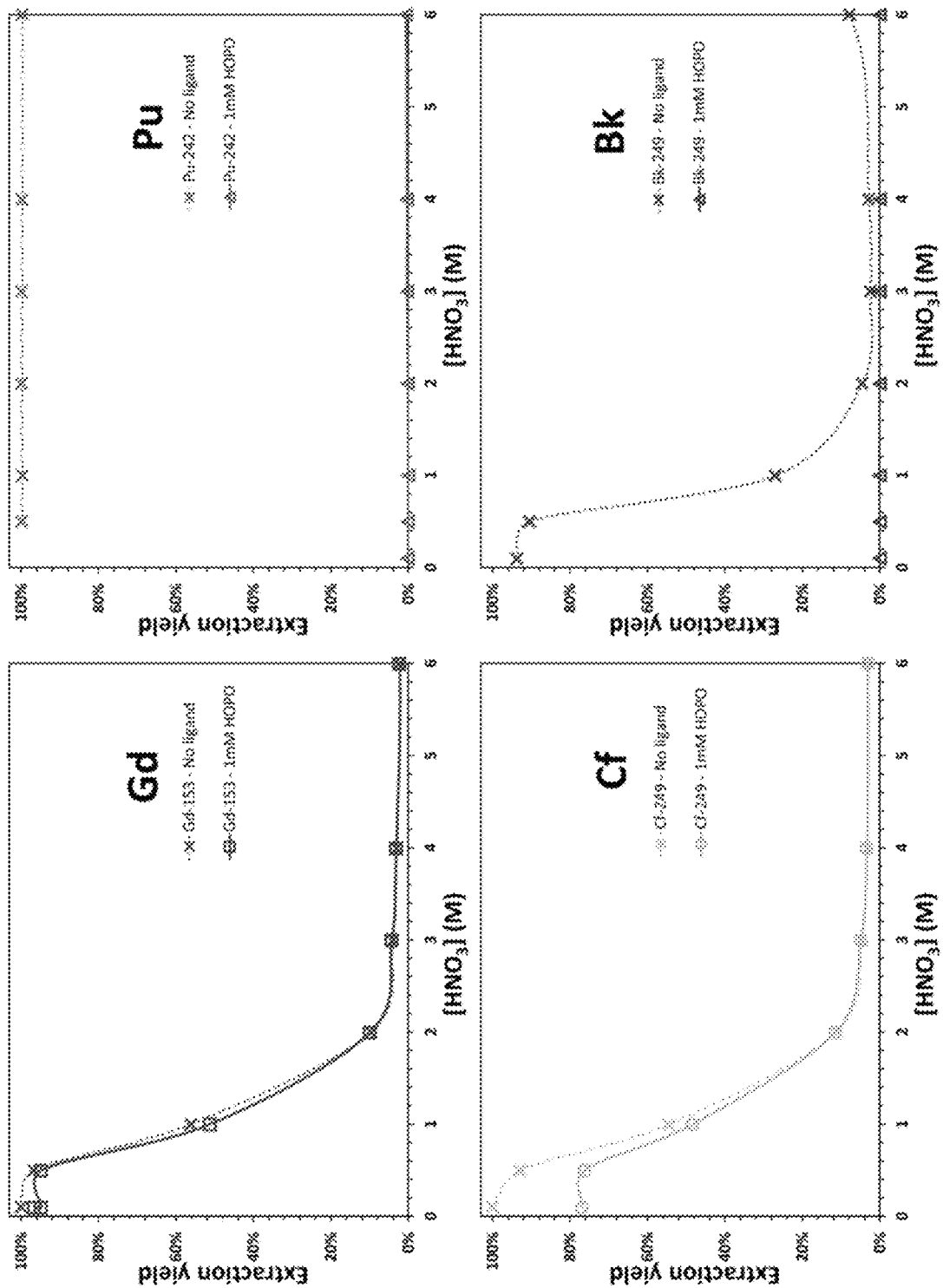
FIG. 56 shows an embodiment of extraction profile of $^{153}$Gd, $^{242}$Pu, $^{249}$Bk, and $^{249}$Cf by HDEHP as a function of the acidity and in the absence (dotted line) or presence (solid line) of 343HOPO. Aqueous phase: 0 or 1 mM 343HOPO in HNO$_3$ (0.1 to 6 M). Organic phase: 0.75 M HDEHP in kerosene. O/A=1. T=25° C. One contact.
Figure 57A:
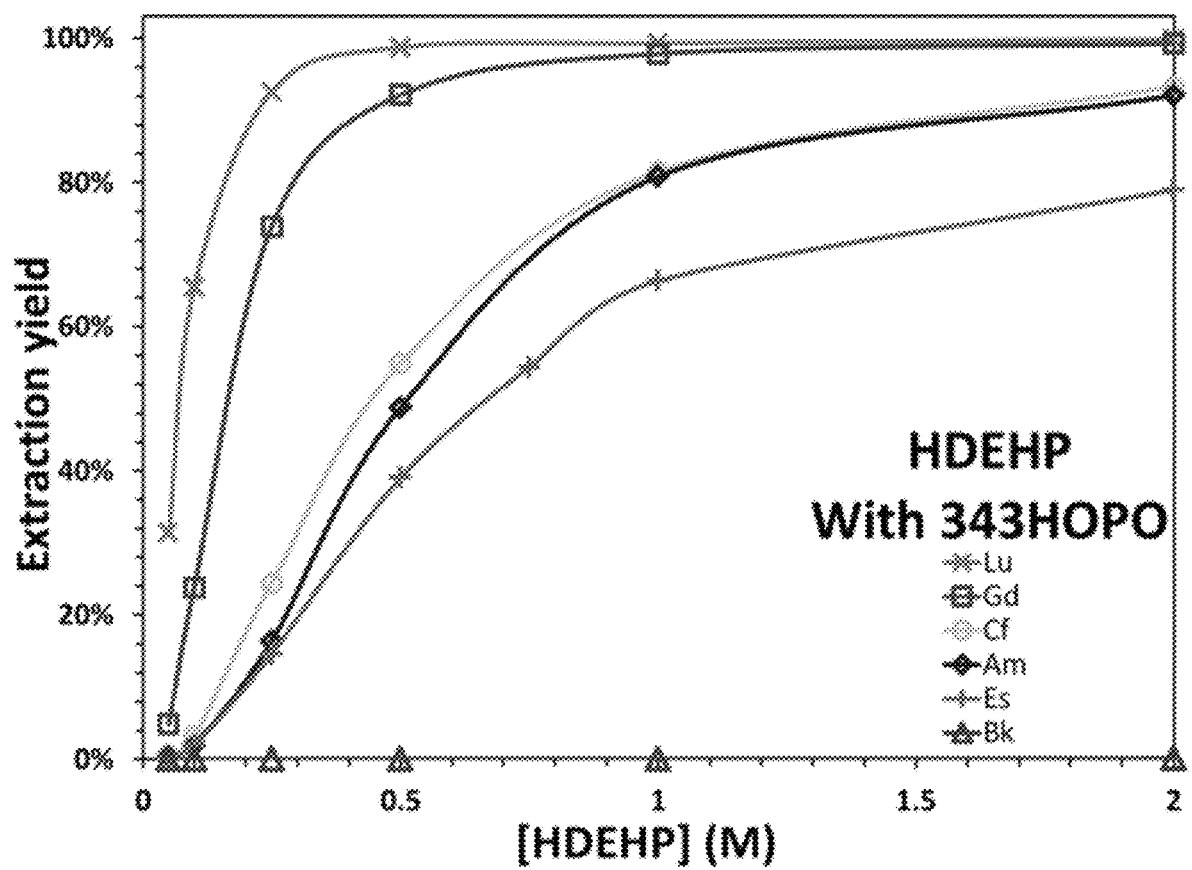
FIG. 57A shows an embodiment of extraction of $^{177}$Lu (crosses), $^{153}$Gd (squares), $^{243}$Am (diamonds), $^{249}$Bk (triangles), $^{249}$Cf (circles) and $^{253}$Es (vertical crosses) by HDEHP as a function of the extractant concentration. Aqueous phase: 1 mM 343HOPO in 0.1 M HNO$_3$ and 1.9 M NaNO$_3$. Organic phase: HDEHP in kerosene.
Figure 57B:
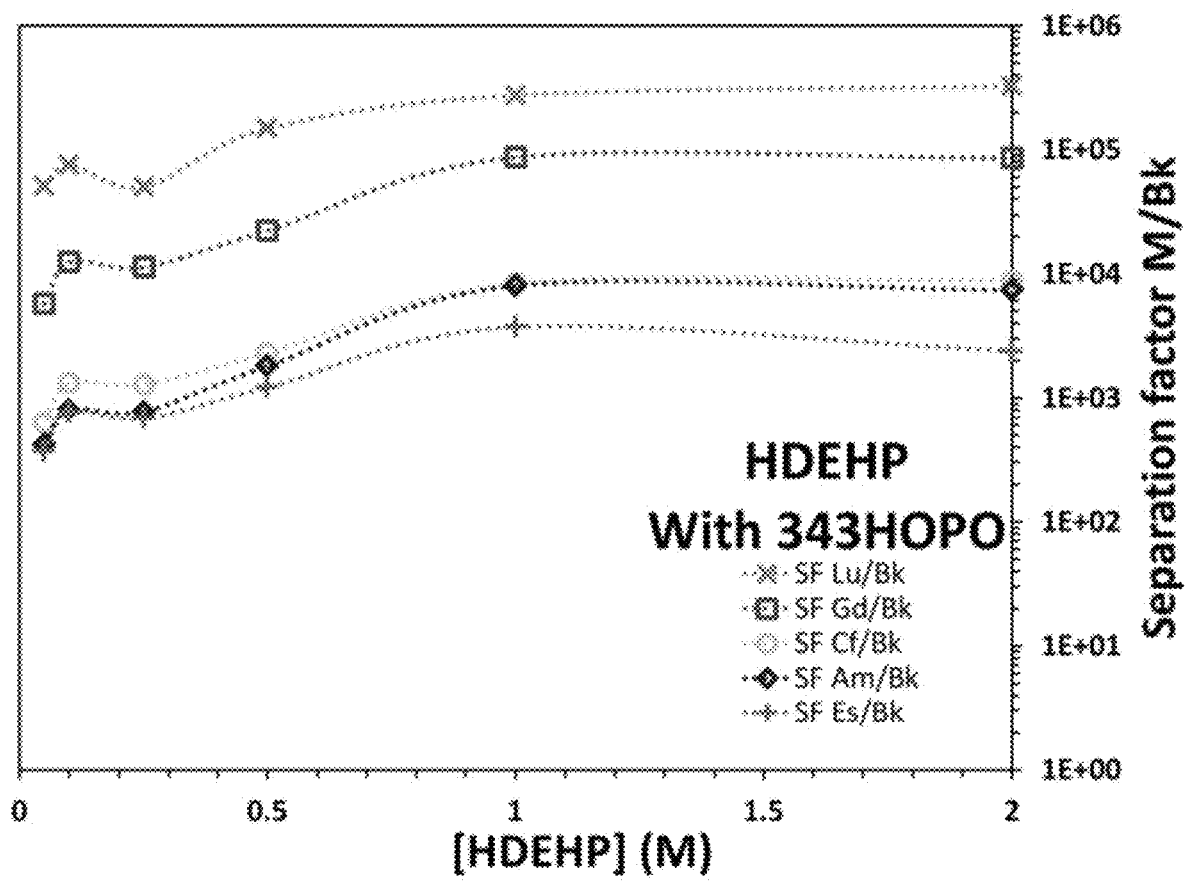
FIG. 57B shows the corresponding separation factors for FIG. 57A. A log scale is used for clarity. See FIGS. 58A and 58B for results as a function of the phase ratio.
Figure 57C:
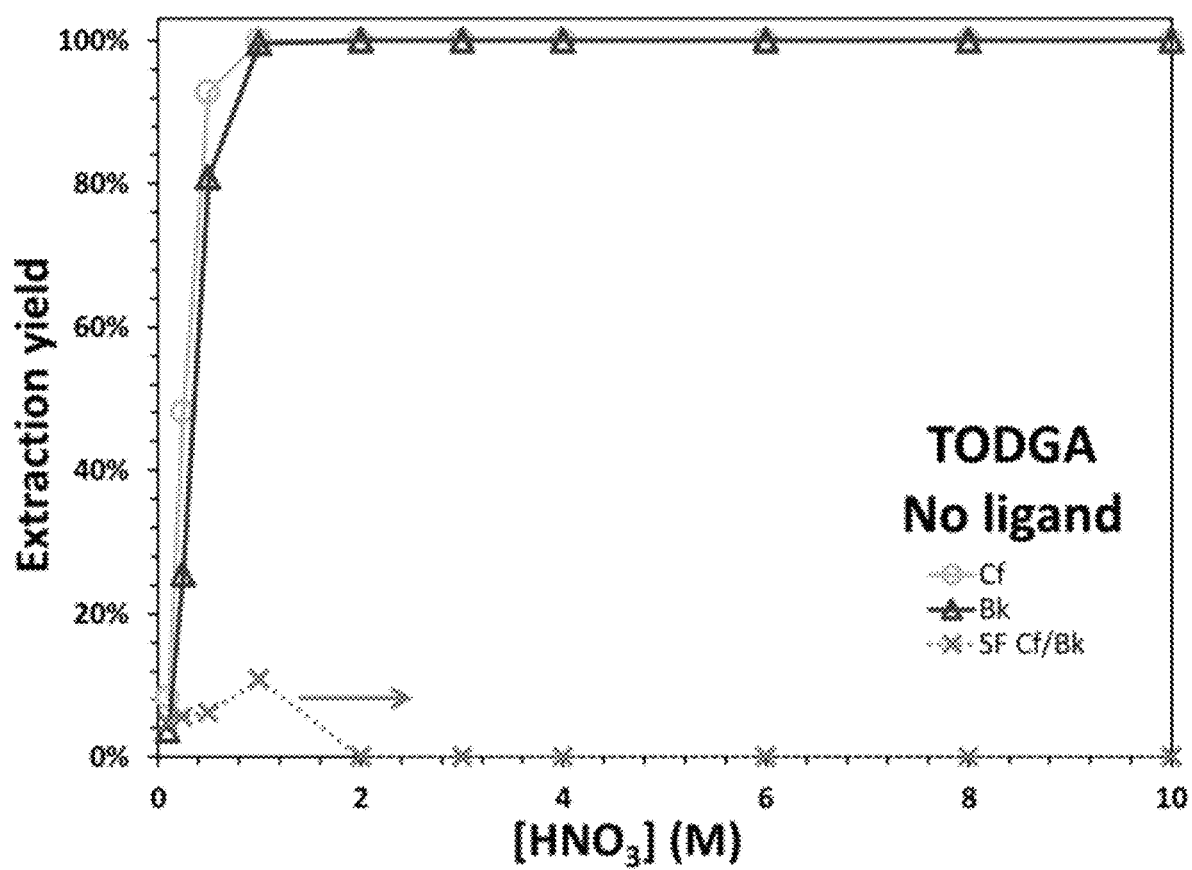
FIG. 57C shows the extraction yields of $^{249}$Bk and $^{249}$Cf by TODGA (solid lines) and separation factors Cf/Bk (dotted lines) as a function of the acidity and in the absence of 1 mM 343HOPO, respectively. Aqueous phase: 0 or 1 mM 343HOPO in HNO$_3$. Organic phase: 0.1 M TODGA in kerosene. T=25° C. O/A=1, one contact. Points with arrows are lower limits.
Figure 57D:
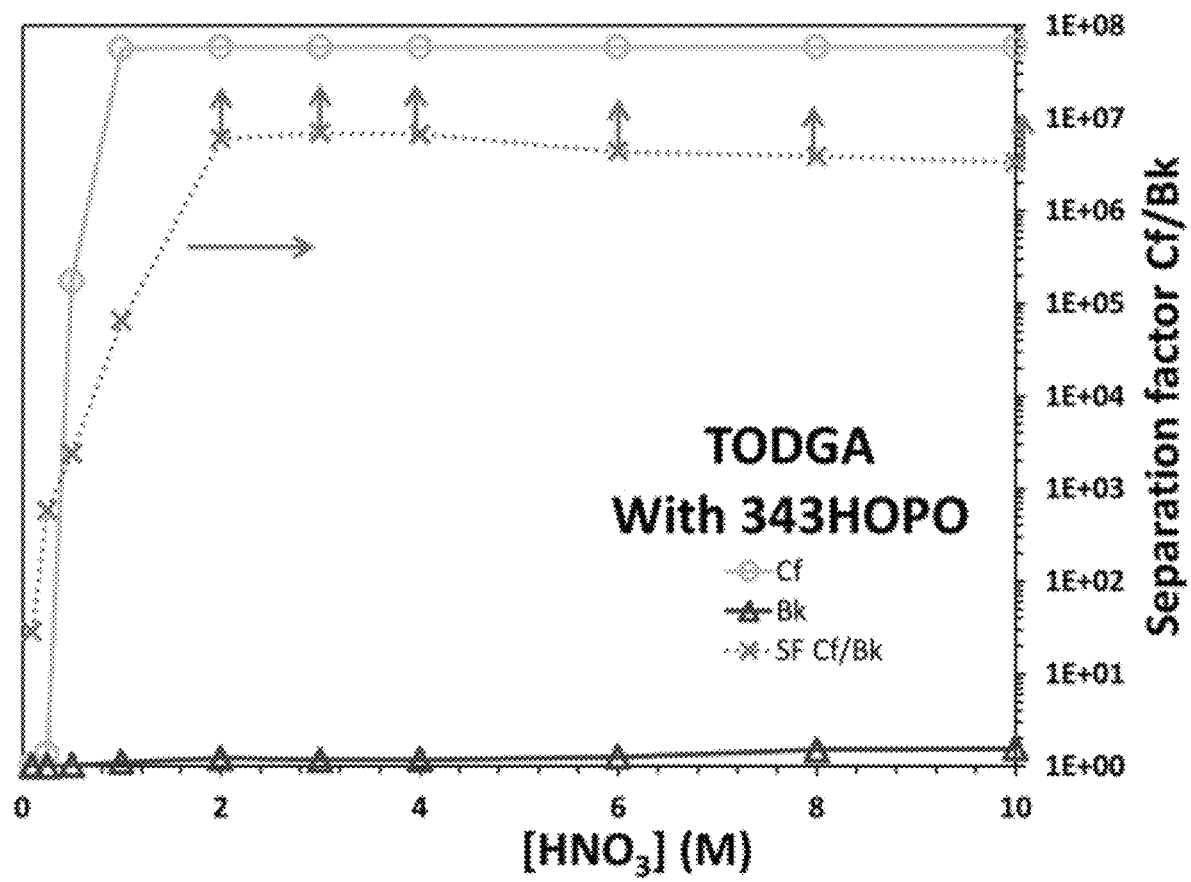
FIG. 57D shows the extraction yields of $^{249}$Bk and $^{249}$Cf by TODGA (solid lines) and separation factors Cf/Bk (dotted lines) as a function of the acidity and in the presence of 1 mM 343HOPO, respectively. Aqueous phase: 0 or 1 mM 343HOPO in HNO$_3$. Organic phase: 0.1 M TODGA in kerosene. T=25° C. O/A=1, one contact. Points with arrows are lower limits.
Figure 58A:
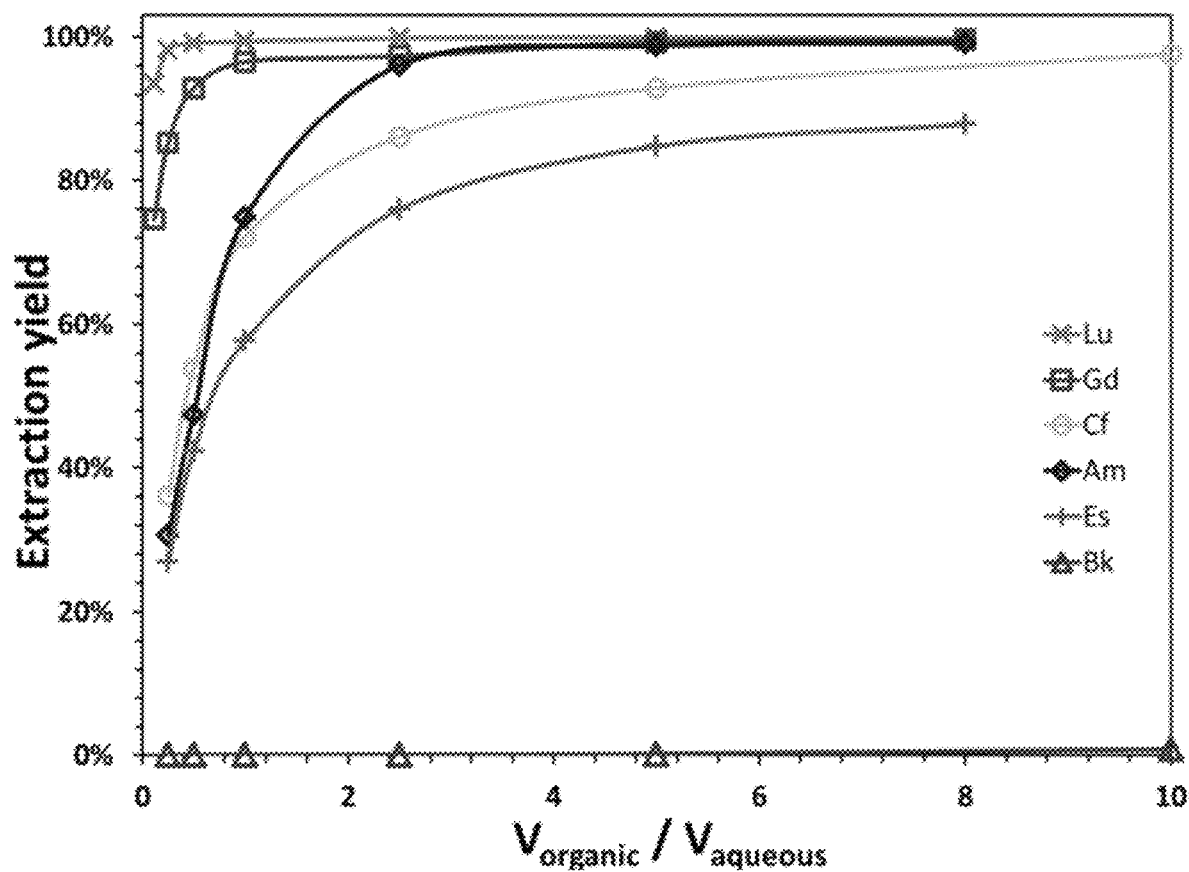
FIG. 58A shows extraction profiles of $^{177}$Lu (crosses), $^{153}$Gd (squares), $^{243}$Am (diamonds), $^{249}$Bk (triangles), and $^{253}$Es (vertical crosses) as a function of the volume phase ratio.
Figure 58B:
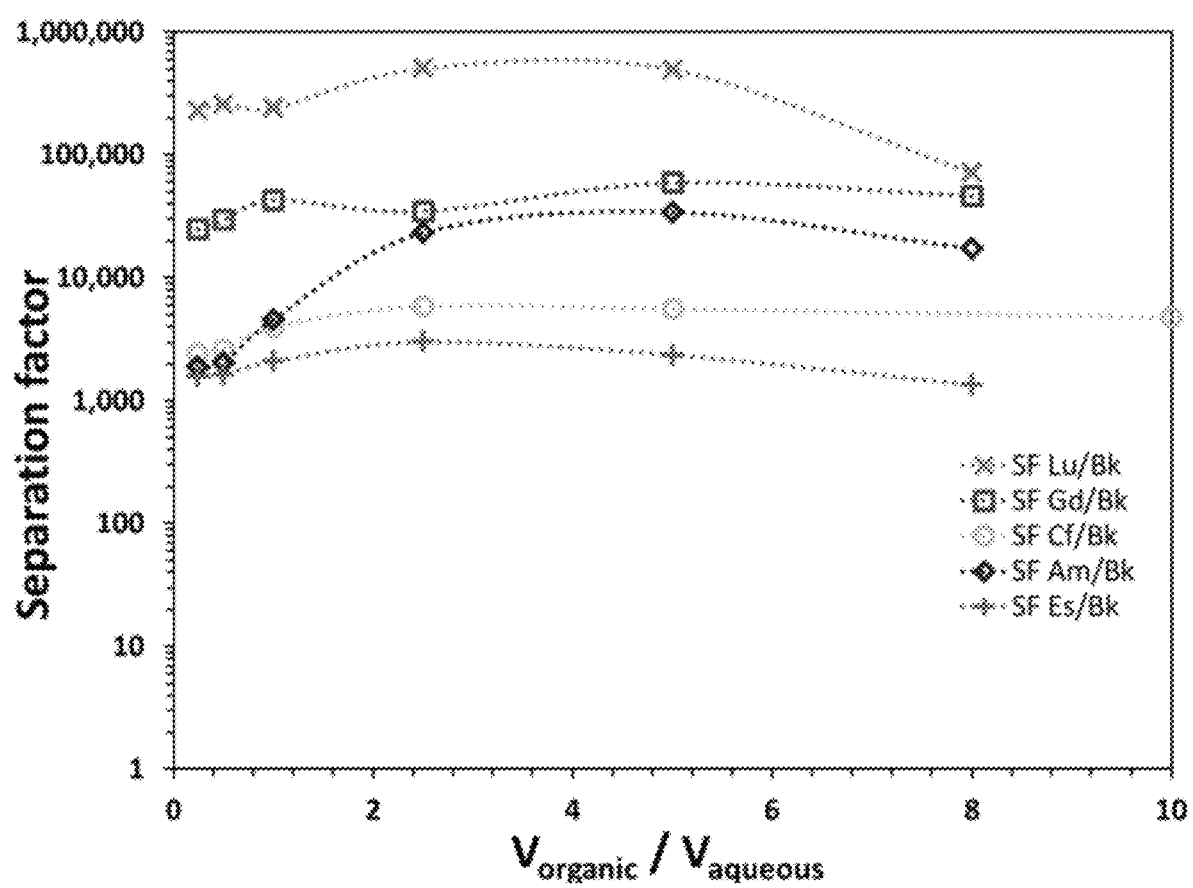
FIG. 58B shows corresponding separation factors for FIG. 58A. Aqueous phase: 1 mM 343HOPO in 0.1 M HNO$_3$ and 1.9 M NaNO$_3$. Organic phase: 0.75 M HDEHP in kerosene. T=25° C. One contact. See FIG. 5 for corresponding data as a function of the extractant concentration.

343HOPO was recently shown (Deblonde, G. J.-P. et al. Chelation and stabilization of berkelium in oxidation state +IV. *Nat. Chem.* 9, 843-849 (2017)) to oxidize $Bk^{3+}$ and stabilize $Bk^{4+}$ in aqueous solution without addition of any redox-active species; a direct consequence of the ligand's thermodynamic preference for tetravalent cations (vide supra). The separation strategy detailed above can therefore be applied to the isolation of Bk from all trivalent ions. Preliminary tests with extractant HDEHP at high acidity (0.1 M to 6 M $HNO_3$) show a drastic influence of 343HOPO on the Bk extraction by HDEHP (FIG. 55). Comparisons with $Pu^{4+}$, $Gd^{3+}$, and $Cf^{3+}$ confirm that Bk exists as $Bk^{3+}$ in nitric media without chelator but forms a $Bk^{4+}$ complex with 343HOPO even under very acidic conditions (FIG. 56). Thus, isolation of Bk from its trivalent neighbors and lanthanides was studied in the HDEHP-$HNO_3$-343HOPO system (FIG. 57). After a single step at room temperature, high extraction yields were observed for all tested trivalent ions, whereas Bk was selectively sequestered in the aqueous phase. $SF_{Bk/Lu}$ values as high as 320,000 were obtained, and SF values between 3,000 and 10,000 were reached between Bk and adjacent actinides $Am^{3+}$, $Cf^{3+}$, and $Es^{3+}$. Similar tests in the presence of NTA, EDTA, CDTA, and DTPA showed no separation at all between Bk and Cf, (similar to what is observed without chelator) since this type of ligands is not strong enough to bind metal ions under acidic conditions and is not selective enough to oxidize $Bk^{3+}$ to $Bk^{4+}$. Importantly (FIGS. 57A-57D and FIGS. 58A-58B), the behavior of Bk in the presence of 343HOPO is completely decoupled from classic extraction parameters (extractant concentration, phase ratio), resulting in stable separation performance and robustness over a wide range of conditions. Given the system SF values, two consecutive steps would yield purification factors similar or higher than the current state-of-the-art process (Roberto, J. B. et al. Actinide targets for the synthesis of super-heavy elements. *Nucl. Phys. A* 944, 99-116 (2015)).

Example 24—Berkelium Purification (2)

Figure 59:
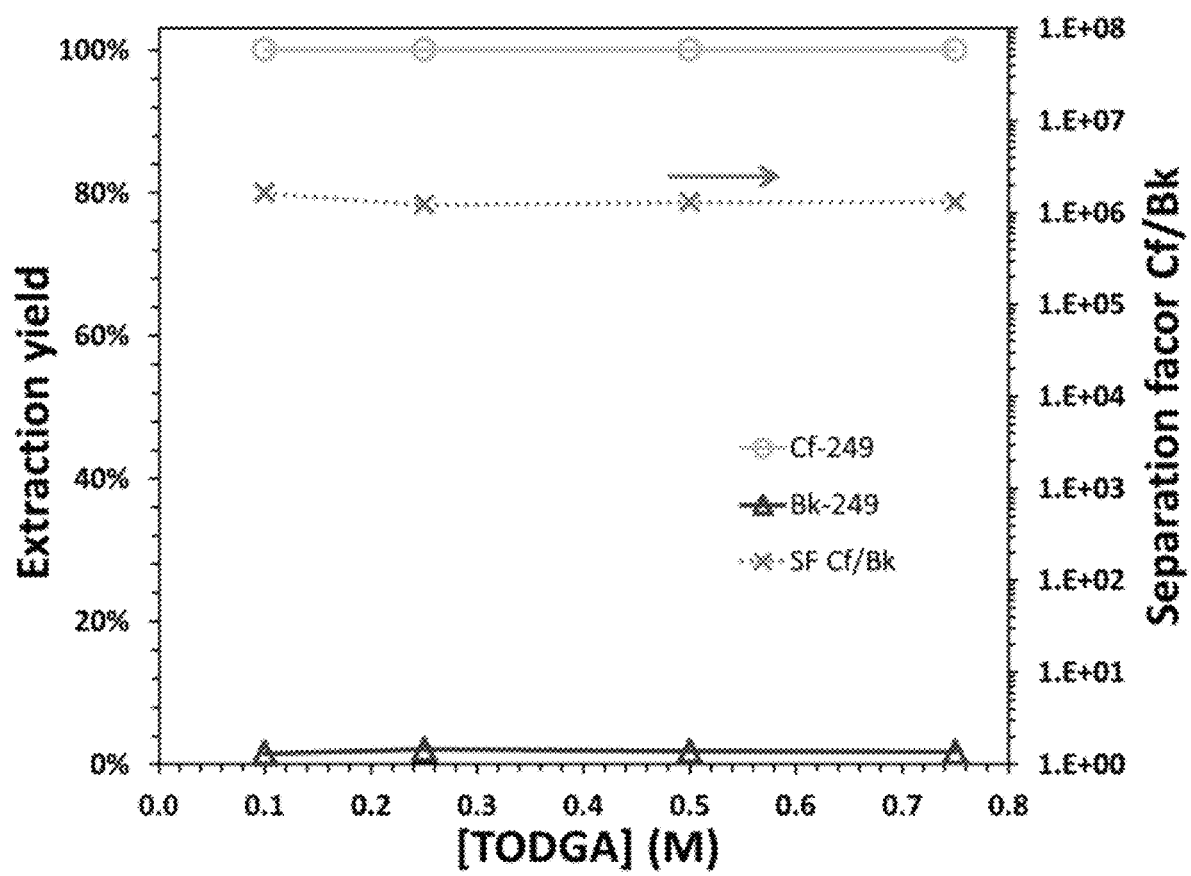
FIG. 59 shows extraction profiles of $^{249}$Bk (triangles), and $^{229}$Cf (circle) and corresponding separation factors (dotted line) as a function of the extractant concentration. Aqueous phase: 1 mM 343HOPO in 3 M HNO$_3$. Organic phase: TODGA in kerosene. O/A=1. One contact. T=25° C. Separation factor values are lower limits due to the quantitative extraction of Cf under these experimental conditions.
Figure 60:
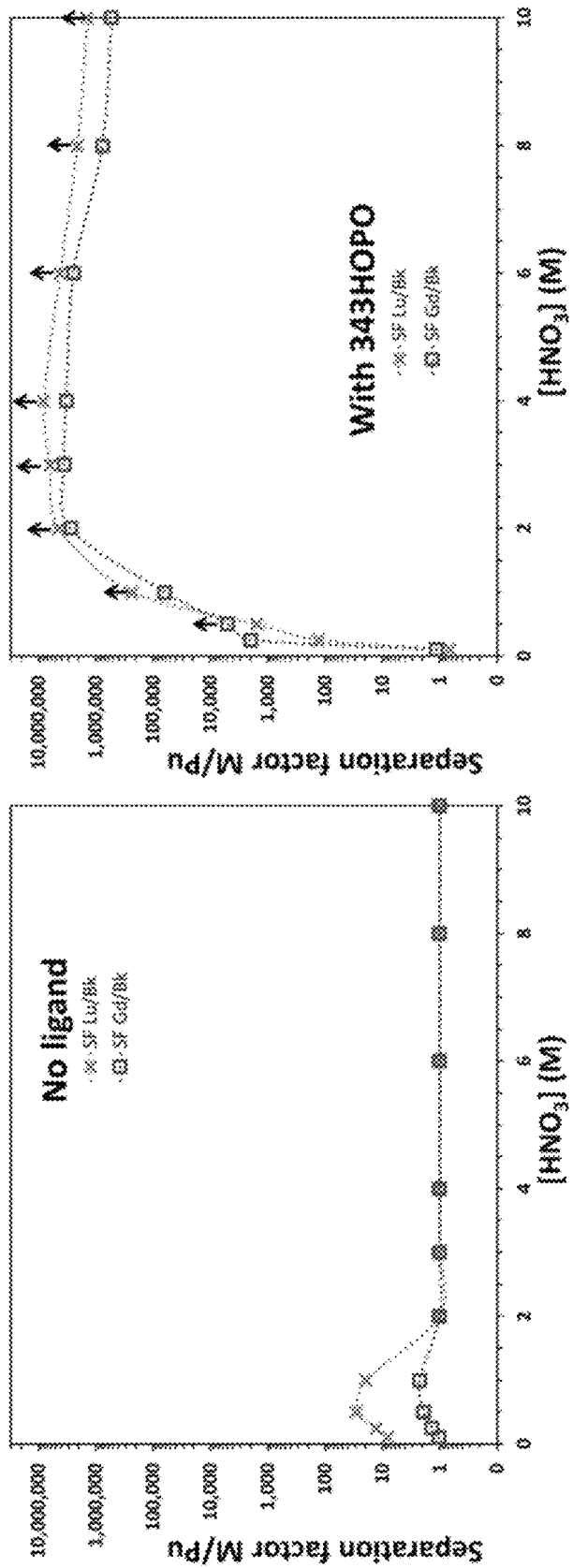
FIG. 60 shows separation factors Lu/Bk and Gd/Bk obtained with the TODGA/343HOPO-HNO$_3$ extraction system. Aqueous phase: 1 mM 343HOPO in HNO$_3$. Organic phase: 0.1 M TODGA in kerosene. O/A=1. One contact. T=25° C. Arrows indicate lower limit due to either the total extraction of Lu$^{3+}$ and Gd$^{3+}$ or the total scavenging of Bk in the aqueous phase.

Bk purification using TODGA as extractant was also investigated. TODGA is more relevant than HDEHP for the production of heavy actinides since it is effective at high acidity and is therefore compatible with the post-irradiation metallic target dissolution step. The extraction behavior of Bk in a TODGA-based system has never been reported (Zhu, Z.-X., Sasaki, Y., Suzuki, H., Suzuki, S. & Kimura, T. Cumulative study on solvent extraction of elements by N,N,N',N'-tetraoctyl-3-oxapentanediamide (TODGA) from nitric acid into n-dodecane. *Anal. Chim. Acta* 527, 163-168 (2004)) but high extraction yields for $Bk^{3+}$ could be expected based on the behavior of $Cf^{3+}$. In nitric solutions without chelator, quantitative co-extraction of $^{249}Bk^{3+}$ and $^{249}Cf^{3+}$ by TODGA was observed, leading to no practical separation between the metals (FIGS. 57A-57D). In stark contrast, addition of 343HOPO drastically changes the Bk extraction profile: less than 1% Bk is extracted throughout the acidity range whereas Cf extraction remains undisturbed, due to the non-interaction between trivalent ions and the aqueous chelator at high acidity. The two adjacent actinides can be separated over a very broad acidity range (0.5 M to 10 M $HNO_3$). Even if an unfavorable initial ratio Cf/Bk was used in those experiments (Cf/Bk ~12,000), $^{249}Bk$ samples completely exempt of $^{249}Cf$ were obtained, notably so after only a single extraction. Experiments at various concentrations of extractant further confirmed the reliability of the $TODGA-HNO_3$-343HOPO separation formulation (FIG. 59) with $SF_{Cf/Bk}$>1,000,000, regardless of the TODGA and $HNO_3$ concentrations. Additional separation experiments with $Gd^{3+}$ and $Lu^{3+}$ further evidenced the reliability of this system for purifying Bk (FIG. 60). Finally, the separation method was tested at the mCi level. Legacy samples of $^{249}Bk/^{249}Cf$ used in previous studies[46,48] were gathered, evaporated, incinerated and reconstituted in 3 M $HNO_3$ solutions containing multiple mCi of $^{249}Bk$ with a Cf/Bk ratio of ~3.4 mol/mol. The solution was split in five, 343HOPO was added, and an extraction step was performed using TODGA. As detailed in TABLE 5, after only a single step and regardless of the conditions used, very efficient separation was observed with the recovery of essentially pure $^{249}Bk$ in the aqueous phase (radiopurity>99.999%, chemical purity>99.8%) and high-purity $^{249}Cf$ in the organic phase (chemical purity>99.5%). These results further confirm the proposed strategy could be used with high-activity samples, and scaled up to either produce high-purity Bk isotopes or to remove Bk traces during Cm, Cf, Es, or Fm production.

TABLE 5

Summary of the separation results obtained for $^{249}Bk$ and $^{249}Cf$ at the mCi level using TODGA and 343HOPO. Separation conditions: 0.1M TODGA in kerosene; 343HOPO in 3M $HNO_3$. T = 25° C. One contact. Activity level: 2 mCi/mL (74 GBq/L).

| Conditions | Phase | Radiopurity | Chemical purity |
|---|---|---|---|
| | Initial | Bk: 99.13% ± 0.13 | Bk: 22.63% ± 0.54 |
| | | Cf: 0.87% ± 0.03 | Cf: 77.37% ± 0.54 |
| O/A = 0.5 [343HOPO] = 1 mM | Organic | Bk: 52.70% Cf: 47.30% | Cf: 99.71% |
| | Aqueous | Bk: >99.999% | Bk: >99.8% |
| O/A = 1.0 [343HOPO] = 1 mM | Organic | Bk: 64.85% Cf: 35.15% | Cf: 99.5% |
| | Aqueous | Bk: >99.999% | Bk: >99.8% |
| O/A = 2.0 [343HOPO] = 1 mM | Organic | Bk: 70.60% Cf: 29.40% | Cf: 99.4% |
| | Aqueous | Bk: >99.999% | Bk: >99.8% |
| O/A = 1.0 [343HOPO] = 5 mM | Organic | Bk: 79.72% Cf: 20.28% | Cf: 99.0% |
| | Aqueous | Bk: >99.999% | Bk: >99.8% |
| O/A = 1.0 [343HOPO] = 25 mM | Organic | Bk: 84.94% Cf: 15.06% | Cf: 98.6% |
| | Aqueous | Bk: >99.999% | Bk: >99.8% |

Noteworthy, the results presented above, although already providing better Cf/Bk separation than with any published method, do not represent optimum system performance since 343HOPO was not initially developed for separation applications and molecules with even higher selectivity could be designed. In addition, the three isotope purification examples examined in this work demonstrate the versatility of the proposed separation strategy, which could undoubtedly be transposed to other critical challenges (NSAC Isotopes Subcommittee. *Meeting isotope needs and capturing opportunities for the future: the* 2015 *long range plan for the DOE-NP isotope program.* 1-160 (US DOE, 2015)) such as those encountered with $^{89}Zr^{4+}/Y^{3+}$, $^{177}Lu^{3+}/Hf^{4+}$, $^{134}La^{3+}/^{134}Ce^{4+}$, or $^{117m}Sn^{4+}/^{116}Cd^{2+}$ purifications. Without being limited by any particular theory, it is anticipated that the use of HOPO ligand derivatives as aqueous chelating hold-back reagents could pave the way to more reliable, flexible and efficient methodologies for metal cation separations.

Example 25—Isotopes

The following isotopes were used in Example 20—Example 24: $^{153}Gd$ (E, $t_{1/2}$=240 d, 130 TBq/g), $^{177}Lu$ ($\beta^-$, $t_{1/2}$=6.6 d, 4,100 TBq/g), $^{225}Ac$ ($\alpha$, $t_{1/2}$=9.95 d, 2,100 TBq/g), $^{233}U$ ($\alpha$, $t_{1/2}$=159200 yr, 0.36 GBq/g), $^{241}Pu$ ($\beta^-$, $t_{1/2}$=14.3 yr, 3.8 TBq/g), $^{242}Pu$ ($\alpha$, $t_{1/2}$=3.74×10$^5$ yr, 0.15 GBq/g), $^{243}Am$ ($\beta$, $t_{1/2}$=7388 yr, 7.4 GBq/g), $^{249}Bk$ ($\beta^-$, $t_{1/2}$=0.9 yr, 61 TBq/g), $^{249}Cf$ ($\alpha$, $t_{1/2}$=352 yr, 0.15 TBq/g), and $^{253}Es$ ($\alpha$, $t_{1/2}$=20.5 d, 932 TBq/g). All are highly radioactive, presenting serious health risks, and were manipulated in facilities specially designed for safe handling of long-lived radioactive materials at the Lawrence Berkeley National Laboratory (LBNL).

Example 26—Materials

For Example 20—Example 24, $^{153}$Gd(III) chloride and $^{233}$U(VI) nitrate were purchased from Eckert & Ziegler Isotope Products (Valencia, Calif.). $^{177}$Lu(III) chloride was purchased from Perkin Elmer Health Sciences (Shelton, Conn.). A Pu(IV) chloride stock solution containing a 50/50 mixture (Bq/Bq) of $^{241}$Pu and $^{242}$Pu and a stock solution of $^{243}$Am(III), prepared by dissolution of $^{243}$Am$_2$O$_3$ in 1 M HNO$_3$, were from LBNL inventory. $^{225}$Ac(III), $^{249}$Bk(III), and $^{249}$Cf(III) were obtained as chlorides from Oak Ridge National Laboratory (ORNL). A $^{253}$Es(III) perchlorate solid sample was provided by Prof. J. Shafer (Colorado School of Mines). 343HOPO was prepared and characterized as previously described (Abergel, R. J. et al. Biomimetic actinide chelators: an update on the preclinical development of the orally active hydroxypyridonate decorporation agents 3,4, 3-LI(1,2-HOPO) and 5-LIO(Me-3,2-HOPO). *Health Phys.* 99, 401-407 (2010)). Standard solutions of 0.1 M and 6.0 M HNO$_3$ (BDH VWR Analytical), 70% HNO$_3$ (Sigma Aldrich), NaNO$_3$ (>99%, ACS grade, VWR), sodium lactate (Sigma Aldrich), TODGA (>99%, Technocomm Ltd.), HDEHP (>95%, Merck), tributyl phosphate "TBP" (>98%, Alpha Aesar), kerosene low odor (Alpha Aesar), DTPA (>98%, TCI), and Ultima Gold LLT (Perkin Elmer) were used as received. All solutions were prepared using deionized water purified by a Millipore Milli-Q reverse osmosis cartridge system. Stocks were stored at 8° C. in the dark between experiments.

Example 27—Method

For Example 20—Example 24, pH measurements were performed with a glass electrode (Metrohm-Micro Combi-response to [H+]) calibrated at 25.0° C. using three NIST standards. Extraction samples were analyzed by liquid scintillation counting (LSC). The distribution coefficient, D(M), of a given metal, M, is defined in Eq. 1, where [M]$_{organic}$ and [M]$_{aqueous}$ are the respective total concentrations of M in the organic and aqueous layers, after extraction. Both concentrations are proportional to the volumetric activity (in Bq/L) determined by LSC. The separation factor, SF$_{M1/M2}$, between two metals, M$_1$ and M$_2$, and extraction yield were calculated according to Eq. 2 and Eq. 3, respectively.

$$D(M) = \frac{[M]_{organic}}{[M]_{aqueous}} = \frac{[Activity]_{organic}}{[Activity]_{aqueous}} \quad \text{Eq. (1)}$$

$$SF_{M1/M2} = \frac{D(M_1)}{D(M_2)} \quad \text{Eq. (2)}$$

$$\% \text{ Extraction} = \frac{[Activity]_{organic} \times V_{organic}}{[Activity]_{organic} \times V_{organic} + [Activity]_{aqueous} \times V_{aqueous}} \times 100 \quad \text{Eq. (3)}$$

In a typical experiment, the solvent (extractant diluted in kerosene) was pre-conditioned by shaking one volume of solvent with three volumes of aqueous phase (typically HNO$_3$) at room temperature for 1 h, thrice. For radioisotope extractions, at least 400 μL aqueous phase (typically containing HNO$_3$, a chelator and a radioisotope) and solvent were placed in air-tight screw-capped plastic tubes, triply-contained, and shaken in a thermoshaker at 300 rpm, 25° C., for at least 30 min. Samples were then centrifuged for 5 min at 3000 rpm and phases separated before analysis. LSC analyses were performed on a Packard Tri-Carb B4430 instrument (Perkin Elmer) after mixing sample aliquots or sample dilution aliquots (10 to 200 μL) with 10 mL of scintillation cocktail (UltimaGold LLT). Samples were counted for at least 6 min and results were background subtracted. The analytical samples contained between 0 and 800,000 CPM. Mixtures of $^{249}$Bk and $^{249}$Cf were analyzed using α/β discrimination and energy windows were set to 0-50 keV for low-energy β particles of $^{249}$Bk and 50-1000 keV for α particles of $^{249}$Cf. $^{243}$Am and $^{225}$Ac samples were counted at secular equilibrium.

REFERENCES

The references cited in this disclosure are incorporated by reference herein in their entireties.

"Designing a Process for Selecting a Site for a Deep-Mined, Geologic Repository for High Level Radioactive Waste and Spent Nuclear Fuel," United States Nuclear Waste Technical Review Board, 1-228 (2015).

Travis S. Grimes, Richard D. Tillotson, and Leigh R. Martin, "Trivalent Lanthanide/Actinide Separation Using Aqueous-Modified TALSPEAK Chemistry," Solvent Extr. Ion Exch. 32(4), 378-390 (2014).

Kenneth L. Nash, "The Chemistry of TALSPEAK: A Review of the Science," Solvent Extr. Ion Exch. 33(1), 1-55 (2015).

Gregg J. Lumetta, Amanda J. Casella, Brian M. Rapko, Tatiana G., Levitskaia, et al., "An Advanced TALSPEAK Concept Using 2-Ethylhexylphosphonic Acid Mono-2-Ethylhexyl Ester as the Extractant," Solvent Extr. Ion Exch. 33(3), 211-223 (2015).

Manuel Sturzbecher-Hoehne, Clara Ng Pak Leung, Anthony D'Aleo, et al. "3,4,3-LI(1,2-HOPO): In vitro formation of highly stable lanthanide complexes translates into efficacious in vivo europium decorporation," Dalton Trans. 40, 8340-8346 (2011).

Ilya Captain, Gauthier J.-P. Deblonde, Peter B. Rupert, et al. "Engineered Recognition of Tetravalent Zirconium and Thorium by Chelator-Protein Systems: Toward Flexible Radiotherapy and Imaging Platforms," Inorg. Chem. 55(22), 11930-11936 (2016).

R. D Shannon, "Revised Effective Ionic Radii and Systematic Studies of Interatomic Distances in Halides and Chalcogenides," Acta Cryst. A 32, 751-767 (1976).

Manuel Sturzbecher-Hoehne, Birgitta Kullgren, Erin E. Jarvis, et al. "Highly Luminescent and Stable Hydroxypyridinonate Complexes: A Step Towards New Curium Decontamination Strategies," Chem.-Eur. J. 20 (32), 9962-9968 (2014).

Manuel Sturzbecher-Hoehne, P. Yang, A. D'Aleo, Rebecca Abergel, "Intramolecular sensitization of americium luminescence in solution: shining light on short-lived forbidden 5f transitions," Dalton Trans. 45, 9912-9919 (2016).

David L. White, Patricai W. Durbin, Nylan Jeung, and Kenneth n. Raymond, "Specific Sequestering Agents for the Actinides. 16. Synthesis and Initial Biological Testing of Polydentate Oxohydroxypyridinecarboxylate Ligands," J. Med. Chem. 31 (1), 11-18 (1988).

Jide Xy, Birgitta Kullgren, Patricia W. Durbin, and Kenneth N. Raymond, "Specific Sequestering Agents for the Actinides. 28. Synthesis and Initial Evaluation of Multidentate 4-Carbamoyl-3-hydroxy-1-methyl-2(1H)-pyridinone Ligands for in Vivo Plutonium (IV) Chelation," J. Med. Chem. 38 (14), 2606-2614 (1988).

Martell, A. E.; Smith, R. M.; Motekaitis, R. J. NIST Standard Reference Database; National Institute of Standards and Technology: Gaithersburg, Md.

Rebecca J. Abergel, Anthony D'Aleo, Clara Ng Pak Leung, David K. Shuh, and Kenneth N. Raymond, "Using the Antenna Effect as a Spectroscopic Tool: Photophysics and Solution Thermodynamics of the Model Luminescent Hydroxypyridonate Complex [Eum(3,4,3-LI(1,2-HOPO))]-," Inorg. Chem. 48, 10868-10870 (2009).

J. T. Harvey, Production of Actinium-225 via High Energy Proton Induced Spallation of Thorium-232. Final Technical Report DE-SC0003602, NorthStar Medical Radioisotopes, LLC, https:1/world wide web.osti.gov/scitech/servlets/purl/1032445/.

M. Sturzbecher-Hoehne, G. J.-P. Deblonde, R. J. Abergel, Solution thermodynamic evaluation of hydroxypyridinonate chelators 3,4,3-LI(1,2-HOPO) and 5-LIO(Me-3,2-HOPO) for UO2(VI) and Th(IV) decorporation, Radiochim. Acta. 101 (2013) 359-366. doi:10.1524/ract.2013.2047.

R. J. Abergel, A. D'Aldo, C. Ng Pak Leung, D. K. Shuh, K. N. Raymond, Using the Antenna Effect as a Spectroscopic Tool: Photophysics and Solution Thermodynamics of the Model Luminescent Hydroxypyridonate Complex [Eu (III)(3,4,3-LI(1,2-HOPO))]-, Inorg. Chem. 48 (2009) 10868-10870. doi:10.1021/ic9013703.

M. Sturzbecher-Hoehne, C. Ng Pak Leung, A. D'Aldo, B. Kullgren, A.-L. Prigent, D. K. Shuh, K. N. Raymond, R. J. Abergel, 3,4,3-LI(1,2-HOPO): In vitro formation of highly stable lanthanide complexes translates into efficacious in vivo europium decorporation, Dalton Trans. 40 (2011) 8340. doi: 10.1039/cldt10840a.

M. Sturzbecher-Hoehne, P. Yang, A. D'Alo, R. J. Abergel, Intramolecular sensitization of americium luminescence in solution: shining light on short-lived forbidden 5f transitions, Dalton Trans. (2016). doi: 10. 1039/$C_6$DT00328A.

M. Sturzbecher-Hoehne, B. Kullgren, E. E. Jarvis, D. D. An, R. J. Abergel, Highly Luminescent and Stable Hydroxypyridinonate Complexes: A Step Towards New Curium Decontamination Strategies, Chem.—Eur. J. 20 (2014) 9962-9968. doi: 10.1002/chem.201402103.

M. Sturzbecher-Hoehne, T. A. Choi, R. J. Abergel, Hydroxypyridinonate Complex Stability of Group (IV) Metals and Tetravalent f-Block Elements: The Key to the Next Generation of Chelating Agents for Radiopharmaceuticals, Inorg. Chem. 54 (2015) 3462-3468. doi: 10.1021/acs.inorgchem.5b00033.

G. J.-P. Deblonde, M. Sturzbecher-Hoehne, R. J. Abergel, Solution Thermodynamic Stability of Complexes Formed with the Octadentate Hydroxypyridinonate Ligand 3,4,3-LI(1,2-HOPO): A Critical Feature for Efficient Chelation of Lanthanide(IV) and Actinide(IV) Ions, Inorg. Chem. 52 (2013) 8805-8811. doi: 10.1021/ic4010246.

G. J.-P. Deblonde, M. Sturzbecher-Hoehne, P. B. Rupert, D. D. An, M.-C. Illy, C. Y. Ralston, J. Brabec, W. A. de Jong, R. K. Strong, R. J. Abergel, Chelation and stabilization of berkelium in oxidation state+IV, Nat. Chem. (2017). doi: 10.1038/nchem.2759.

A. E. Martell, R. M. Smith, R. J. Motekaitis, NIST Standard Reference Database 46, (n.d.).

D. Lundberg, I. Persson, The size of actinoid(III) ions—structural analysis vs. common misinterpretations, Coord. Chem. Rev. 318 (2016) 131-134. doi: 10.1016/j.ccr.2016.04.003.

D. Lundberg, I. Persson, L. Eriksson, P. D'Angelo, S. De Panfilis, Structural Study of the N,N'-Dimethylpropyleneurea Solvated Lanthanoid(III) Ions in Solution and Solid State with an Analysis of the Ionic Radii of Lanthanoid(III) Ions, Inorg. Chem. 49 (2010) 4420-4432. doi:10.1021/ic100034q.

C. Wai, D. Fisher, others, Carboxylate-derived calixarenes with high selectivity for actinium-225, Chem. Commun. (1998) 377-378.

V. Radchenko, J. W. Engle, J. J. Wilson, J. R. Maassen, F. M. Nortier, W. A. Taylor, E. R. Birnbaum, L. A. Hudston, K. D. John, M. E. Fassbender, Application of ion exchange and extraction chromatography to the separation of actinium from proton-irradiated thorium metal for analytical purposes, J. Chromatogr. A. 1380 (2015) 55-63. doi: 10.1016/j.chroma.2014.12.045.

V. Ostapenko, A. Vasiliev, E. Lapshina, S. Ermolaev, R. Aliev, Y. Totskiy, B. Zhuikov, S. Kalmykov, Extraction chromatographic behavior of actinium and REE on DGA, Ln and TRU resins in nitric acid solutions, J. Radioanal. Nucl. Chem. 306 (2015) 707-711. doi:10.1007/s10967-015-4331-y.

L. R. Morss, N. M. Edelstein, J. Fuger, The Chemistry of the Actinide and Transactinide Elements, 4th ed., Springer, 2010.

K. L. Nash, The Chemistry of TALSPEAK: A Review of the Science, Solvent Extr. Ion Exch. 33 (2015) 1-55. doi: 10.1080/07366299.2014.985912.

K. V. Lohithakshan, P. Patil, S. K. Aggarwal, Solvent extraction studies of plutonium(IV) and americium(III) in room temperature ionic liquid (RTIL) by di-2-ethyl hexyl phosphoric acid (HDEHP) as extractant, J. Radioanal. Nucl. Chem. 301 (2014) 153-157. doi:10.1007/s 10967-014-3119-9.

J. T. Harvey, Production of Actinium-225 via High Energy Proton Induced Spallation of Thorium-232. Final Technical Report DE-SC0003602, NorthStar Medical Radioisotopes, LLC, n.d. https:1/world wide web.osti.gov/scitech/servlets/purl/1032445/.

NSAC Isotopes Subcommittee. *Meeting isotope needs and capturing opportunities for the future: the* 2015 *long range plan for the DOE-NP isotope program.* 1-160 (US DOE, 2015).

Hagemann, U. B. et al. In Vitro and In Vivo Efficacy of a Novel CD33-Targeted Thorium-227 Conjugate for the Treatment of Acute Myeloid Leukemia. *Mol. Cancer Therapeutics* 15, 2422-2431 (2016).

Witze, A. Nuclear power: Desperately seeking plutonium. Nature News 515, 484-486 (2014).

Veliscek-Carolan, J. Separation of actinides from spent nuclear fuel: A review. *J. Hazard. Mater.* 318, 266-281 (2016).

Roberto, J. B. et al. Actinide targets for the synthesis of super-heavy elements. *Nucl. Phys. A* 944, 99-116 (2015).

Oganessian, Y. T. et al. Experimental studies of the 249 Bk+48 Ca reaction including decay properties and excitation function for isotopes of element 117, and discovery of the new isotope 277 Mt. *Phys. Rev. C* 87, (2013).

Beltrami, D. et al. Recovery of Uranium from Wet Phosphoric Acid by Solvent Extraction Processes. *Chem. Rev.* 114, 12002-12023 (2014).

Leydier, A. et al. Recovery of uranium (VI) from concentrated phosphoric acid using bifunctional reagents. Hydrometallurgy 171, 262-266 (2017).

Zhu, Z.-X., Sasaki, Y., Suzuki, H., Suzuki, S. & Kimura, T. Cumulative study on solvent extraction of elements by N,N,N',N'-tetraoctyl-3-oxapentanediamide (TODGA) from nitric acid into n-dodecane. *Anal. Chim. Acta* 527, 163-168 (2004).

Horwitz, E. P. & Bloomquist, C. A. A. Chemical separations for super-heavy element searches in irradiated uranium targets. *J. Inorg. Nucl. Chem.* 37, 425-434 (1975).

Cary, S. K. et al. Advancing Understanding of the +4 Metal Extractant Thenoyltrifluoroacetonate (TTA−); Synthesis and Structure of $M_{IV}TTA_4$ ($M^{IV}$=Zr, Hf, Ce, Th, U, Np, Pu) and $M^{III}(TTA)_4$ ($M^{III}$=Ce, Nd, Sm, Yb). *Inorg. Chem.* 57, 3782-3797 (2018).

Abergel, R. J. et al. Biomimetic actinide chelators: an update on the preclinical development of the orally active hydroxypyridonate decorporation agents 3,4,3-LI(1,2-HOPO) and 5-LIO(Me-3,2-HOPO). *Health Phys.* 99, 401-407 (2010).

Gorden, A. E. V., Xu, J., Raymond, K. N. & Durbin, P. Rational Design of Sequestering Agents for Plutonium and Other Actinides. *Chem. Rev.* 103, 4207-4282 (2003).

Deri, M. A. et al. p-SCN-Bn-HOPO: A Superior Bifunctional Chelator for 89Zr ImmunoPET. *Bioconj. Chem.* 26, 2579-2591 (2015).

Captain, I. et al. Engineered Recognition of Tetravalent Zirconium and Thorium by Chelator-Protein Systems: Toward Flexible Radiotherapy and Imaging Platforms. *Inorg. Chem.* 55, 11930-11936 (2016).

Xu, J., Radkov, E., Ziegler, M. & Raymond, K. N. Plutonium(IV) Sequestration: Structural and Thermodynamic Evaluation of the Extraordinarily Stable Cerium(IV) Hydroxypyridinonate Complexes[1]. *Inorg. Chem.* 39, 4156-4164 (2000).

Deblonde, G. J.-P. et al. Solution Thermodynamics and Kinetics of Metal Complexation with a Hydroxypyridinone Chelator Designed for Thorium-227 Targeted Alpha Therapy. *Inorg. Chem.* (2018). doi: 10.1021/acs.inorgchem.8b02430

Pham, T. A. et al. A Macrocyclic Chelator That Selectively Binds Ln4+ over Ln3+ by a Factor of 1029. *Inorg. Chem.* 55, 9989-10002 (2016).

D'Aléo, A., Moore, E. G., Xu, J., Daumann, L. J. & Raymond, K. N. Optimization of the Sensitization Process and Stability of Octadentate Eu(III) 1,2-HOPO Complexes. *Inorg. Chem.* 54, 6807-6820 (2015).

Xu, J. et al. Synthesis and Initial Evaluation for In Vivo Chelation of Pu(IV) of a Mixed Octadentate Spermine-Based Ligand Containing 4-Carbamoyl-3-hydroxy-1-methyl-2(1H)-pyridinone and 6-Carbamoyl-1-hydroxy-2(1H)-pyridinone. *J. Med. Chem.* 45, 3963-3971 (2002).

Allott, L. et al. Evaluation of DFO-HOPO as an octadentate chelator for zirconium-89. *Chem. Comm.* 53, 8529-8532 (2017).

Deblonde, G. J.-P., Sturzbecher-Hoehne, M. & Abergel, R. J. Solution Thermodynamic Stability of Complexes Formed with the Octadentate Hydroxypyridinonate Ligand 3,4,3-LI(1,2-HOPO): A Critical Feature for Efficient Chelation of Lanthanide(IV) and Actinide(IV) Ions. *Inorg. Chem.* 52, 8805-8811 (2013).

Sturzbecher-Hoehne, M. et al. 3,4,3-LI(1,2-HOPO): In vitro formation of highly stable lanthanide complexes translates into efficacious in vivo europium decorporation. *Dalton Trans.* 40, 8340 (2011).

Deblonde, G. J.-P. et al. Chelation and stabilization of berkelium in oxidation state +IV. *Nat. Chem.* 9, 843-849 (2017). Sturzbecher-Hoehne, M., Kullgren, B., Jarvis, E. E., An, D. D. & Abergel, R. J. Highly Luminescent and Stable Hydroxypyridinonate Complexes: A Step Towards New Curium Decontamination Strategies. *Chem. Eur. J.* 20, 9962-9968 (2014).

Sturzbecher-Hoehne, M., Yang, P., D'Alo, A. & Abergel, R. J. Intramolecular sensitization of americium luminescence in solution: shining light on short-lived forbidden 5f transitions. *Dalton Trans.* 45, 9912-9919 (2016).

Deblonde, G. J.-P., Lohrey, T. D., An, D. D. & Abergel, R. J. Toxic heavy metal—Pb, Cd, Sn—complexation by the octadentate hydroxypyridinonate ligand archetype 3,4,3-LI(1,2-HOPO). *New J. Chem.* 42, 7649-7658 (2018).

Sturzbecher-Hoehne, M., Deblonde, G. J.-P. & Abergel, R. J. Solution thermodynamic evaluation of hydroxypyridinonate chelators 3,4,3-LI(1,2-HOPO) and 5-LIO(Me-3,2-HOPO) for UO2(VI) and Th(IV) decorporation. *Radiochim. Acta* 101, 359-366 (2013).

Wilson, J. J. et al. Evaluation of nitrogen-rich macrocyclic ligands for the chelation of therapeutic bismuth radioisotopes. *Nucl. Med. Biol.* 42, 428-438 (2015).

Ferrier, M. G. et al. Synthesis and Characterization of the Actinium Aquo Ion. *ACS Cent. Sci.* 3, 176-185 (2017).

Lundberg, D. & Persson, I. The size of actinoid(III) ions—structural analysis vs. common misinterpretations. *Coord. Chem. Rev.* 318, 131-134 (2016).

Radchenko, V. et al. Application of ion exchange and extraction chromatography to the separation of actinium from proton-irradiated thorium metal for analytical purposes. *J. Chromat. A* 1380, 55-63 (2015).

Nash, K. L. The Chemistry of TALSPEAK: A Review of the Science. *Solv. Extract. Ion Exchange* 33, 1-55 (2015).

Braley, J. C., Grimes, T. S. & Nash, K. L. Alternatives to HDEHP and DTPA for Simplified TALSPEAK Separations. *Ind. Eng. Chem. Res.* 51, 629-638 (2012).

Glaser, A. & Mian, Z. Fissile Material Stocks and Production, 2008. *Bull. Atom. Sci.* 65, 35-47 (2009).

Zhao, P. et al. Plutonium(IV) and (V) Sorption to Goethite at Sub-Femtomolar to Micromolar Concentrations: Redox Transformations and Surface Precipitation. *Environ. Sci. Technol.* 50, 6948-6956 (2016).

Albright, D. & Kramer, K. Stockpiles still growing. *Bull. Atom. Sci.* 60, 14-16 (2004).

Herbst, R. S., Baron, P. & Nilsson, M. 6—Standard and advanced separation: PUREX processes for nuclear fuel reprocessing. in *Advanced Separation Techniques for Nuclear Fuel Reprocessing and Radioactive Waste Treatment* (eds. Nash, K. L. & Lumetta, G. J.) 141-175 (Woodhead Publishing, 2011). doi: 10.1533/9780857092274.2.141

Paviet-Hartmann, P., Riddle, C., Campbell, K. & Mausolf, E. Overview of reductants utilized in nuclear fuel reprocessing/recycling. in 79-86 (2013).

Whittaker, D. et al. Applications of Diglycolamide Based Solvent Extraction Processes in Spent Nuclear Fuel Reprocessing, Part 1: TODGA. *Solv. Extract. Ion Exchange* 36, 223-256 (2018).

Modolo, G., Asp, H., Schreinemachers, C. & Vijgen, H. Recovery of actinides and lanthanides from high-level liquid waste by extraction chromatography using TODGA+TBP impregnated resins. *Radiochim. Acta* 95, (2007).

Carrott, M. et al. Distribution of plutonium, americium and interfering fission products between nitric acid and a mixed organic phase of TODGA and DMDOHEMA in kerosene, and implications for the design of the "EURO-GANEX" process. *Hydrometallurgy* 152, 139-148 (2015).

Modolo, G., Asp, H., Schreinemachers, C. & Vijgen, H. Development of a TODGA based Process for Partitioning of Actinides from a PUREX Raffinate Part I: Batch Extraction Optimization Studies and Stability Tests. *Solv. Extract. Ion Exchange* 25, 703-721 (2007).

Öhrström, L. & Reedijk, J. Names and symbols of the elements with atomic numbers 113, 115, 117 and 118 (IUPAC Recommendations 2016). *Pure Appl. Chem.* 88, (2016).

Oganessian, Y. T. et al. *Results from the First 249Cf+48Ca Experiment.* 11 (Lawrence Livermore National Laboratory, 02/0302003).

Deblonde, G. J.-P. et al. Spectroscopic and Computational Characterization of Diethylenetriaminepentaacetic Acid/Transplutonium Chelates: Evidencing Heterogeneity in the Heavy Actinide(III) Series. *Angew. Chem. Int. Ed.* 57, 4521-4526 (2018).

Du, M., Tan, R. & Boll, R. Applications of MP-1 anion exchange resin and Eichrom LN resin in berkelium-249 purification. *J. Radioanal. Nucl. Chem.* 318, 619-629 (2018).

Kelley, M. P. et al. Bond Covalency and Oxidation State of Actinide Ions Complexed with Therapeutic Chelating Agent 3,4,3-LI(1,2-HOPO). *Inorg. Chem.* 57, 5352-5363 (2018).

What is claimed is:

1. A method of separating metal ions, comprising:
   contacting a liquid composition comprising a plurality of metal ions with an octadentate ligand, under conditions sufficient to form a metal ion-ligand complex comprising a metal ion of the plurality of metal ions, to generate a mixture enriched for the metal ion-ligand complex; and
   separating a first fraction of the mixture enriched for the metal ion-ligand complex from a second fraction depleted for the metal ion-ligand complex, wherein the first fraction of the mixture has an acidic pH of less than 1,
   wherein the plurality of metal ions are plutonium ions.

2. The method of claim 1, wherein acidic denotes a pH of between about 1 to about 0.

3. The method of claim 1, wherein the octadentate ligand is a hydroxypyridonate ligand.

4. The method of claim 3, wherein the octadentate ligand is built on a spermine scaffold.

5. The method of claim 3, wherein the octadentate ligand is 3,4,3-LI(1,2-HOPO).

6. The method of claim 1, further comprising dissolving a metal in an acidic solution to obtain the liquid composition.

7. The method of claim 1, further comprising lowering a pH beneath 0 to separate tetravalent ions.

8. The method of claim 1, further comprising an extractant.

9. The method of claim 8, wherein the extractant is selected from the group consisting of TODGA, di-(2-ethylhexyl)phosphoric acid (HDEHP), a derivative of HDEHP, calixarenes, diglycoamide derivatives, carbamoylphosphine oxide derivatives, tributylphosphate (TBP), monoamide derivatives, and tertiary amines, and quaternary ammonium salts.

10. The method of claim 1, wherein separating comprises filtering, precipitating, liquid-liquid extraction or chromatography, or wherein the method further comprises filtering, precipitating, liquid-liquid extraction or chromatography.

11. The method of claim 1, wherein
    1) the separating comprises contacting the liquid composition with an organic phase or
    2) further comprising contacting the liquid composition with an organic phase.

12. The method of claim 6, wherein the method does not comprise adjusting the pH of the liquid composition after dissolving the metal.

13. The method of claim 6, wherein the method does not comprise raising the pH of the liquid composition after dissolving the metal.

14. The method of claim 11, wherein the organic phase comprises a non-selective extractant.

15. The method of claim 11, wherein the organic phase does not comprise an extractant that selectively binds to the first or second fraction.

* * * * *